(12) United States Patent
Wong et al.

(10) Patent No.: US 11,624,093 B2
(45) Date of Patent: Apr. 11, 2023

(54) TUMOR SUPPRESSOR AND ONCOGENE BIOMARKERS PREDICTIVE OF ANTI-IMMUNE CHECKPOINT INHIBITOR RESPONSE

(71) Applicants: Dana-Farber Cancer Institute, Inc., Boston, MA (US); Children's Medical Center Corporation, Boston, MA (US)

(72) Inventors: Kwok-Kin Wong, Arlington, MA (US); Chunxiao Xu, Boston, MA (US); Christine F. Brainson, Boston, MA (US); Carla F. Kim, Boston, MA (US); Glenn Dranoff, Lexington, MA (US); Peter Hammerman, Newton, MA (US)

(73) Assignees: Dana-Farber Cancer Institute, Inc., Boston, MA (US); Children's Medical Center Corporation, Boston, MA (US)

( * ) Notice: Subject to any disclaimer, the term of this patent is extended or adjusted under 35 U.S.C. 154(b) by 0 days.

(21) Appl. No.: 15/305,498

(22) PCT Filed: Apr. 24, 2015

(86) PCT No.: PCT/US2015/027515
§ 371 (c)(1),
(2) Date: Oct. 20, 2016

(87) PCT Pub. No.: WO2015/164743
PCT Pub. Date: Oct. 29, 2015

(65) Prior Publication Data
US 2017/0130271 A1    May 11, 2017

Related U.S. Application Data

(60) Provisional application No. 62/012,689, filed on Jun. 16, 2014, provisional application No. 61/983,602, filed on Apr. 24, 2014.

(51) Int. Cl.
| | | |
|---|---|---|
| *C12Q 1/6886* | (2018.01) | |
| *A61K 31/69* | (2006.01) | |
| *A61K 45/06* | (2006.01) | |
| *G01N 33/50* | (2006.01) | |
| *G01N 33/574* | (2006.01) | |

(52) U.S. Cl.
CPC ............ *C12Q 1/6886* (2013.01); *A61K 31/69* (2013.01); *A61K 45/06* (2013.01); *G01N 33/5011* (2013.01); *G01N 33/57423* (2013.01); *C12Q 2600/106* (2013.01); *C12Q 2600/118* (2013.01); *C12Q 2600/136* (2013.01); *C12Q 2600/156* (2013.01); *C12Q 2600/158* (2013.01); *G01N 2333/70596* (2013.01)

(58) Field of Classification Search
CPC ............ C12Q 1/6886; G01N 33/5011; G01N 33/57423; G01N 2333/70596; A61K 31/69; A61K 45/06
See application file for complete search history.

(56) References Cited

U.S. PATENT DOCUMENTS

| | | | |
|---|---|---|---|
| 6,054,308 | A | 4/2000 | Vockley et al. |
| 9,040,703 | B2 * | 5/2015 | Van Zandt .............. C07F 5/025 546/13 |
| 2009/0264398 | A1 | 10/2009 | Bauer |
| 2010/0021472 | A1 | 1/2010 | Srikrishna et al. |
| 2012/0171116 | A1 | 7/2012 | Tomczuk et al. |
| 2013/0196873 | A1 | 8/2013 | Wurdinger et al. |
| 2013/0338040 | A1 | 12/2013 | Hayes et al. |
| 2014/0099254 | A1 | 4/2014 | Chang et al. |

FOREIGN PATENT DOCUMENTS

| | | |
|---|---|---|
| WO | WO-2008/097908 A2 | 8/2008 |
| WO | WO-2010/085797 A2 | 7/2010 |
| WO | WO-2011/068810 A1 | 6/2011 |
| WO | WO-2012/019127 A2 | 2/2012 |
| WO | WO-2012/058065 A1 | 5/2012 |
| WO | WO-2013/103836 A2 | 7/2013 |
| WO | WO-2013/151666 A2 | 10/2013 |

OTHER PUBLICATIONS

Feun et al., Curr Pharm Des 2008, 14(11), 1049-1057.*
Zea et al., Cancer Res. 2005, 65 (8), Apr. 2005, 3044-3048.*
Chatela et al., J. Thoracic Disease, 2017, 9(7), 2142-2158.*
SSC, 2018, https://www.skincancer.org/skin-cancer-information/squamous-cell-carcinoma.*
Extended European Search Report issued by the European Patent Office in corresponding Application No. EP 15782674.4, dated Nov. 7, 2017.
Ji et al., "LKB1 modulates lung cancer differentiation and metastasis," Nature, 448(7155):807-810 (2007).
She-Juan et al., "Identification of enriched driver gene alterations in subgroups of non-small cell lung cancer patients based on histology and smoking status," PLoS One, 7(6):e40109 (2012).
Stjernström et al., "Alterations of INPP4B, PIK3CA and pAkt of the PI3K pathway are associated with squamous cell carcinoma of the lung," Cancer Med, 3(2):337-348 (2014).
Bayne et al., "Tumor-derived granulocyte-macrophage colony-stimulating factor regulates myeloid inflammation and t cell immunity in pancreatic cancer," Cancer Cell, 21:822-835 (2012).
GenBank Accession No. BC020653.1 submitted by Strausberg et al., "Generation and initial analysis of more than 15,000 full-length human and mouse cDNA sequences," Proc. Natl. Acad. Sci. USA 99:16899-16903 (Jul. 15, 2006).
Van Zandt et al., "Discovery of (R)-2-Amino-6-borono-2-(2-(piperidin-1-yl)ethyl)hexanoic acid and congeners as highly potent inhibitors of human arginases I and II for treatment of myocardial reperfusion injury," J Med Chem, 56: 2568-2580 (2013).
International Search Report dated Oct. 28, 2015 for International Application No. PCT/US2015/027515 filed on Apr. 24, 2015.
Declerck et al., "Immunotherapy for lung cancer: ongoing clinical trials," Future Oncology, 10(1):91-105 (2014).
Heuvers et al., "Arginase-1 mRNA expression correlates with myeloid-derived suppressor cell levels in peripheral blood of NSCLC patients," Lung Cancer, 81:468-474 (2013).

* cited by examiner

*Primary Examiner* — Sun Jae Yoo
(74) *Attorney, Agent, or Firm* — Foley Hoag LLP

(57) ABSTRACT

The present invention is based on the identification of novel biomarkers predictive of responsiveness to anti-immune checkpoint inhibitor therapies.

21 Claims, 22 Drawing Sheets

Specification includes a Sequence Listing.

A

B

SCC: LP SCC whole tumor; S:Sca1; N:Ngfr
EC: epithelial cells; Kras: Kras$^{G12D}$ tumor

A

Lkb1;Pten mice SCCs vs normal lung (n=3)

TCGA Lung SCC with LKB or PTEN alteration vs normal lung (n=34)

B

SEQUENCE LISTING

<160> NUMBER OF SEQ ID NOS: 19

<210> SEQ ID NO 1
<211> LENGTH: 993
<212> TYPE: DNA
<213> ORGANISM: Homo sapiens

<400> SEQUENCE: 1

```
atgagcgcca agtccagaac cataggatt attggagctc ctttctcaaa gggacagcca    60
cgaggagggg tggaagaagg ccctacagta ttgagaaagg ctggtctgct tgagaaactt   120
aaagaacaag taactcaaaa cttttaatt ttagagtgtg atgtgaagga ttatgggac    180
ctgccctttg ctgacatccc taatgacagt cccttcaaa ttgtgaagaa tccaaggtct   240
gtgggaaaag caagcgagca gctggctggc aaggtggcag aagtcaagaa gaacggaaga   300
atcagcctgg tgctgggcgg agaccacagt ttggcaattg gaagcatctc tggccatgcc   360
agggtccacc ctgatcttgg agtcatctgg gtggatgctc acactgatat caacactcca   420
ctgacaacca caagtggaaa cttgcatgga caacctgtat cttcctcct gaaggaacta    480
aaaggaaaga ttcccgatgt gccaggattc tcctgggtga ctccctgtat atctgccaag   540
gatattgtgt atattggctt gagagacgtg gaccctgggg aacactacat tttgaaaact   600
ctaggcatta aatactttc aatgactgaa gtggacagac taggaattgg caaggtgatg   660
gaagaaacac tcagctatct actaggaaga agaaaaggc caattcatct aagttttgat   720
gttgacggac tggacccatc tttcacacca gctactggca caccagtcgt gggaggtctg   780
acatacagag aaggtctcta catcacgaaa gaaatctaca aaacagggct actctcagga   840
ttagatataa tggaagtgaa cccatccctg gggaagacac cagaagaagt aactcgaaca   900
gtgaacacag cagttgcaat aaccttggct tgtttcggac ttgctcggga gggtaatcac   960
aagcctattg actaccttaa cccacctaag taa                                 993
```

<210> SEQ ID NO 2
<211> LENGTH: 330
<212> TYPE: PRT
<213> ORGANISM: Homo sapiens

<400> SEQUENCE: 2

```
Met Ser Ala Lys Ser Arg Thr Ile Gly Ile Ile Gly Ala Pro Phe Ser
1               5                   10                  15

Lys Gly Gln Pro Arg Gly Gly Val Glu Glu Gly Pro Thr Val Leu Arg
            20                  25                  30

Lys Ala Gly Leu Leu Glu Lys Leu Lys Glu Gln Val Thr Gln Asn Phe
        35                  40                  45

Leu Ile Leu Glu Cys Asp Val Lys Asp Tyr Gly Asp Leu Pro Phe Ala
    50                  55                  60

Asp Ile Pro Asn Asp Ser Pro Phe Gln Ile Val Lys Asn Pro Arg Ser
65                  70                  75                  80

Val Gly Lys Ala Ser Glu Gln Leu Ala Gly Lys Val Ala Glu Val Lys
                85                  90                  95

Lys Asn Gly Arg Ile Ser Leu Val Leu Gly Gly Asp His Ser Leu Ala
            100                 105                 110

Ile Gly Ser Ile Ser Gly His Ala Arg Val His Pro Asp Leu Gly Val
        115                 120                 125

Ile Trp Val Asp Ala His Thr Asp Ile Asn Thr Pro Leu Thr Thr Thr
    130                 135                 140

Ser Gly Asn Leu His Gly Gln Pro Val Ser Phe Leu Leu Lys Glu Leu
145                 150                 155                 160

Lys Gly Lys Ile Pro Asp Val Pro Gly Phe Ser Trp Val Thr Pro Cys
                165                 170                 175

Ile Ser Ala Lys Asp Ile Val Tyr Ile Gly Leu Arg Asp Val Asp Pro
            180                 185                 190
```

```
Gly Glu His Tyr Ile Leu Lys Thr Leu Gly Ile Lys Tyr Phe Ser Met
        195                 200                 205

Thr Glu Val Asp Arg Leu Gly Ile Gly Lys Val Met Glu Glu Thr Leu
    210                 215                 220

Ser Tyr Leu Leu Gly Arg Lys Lys Arg Pro Ile His Leu Ser Phe Asp
225                 230                 235                 240

Val Asp Gly Leu Asp Pro Ser Phe Thr Pro Ala Thr Gly Thr Pro Val
            245                 250                 255

Val Gly Gly Leu Thr Tyr Arg Glu Gly Leu Tyr Ile Thr Glu Glu Ile
            260                 265                 270

Tyr Lys Thr Gly Leu Leu Ser Gly Leu Asp Ile Met Glu Val Asn Pro
        275                 280                 285

Ser Leu Gly Lys Thr Pro Glu Glu Val Thr Arg Thr Val Asn Thr Ala
        290                 295                 300

Val Ala Ile Thr Leu Ala Cys Phe Gly Leu Ala Arg Glu Gly Asn His
305                 310                 315                 320

Lys Pro Ile Asp Tyr Leu Asn Pro Pro Lys
                325                 330

<210> SEQ ID NO 3
<211> LENGTH: 969
<212> TYPE: DNA
<213> ORGANISM: Homo sapiens

<400> SEQUENCE: 3
atgagcgcca agtccagaac cataggggatt attggagctc ctttctcaaa gggacagcca      60
cgaggagggg tggaagaagg ccctacagta ttgagaaagg ctggtctgct tgagaaactt     120
aaagaacaag agtgtgatgt gaaggattat ggggacctgc cctttgctga catccctaat     180
gacagtccct ttcaaattgt gaagaatcca aggtctgtgg aaaagcaag cgagcagctg      240 gctggcaagg tggcagaagt caagaagaac ggaagaatca gcctggtgct gggcggagac     300
cacagtttgg caattggaag catctctggc catgccaggg tccaccctga tcttggagtc     360
atctgggtgg atgctcacac tgatatcaac actccactga caaccacaag tggaaacttg     420
catggacaac tgtatctttt cctcctgaag aactaaaaag gaaagattcc cgatgtgcca     480
ggattctcct gggtgactcc ctgtatatct gccaaggata ttgtgtatat ggcttgaga      540 gacgtggacc ctggggaaca ctacattttg aaaactctag cattaaata ctttcaatg      600 actgaagtgg acagactagg aattggcaag gtgatggaag aaacactcag ctatctacta     660
ggaagaaaga aaaggccaat tcatctaagt tttgatgttg acggactgga cccatctttc     720
acaccagcta ctggcacacc agtcgtggga ggtctgacat acagagaagg tctctacatc     780
acagaagaaa tctacaaaac agggctactc tcaggattag atataatgga agtgaaccca     840
tccctgggga gacaccaga agaagtaact cgaacagtga acacagcagt tgcaataacc     900
ttggcttgtt tcggacttgc tcgggagggt aatcacaagc ctattgacta ccttaaccca     960
cctaagtaa                                                             969

<210> SEQ ID NO 4
<211> LENGTH: 322
<212> TYPE: PRT
<213> ORGANISM: Homo sapiens
```

<400> SEQUENCE: 4

```
Met Ser Ala Lys Ser Arg Thr Ile Gly Ile Ile Gly Ala Pro Phe Ser
1               5                   10                  15

Lys Gly Gln Pro Arg Gly Val Glu Glu Gly Pro Thr Val Leu Arg
            20                  25                  30

Lys Ala Gly Leu Leu Glu Lys Leu Lys Glu Gln Glu Cys Asp Val Lys
            35                  40                  45

Asp Tyr Gly Asp Leu Pro Phe Ala Asp Ile Pro Asn Asp Ser Pro Phe
    50                  55                  60

Gln Ile Val Lys Asn Pro Arg Ser Val Gly Lys Ala Ser Glu Gln Leu
65                  70                  75                  80

Ala Gly Lys Val Ala Glu Val Lys Lys Asn Gly Arg Ile Ser Leu Val
                85                  90                  95

Leu Gly Gly Asp His Ser Leu Ala Ile Gly Ser Ile Ser Gly His Ala
            100                 105                 110

Arg Val His Pro Asp Leu Gly Val Ile Trp Val Asp Ala His Thr Asp
        115                 120                 125

Ile Asn Thr Pro Leu Thr Thr Thr Ser Gly Asn Leu His Gly Gln Pro
130                 135                 140

Val Ser Phe Leu Leu Lys Glu Leu Lys Gly Lys Ile Pro Asp Val Pro
145                 150                 155                 160

Gly Phe Ser Trp Val Thr Pro Cys Ile Ser Ala Lys Asp Ile Val Tyr
                165                 170                 175

Ile Gly Leu Arg Asp Val Asp Pro Gly Glu His Tyr Ile Leu Lys Thr
            180                 185                 190

Leu Gly Ile Lys Tyr Phe Ser Met Thr Glu Val Asp Arg Leu Gly Ile
        195                 200                 205

Gly Lys Val Met Glu Glu Thr Leu Ser Tyr Leu Leu Gly Arg Lys Lys
    210                 215                 220

Arg Pro Ile His Leu Ser Phe Asp Val Asp Gly Leu Asp Pro Ser Phe
225                 230                 235                 240

Thr Pro Ala Thr Gly Thr Pro Val Val Gly Gly Leu Thr Tyr Arg Glu
                245                 250                 255

Gly Leu Tyr Ile Thr Glu Glu Ile Tyr Lys Thr Gly Leu Leu Ser Gly
            260                 265                 270

Leu Asp Ile Met Glu Val Asn Pro Ser Leu Gly Lys Thr Pro Glu Glu
        275                 280                 285

Val Thr Arg Thr Val Asn Thr Ala Val Ala Ile Thr Leu Ala Cys Phe
    290                 295                 300

Gly Leu Ala Arg Glu Gly Asn His Lys Pro Ile Asp Tyr Leu Asn Pro
305                 310                 315                 320

Pro Lys
```

<210> SEQ ID NO 5
<211> LENGTH: 570
<212> TYPE: DNA
<213> ORGANISM: Homo sapiens

<400> SEQUENCE: 5

```
atgactgaat ataaacttgt ggtagttgga gctggtggcg taggcaagag tgccttgacg    60
atacagctaa ttcagaatca ttttgtggac gaatatgatc caacaataga ggattcctac   120
aggaagcaag tagtaattga tggagaaacc tgtctcttgg atattctcga cacagcaggt   180
caagaggagt acagtgcaat gagggaccag tacatgagga ctgggagggc ttttctttgt   240
```

```
gtatttgcca taaataatac taaatcattt gaagatattc accattatag agaacaaatt    300
aaaagagtta aggactctga agatgtacct atggtcctag taggaaataa atgtgatttg    360
ccttctagaa cagtagacac aaaacaggct caggacttag caagaagtta tggaattcct    420
tttattgaaa catcagcaaa gacaagacag agagtggagg atgctttta  tacattggtg    480 agggagatcc gacaatacag attgaaaaaa atcagcaaag aagaaaagac tcctggctgt    540
gtgaaaatta aaaatgcat  tataatgtaa                                     570
```

<210> SEQ ID NO 6
<211> LENGTH: 189
<212> TYPE: PRT
<213> ORGANISM: Homo sapiens

<400> SEQUENCE: 6

```
Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Arg Val Glu Asp Ala Phe Tyr Thr Leu Val
145                 150                 155                 160

Arg Glu Ile Arg Gln Tyr Arg Leu Lys Lys Ile Ser Lys Glu Glu Lys
                165                 170                 175

Thr Pro Gly Cys Val Lys Ile Lys Lys Cys Ile Ile Met
            180                 185
```

<210> SEQ ID NO 7
<211> LENGTH: 567
<212> TYPE: DNA
<213> ORGANISM: Homo sapiens

<400> SEQUENCE: 7

```
atgactgaat ataaacttgt ggtagttgga gctggtggcg taggcaagag tgccttgacg     60
atacagctaa ttcagaatca ttttgtggac gaatatgatc caacaataga ggattcctac    120
aggaagcaag tagtaattga tggagaaacc tgtctcttgg atattctcga cacagcaggt    180
caagaggagt acagtgcaat gagggaccag tacatgagga ctggggaggg ctttctttgt    240
gtatttgcca taaataatac taaatcattt gaagatattc accattatag agaacaaatt    300
aaaagagtta aggactctga agatgtacct atggtcctag taggaaataa atgtgatttg    360
ccttctagaa cagtagacac aaaacaggct caggacttag caagaagtta tggaattcct    420
tttattgaaa catcagcaaa gacaagacag ggtgttgatg atgccttcta tacattagtt    480
```

```
cgagaaattc gaaacataa agaaaagatg agcaaagatg gtaaaagaa gaaaagaag      540 tcaaagacaa agtgtgtaat tatgtaa                                       567
```

<210> SEQ ID NO 8
<211> LENGTH: 188
<212> TYPE: PRT
<213> ORGANISM: Homo sapiens

<400> SEQUENCE: 8

```
Met Thr Glu Tyr Lys Leu Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
            180                 185
```

<210> SEQ ID NO 9
<211> LENGTH: 570
<212> TYPE: DNA
<213> ORGANISM: Homo sapiens

<400> SEQUENCE: 9

```
atgactgagt acaaactggt ggtggttgga gcaggtggtg ttgggaaaag cgcactgaca      60
atccagctaa tccagaacca ctttgtagat gaatatgatc ccaccataga ggattcttac    120
agaaaacaag tggttataga tggtgaaacc tgtttgttgg acatactgga tacagctgga    180
caagaagagt acagtgccat gagagaccaa tacatgagga caggcgaagg cttcctctgt    240
gtatttgcca tcaataatag caagtcattt gcggatatta acctctacag ggagcagatt    300
aagcgagtaa aagactcgga tgatgtacct atggtgctag tgggaaacaa gtgtgatttg    360
ccaacaagga cagttgatac aaaacaagcc cacgaactgg ccaagagtta cgggattcca    420
ttcattgaaa cctcagccaa gaccagacag ggtgttgaag atgcttttta cacactggta    480
agagaaatac gccagtaccg aatgaaaaaa ctcaacagca gtgatgatgg gactcagggt    540
tgtatgggat tgccatgtgt ggtgatgtaa                                      570
```

```
<210> SEQ ID NO 10
<211> LENGTH: 189
<212> TYPE: PRT
<213> ORGANISM: Homo sapiens

<400> SEQUENCE: 10

Met Thr Glu Tyr Lys Leu Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Ser Lys Ser Phe Ala Asp Ile Asn Leu Tyr
                85                  90                  95

Arg Glu Gln Ile Lys Arg Val Lys Asp Ser Asp Val Pro Met Val
            100                 105                 110

Leu Val Gly Asn Lys Cys Asp Leu Pro Thr Arg Thr Val Asp Thr Lys
            115                 120                 125

Gln Ala His Glu Leu Ala Lys Ser Tyr Gly Ile Pro Phe Ile Glu Thr
            130                 135                 140

Ser Ala Lys Thr Arg Gln Gly Val Glu Asp Ala Phe Tyr Thr Leu Val
145                 150                 155                 160

Arg Glu Ile Arg Gln Tyr Arg Met Lys Lys Leu Asn Ser Ser Asp Asp
                165                 170                 175

Gly Thr Gln Gly Cys Met Gly Leu Pro Cys Val Val Met
            180                 185

<210> SEQ ID NO 11
<211> LENGTH: 570
<212> TYPE: DNA
<213> ORGANISM: Homo sapiens

<400> SEQUENCE: 11
atgacggaat ataagctggt ggtggtgggc gccggcggtg tgggcaagag tgcgctgacc      60
atccagctga tccagaacca ttttgtggac gaatacgacc ccactataga ggattcctac     120
cggaagcagg tggtcattga tggggagacg tgcctgttgg acatcctgga taccgccggc     180
caggaggagt acagcgccat gcgggaccag tacatgcgca ccggggaggg cttcctgtgt     240
gtgtttgcca tcaacaacac caagtctttt gaggacatcc accagtacag ggagcagatc     300
aaacgggtga aggactcgga tgacgtgccc atggtgctgg tggggaacaa gtgtgacctg     360
gctgcacgca ctgtggaatc tcggcaggct caggacctcg cccgaagcta cggcatcccc     420
tacatcgaga cctcggccaa gacccggcag ggagtggagg atgccttcta cacgttggtg     480
cgtgagatcc ggcagcacaa gctgcggaag ctgaaccctc tgatgagag tggccccggc     540 tgcatgagct gcaagtgtgt gctctcctga                                      570

<210> SEQ ID NO 12
<211> LENGTH: 570
<212> TYPE: DNA
<213> ORGANISM: Homo sapiens
```

<400> SEQUENCE: 12

```
atgacggaat ataagctggt ggtggtgggc gccggcggtg tgggcaagag tgcgctgacc    60
atccagctga tccagaacca ttttgtggac gaatacgacc ccactataga ggattcctac   120
cggaagcagg tggtcattga tggggagacg tgcctgttgg acatcctgga taccgccggc   180
caggaggagt acagcgccat gcgggaccag tacatgcgca ccggggaggg cttcctgtgt   240
gtgtttgcca tcaacaacac caagtctttt gaggacatcc accagtacag ggagcagatc   300
aaacgggtga aggactcgga tgacgtgccc atggtgctgg tggggaacaa gtgtgacctg   360
gctgcacgca ctgtggaatc tcggcaggct caggacctcg cccgaagcta cggcatcccc   420
tacatcgaga ccctcggcca agacccggca ggagtggagg atgccttcta cacgttggtg   480
cgtgagatcc ggcagcacaa gctgcggaag ctgaaccctc ctgatgagag tggccccggc   540
tgcatgagct gcaagtgtgt gctctcctga                                    570
```

<210> SEQ ID NO 13
<211> LENGTH: 189
<212> TYPE: PRT
<213> ORGANISM: Homo sapiens

<400> SEQUENCE: 13

```
Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His Gln Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Ala Ala Arg Thr Val Glu Ser Arg
        115                 120                 125

Gln Ala Gln Asp Leu Ala Arg Ser Tyr Gly Ile Pro Tyr Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln His Lys Leu Arg Lys Leu Asn Pro Pro Asp Glu
                165                 170                 175

Ser Gly Pro Gly Cys Met Ser Cys Lys Cys Val Leu Ser
            180                 185
```

<210> SEQ ID NO 14
<211> LENGTH: 513
<212> TYPE: DNA
<213> ORGANISM: Homo sapiens

<400> SEQUENCE: 14

```
atgacggaat ataagctggt ggtggtgggc gccggcggtg tgggcaagag tgcgctgacc    60
atccagctga tccagaacca ttttgtggac gaatacgacc ccactataga ggattcctac   120
cggaagcagg tggtcattga tggggagacg tgcctgttgg acatcctgga taccgccggc   180
```

| | |
|---|---|
| caggaggagt acagcgccat gcgggaccag tacatgcgca ccggggaggg cttcctgtgt | 240 |
| gtgtttgcca tcaacaacac caagtctttt gaggacatcc accagtacag ggagcagatc | 300 |
| aaacgggtga aggactcgga tgacgtgccc atggtgctgg tggggaacaa gtgtgacctg | 360 |
| gctgcacgca ctgtggaatc tcggcaggct caggacctcg cccgaagcta cggcatcccc | 420 |
| tacatcgaga cctcggccaa gacccggcag gcagccgct ctggctctag ctccagctcc | 480 |
| gggaccctct gggaccccc gggacccatg tga | 513 |

<210> SEQ ID NO 15
<211> LENGTH: 170
<212> TYPE: PRT
<213> ORGANISM: Homo sapiens

<400> SEQUENCE: 15

Met Thr Glu Tyr Lys Leu Val Val Gly Ala Gly Gly Val Gly Lys
1               5                   10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
        50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His Gln Tyr
                85                  90                  95

Arg Glu Gln Ile Lys Arg Val Lys Asp Ser Asp Val Pro Met Val
            100                 105                 110

Leu Val Gly Asn Lys Cys Asp Leu Ala Ala Arg Thr Val Glu Ser Arg
        115                 120                 125

Gln Ala Gln Asp Leu Ala Arg Ser Tyr Gly Ile Pro Tyr Ile Glu Thr
    130                 135                 140

Ser Ala Lys Thr Arg Gln Gly Ser Arg Ser Gly Ser Ser Ser Ser
145                 150                 155                 160

Gly Thr Leu Trp Asp Pro Pro Gly Pro Met
                165                 170

<210> SEQ ID NO 16
<211> LENGTH: 1302
<212> TYPE: DNA
<213> ORGANISM: Homo sapiens

<400> SEQUENCE: 16

| | |
|---|---|
| atggaggtgg tggacccgca gcagctgggc atgttcacgg agggcgagct gatgtcggtg | 60 |
| ggtatggaca cgttcatcca ccgcatcgac tccaccgagg tcatctacca gccgcgccgc | 120 |
| aagcgggcca agctcatcgg caagtacctg atggggacc tgctggggga aggctcttac | 180 |
| ggcaaggtga aggaggtgct ggactcggag acgctgtgca ggagggccgt caagatcctc | 240 |
| aagaagaaga agttgcgaag gatccccaac ggggaggcca acgtgaagaa ggaaattcaa | 300 |
| ctactgagga ggttacggca caaaaatgtc atccagctgg tggatgtgtt atacaacgaa | 360 |
| gagaagcaga aaatgtatat ggtgatggag tactgcgtgt gtggcatgca ggaaatgctg | 420 |
| gacagcgtgc cggagaagcg tttcccagtg tgccaggccc acgggtactt ctgtcagctg | 480 |
| attgacggcc tggagtacct gcatagccag ggcattgtgc acaaggacat caagccgggg | 540 |

```
aacctgctgc tcaccaccgg tggcaccctc aaaatctccg acctgggcgt ggccgaggca      600
ctgcacccgt cgcggcgga cgacacctgc cggaccagcc agggctcccc ggctttccag      660
ccgcccgaga ttgccaacgg cctggacacc ttctccggct caaggtgga catctggtcg      720 gctggggtca ccctctacaa catcaccacg ggtctgtacc ccttcgaagg ggacaacatc      780
tacaagttgt ttgagaacat cgggaagggg agctacgcca tcccgggcga ctgtggcccc      840
ccgctctctg acctgctgaa agggatgctt gagtacgaac cggccaagag gttctccatc      900
cggcagatcc ggcagcacag ctggttccgg aagaaacatc ctccggctga agcaccagtg      960
cccatcccac cgagcccaga caccaaggac cggtggcgca gatgactgt ggtgccgtac     1020 ttggaggacc tgcacggcgc ggacgaggac gaggacctct tcgacatcga ggatgacatc     1080
atctacactc aggacttcac ggtgcccgga caggtcccag aagaggaggc cagtcacaat     1140
ggacagcgcc ggggcctccc caaggccgtg tgtatgaacg gcacagaggc ggcgcagctg     1200
agcaccaaat ccagggcgga gggcggggcc cccaaccctg cccgcaaggc ctgctccgcc     1260
agcagcaaga tccgccggct gtcggcctgc aagcagcagt ga                       1302
```

<210> SEQ ID NO 17
<211> LENGTH: 433
<212> TYPE: PRT
<213> ORGANISM: Homo sapiens

<400> SEQUENCE: 17

```
Met Glu Val Val Asp Pro Gln Gln Leu Gly Met Phe Thr Glu Gly
1               5                   10                  15

Leu Met Ser Val Gly Met Asp Thr Phe Ile His Arg Ile Asp Ser Thr
                20                  25                  30

Glu Val Ile Tyr Gln Pro Arg Arg Lys Arg Ala Lys Leu Ile Gly Lys
            35                  40                  45

Tyr Leu Met Gly Asp Leu Leu Gly Glu Gly Ser Tyr Gly Lys Val Lys
        50                  55                  60

Glu Val Leu Asp Ser Glu Thr Leu Cys Arg Arg Ala Val Lys Ile Leu
65                  70                  75                  80

Lys Lys Lys Lys Leu Arg Arg Ile Pro Asn Gly Glu Ala Asn Val Lys
                85                  90                  95

Lys Glu Ile Gln Leu Leu Arg Arg Leu Arg His Lys Asn Val Ile Gln
            100                 105                 110

Leu Val Asp Val Leu Tyr Asn Glu Glu Lys Gln Lys Met Tyr Met Val
        115                 120                 125

Met Glu Tyr Cys Val Cys Gly Met Gln Glu Met Leu Asp Ser Val Pro
130                 135                 140

Glu Lys Arg Phe Pro Val Cys Gln Ala His Gly Tyr Phe Cys Gln Leu
145                 150                 155                 160

Ile Asp Gly Leu Glu Tyr Leu His Ser Gln Gly Ile Val His Lys Asp
                165                 170                 175

Ile Lys Pro Gly Asn Leu Leu Leu Thr Thr Gly Gly Thr Leu Lys Ile
            180                 185                 190

Ser Asp Leu Gly Val Ala Glu Ala Leu His Pro Phe Ala Ala Asp Asp
        195                 200                 205

Thr Cys Arg Thr Ser Gln Gly Ser Pro Ala Phe Gln Pro Pro Glu Ile
        210                 215                 220

Ala Asn Gly Leu Asp Thr Phe Ser Gly Phe Lys Val Asp Ile Trp Ser
225                 230                 235                 240
```

```
Ala Gly Val Thr Leu Tyr Asn Ile Thr Thr Gly Leu Tyr Pro Phe Glu
            245                 250                 255

Gly Asp Asn Ile Tyr Lys Leu Phe Glu Asn Ile Gly Lys Gly Ser Tyr
        260                 265                 270

Ala Ile Pro Gly Asp Cys Gly Pro Pro Leu Ser Asp Leu Leu Lys Gly
        275                 280                 285

Met Leu Glu Tyr Glu Pro Ala Lys Arg Phe Ser Ile Arg Gln Ile Arg
    290                 295                 300

Gln His Ser Trp Phe Arg Lys Lys His Pro Ala Glu Ala Pro Val
305                 310                 315                 320

Pro Ile Pro Pro Ser Pro Asp Thr Lys Asp Arg Trp Arg Ser Met Thr
                325                 330                 335

Val Val Pro Tyr Leu Glu Asp Leu His Gly Ala Asp Glu Asp Glu Asp
            340                 345                 350

Leu Phe Asp Ile Glu Asp Asp Ile Ile Tyr Thr Gln Asp Phe Thr Val
        355                 360                 365

Pro Gly Gln Val Pro Glu Glu Glu Ala Ser His Asn Gly Gln Arg Arg
    370                 375                 380

Gly Leu Pro Lys Ala Val Cys Met Asn Gly Thr Glu Ala Ala Gln Leu
385                 390                 395                 400

Ser Thr Lys Ser Arg Ala Glu Gly Arg Ala Pro Asn Pro Ala Arg Lys
                405                 410                 415

Ala Cys Ser Ala Ser Ser Lys Ile Arg Arg Leu Ser Ala Cys Lys Gln
            420                 425                 430

Gln

<210> SEQ ID NO 18
<211> LENGTH: 403
<212> TYPE: PRT
<213> ORGANISM: Homo sapiens

<400> SEQUENCE: 18

Met Thr Ala Ile Ile Lys Glu Ile Val Ser Arg Asn Lys Arg Arg Tyr
1               5                   10                  15

Gln Glu Asp Gly Phe Asp Leu Asp Leu Thr Tyr Ile Tyr Pro Asn Ile
            20                  25                  30

Ile Ala Met Gly Phe Pro Ala Glu Arg Leu Glu Gly Val Tyr Arg Asn
        35                  40                  45

Asn Ile Asp Asp Val Val Arg Phe Leu Asp Ser Lys His Lys Asn His
    50                  55                  60

Tyr Lys Ile Tyr Asn Leu Cys Ala Glu Arg His Tyr Asp Thr Ala Lys
65                  70                  75                  80

Phe Asn Cys Arg Val Ala Gln Tyr Pro Phe Glu Asp His Asn Pro Pro
                85                  90                  95

Gln Leu Glu Leu Ile Lys Pro Phe Cys Glu Asp Leu Asp Gln Trp Leu
            100                 105                 110

Ser Glu Asp Asp Asn His Val Ala Ala Ile His Cys Lys Ala Gly Lys
        115                 120                 125

Gly Arg Thr Gly Val Met Ile Cys Ala Tyr Leu Leu His Arg Gly Lys
    130                 135                 140

Phe Leu Lys Ala Gln Glu Ala Leu Asp Phe Tyr Gly Glu Val Arg Thr
145                 150                 155                 160

Arg Asp Lys Lys Gly Val Thr Ile Pro Ser Gln Arg Arg Tyr Val Tyr
                165                 170                 175
```

```
Tyr Tyr Ser Tyr Leu Leu Lys Asn His Leu Asp Tyr Arg Pro Val Ala
            180                 185                 190

Leu Leu Phe His Lys Met Met Phe Glu Thr Ile Pro Met Phe Ser Gly
        195                 200                 205

Gly Thr Cys Asn Pro Gln Phe Val Val Cys Gln Leu Lys Val Lys Ile
    210                 215                 220

Tyr Ser Ser Asn Ser Gly Pro Thr Arg Arg Glu Asp Lys Phe Met Tyr
225                 230                 235                 240

Phe Glu Phe Pro Gln Pro Leu Pro Val Cys Gly Asp Ile Lys Val Glu
                245                 250                 255

Phe Phe His Lys Gln Asn Lys Met Leu Lys Lys Asp Lys Met Phe His
            260                 265                 270

Phe Trp Val Asn Thr Phe Phe Ile Pro Gly Pro Glu Glu Thr Ser Glu
        275                 280                 285

Lys Val Glu Asn Gly Ser Leu Cys Asp Gln Glu Ile Asp Ser Ile Cys
    290                 295                 300

Ser Ile Glu Arg Ala Asp Asn Asp Lys Glu Tyr Leu Val Leu Thr Leu
305                 310                 315                 320

Thr Lys Asn Asp Leu Asp Lys Ala Asn Lys Asp Lys Ala Asn Arg Tyr
                325                 330                 335

Phe Ser Pro Asn Phe Lys Val Lys Leu Tyr Phe Thr Lys Thr Val Glu
            340                 345                 350

Glu Pro Ser Asn Pro Glu Ala Ser Ser Thr Ser Val Thr Pro Asp
        355                 360                 365

Val Ser Asp Asn Glu Pro Asp His Tyr Arg Tyr Ser Asp Thr Thr Asp
    370                 375                 380

Ser Asp Pro Glu Asn Glu Pro Phe Asp Glu Asp Gln His Thr Gln Ile
385                 390                 395                 400

Thr Lys Val

<210> SEQ ID NO 19
<211> LENGTH: 403
<212> TYPE: PRT
<213> ORGANISM: Homo sapiens

<400> SEQUENCE: 19

Met Thr Ala Ile Ile Lys Glu Ile Val Ser Arg Asn Lys Arg Arg Tyr
1               5                   10                  15

Gln Glu Asp Gly Phe Asp Leu Asp Leu Thr Tyr Ile Tyr Pro Asn Ile
            20                  25                  30

Ile Ala Met Gly Phe Pro Ala Glu Arg Leu Glu Gly Val Tyr Arg Asn
        35                  40                  45

Asn Ile Asp Asp Val Val Arg Phe Leu Asp Ser Lys His Lys Asn His
    50                  55                  60

Tyr Lys Ile Tyr Asn Leu Cys Ala Glu Arg His Tyr Asp Thr Ala Lys
65                  70                  75                  80

Phe Asn Cys Arg Val Ala Gln Tyr Pro Phe Glu Asp His Asn Pro Pro
                85                  90                  95

Gln Leu Glu Leu Ile Lys Pro Phe Cys Glu Asp Leu Asp Gln Trp Leu
            100                 105                 110

Ser Glu Asp Asp Asn His Val Ala Ala Ile His Cys Lys Ala Gly Lys
        115                 120                 125

Gly Arg Thr Gly Val Met Ile Cys Ala Tyr Leu Leu His Arg Gly Lys
    130                 135                 140
```

```
Phe Leu Lys Ala Gln Glu Ala Leu Asp Phe Tyr Gly Glu Val Arg Thr
145                 150                 155                 160

Arg Asp Lys Lys Gly Val Thr Ile Pro Ser Gln Arg Arg Tyr Val Tyr
                165                 170                 175

Tyr Tyr Ser Tyr Leu Leu Lys Asn His Leu Asp Tyr Arg Pro Val Ala
            180                 185                 190

Leu Leu Phe His Lys Met Met Phe Glu Thr Ile Pro Met Phe Ser Gly
        195                 200                 205

Gly Thr Cys Asn Pro Gln Phe Val Val Cys Gln Leu Lys Val Lys Ile
        210                 215                 220

Tyr Ser Ser Asn Ser Gly Pro Thr Arg Arg Glu Asp Lys Phe Met Tyr
225                 230                 235                 240

Phe Glu Phe Pro Gln Pro Leu Pro Val Cys Gly Asp Ile Lys Val Glu
                245                 250                 255

Phe Phe His Lys Gln Asn Lys Met Leu Lys Lys Asp Lys Met Phe His
            260                 265                 270

Phe Trp Val Asn Thr Phe Phe Ile Pro Gly Pro Glu Glu Thr Ser Glu
        275                 280                 285

Lys Val Glu Asn Gly Ser Leu Cys Asp Gln Glu Ile Asp Ser Ile Cys
        290                 295                 300

Ser Ile Glu Arg Ala Asp Asn Asp Lys Glu Tyr Leu Val Leu Thr Leu
305                 310                 315                 320

Thr Lys Asn Asp Leu Asp Lys Ala Asn Lys Asp Lys Ala Asn Arg Tyr
                325                 330                 335

Phe Ser Pro Asn Phe Lys Val Lys Leu Tyr Phe Thr Lys Thr Val Glu
            340                 345                 350

Glu Pro Ser Asn Pro Glu Ala Ser Ser Ser Thr Ser Val Thr Pro Asp
        355                 360                 365

Val Ser Asp Asn Glu Pro Asp His Tyr Arg Tyr Ser Asp Thr Thr Asp
    370                 375                 380

Ser Asp Pro Glu Asn Glu Pro Phe Asp Glu Asp Gln His Thr Gln Ile
385                 390                 395                 400

Thr Lys Val
```

TUMOR SUPPRESSOR AND ONCOGENE BIOMARKERS PREDICTIVE OF ANTI-IMMUNE CHECKPOINT INHIBITOR RESPONSE

CROSS-REFERENCE TO RELATED APPLICATIONS

This application claims the benefit of U.S. Provisional Application Nos. 62/012,689, filed on 16 Jun. 2014, and 61/983,602, filed on 24 Apr. 2014; the entire contents of each of said applications are incorporated herein in their entirety by this reference.

STATEMENT OF RIGHTS

This invention was made with government support under Grant Numbers HL090136, HL100402, CA122794, CA140594, CA163896, CA166480, CA154303, CA098101, CA141576, CA137181, CA120964, CA143083, and CA163677 awarded by the National Institutes of Health. The U.S. government has certain rights in the invention. This statement is included solely to comply with 37 C.F.R § 401.14(a)(f)(4) and should not be taken as an assertion or admission that the application discloses and/or claims only one invention.

BACKGROUND OF THE INVENTION

Lung squamous cell carcinoma (SCC) is a common type of non-small cell lung cancer and the second leading cause of lung cancer related-death, causing approximately 400,000 deaths per year worldwide (Cancer Genome Atlas Research (2012) *Nature* 489:519-525; Siegel et al. (2013) *CA Cancer J. Clin.* 63:11-30). Unlike lung adenocarcinoma (ADC), for which many relevant oncogenic mutations have been defined and used to develop strategies for targeted therapies, the genomic landscape of lung SCC is only now emerging. There are not yet any approved targeted therapies for lung SCC. Unfortunately, therapeutic targets in lung ADC, such as EGFR and EML4-ALK, do not appear to play major roles in lung SCC (Rekhtman et al. (2012) *Clin. Cancer Res.* 18:1167-1176). This fact underscores the need to develop a preclinical model of lung squamous cell carcinoma in which to define and test novel therapeutic approaches.

Currently, the field lacks a mouse model in which introduction of genetic alterations found in human squamous lung cancers leads to tumors of purely squamous phenotype. Simultaneous activation of $Kras^{G12D}$ (Kras) and inactivation of Lkb1 (also known as serine-threonine kinase 11, Stk11) gives rise to multiple lung cancer histologies, including squamous cell carcinomas (Ji et al, (2007) *Nature* 448:807-810); however, KRAS mutations are very rarely found in human squamous lung tumors. Recently, it was reported that kinase-dead Ikkα knock-in mice developed spontaneous lung squamous cell carcinomas characterized by Ikkα down-regulation and marked pulmonary inflammation (Xiao et al. (2013) *Cancer Cell* 23:527-540). Significant down-regulation of Lkb1 was found in $Ikk\alpha^{KA/KA}$ lung SCCs and adjacent lung tissues as compared to wild-type lungs.

Deletion of Lkb1 alone is unable to drive tumor formation (Ji et al. (2007) *Nature* 448:807-810). PTEN (Phosphatase and tensin homolog) is another commonly mutated, deleted, or epigenetically silenced tumor suppressor in human lung cancers (Salmena et al. (2008) *Cell* 133:403-414). PTEN is altered in 15% of human SCCs (Cancer Genome Atlas Research (2012) *Nature* 489:519-525). PTEN negatively regulates the PI3K/AKT pathway and PI3K pathway gene alterations are found in more than half of human lung SCCs (Cancer Genome Atlas Research (2012) *Nature* 489:519-525). In the mouse model, Pten deletion alone in airway basal cells can initiate lung tumor formation, but with low tumor incidence, long latency, and mixed ADC and SCC phenotype (Malkoski et al. (2013) *Mol. Carcinog.* (e-pub) doi:10.1002/mc/22030).

One key feature of tumor development that autochthonous genetically engineered mouse models provide is a physiologically relevant tumor microenvironment. All of the models of lung SCC to date, including the Ikkα knock-in mice and a model driven by chronic tuberculosis infection, show marked pulmonary inflammation (Nalbandian et al. (2009) *Oncogen* 28:1928-1938: Xiao et al. (2013) *Cancer Cell* 23:527-540), suggesting that an inflammatory microenvironment is central to the development of lung SCCs. This is not surprising given that nearly all humans with lung SCCs have a history of tobacco use that drives squamous metaplasia and the development of SCCs is associated with inflammatory diseases and chronic immunosuppression. Both tumor-associated macrophages (TAMs) and tumor-associated neutrophils (TANs) comprise significant proportions of the inflammatory infiltrates in a wide variety of mouse tumor models and human cancers (Murdoch et al. (2008) *Nat. Rev. Cancer* 8:618-631). Neutrophils were shown to predominate in human head/neck squamous carcinomas (Trellakis et al. (2011) *Int. J. Cancer* 129:2183-2193). Neutrophils found in mouse tumors are phenotypically characterized as polymorphonuclear $CD11b^+Ly6G^+$ cells, and may be related to a subtype of myeloid derived suppressive cells (MDSCs). MDSCs encompass a heterogeneous population of myeloid cells, which share the ability to suppress T cells through the production of arginase, the expression of inducible nitric oxide synthase (iNOS), and other mechanisms (Dumitru et al. (2012) *Cancer Immunol. Immunother.* 61:1155-1167). In the tumor microenvironment, accumulated MDSCs are thought to promote tumor progression through enhancing matrix degradation, tumor cell proliferation, metastasis and angiogenesis (Welch et al. (1989) *Proc. Natl. Acad. Sci. U.S.A.* 86:5859-5863). MDSCs have also been shown to antagonize effector T cell function, support the generation of immunosuppressive T cell populations and inhibit the lysis of tumor cells by cytotoxic T cells or NK cells (Dumitru et al. (2012) *Cancer Immunol. Immunother.* 61:1155-1167). Some MDSCs have neutrophilic features, but the precise relationship between these cells and normal polymorphonuclear leukocytes remains under active investigation. Polymorphonuclear cells infiltrating lung cancers are referred to herein as TANs.

Tumors can also evade immune surveillance by expressing molecules that maintain immune tolerance in peripheral tissues, such as Pd-ligand-1 (PD-L1), which interacts with the immune receptor Programmed cell death-1 (PDCD1 or PD-1) (Barber et al. (2006) *Nature* 439:682-687). The PD-1/PD-L1 interaction inhibits $CD8^+$ cytotoxic T lymphocyte (CTL) proliferation, survival and effector function, and can induce apoptosis of tumor-infiltrating T cells (Barber et al. (2006) *Nature* 439:682-687). PD-1/PD-L1 interactions can also promote the differentiation of $CD4^+$ T cells into $FOXP3^+$ Tregs (Francisco et al. (2009) *J. Exp. Med.* 206: 3015-3029), which are known to further suppress the immune system and cause peripheral immune tolerance in lung cancer patients (Adeegbe and Nishikawa (2013) *Front. Immunol.* 4:190). Ectopic PD-L1 expression in tumor cells in a syngeneic transplant model facilitated the escape of the tumor cells from CTL control (Iwai et al. (2002) *Proc. Natl.*

Acad. Sci. U.S.A. 99:12293-12297). Consistent with these findings in pre-clinical systems, infusing lung cancer patients with blocking anti-PD-1/PDL-1 monoclonal antibodies has shown efficacy in early stage trials, despite limited activity of prior immunotherapies for lung malignancies (Brahmer et al. (2012) N. Eng. J. Med. 366:2455-2465; Topalian et al. (2012) N. Engl. J. Med. 366:2443-2454).

Tumor-propagating cells have the ability to self-renew and differentiate into the bulk population of the tumor and are thought to drive both disease recurrence and metastatic spread (Visvader and Lindeman (2012) Cell Stem Cell 10:717-728). Stem cell antigen-1 (Sca1 or Ly6a) was reported as a bronchioalveolar stem cell (BASC) marker in the distal lung and is also enriched in bronchiolar progenitor cells (Kim et al. (2005) Cell 121:823-835; Lee et al. (2014) Cell 156:440-455). SCA1$^+$ cells, located at the bronchioalveolar duct junction (BADJ), are hyper-proliferative in response to both oncogenic Kras and deletion of Pten, suggesting that they are susceptible to neoplastic transformation (Kim et al. (2005) Cell 121:823-835; Tiozzo et al. (2009) Am. J. Respir. Crit. Care Med. 180:701-712). In addition, SCA1 can be used to enrich for tumor propagating cells (TPCs) in the lung adenocarcinoma Kras$^{G12D}$;p53$^{fl/fl}$ (Kras;p53) model (Curtis et al. (2010) Cell Stem Cell 7:127-133). In the more proximal lung, nerve growth factor receptor (TNFR superfamily, member 16, Ngfr) is a stem cell marker for the pseudostratified tracheal epithelium in both human and mouse, NGFR expression is specifically observed in the p63$^+$ mouse basal stem cells (Rock et al. (2009) Proc. Natl. Acad. Sci. U.S.A. 106:12771-12775). NGFR$^+$ basal cells appear to be the cells-of-origin in a SOX2-induced model of esophageal SCC, and NGFR has been suggested as a putative marker for human esophageal SCC TPCs (Huang et al. (2009) BMC Cancer 9:9; Liu et al. (2013) Cell Stem Cell 12:304-315).

Despite these clues as to the molecular phenotype of a potential tumor propagating cell in SCC, no TPC population able to propagate disease serially has been identified for lung SCC. Moreover, since therapies that negatively regulate immune checkpoint inhibitors, such as anti-PD-1, anti-PD-L1, and anti-CTLA-4 antibodies, are both significantly toxic in combination and very expensive, there is a great need in the art to identify biomarkers which are predictive of patient responsiveness to such therapies in order to appropriately determine an efficacious and cost-effective course of therapeutic intervention.

SUMMARY OF THE INVENTION

The present invention is based, at least in part, on the discovery that the presence of activating oncogenes (e.g., activating KRAS, NRAS, and/or HRAS mutations), the presence of inhibiting tumor suppressors (e.g., inhibiting Lkb1 and/or Pten mutations), and the amount (e.g., copy number or level of expression) and/or activity of such biomarkers, are predictive of hyperproliferative cell responsiveness to anti-immune checkpoint inhibitor therapies.

In one aspect, a method of treating a subject afflicted with a cancer, wherein the cancer comprises at least one mutation selected from the group consisting of an activating KRAS mutation, an activating NRAS mutation, an activating HRAS mutation, an inhibiting LKB1 mutation, and an inhibiting PTEN mutation, comprising administering to the subject an agent that inhibits the copy number, amount, and/or activity of arginase 1, thereby treating the subject afflicted with the cancer, is provided. In one embodiment, the agent is administered in a pharmaceutically acceptable formulation. In another embodiment, the agent directly binds arginase 1. In still another embodiment, arginase 1 is human arginase 1. In yet another embodiment, the method further comprises administering one or more additional anti-cancer agents.

In another aspect, a method of inhibiting hyperproliferative growth of a cancer cell or cells, wherein the cancer cell or cells comprise at least one mutation selected from the group consisting of an activating KRAS mutation, an activating NRAS mutation, an activating HRAS mutation, an inhibiting LKB1 mutation, and an inhibiting PTEN mutation, the method comprising contacting the cancer cell or cells with an agent that inhibits the copy number, amount, and/or activity of arginase 1, thereby inhibiting hyperproliferative growth of the cancer cell or cells, is provided. In one embodiment, the step of contacting occurs in viva, ex vivo, or in vitro. In another embodiment, the agent is administered in a pharmaceutically acceptable formulation. In still another embodiment, the agent directly binds arginase 1. In yet another embodiment, arginase 1 is human arginase 1. In another embodiment, the method further comprises administering one or more additional anti-cancer agents.

In still another aspect, a method of determining whether a subject afflicted with a cancer or at risk for developing a cancer, wherein the cancer comprises at least one mutation selected from the group consisting of an activating KRAS mutation, an activating NRAS mutation, an activating HRAS mutation, an inhibiting LKB1 mutation, and an inhibiting PTEN mutation, would benefit from anti-immune checkpoint inhibitor therapy, the method comprising: a) obtaining a biological sample from the subject; b) determining the presence, copy number, amount, and/or activity of at least one biomarker listed in Table 1 in a subject sample; c) determining the presence, copy number, amount, and/or activity of the at least one biomarker in a control; and d) comparing the presence, copy number, amount, and/or activity of said at least one biomarker detected in steps b) and c); wherein the presence or a significant increase in the copy number, amount, and/or activity of the at least one biomarker in the subject sample relative to the control indicates that the subject afflicted with the cancer or at risk for developing the cancer would benefit from anti-immune checkpoint inhibitor therapy, is provided. In one embodiment, the method further comprises recommending, prescribing, or administering anti-immune checkpoint inhibitor therapy if the cancer is determined to benefit from anti-immune checkpoint inhibitor therapy. In another embodiment, the method further comprises recommending, prescribing, or administering anti-cancer therapy other than anti-immune checkpoint inhibitor therapy if the cancer is determined to not benefit from anti-immune checkpoint inhibitor therapy. In still another embodiment, the anti-cancer therapy is selected from the group consisting of targeted therapy, chemotherapy, radiation therapy, and/or hormonal therapy. In yet another embodiment, the control sample is determined from a cancerous or non-cancerous sample from either the patient or a member of the same species to which the patient belongs. In another embodiment, the control sample comprises cells. In still another embodiment, the method further comprises determining responsiveness to anti-immune checkpoint inhibitor therapy measured by at least one criteria selected from the group consisting of clinical benefit rate, survival until mortality, pathological complete response, semi-quantitative measures of pathologic response, clinical complete remission, clinical partial remission, clinical stable disease, recurrence-free survival, metastasis free survival, disease free survival, circulating tumor cell decrease, circulating marker response, and RECIST criteria.

In yet another aspect, a method of assessing the efficacy of an agent for treating a cancer in a subject, wherein the cancer comprises at least one mutation selected from the group consisting of an activating KRAS mutation, an activating NRAS mutation, an activating HRAS mutation, an inhibiting LKB1 mutation, and an inhibiting PTEN mutation, comprising: a) detecting in a first subject sample and maintained in the presence of the agent the presence, copy number, amount and/or activity of at least one biomarker listed in Table 1; b) detecting the presence, copy number, amount and/or activity of the at least one biomarker listed in Table 1 in a second subject sample and maintained in the absence of the test compound; and c) comparing the presence, copy number, amount and/or activity of the at least one biomarker listed in Table 1 from steps a) and b), wherein the presence or a significantly increased copy number, amount, and/or activity of the at least one biomarker listed in Table 1 in the first subject sample relative to the second subject sample, indicates that the agent treats the cancer in the subject, is provided.

Similarly, in another aspect, a method of monitoring the progression of a cancer in a subject, wherein the cancer comprises at least one mutation selected from the group consisting of an activating KRAS mutation, an activating NRAS mutation, an activating HRAS mutation, an inhibiting LKB1 mutation, and an inhibiting PTEN mutation, comprising: a) detecting in a subject sample at a first point in time the presence, copy number, amount, and/or activity of at least one biomarker listed in Table 1; b) repeating step a) during at least one subsequent point in time after administration of a therapeutic agent; and c) comparing the presence, copy number, amount, and/or activity detected in steps a) and b), wherein the presence or a significantly increased copy number, amount, and/or activity of the at least one biomarker listed in Table 1 in the first subject sample relative to at least one subsequent subject sample, indicates that the agent treats the cancer in the subject, is provided.

For such methods of assessment or monitoring, in one embodiment, the subject has undergone treatment, completed treatment, and/or is in remission for the cancer in between the first point in time and the subsequent point in time. In another embodiment, the subject has undergone anti-immune checkpoint inhibitor therapy in between the first point in time and the subsequent point in time. In still another embodiment, the first and/or at least one subsequent sample is selected from the group consisting of ex vivo and in vivo samples. In yet another embodiment, the first and/or at least one subsequent sample is obtained from an animal model of the cancer. In another embodiment, the first and/or at least one subsequent sample is a portion of a single sample or pooled samples obtained from the subject.

In another aspect, a cell-based method for identifying an agent that inhibits a cancer, the method comprising: a) contacting a cell expressing at least one biomarker listed in Table 1 with a test agent; and b) determining the effect of the test agent on the copy number, level of expression, and/or level of activity of the at least one biomarker in Table 1 to thereby identify an agent that inhibits the cancer, is provided. In one embodiment, the cells are isolated from an animal model of a cancer. In another embodiment, the cells are from a subject afflicted with a cancer or wherein the cell comprises at least one mutation selected from the group consisting of an activating KRAS mutation, an activating NRAS mutation, an activating HRAS mutation, an inhibiting LKB1 mutation, and an inhibiting PTEN mutation. In still another embodiment, the cells are unresponsive to anti-immune checkpoint inhibitor therapy. In yet another embodiment, the step of contacting occurs in vivo, ex vivo, or in vitro. In another embodiment, the method further comprises determining the ability of the test agent to bind to the at least one biomarker listed in Table 1 before or after determining the effect of the test agent on the copy number, level of expression, or level of activity of the at least one biomarker listed in Table 1.

Certain embodiments can be applied to any method, assay, and the like of the present invention. For example, in one embodiment, the sample comprises cells, cell lines, histological slides, paraffin embedded tissue, fresh frozen tissue, fresh tissue, biopsies, bronchoalveolar lavage (BAL) fluid, blood, plasma, serum, buccal scrape, saliva, cerebrospinal fluid, urine, stool, mucus, or bone marrow, obtained from the subject. In another embodiment, the presence or copy number is assessed by microarray, quantitative PCR (qPCR), high-throughput sequencing, comparative genomic hybridization (CGH), or fluorescent in situ hybridization (FISH). In still another embodiment, the amount of the at least one biomarker listed in Table 1 is assessed by detecting the presence in the samples of a polynucleotide molecule encoding the biomarker or a portion of said polynucleotide molecule. In yet another embodiment, the polynucleotide molecule is a mRNA, cDNA, or functional variants or fragments thereof. In another embodiment, the step of detecting further comprises amplifying the polynucleotide molecule. In still another embodiment, the amount of the at least one biomarker is assessed by annealing a nucleic acid probe with the sample of the polynucleotide encoding the one or more biomarkers or a portion of said polynucleotide molecule under stringent hybridization conditions. In yet another embodiment, the amount of the at least one biomarker is assessed by detecting the presence a polypeptide of the at least one biomarker. In another embodiment, the presence of said polypeptide is detected using a reagent which specifically binds with said polypeptide (e.g., a reagent selected from the group consisting of an antibody, an antibody derivative, and an antibody fragment). In still another embodiment, the activity of the at least one biomarker is assessed by determining the magnitude of cellular proliferation, cell death, or cytokine production. In yet another embodiment, the agent or anti-immune checkpoint inhibitor therapy is selected from the group consisting of a blocking antibody, small molecule, antisense nucleic acid, interfering RNA, shRNA, siRNA, aptamer, ribozyme, dominant-negative protein, and combinations thereof (e.g., an agent or anti-immune checkpoint inhibitor therapy selected from the group consisting of inhibitors of PD-1, PD-L1, PD-L2, CTLA-4, arginase 1, and combinations thereof). In another embodiment, the agent or anti-immune checkpoint inhibitor therapy is an inhibitor of arginase 1 in combination with inhibitors of PD-1, PD-L1, PD-L2, or CTLA-4. In still another embodiment, the at least one biomarker is selected from the group consisting of 1, 2, 3, 4, 5, 6, 7, 8, 9, 10, or more biomarkers. In yet another embodiment, the at least one biomarker is selected from the group consisting of KRAS, NRAS, HRAS, LKB1, PTEN, arginase 1, and combinations thereof. In another embodiment, the cancer is selected from the group consisting of lung cancer, lung squamous cell carcinoma (SCC), melanoma, cervical cancer, and pancreatic cancer. In still another embodiment, the cancer comprises 1) at least one inhibiting LKB1 mutation and at least one inhibiting PTEN mutation or 2) at least one activating RAS mutation selected from the group consisting of KRAS, NRAS, HRAS, and any combination thereof. In yet another embodiment, the subject is a mammal (e.g., an animal model of cancer or a human).

Figure 1:
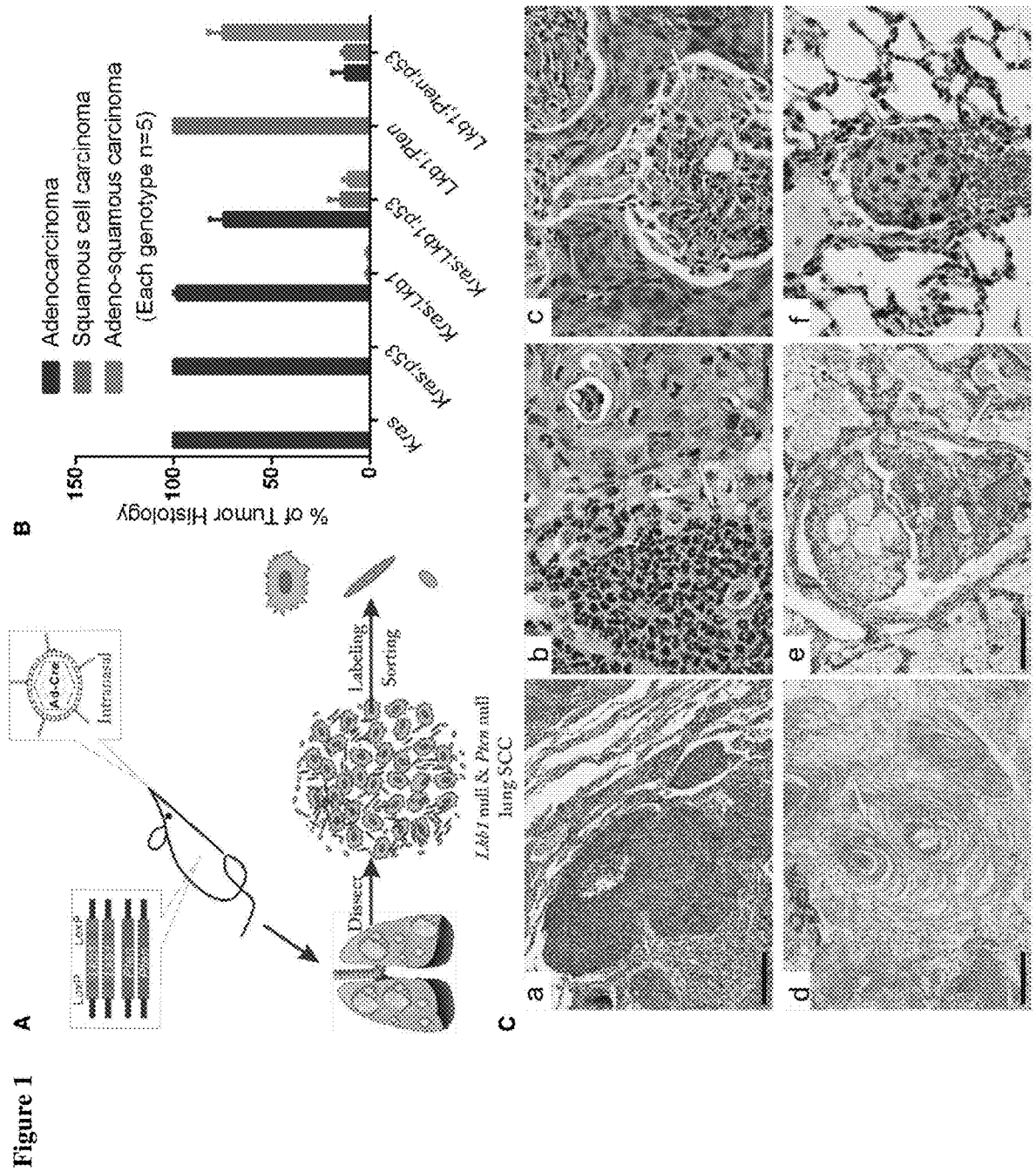
FIG. 1 includes 3 panels, identified as panels A, B, and C, which show that bi-allelic inactivation of both Lkb1 and Pten in the mouse lung leads to squamous cell carcinoma. Panel A shows a schematic of bi-allelic inactivation of both Lkb1 and Pten in the mouse lung by Ad-Cre inhalation, followed by tumor dissociation and sorting. Panel B shows the results of phenotypic quantification of lung tumor histologies from the indicated conditional mouse models, including $Kras^{G12D}$ (Kras), $Kras^{G12D}$;$p53^{fl/fl}$ (Kras;p53), $Kras^{G12D}$;$Lkb1^{fl/fl}$ (Kras;Lkb1) and $Kras^{G12D}$;$p53^{fl/fl}$ (Kras; p53;Lkb1), $Lkb1^{fl/fl}$;$Pten^{fl/fl}$ (Lkb1, Pten) $Lkb1^{fl/fl}$;$Pten^{fl/fl}$; $p53^{fl/fl}$ (Lkb1;Pten;p53), which all rely upon Ad-Cre inhalation for tumor initiation (mean+/−SEM; n=5 mice per genotype). Panel C shows representative H&E stained sections derived from tumors arising in the Lkb1;Pten mouse model. Arrows indicate specific features on individual images, which include (a) mature squamous cells with aberrant nuclear morphology; (b) large infiltrates of neutrophils in SCC nodules; (c) keratinized cells with markedly dense eosinophilic cytoplasm surrounded by epithelial cells; (d) well-differentiated SCC with keratin pearls: (e) SCC nodules in large airways; and (f) squamous-like tumor cell lymphovascular invasion. Scale bar in Panels C(a), C(d), and C(e)=200 µm; scale bar in Panels C(c) and C(f)=50 µm; scale bar in Panel C(b)=25 µm.

For any figure showing a bar histogram, curve, or other data associated with a legend, the bars, curve, or other data presented from left to right for each indication correspond directly and in order to the boxes from top to bottom of the legend.

DETAILED DESCRIPTION OF THE INVENTION

The present invention is based, at least in part, on the discovery that bi-allelic inactivation of the tumor suppressors, Lkb1 and Pten, in the lung causes lung tumors with a purely squamous cell phenotype. These squamous lung tumors were 100% penetrant and recapitulated the genetic, molecular and microenvironmental aspects of the human disease. With this model, the molecular and genetic mechanisms involved in the pathogenesis of lung squamous tumors, including tumor propagating cells, microenvironmental factors, immune tolerance, and therapeutic targets were identified. For example, Lkb1;Pten-null (LP) tumors expressed the squamous markers KRT5, p63 and SOX2, and transcriptionally resembled the basal subtype of human SCC. In contrast to mouse adenocarcinomas, the LP tumors contained immune populations enriched for tumor-associated neutrophils. SCA1+NGFR+ fractions were enriched for tumor propagating cells (TPCs) that could serially transplant the disease in orthotopic assays. TPCs in the LP model and NGFR+ cells in human SCCs highly expressed PD-L1, suggesting a mechanism of immune escape for TPCs.

Accordingly, the present invention relates, in part, to methods for predicting response of a cancer in a subject to anti-immune checkpoint inhibitor therapy based upon a determination and analysis of specific biomarkers, such as the presence of activating oncogenes (e.g., activating KRAS, NRAS, and/or HRAS mutations), the presence of inhibiting tumor suppressors (e.g., inhibiting Lkb1 and/or Pten mutations), and the amount (e.g., copy number or level of expression) and/or activity of such biomarkers. In addition, such analyses can be used in order to provide useful anti-immune checkpoint inhibitor treatment regimens (e.g., based on predictions of subject survival or relapse, timing of adjuvant or neoadjuvant treatment, etc.).

I. DEFINITIONS

The articles "a" and "an" are used herein to refer to one or to more than one (i.e. to at least one) of the grammatical object of the article. By way of example, "an element" means one element or more than one element.

The term "altered amount" or "altered level" refers to increased or decreased copy number (e.g., germline and/or somatic) of a biomarker nucleic acid, e.g., increased or decreased expression level in a cancer sample, as compared to the expression level or copy number of the biomarker nucleic acid in a control sample. The term "altered amount" of a biomarker also includes an increased or decreased protein level of a biomarker protein or metabolite level of a biomarker metabolite, such as L-arginine or creatine, in a sample, e.g., a cancer sample, as compared to the corresponding protein or metabolite level in a normal, control sample. Furthermore, an altered amount of a biomarker protein may be determined by detecting posttranslational modification such as methylation status of the marker, which may affect the expression or activity of the biomarker protein.

The amount of a biomarker in a subject is "significantly" higher or lower than the normal amount of the biomarker, if the amount of the biomarker is greater or less, respectively, than the normal level by an amount greater than the standard error of the assay employed to assess amount, and preferably at least 20%, 30%, 40%, 50%, 60%, 70%, 80%, 90%, 100%, 150%, 200%, 300%, 350%, 400%, 500%, 600%, 700%, 800%, 900%, 1000% or than that amount. Alternately, the amount of the biomarker in the subject can be considered "significantly" higher or lower than the normal amount if the amount is at least about two, and preferably at least about three, four, or five times, higher or lower, respectively, than the normal amount of the biomarker. Such "significance"

can also be applied to any other measured parameter described herein, such as for expression, inhibition, cytotoxicity, cell growth, and the like.

The term "altered level of expression" of a biomarker refers to an expression level or copy number of the biomarker in a test sample, e.g., a sample derived from a patient suffering from cancer, that is greater or less than the standard error of the assay employed to assess expression or copy number, and is preferably at least twice, and more preferably three, four, five or ten or more times the expression level or copy number of the biomarker in a control sample (e.g., sample from a healthy subjects not having the associated disease) and preferably, the average expression level or copy number of the biomarker in several control samples. The altered level of expression is greater or less than the standard error of the assay employed to assess expression or copy number, and is preferably at least twice, and more preferably three, four, five or ten or more times the expression level or copy number of the biomarker in a control sample (e.g., sample from a healthy subjects not having the associated disease) and preferably, the average expression level or copy number of the biomarker in several control samples.

The term "altered activity" of a biomarker refers to an activity of the biomarker which is increased or decreased in a disease state, e.g., in a cancer sample, as compared to the activity of the biomarker in a normal, control sample. Altered activity of the biomarker may be the result of, for example, altered expression of the biomarker, altered protein level of the biomarker, altered structure of the biomarker, or, e.g., an altered interaction with other proteins involved in the same or different pathway as the biomarker or altered interaction with transcriptional activators or inhibitors.

The term "altered structure" of a biomarker refers to the presence of mutations or allelic variants within a biomarker nucleic acid or protein, e.g., mutations which affect expression or activity of the biomarker nucleic acid or protein, as compared to the normal or wild-type gene or protein. For example, mutations include, but are not limited to substitutions, deletions, or addition mutations. Mutations may be present in the coding or non-coding region of the biomarker nucleic acid.

Unless otherwise specified here within, the terms "antibody" and "antibodies" broadly encompass naturally-occurring forms of antibodies (e.g. IgG, IgA, IgM, IgE) and recombinant antibodies such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody.

The term "antibody" as used herein also includes an "antigen-binding portion" of an antibody (or simply "antibody portion"). The term "antigen-binding portion", as used herein, refers to one or more fragments of an antibody that retain the ability to specifically bind to an antigen (e.g., a biomarker polypeptide, fragment thereof, or biomarker metabolite). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent polypeptides (known as single chain Fv (scFv); see e.g., Bird et al. (1988) *Science* 242:423-426; and Huston et al. (1988) *Proc. Natl. Acad. Sci. USA* 85:5879-5883; and Osbourn et al. 1998, Nature Biotechnology 16: 778). Such single chain antibodies are also intended to be encompassed within the term "antigen-binding portion" of an antibody. Any VH and VL sequences of specific scFv can be linked to human immunoglobulin constant region cDNA or genomic sequences, in order to generate expression vectors encoding complete IgG polypeptides or other isotypes. VH and VL can also be used in the generation of Fab, Fv or other fragments of immunoglobulins using either protein chemistry or recombinant DNA technology. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123).

Still further, an antibody or antigen-binding portion thereof may be part of larger immunoadhesion polypeptides, formed by covalent or noncovalent association of the antibody or antibody portion with one or more other proteins or peptides. Examples of such immunoadhesion polypeptides include use of the streptavidin core region to make a tetrameric scFv polypeptide (Kipriyanov, S. M., et al. (1995) *Human Antibodies and Hybridomas* 6:93-101) and use of a cysteine residue, biomarker peptide and a C-terminal polyhistidine tag to make bivalent and biotinylated scFv polypeptides (Kipriyanov, S. M., et al. (1994) *Mol. Immunol.* 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion polypeptides can be obtained using standard recombinant DNA techniques, as described herein.

Antibodies may be polyclonal or monoclonal; xenogeneic, allogeneic, or syngeneic; or modified forms thereof (e.g. humanized, chimeric, etc.). Antibodies may also be fully human. Preferably, antibodies of the invention bind specifically or substantially specifically to a biomarker polypeptide or fragment thereof. The terms "monoclonal antibodies" and "monoclonal antibody composition," as used herein, refer to a population of antibody polypeptides that contain only one species of an antigen binding site capable of immunoreacting with a particular epitope of an antigen, whereas the term "polyclonal antibodies" and "polyclonal antibody composition" refer to a population of antibody polypeptides that contain multiple species of antigen binding sites capable of interacting with a particular antigen. A monoclonal antibody composition typically displays a single binding affinity for a particular antigen with which it immunoreacts.

Antibodies may also be "humanized", which is intended to include antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. The humanized antibodies of the invention may include amino acid residues not encoded by human germline immunoglobulin sequences (e.g., mutations introduced by random or site-specific mutagenesis in vitro or by somatic mutation in vivo), for example in the CDRs. The term "humanized antibody", as used herein, also includes antibodies in which CDR sequences derived from the germline of another mammalian species, such as a mouse, have been grafted onto human framework sequences.

The term "assigned score" refers to the numerical value designated for each of the biomarkers after being measured in a patient sample. The assigned score correlates to the absence, presence or inferred amount of the biomarker in the sample. The assigned score can be generated manually (e.g., by visual inspection) or with the aid of instrumentation for image acquisition and analysis. In certain embodiments, the assigned score is determined by a qualitative assessment, for example, detection of a fluorescent readout on a graded scale, or quantitative assessment. In one embodiment, an "aggregate score," which refers to the combination of assigned scores from a plurality of measured biomarkers, is determined. In one embodiment the aggregate score is a summation of assigned scores. In another embodiment, combination of assigned scores involves performing mathematical operations on the assigned scores before combining them into an aggregate score. In certain, embodiments, the aggregate score is also referred to herein as the predictive score."

The term "biomarker" refers to a measurable entity of the present invention that has been determined to be predictive of anti-immune checkpoint inhibitor therapy effects on a cancer. Biomarkers can include, without limitation, nucleic acids, proteins, and metabolites, particularly those relating to oncogene biomarkers (e.g., activating mutations in oncogene biomarkers) and tumor suppressor biomarkers (e.g., inhibiting mutations in tumor suppressors) as shown in Table 1.

A "blocking" antibody or an antibody "antagonist" is one which inhibits or reduces at least one biological activity of the antigen(s) it binds. In certain embodiments, the blocking antibodies or antagonist antibodies or fragments thereof described herein substantially or completely inhibit a given biological activity of the antigen(s).

The term "body fluid" refers to fluids that are excreted or secreted from the body as well as fluid that are normally not (e.g., bronchoalveolar lavage fluid, amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, vomit).

The terms "cancer" or "tumor" or "hyperproliferative" refer to the presence of cells possessing characteristics typical of cancer-causing cells, such as uncontrolled proliferation, immortality, metastatic potential, rapid growth and proliferation rate, and certain characteristic morphological features. In some embodiments, such cells exhibit such characteristics in part or in full due to the expression and activity of immune checkpoint inhibitors, such as PD-1, PD-L1, PD-L2, and/or CTLA-4. Cancer cells are often in the form of a tumor, but such cells may exist alone within an animal, or may be a non-tumorigenic cancer cell, such as a leukemia cell. As used herein, the term "cancer" includes premalignant as well as malignant cancers. Cancers include, but are not limited to, B cell cancer, e.g., multiple myeloma, Waldenström's macroglobulinemia, the heavy chain diseases, such as, for example, alpha chain disease, gamma chain disease, and mu chain disease, benign monoclonal gammopathy, and immunocytic amyloidosis, melanomas, breast cancer, lung cancer, bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematologic tissues, and the like. Other non-limiting examples of types of cancers applicable to the methods encompassed by the present invention include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, choriocarcinoma, seminoma, embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. In some embodiments, cancers are epithelial in nature and include but are not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers may be characterized in various other ways including, but not limited to, serous, endometrioid, mucinous, clear cell, Brenner, or undifferentiated.

In some embodiments, lung cancer subtypes are included. For example, according to the American Cancer Society, there are two major types of lung cancer: small cell lung cancer (SCLC) and non-small cell lung cancer (NSCLC). SCLC comprises about 15% of all cancers. NSCLC, however, comprises about 85% of all lung cancers and is divided into three distinct sub-types: squamous cell carcinoma (about 25-30% of the cases), large cell carcinomas (about 10-15%), and adenocarcinomas (about 40%). The cells in these sub-types differ in size, shape, and chemical make-up. These lung cancers are inclusive of bronchogenic carcinoma, bronchial carcinoids, chondromatous hamartoma, solitary pulmonary nodules, pulmonary sarcomas, undifferentiated small cell carcinoma, undifferentiated large cell carcinoma, and bronchoalveolar carcinomas. Each such lung cancer subtype is contemplated for use according to the present invention, either alone or in any combination.

The term "coding region" refers to regions of a nucleotide sequence comprising codons which are translated into amino acid residues, whereas the term "noncoding region" refers to regions of a nucleotide sequence that are not translated into amino acids (e.g., 5' and 3' untranslated regions).

The term "complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

The term "control" refers to any reference standard suitable to provide a comparison to the expression products in the test sample. In one embodiment, the control comprises obtaining a "control sample" from which expression product levels are detected and compared to the expression product levels from the test sample. Such a control sample may comprise any suitable sample, including but not limited to a sample from a control cancer patient (can be stored sample or previous sample measurement) with a known outcome; normal tissue or cells isolated from a subject, such as a normal patient or the cancer patient, cultured primary cells/tissues isolated from a subject such as a normal subject or the cancer patient, adjacent normal cells/tissues obtained from the same organ or body location of the cancer patient, a tissue or cell sample isolated from a normal subject, or a primary cells/tissues obtained from a depository. In another preferred embodiment, the control may comprise a reference standard expression product level from any suitable source, including but not limited to housekeeping genes, an expression product level range from normal tissue (or other previously analyzed control sample), a previously determined expression product level range within a test sample from a group of patients, or a set of patients with a certain outcome (for example, survival for one, two, three, four years, etc.) or receiving a certain treatment (for example, standard of care cancer therapy). It will be understood by those of skill in the art that such control samples and reference standard expression product levels can be used in combination as controls in the methods of the present invention. In one embodiment, the control may comprise normal or non-cancerous cell/tissue sample. In another preferred embodiment, the control may comprise an expression level for a set of patients, such as a set of cancer patients, or for a set of cancer patients receiving a certain treatment, or for a set of patients with one outcome versus another outcome. In the former case, the specific expression product level of each patient can be assigned to a percentile level of expression, or expressed as either higher or lower than the mean or average of the reference standard expression level. In another preferred embodiment, the control may comprise normal cells, cells from patients treated with combination chemotherapy, and cells from patients having benign cancer. In another embodiment, the control may also comprise a measured value for example, average level of expression of a particular gene in a population compared to the level of expression of a housekeeping gene in the same population. Such a population may comprise normal subjects, cancer patients who have not undergone any treatment (i.e., treatment naive), cancer patients undergoing standard of care therapy, or patients having benign cancer. In another preferred embodiment, the control comprises a ratio transformation of expression product levels, including but not limited to determining a ratio of expression product levels of two genes in the test sample and comparing it to any suitable ratio of the same two genes in a reference standard; determining expression product levels of the two or more genes in the test sample and determining a difference in expression product levels in any suitable control; and determining expression product levels of the two or more genes in the test sample, normalizing their expression to expression of housekeeping genes in the test sample, and comparing to any suitable control. In particularly preferred embodiments, the control comprises a control sample which is of the same lineage and/or type as the test sample. In another embodiment, the control may comprise expression product levels grouped as percentiles within or based on a set of patient samples, such as all patients with cancer. In one embodiment a control expression product level is established wherein higher or lower levels of expression product relative to, for instance, a particular percentile, are used as the basis for predicting outcome. In another preferred embodiment, a control expression product level is established using expression product levels from cancer control patients with a known outcome, and the expression product levels from the test sample are compared to the control expression product level as the basis for predicting outcome. As demonstrated by the data below, the methods of the invention are not limited to use of a specific cut-point in comparing the level of expression product in the test sample to the control.

The "copy number" of a biomarker nucleic acid refers to the number of DNA sequences in a cell (e.g., germline and/or somatic) encoding a particular gene product. Generally, for a given gene, a mammal has two copies of each gene. The copy number can be increased, however, by gene amplification or duplication, or reduced by deletion. For example, germline copy number changes include changes at one or more genomic loci, wherein said one or more genomic loci are not accounted for by the number of copies in the normal complement of germline copies in a control (e.g., the normal copy number in germline DNA for the same species as that from which the specific germline DNA and corresponding copy number were determined). Somatic copy number changes include changes at one or more genomic loci, wherein said one or more genomic loci are not accounted for by the number of copies in germline DNA of a control (e.g., copy number in germline DNA for the same subject as that from which the somatic DNA and corresponding copy number were determined).

The "normal" copy number (e.g., germline and/or somatic) of a biomarker nucleic acid or "normal" level of expression of a biomarker nucleic acid, protein, or metabolite is the activity/level of expression or copy number in a biological sample, e.g., a sample containing tissue, whole blood, serum, plasma, buccal scrape, saliva, cerebrospinal fluid, urine, stool, and bone marrow, from a subject, e.g., a human, not afflicted with cancer, or from a corresponding non-cancerous tissue in the same subject who has cancer.

The term "determining a suitable treatment regimen for the subject" is taken to mean the determination of a treatment regimen (i.e., a single therapy or a combination of different therapies that are used for the prevention and/or treatment of the cancer in the subject) for a subject that is started, modified and/or ended based or essentially based or at least partially based on the results of the analysis according to the present invention. One example is determining whether to provide targeted therapy against a cancer to provide immunotherapy that generally increases immune responses against the cancer (e.g., anti-immune checkpoint inhibitor therapy). Another example is starting an adjuvant therapy after surgery whose purpose as to decrease the risk of recurrence, another would be to modify the dosage of a particular chemotherapy. The determination can, in addition to the results of the analysis according to the present invention, be based on personal characteristics of the subject to be treated. In most cases, the actual determination of the suitable treatment regimen for the subject will be performed by the attending physician or doctor.

A molecule is "fixed" or "affixed" to a substrate if it is covalently or non-covalently associated with the substrate such that the substrate can be rinsed with a fluid (e.g. standard saline citrate, pH 7.4) without a substantial fraction of the molecule dissociating from the substrate.

The term "expression signature" or "signature" refers to a group of two or more coordinately expressed biomarkers. For example, the genes, proteins, metabolites, and the like making up this signature may be expressed in a specific cell lineage, stage of differentiation, or during a particular biological response. The biomarkers can reflect biological aspects of the tumors in which they are expressed, such as the cell of origin of the cancer, the nature of the non-malignant cells in the biopsy, and the oncogenic mechanisms responsible for the cancer. Expression data and gene expression levels can be stored on computer readable media, e.g., the computer readable medium used in conjunction with a microarray or chip reading device. Such expression data can be manipulated to generate expression signatures.

"Homologous" as used herein, refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue. By way of example, a region having the nucleotide sequence 5'-ATTGCC-3' and a region having the nucleotide sequence 5'-TATGGC-3' share 50% homology. Preferably, the first region comprises a first portion and the second region comprises a second portion, whereby, at least about 50%, and preferably at least about 75%, at least about 90%, or at least about 95% of the nucleotide residue positions of each of the portions are occupied by the same nucleotide residue. More preferably, all nucleotide residue positions of each of the portions are occupied by the same nucleotide residue.

The term "immune cell" refers to cells that play a role in the immune response. Immune cells are of hematopoietic origin, and include lymphocytes, such as B cells and T cells; natural killer cells; myeloid cells, such as monocytes, macrophages, eosinophils, mast cells, basophils, and granulocytes.

The term "immune checkpoint inhibitor" means a group of molecules on the cell surface of CD4+ and/or CD8+ T cells that fine-tune immune responses by down-modulating or inhibiting an anti-tumor immune response. Immune checkpoint proteins are well known in the art and include, without limitation, CTLA-4, PD-1, VISTA, B7-H2, B7-H3, PD-L1, B7-H4, B7-H6, 2B4, ICOS, HVEM, PD-L2, CD160, gp49B, PIR-B, KIR family receptors, TIM-1, TIM-3, TIM-4, LAG-3, BTLA, SIRPalpha (CD47), CD48, 2B4 (CD244), B7.1, B7.2, ILT-2, ILT-4, TIGIT, and A2aR (see, for example, WO 2012/177624). "Anti-immune checkpoint inhibitor therapy" refers to the use of agents that inhibit immune checkpoint inhibitors. Inhibition of one or more immune checkpoint inhibitors can block or otherwise neutralize inhibitory signaling to thereby upregulate an immune response in order to more efficaciously treat cancer. Exemplary agents useful for inhibiting immune checkpoint inhibitors include antibodies, small molecules, peptides, peptidomimetics, natural ligands, and derivatives of natural ligands, that can either bind and/or inactivate or inhibit immune checkpoint proteins, or fragments thereof; as well as RNA interference, antisense, nucleic acid aptamers, etc. that can downregulate the expression and/or activity of immune checkpoint inhibitor nucleic acids, or fragments thereof. Exemplary agents for upregulating an immune response include antibodies against one or more immune checkpoint inhibitor proteins block the interaction between the proteins and its natural receptor(s); a non-activating form of one or more immune checkpoint inhibitor proteins (e.g., a dominant negative polypeptide); small molecules or peptides that block the interaction between one or more immune checkpoint inhibitor proteins and its natural receptor(s); fusion proteins (e.g. the extracellular portion of an immune checkpoint inhibition protein fused to the Fc portion of an antibody or immunoglobulin) that bind to its natural receptor(s); nucleic acid molecules that block immune checkpoint inhibitor nucleic acid transcription or translation; and the like. Such agents can directly block the interaction between the one or more immune checkpoint inhibitors and its natural receptor(s) (e.g., antibodies) to prevent inhibitory signaling and upregulate an immune response. Alternatively, agents can indirectly block the interaction between one or more immune checkpoint proteins and its natural receptor(s) to prevent inhibitory signaling and upregulate an immune response. For example, a soluble version of an immune checkpoint protein ligand such as a stabilized extracellular domain can binding to its receptor to indirectly reduce the effective concentration of the receptor to bind to an appropriate ligand. In one embodiment, anti-PD-1 antibodies, anti-PD-L1 antibodies, and anti-CTLA-4 antibodies, either alone or in combination or in combination with anti-ARG1 therapeutics described below, are used to inhibit immune checkpoint inhibitors.

In some embodiments, arginase 1 (ARG1) is included within the definition of "immune checkpoint inhibitor" by virtue of the fact that it has immunoinhibitory functions. The term "arginase 1" refers to a manganese-containing enzyme that catalyzes the reaction of arginine and water to ornithine and urea. At least two isoforms of mammalian arginase exist (types I and II), which differ in their tissue distribution, subcellular localization, immunologic crossreactivity and physiologic function. The type I isoform encoded by this gene, is a cytosolic enzyme and expressed predominantly in the liver as a component of the urea cycle. Representative human ARG1 cDNA and protein sequences are well-known in the art and are publicly available from the National Center for Biotechnology Information (NCBI). For example, ARG1 isoform 1 is available under accession numbers NM_001244438.1 and NP_001231367.1. ARG1 isoform 2, available under accession numbers NM_000045.3 and NP_000036.2, uses an alternate in-frame splice site at the 5' end of an exon compared to variant 1 resulting in the same N- and C-termini, but is shorter in comparison to isoform 1. Nucleic acid and polypeptide sequences of ARG1 orthologs in organisms other than humans are well known and include, for example, mouse ARG1 (NM_007842.3 and NP_031508.1), chimpanzee ARG1 (XM_003311489.2 and XP_003311537.1), monkey ARG1 (XM_001103609.2 and XP_001103609.2), dog ARG1 (XM_532053.4, XP_532053.3, XM_003639427.2, and XP_003639475.1), cow ARG1 (NM_001046154.1 and NP_001039619.1), rat ARG1 (NM_017134.3 and NP_058830.2), and zebrafish ARG1 (NM_001045197.1 and NP_001038662.1). Representative ARG1 sequences are presented below in Table 1. Anti-ARG1 antibodies are well-known in the art and include, for example, 16001-1-AP (Proteintech Group), AMAb90545 (Atlas Antibodies), and PA1783 (Boster Immunoleader). In addition, other inhibitors of ARG1 (e.g., small molecules) are known and include, for example, N-hydroxy-L-arginine and 2(S)-amino-6-boronohexonic acid (ABH). Moreover, assays for measuring ARG1 amount, activity, and metabolites are well-known in the art (see, for example, U.S. Pat. Publ. 2011-026348). It is to be noted that the term can further be used to refer to any combination of features described herein regarding ARG1 molecules. For example, any combination of sequence composition, percentage identify, sequence length, domain structure, functional activity, etc. can be used to describe an ARG1 molecule of the present invention.

"PD-1" is an immune checkpoint inhibitor that refers to a member of the immunoglobulin gene superfamily that functions as a coinhibitory receptor having PD-L1 and PD-L2 as known ligands. PD-1 was previously identified using a subtraction cloning based approach to select for proteins involved in apoptotic cell death. PD-1 is a member of the CD28/CTLA-4 family of molecules based on its ability to bind to PD-L1. Like CTLA-4, PD-1 is rapidly induced on the surface of T-cells in response to anti-CD3 (Agata et al. (1996) Int. Immunol. 8:765). In contrast to CTLA-4, however, PD-1 is also induced on the surface of B-cells (in response to anti-IgM). PD-1 is also expressed on a subset of thymocytes and myeloid cells (Agata et al. (1996) supra; Nishimura et al. (1996) Int. Immunol. 8:773).

The nucleic acid and amino acid sequences of a representative human PD-1 biomarker is available to the public at the GenBank database under NM_005018.2 and NP_005009.2 (see also Ishida e al. (1992) 20 EMBO J 11:3887; Shinohara et al. (1994) Genomics 23:704; U.S. Pat. No. 5,698,520). PD-1 has an extracellular region containing immunoglobulin superfamily domain, a transmembrane domain, and an intracellular region including an immunoreceptor tyrosine-based inhibitory motif (ITIM) (Ishida et al. (1992) EMBO J. 11:3887; Shinohara et al. (1994) Genomics 23:704; and U.S. Pat. No. 5,698,520). These features also define a larger family of polypeptides, called the immunoinhibitory receptors, which also includes gp49B, PIR-B, and the killer inhibitory receptors (KIRs) (Vivier and Daeron (1997) Immunol. Today 18:286). It is often assumed that the tyrosyl phosphorylated ITIM motif of these receptors interacts with SH2-domain containing phosphatases, which leads to inhibitory signals. A subset of these immunoinhibitory receptors bind to MHC polypeptides, for example the KIRs, and CTLA4 binds to B7-1 and B7-2. It has been proposed that there is a phylogenetic relationship between the MHC and B7 genes (Henry et al. (1999) Immunol. Today 20(6): 285-8). Nucleic acid and polypeptide sequences of PD-1 orthologs in organisms other than humans are well known and include, for example, mouse PD-1 (NM_008798.2 and NP_032824.1), rat PD-1 (NM_001106927.1 and NP_001100397.1), dog PD-1 (XM_543338.3 and XP_543338.3), cow PD-1 (NM_001083506.1 and NP_001076975.1), and chicken PD-1 (XM_422723.3 and XP_422723.2).

PD-1 polypeptides are inhibitory receptors capable of transmitting an inhibitory signal to an immune cell to thereby inhibit immune cell effector function, or are capable of promoting costimulation (e.g., by competitive inhibition) of immune cells, e.g., when present in soluble, monomeric form. Preferred PD-1 family members share sequence identity with PD-1 and bind to one or more B7 family members, e.g., B7-1, B7-2, PD-1 ligand, and/or other polypeptides on antigen presenting cells.

The term "PD-1 activity" includes the ability of a PD-1 polypeptide to modulate an inhibitory signal in an activated immune cell, e.g., by engaging a natural PD-1 ligand on an antigen presenting cell. PD-1 transmits an inhibitory signal to an immune cell in a manner similar to CTLA4. Modulation of an inhibitory signal in an immune cell results in modulation of proliferation of, and/or cytokine secretion by, an immune cell. Thus, the term "PD-1 activity" includes the ability of a PD-1 polypeptide to bind its natural ligand(s), the ability to modulate immune cell costimulatory or inhibitory signals, and the ability to modulate the immune response.

The term "PD-1 ligand" refers to binding partners of the PD-1 receptor and includes both PD-L1 (Freeman et al. (2000) J. Exp. Med. 192:1027) and PD-L2 (Latchman er al. (2001) Nat. Immunol. 2:261). At least two types of human PD-1 ligand polypeptides exist. PD-1 ligand proteins comprise a signal sequence, and an IgV domain, an IgC domain, a transmembrane domain, and a short cytoplasmic tail. Both PD-L1 (See Freeman et al. (2000) J. Exp. Med. 192:1027 for sequence data) and PD-L2 (See Latchman et al. (2001) Nat. Immunol. 2:261 for sequence data) are members of the B7 family of polypeptides. Both PD-L1 and PD-L2 are expressed in placenta, spleen, lymph nodes, thymus, and heart. Only PD-L2 is expressed in pancreas, lung and liver, while only PD-L1 is expressed in fetal liver. Both PD-1 ligands are upregulated on activated monocytes and dendritic cells, although PD-L1 expression is broader. For example, PD-L1 is known to be constitutively expressed and upregulated to higher levels on murine hematopoietic cells (e.g., T cells, B cells, macrophages, dendritic cells (DCs), and bone marrow-derived mast cells) and non-hematopoietic cells (e.g., endothelial, epithelial, and muscle cells), whereas PD-L2 is inducibly expressed on DCs, macrophages, and bone marrow-derived mast cells (see, Butte et al. (2007) Immunity 27:111).

PD-1 ligands comprise a family of polypeptides having certain conserved structural and functional features. The term "family" when used to refer to proteins or nucleic acid molecules, is intended to mean two or more proteins or nucleic acid molecules having a common structural domain or motif and having sufficient amino acid or nucleotide sequence homology, as defined herein. Such family members can be naturally or non-naturally occurring and can be from either the same or different species. For example, a family can contain a first protein of human origin, as well as other, distinct proteins of human origin or alternatively, can contain homologues of non-human origin. Members of a family may also have common functional characteristics. PD-1 ligands are members of the B7 family of polypeptides. The term "B7 family" or "B7 polypeptides" as used herein includes costimulatory polypeptides that share sequence homology with B7 polypeptides, e.g., with B7-1 (CD80), B7-2 (CD86), inducible costimulatory ligand (ICOS-L), B7-H3, B7-H4. VISTA, B7-H6, B7h (Swallow et al. (1999) *Immunity* 11:423), and/or PD-1 ligands (e.g., PD-L1 or PD-L2). For example, human B7-1 and B7-2 share approximately 26% amino acid sequence identity when compared using the BLAST program at NCBI with the default parameters (Blosum62 matrix with gap penalties set at existence 11 and extension 1 (see the NCBI website). The term B7 family also includes variants of these polypeptides which are capable of modulating immune cell function. The B7 family of molecules share a number of conserved regions, including signal domains, IgV domains and the IgC domains. IgV domains and the IgC domains are art-recognized Ig superfamily member domains. These domains correspond to structural units that have distinct folding patterns called Ig folds. Ig folds are comprised of a sandwich of two β sheets, each consisting of anti-parallel β strands of 5-10 amino acids with a conserved disulfide bond between the two sheets in most, but not all, IgC domains of Ig, TCR, and MHC molecules share the same types of sequence patterns and are called the C1-set within the Ig superfamily. Other IgC domains fall within other sets. IgV domains also share sequence patterns and are called V set domains. IgV domains are longer than IgC domains and contain an additional pair of β strands.

The term "PD-L1" refers to a specific PD-1 ligand. Two forms of human PD-L1 molecules have been identified. One form is a naturally occurring PD-L1 soluble polypeptide, i.e., having a short hydrophilic domain at the COOH-terminal end and no transmembrane domain, and is referred to herein as PD-L1S. The second form is a cell-associated polypeptide, i.e., having a transmembrane and cytoplasmic domain, referred to herein as PD-L1M. The nucleic acid and amino acid sequences of representative human PD-L1 biomarkers regarding PD-L1M are also available to the public at the GenBank database under NM_014143.3 and NP_054862.1. PD-L1 proteins comprise a signal sequence, and an IgV domain and an IgC domain. The signal sequence is from about amino acid 1 to about amino acid 18. The signal sequence is from about amino acid 1 to about amino acid 18. The IgV domain is from about amino acid 19 to about amino acid 134 and the IgV domain is from about amino acid 19 to about amino acid 134. The IgC domain is from about amino acid 135 to about amino acid 227 and the IgC domain of SEQ ID NO: 6 is shown from about amino acid 135 to about amino acid 227. The hydrophilic tail of PD-L1 comprises a hydrophilic tail shown from about amino acid 228 to about amino acid 245. The PD-L1 polypeptide comprises a transmembrane domain shown from about amino acids 239 to about amino acid 259 and a cytoplasmic domain shown of about 30 amino acids from 260 to about amino acid 290. In addition, nucleic acid and polypeptide sequences of PD-L1 orthologs in organisms other than humans are well known and include, for example, mouse PD-L1 (NM_021893.3 and NP_068693.1), rat PD-L1 (NM_001191954.1 and NP_0.001178883.1), dog PD-L1 (XM_541302.3 and XP_541302.3), cow PD-L1 (NM_001163412.1 and NP_001156884.1), and chicken PD-L1 (XM_424811.3 and XP_424811.3).

The term "PD-L2" refers to another specific PD-1 ligand. PD-L2 is a B7 family member expressed on various APCs, including dendritic cells, macrophages and bone-marrow derived mast cells (Zhong et al. (2007) *Eur. J. Immunol.* 37:2405). APC-expressed PD-L2 is able to both inhibit T cell activation through ligation of PD-1 and costimulate T cell activation, through a PD-1 independent mechanism (Shin et al. (2005) *J. Exp. Med.* 201:1531). In addition, ligation of dendritic cell-expressed PD-L2 results in enhanced dendritic cell cytokine expression and survival (Radhakrishnan et al. (2003) *J. Immunol.* 37:1827; Nguyen et al. (2002) *J. Exp. Med.* 196:1393). The nucleic acid and amino acid sequences of representative human PD-L2 biomarkers are well known in the art and are also available to the public at the GenBank database under NM_025239.3 and NP_079515.2. PD-L2 proteins are characterized by common structural elements. In some embodiments, PD-L2 proteins include at least one or more of the following domains: a signal peptide domain, a transmembrane domain, an IgV domain, an IgC domain, an extracellular domain, a transmembrane domain, and a cytoplasmic domain. For example, amino acids 1-19 comprise a signal sequence. As used herein, a "signal sequence" or "signal peptide" serves to direct a polypeptide containing such a sequence to a lipid bilayer, and is cleaved in secreted and membrane bound polypeptides and includes a peptide containing about 15 or more amino acids which occurs at the N-terminus of secretory and membrane bound polypeptides and which contains a large number of hydrophobic amino acid residues. For example, a signal sequence contains at least about 10-30 amino acid residues, preferably about 15-25 amino acid residues, more preferably about 18-20 amino acid residues, and even more preferably about 19 amino acid residues, and has at least about 35-65%, preferably about 38-50%, and more preferably about 40-45% hydrophobic amino acid residues (e.g., valine, leucine, isoleucine or phenylalanine). In another embodiment, amino acid residues 220-243 of the native human PD-L2 polypeptide and amino acid residues 201-243 of the mature polypeptide comprise a transmembrane domain. As used herein, the term "transmembrane domain" includes an amino acid sequence of about 15 amino acid residues in length which spans the plasma membrane. More preferably, a transmembrane domain includes about at least 20, 25, 30, 35, 40, or 45 amino acid residues and spans the plasma membrane. Transmembrane domains are rich in hydrophobic residues, and typically have an alpha-helical structure. In a preferred embodiment, at least 50%, 60%, 70%, 80%, 90%, 95% or more of the amino acids of a transmembrane domain are hydrophobic, e.g., leucines, isoleucines, tyrosines, or tryptophans. Transmembrane domains are described in, for example, Zagotta et al. (1996) *Annu. Rev. Neurosci.* 19: 235-263. In still another embodiment, amino acid residues 20-120 of the native human PD-L2 polypeptide and amino acid residues 1-101 of the mature polypeptide comprise an IgV domain. Amino acid residues 121-219 of the native human PD-L2 polypeptide and amino acid residues 102-200 of the mature polypeptide comprise an IgC domain. As used herein, IgV and IgC domains are recognized in the art as Ig superfamily member domains. These domains correspond to structural units that have distinct folding patterns called Ig folds. Ig folds are comprised of a sandwich of two β sheets, each consisting of antiparallel (3 strands of 5-10 amino acids with a conserved disulfide bond between the two sheets in most, but not all, domains. IgC domains of Ig, TCR, and MHC molecules share the same types of sequence patterns and are called the C1 set within the Ig superfamily. Other IgC domains fall within other sets. IgV domains also share sequence patterns and are called V set domains. IgV domains are longer than C-domains and form an additional pair of strands. In yet another embodiment, amino acid residues 1-219 of the native human PD-L2 polypeptide and amino acid residues 1-200 of the mature polypeptide comprise an extracellular domain. As used herein, the term "extracellular domain" represents the N-terminal amino acids which extend as a tail from the surface of a cell. An extracellular domain of the present invention includes an IgV domain and an IgC domain, and may include a signal peptide domain. In still another embodiment, amino acid residues 244-273 of the native human PD-L2 polypeptide and amino acid residues 225-273 of the mature polypeptide comprise a cytoplasmic domain. As used herein, the term "cytoplasmic domain" represents the C-terminal amino acids which extend as a tail into the cytoplasm of a cell. In addition, nucleic acid and polypeptide sequences of PD-L2 orthologs in organisms other than humans are well known and include, for example, mouse PD-L2 (NM_021396.2 and NP_067371.1), rat PD-L2 (NM_001107582.2 and NP_001101052.2), dog PD-L2 (XM_847012.2 and XP_852105.2), cow PD-L2 (XM_586846.5 and XP_586846.3), and chimpanzee PD-L2 (XM_001140776.2 and XP_001140776.1).

The term "PD-12 activity," "biological activity of PD-L2," or "functional activity of PD-L2," refers to an activity exerted by a PD-L2 protein, polypeptide or nucleic acid molecule on a PD-L2-responsive cell or tissue, or on a PD-L2 polypeptide binding partner, as determined in vivo, or in vitro, according to standard techniques. In one embodiment, a PD-L2 activity is a direct activity, such as an association with a PD-L2 binding partner. As used herein, a "target molecule" or "binding partner" is a molecule with which a PD-L2 polypeptide binds or interacts in nature, such that PD-L2-mediated function is achieved. In an exemplary embodiment, a PD-L2 target molecule is the receptor RGMb. Alternatively, a PD-L2 activity is an indirect activity, such as a cellular signaling activity mediated by interaction of the PD-L2 polypeptide with its natural binding partner, e.g., RGMb. The biological activities of PD-L2 are described herein. For example, the PD-L2 polypeptides of the present invention can have one or more of the following activities: 1) bind to and/or modulate the activity of the receptor RGMb, PD-1, or other PD-L2 natural binding partners, 2) modulate intra- or intercellular signaling, 3) modulate activation of immune cells, e.g., T lymphocytes, and 4) modulate the immune response of an organism, e.g., a mouse or human organism.

The term "immune response" includes T cell mediated and/or B cell mediated immune responses. Exemplary immune responses include T cell responses, e.g., cytokine production and cellular cytotoxicity. In addition, the term immune response includes immune responses that are indirectly effected by T cell activation, e.g., antibody production (humoral responses) and activation of cytokine responsive cells, e.g., macrophages.

The term "immunotherapeutic agent" can include any molecule, peptide, antibody or other agent which can stimulate a host immune system to generate an immune response to a tumor or cancer in the subject. Various immunotherapeutic agents are useful in the compositions and methods described herein.

The term "inhibit" includes the decrease, limitation, or blockage, of, for example a particular action, function, or interaction. In some embodiments, cancer is "inhibited" if at least one symptom of the cancer is alleviated, terminated, slowed, or prevented. As used herein, cancer is also "inhibited" if recurrence or metastasis of the cancer is reduced, slowed, delayed, or prevented.

The term "interaction", when referring to an interaction between two molecules, refers to the physical contact (e.g., binding) of the molecules with one another. Generally, such an interaction results in an activity (which produces a biological effect) of one or both of said molecules.

An "isolated protein" refers to a protein that is substantially free of other proteins, cellular material, separation medium, and culture medium when isolated from cells or produced by recombinant DNA techniques, or chemical precursors or other chemicals when chemically synthesized. An "isolated" or "purified" protein or biologically active portion thereof is substantially free of cellular material or other contaminating proteins from the cell or tissue source from which the antibody, polypeptide, peptide or fusion protein is derived, or substantially free from chemical precursors or other chemicals when chemically synthesized. The language "substantially free of cellular material" includes preparations of a biomarker polypeptide or fragment thereof, in which the protein is separated from cellular components of the cells from which it is isolated or recombinantly produced. In one embodiment, the language "substantially free of cellular material" includes preparations of a biomarker protein or fragment thereof, having less than about 30% (by dry weight) of non-biomarker protein (also referred to herein as a "contaminating protein"), more preferably less than about 20% of non-biomarker protein, still more preferably less than about 10% of non-biomarker protein, and most preferably less than about 5% non-biomarker protein. When antibody, polypeptide, peptide or fusion protein or fragment thereof, e.g., a biologically active fragment thereof, is recombinantly produced, it is also preferably substantially free of culture medium, i.e., culture medium represents less than about 20%, more preferably less than about 10%, and most preferably less than about 5% of the volume of the protein preparation.

A "kit" is any manufacture (e.g. a package or container) comprising at least one reagent, e.g. a probe or small molecule, for specifically detecting and/or affecting the expression of a marker of the invention. The kit may be promoted, distributed, or sold as a unit for performing the methods of the present invention. The kit may comprise one or more reagents necessary to express a composition useful in the methods of the present invention. In certain embodiments, the kit may further comprise a reference standard, e.g., a nucleic acid encoding a protein that does not affect or regulate signaling pathways controlling cell growth, division, migration, survival or apoptosis. One skilled in the art can envision many such control proteins, including, but not limited to, common molecular tags (e.g., green fluorescent protein and beta-galactosidase), proteins not classified in any of pathway encompassing cell growth, division, migration, survival or apoptosis by GeneOntology reference, or ubiquitous housekeeping proteins. Reagents in the kit may be provided in individual containers or as mixtures of two or more reagents in a single container. In addition, instructional materials which describe the use of the compositions within the kit can be included.

The term "neoadjuvant therapy" refers to a treatment given before the primary treatment. Examples of neoadjuvant therapy can include chemotherapy, radiation therapy, and hormone therapy. For example, in treating breast cancer, neoadjuvant therapy can allows patients with large breast cancer to undergo breast-conserving surgery.

The "normal" level of expression of a biomarker is the level of expression of the biomarker in cells of a subject, e.g., a human patient, not afflicted with a cancer. An "overexpression" or "significantly higher level of expression" of a biomarker refers to an expression level in a test sample that is greater than the standard error of the assay employed to assess expression, and is preferably at least twice, and more preferably 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher than the expression activity or level of the biomarker in a control sample (e.g., sample from a healthy subject not having the biomarker associated disease) and preferably, the average expression level of the biomarker in several control samples. A "significantly lower level of expression" of a biomarker refers to an expression level in a test sample that is at least twice, and more preferably 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more lower than the expression level of the biomarker in a control sample (e.g., sample from a healthy subject not having the biomarker associated disease) and preferably, the average expression level of the biomarker in several control samples.

The term "oncogene" refers to a well-known class of proteins that have the potential to cause cancer or a nucleic acid encoding same. Non-limiting examples of oncogenes include growth factors or mitogens such as c-Sis; receptor tyrosine kinases such as EGFR. HER2, PDGFR, and VEGFR; cytoplasmic tyrosine kinases such as Abl and kinases in the Src-family, Syk-ZAP-70 family, and BTK family of tyrosine kinases; cytoplasmic serine/threonine kinases and their regulatory subunits such as PIK3CA, PIK3R1, and RAF (e.g., RAF-1, A-RAF, B-RAF); regulatory GTPases such as RAS (e.g., KRAS); transcription factors such as MYC; and combinations thereof.

By contrast, the term "tumor suppressor" refers to a well-known class of proteins that have the potential to protect a cell from becoming a cancerous cell. Non-limiting examples of tumor suppressor genes include the TP53 gene (also known as the P53 gene), which encodes p53 (also known as protein 53 or tumor protein 53); kinases such as, e.g., tyrosine kinases or serine/threonine kinases including serine/threonine kinase 11 (STK11); the RB1 gene, which encodes the Retinoblastoma protein (pRb); LKB1; PTEN; VHL; APC; CD95; ST5; YPEL3; ST7; ST14; and combinations thereof.

The term "at least one mutation" in a polypeptide or a gene encoding a polypeptide and grammatical variations thereof means a polypeptide or gene encoding a polypeptide having one or more allelic variants, splice variants, derivative variants, substitution variants, deletion variants, truncation variants, and/or insertion variants, fusion polypeptides, orthologs, and/or interspecies homologs. By way of example, at least one mutation of a Ras protein would include a Ras protein in which part of all of the sequence of a polypeptide or gene encoding the Ras protein is absent or not expressed in the cell for at least one Ras protein produced in the cell. For example, a Ras protein may be produced by a cell in a truncated form and the sequence of the truncated form may be wild type over the sequence of the truncate. A deletion may mean the absence of all or part of a gene or protein encoded by a gene. Additionally, some of a protein expressed in or encoded by a cell may be mutated while other copies of the same protein produced in the same cell may be wild type. By way of another example a mutation in a Ras protein would include a Ras protein having one or more amino acid differences in its amino acid sequence compared with wild type of the same Ras protein. By way of another example, a mutation LKB1 includes, but is not limited to, an LKB1 having at least one amino acid difference compared to wild type LKB1. Mutation may be somatic or germline. Mutations in a polypeptide, including, but not limited to, LKB1, can lead to expression of truncated protein.

Mutations in an oncogene that cause increased activity of the oncogene to therefore promote cancer are known as "activating mutations." Such activating mutations are well known in the art for many oncogenes and particularly for the activating mutant oncogenes described herein. Such mutations can be constitutive (i.e., always causing increased activity) or inducible. Such mutations can also cause variable increases in oncogene activity.

For example, the term "KRAS" and "NRAS" and "HRAS" refer to specific members of the rat sarcoma (RAS) superfamily of proteins. V-Ki-ras2 Kirsten rat sarcoma viral oncogene homolog (KRAS), v-Ha-ras Harvey rat sarcoma viral oncogene homolog (HRAS), and neuroblastoma RAS viral (v-ras) oncogene homolog (NRAS) are the founding members of the rat sarcoma (RAS) superfamily of small guanosine triphosphatases (GTPases) that is known to comprise >150 members in humans (Colicelli (2004) *Sci. STKE* 2004:RE13). Five subgroups of these small GTPases have been identified and designated as the RAS; ras homolog family member (RHO); RABIA, member RAS oncogene family (RAB); RAN, member RAS oncogene family (RAN); and ADP-ribosylation factor (ARF) families. All small GTPases function as binary switches that transition between GDP-bound, inactive and GTP-bound, active forms and thereby contribute to intracellular signaling that underlies a wide array of cellular activities, including cell proliferation, differentiation, survival, motility, cytoskeleton rearrangements, and transformation (Cox and Der (2010) *Small GTPases* 1:2-27; Lowy et al. (1993) *Annu. Rev. Biochem.* 62:851-891). Somatic point mutations that activate KRAS, HRAS, or NRAS have been identified in a variety of human tumors, with KRAS being the most frequently activated oncoprotein in humans. Somatic activating mutations of KRAS are thus present in >90% of pancreatic adenocarcinomas, for example (Jaffee et al. (2002) *Cancer Cell* 2:25-28). Since members of the Ras family communicate signals from outside the cell to the nucleus, mutations in Ras pathway signalling can permanently activate it and cause inappropriate transmission inside the cell even in the absence of extracellular signals. Because these signals result in cell growth and division, dysregulated RAS pathway signaling, such as promoted by activatin RAS mutations, can ultimately lead to oncogenesis and cancer (Goodsell et al. (1999) *Oncologist* 4: 263-264). Activated mutations in the Ras family (e.g., H-Ras, N-Ras and K-Ras) are found in 20-25% of all human tumors and up to 90% in specific tumor types (Downward et al. (2003) *Nat. Rev. Cancer* 3:11-22; Bos et al. (1989) *Cancer Res.* 49:4682-4689; Kranenburg et al. (2005) *Biochim. Biophys. Acta* 1756:81-82).

Representative human KRAS cDNA and protein sequences are well-known in the art and are publicly available from the National Center for Biotechnology Information (NCBI). For example, KRAS isoform 1 is available under accession numbers NM_033360.3 and NP_203524.1 and is composed of six exons, including exon 4a, which the shorter transcript variant 2 lacks. This rare variant has a coding sequence that terminates in exon 4a and encodes a unique C-terminus, compared to isoform 2. KRAS isoform 2, available under accession numbers NM_004985.4 and NP_004976.2, is composed of five exons and lacks exon 4a which the longer transcript variant 1 includes. This predominant variant as a cds that terminates in exon 4b and encodes isoform 2. Nucleic acid and polypeptide sequences of KRAS orthologs in organisms other than humans are well known and include, for example, canine KRAS (NCBI Accession XM_540523.3, XP_540523.3, XM_003432429.1, and XP_00343247.1), chimpanzee KRAS (NCBI Accession XM_003313794.1. XP_003313842.1. XM_528758.3, and XP_528758.3), cow KRAS (NCBI Accession NM_001110001.1 and NP_001103471.1), mouse KRAS (NCBI Accession NM_021284.6 and NP_067259.4), rat KRAS (NCBI Accession NM_031515.3 and NP_13703.1), chicken KRAS (NCBI Accession NM_001256162.1 and NP_001243091.1), and zebrafish KRAS (NCBI Accession NM_001003744.1 and NP_001003744.1). Representative KRAS sequences are presented below in Table 1. It is to be noted that the term can further be used to refer to any combination of features described herein regarding KRAS molecules. For example, any combination of sequence composition, percentage identify, sequence length, domain structure, functional activity, etc. can be used to describe a KRAS molecule of the present invention.

Representative human NRAS cDNA and protein sequences are well-known in the art and are publicly available from the National Center for Biotechnology Information (NCBI). For example, NRAS sequences are available under accession numbers NM_002524.4 and NP_002515.1. Nucleic acid and polypeptide sequences of KRAS orthologs in organisms other than humans are well known and include, for example, dog NRAS (NM_001287065.1 and NP_001273994.1), chimpanzee NRAS (XM_001149822.3 and XP_001149822.1), cow NRAS (NM_001097989.1 and NP_001091458.1), mouse NRAS (XM_006501122.1, XP_006501185.1, XM_006501119.1, XP_006501182.1, XM_006501118.1, XP_006501181.1, XM_006501120.1, XP_006501183.1, XM_006501121.1, XP_006501184.1, XM_006501123.1, and XP_006501186.1), rat NRAS (NM_080766.2 and NP_542944.1), chicken NRAS (NM_001012549.1 and NP_001012567.1), and zebrafish NRAS (NM_131145.1 and NP_571220.1). Representative NRAS sequences are presented below in Table 1. It is to be noted that the term can further be used to refer to any combination of features described herein regarding NRAS molecules. For example, any combination of sequence composition, percentage identify, sequence length, domain structure, functional activity, etc. can be used to describe an NRAS molecule of the present invention.

Representative human HRAS cDNA and protein sequences are well-known in the art and are publicly available from the National Center for Biotechnology Information (NCBI). For example, HRAS isoform 1 is available under accession numbers NP_005334.1 and NP_001123914.1 and is encoded by two different splice variants. Transcript 1 (NM_005343.2) differs from transcript 3 (NM_001130442.1) in the 3' UTR, but otherwise encodes the same protein. Transcript 2 (NM_005343.2) encodes an alternate exon in its 3' coding region and a different 3'UTR from transcripts 1 and 2 resulting in a shorter isoform 2 (NP_789765.1) compared to isoform 1 and contains a distinct C-terminus as well. Nucleic acid and polypeptide sequences of HRAS orthologs in organisms other than humans are well known and include, for example, dog HRAS (NCBI Accession NM_001287070.1, NP_001273999.1, NM_001287069.1, and NP_001273998.1), chimpanzee HRAS (NCBI Accession XM_521702.4 and XP_521702.2), monkey HRAS (NCBI Accession NM_001266421.1 and NP_001253350.1), cow HRAS (NCBI Accession NM_001242347.1, NP_001229276.1, NM_001242346.1, and NP_001229275.1), mouse HRAS (NCBI Accession NM_008284.2, NP_032310.2, NM_001130444.1, NP_001123916.1, NM_001130443.1, and NP_001123915.1), rat HRAS (NCBI Accession NM_001130441.1, NP_001123913.1, NM_001098241.1, and NP_001091711.1), and chicken HRAS (NCBI Accession NM_205292.1 and NP_990623.1). Representative HRAS sequences are presented below in Table 1. It is to be noted that the term can further be used to refer to any combination of features described herein regarding HRAS molecules. For example, any combination of sequence composition, percentage identify, sequence length, domain structure, functional activity, etc. can be used to describe an HRAS molecule of the present invention.

The terms "mutant KRAS protein" and "mutant NRAS protein" and "mutant HRAS protein" and "KRAS mutation" and "NRAS mutation" and "HRAS mutation" refer to KRAS, NRAS, and HRAS proteins having at least one mutation, respectively. The term "activating KRAS mutation" refers to a mutation in a KRAS polypeptide that causes enhanced KRAS activity relative to the control wild-type KRAS polypeptide without the mutation and are well known in the art (see, for example, U.S. Pat. Publ. 2013-0231346 and U.S. Pat. Publ. 2014-0057798). In certain embodiments, the activating KRAS, NRAS, or HRAS mutations include G12S, G12V, G12D, G12A, G12C, G12F, G12R, G13A, G13C, G13D, V14I, G60E, Q61H, Q61K, T74P, E76G, E76K, E76Q and A146T. Certain NRAS mutations include, but are not limited to G12S, G12V, G12D, G12A, G12C, G13A, G13D, G60E Q61H, and Q61K. Certain KRAS mutations can occur at positions 12, 13, 14, 61, and 76 and include, but are not limited to, G12S, G12V, G12D, G12A, G12C, G12F, G12R, G13A, G13C, G13D, V14I, G60E, Q61H, Q61K, T74P, E76G, E76K, E76Q and A146T. Certain HRAS mutations include, but are not limited to, substitution of Gly12 with Val (G12V caused by, for example, a GGC to GTC mutation at codon 12) and substitution of Gln61 with Lys (Q61K caused by, for example, a CAG to AAG mutation at codon 61). Ras protein mutation may occur at amino acid 12, 13, 14, 59, 60, 61, 76, and/or 146. Certain exemplary mutant KRAS and NRAS polypeptides include, but are not limited to, allelic variants, splice variants, derivative variants, substitution variants, deletion variants, and/or insertion variants, fusion polypeptides, orthologs, and interspecies homologs. In certain embodiments, a mutant KRAS and NRAS polypeptide includes additional residues at the C- or N-terminus, such as, but not limited to, leader sequence residues, targeting residues, amino terminal methionine residues, lysine residues, tag residues and/or fusion protein residues.

Mutations in a tumor suppressor that cause reduced activity of the tumor suppressor to therefore promote cancer are known as "inhibiting mutations." Such inhibiting mutations, such as missense, frameshift, nonsense, deletion, addition, catalytic reduction, or other mutations, are well known in the art for many tumor suppressors and particularly for the inhibiting mutant tumor suppressors described herein. Such mutations can be constitutive (i.e., always causing decreased activity) or inducible. Such mutations can also cause variable decreases in tumor suppressor activity or be loss-of-function mutations.

For example, the term "LKB1" is synonymous with Serine/Threonine Kinase 11 (STK11) and is a serine/threonine protein kinase. LKB1 is a primary upstream kinase of adenine monophosphate-activated protein kinase (AMPK), a key regulator of cell metabolism and maintenance of energy homeostasis. LKB1 suppresses cellular growth by activating a group of other kinases, comprising AMPK and AMPK-related kinases. Activation of AMPK by LKB1 suppresses growth and proliferation when energy and nutrient levels are scarce. The human LKB gene is defective in patients with Peutz-Jeghers syndrome (PJS). PJS is an autosomal dominantly inherited syndrome characterized by hamartomatous polyposis of the gastrointestinal tract and mucocutaneous pigmentation. Over 145 different germline LKB1 mutations are known and the majority of the mutations lead to a truncated protein product. At least 40 different somatic LKB1 mutations are known in 41 sporadic tumors and seven cancer cell lines. Mutations occur particularly in lung and colorectal cancer. Most of the somatic LKB1 mutations result in truncation of the protein.

Representative human LKB1 cDNA and protein sequences are well-known in the art and are publicly available from the National Center for Biotechnology Information (NCBI). For example, LKB1 sequences are available under accession numbers NM_00455.4 and NP_000446.1. Nucleic acid and polypeptide sequences of LKB1 orthologs in organisms other than humans are well known and include, for example, chimpanzee LKB1 (XM_524028.3 and XP_524028.2), monkey LKB1 (XM_001093806.2 and XP_001093806.1), mouse LKB1 (XM_006513439.1, XP_006513502.1, XM_006513440.1, XP_006513503.1, XM_006513442.1, XP_006513505.1, XM_006513441.1, XP_006513504.1, XM_006513443.1, and XP_006513506.1), rat LKB1 (XM_006240910.1 and XP_006240972.1), chicken LKB1 (NM_001045833.1 and NP_001039298.1), and zebrafish LKB1 (NM_001017839.1 and NP_001017839.1). Representative LKB1 sequences are presented below in Table 1. It is to be noted that the term can further be used to refer to any combination of features described herein regarding LKB1 molecules. For example, any combination of sequence composition, percentage identify, sequence length, domain structure, functional activity, etc. can be used to describe an LKB1 molecule of the present invention.

The term "inhibiting LKB1 mutation" includes any one or more mutations in the LKB1 gene that reduce or eliminate LKB1 tumor suppressor activity. Examples of LKB1 mutations include, but are not limited to, C109T (Q37Ter), G595T (E199Ter), C108A (Y36Ter). T145G (Y49D), G169T (E57Ter), T200C (L67P), A250T (K84Ter), G290+36T, G403C (G135R), G488A (G163D), C508T (Q170Ter), G580A (D194N), G580T (D194Y), A581T (D194V), G595A (E199K), G717C (W239C), C738G (Y246Ter), C759A(Y253Ter), C842T (P281L), G996A (W332Ter), C1062G (F354L), G169del (E57K frameshift), TTGT787-790del (L263-F264 frameshift), C842del (P281R frameshift), a kinase domain mutation, and combinations thereof. In another embodiment, the deletion, insertion or mutation of LKB1 is in the catalytic kinase domain. The deletion, insertion or mutation of LKB1 may be in codons 50-337. In one embodiment, a mutation, deletion or insertion in LKB1 causes a truncated protein. Additional inhibiting LKB1 mutations are well known in the art (see, for example, U.S. Pat. Publ. 2013-0231346 and U.S. Pat. Publ. 2014-0057798).

Similarly, "PTEN" is a tumor suppressor known as Phosphatase and Tensin homolog deleted on chromosome Ten and is party of the PI-3 Kinase-AKT pathway. The PI-3 kinase pathway controls a number of cellular functions including cell growth, metabolism, differentiation, and apoptosis. Many types of cancer are thought to arise in response to abnormalities in signal transduction pathways of which the PI-3 kinase pathway is a major example. The PI-3 kinase pathway comprises a number of enzymes in addition to PTEN, including PI-3 kinase and AKT (a serine/threonine kinase) all of which are involved in producing and maintaining intracellular levels of second messenger molecule PtdIns(3,4,5)P3 ($PIP_3$). Homeostasis in the levels of this important second messenger is maintained by the interaction between PI-3 kinase and PTEN. Specifically, the PTEN gene encodes a lipid phosphatase that regulates signaling through the phosphatidylinositol 3-kinase (PI-3 kinase) pathway. PTEN dephosphorylates PIP3, the product of PI-3 kinase (for review, see Cantley et al. (1999) Proc. Natl. Acad. Sci. U.S.A. 96:4240-4245). As a consequence of PTEN loss and the resultant increase in PIP3 levels, signal propagation through downstream kinases such as AKT is constitutively elevated. When either PI-3 kinase or PTEN are mutated and/or reduced in activity PIP: levels are perturbed and it is believed that this perturbation acts as a trigger in the development of cancer. Such perturbation of metabolites can be detected according to well known methods in the art. Preclinical studies indicate that this indirect mode of constitutive kinase activation in tumor cells, through loss of the PTEN suppressor gene, creates a kinase dependency analogous to that seen in tumors with direct, activating mutations in the kinase itself. Tumors with loss-of-function mutations in PTEN exhibit constitutive activation of AKT.

The PTEN protein comprises, from amino- to carboxy-terminus, a protein tyrosine phosphatase catalytic domain that has considerable homology to the cytoskeletal protein tensin, a C2 domain that confers lipid-binding and membrane-targeting, and a PDZ domain-binding site that contributes to membrane localization and protein stability (Lee et al. (1999) Cell; Wu et al. (2000) PNAS). The amino-terminal catalytic domain includes the $HC(X)_{5R}$ sequence, which is the signature motif of protein tyrosine phosphatases. Dual specificity phosphatase, whose substrate targets include phosphorylated proteins and inositol phospholipids. PTEN is distinguished by the fact that, unlike other dual specificity phosphatases, it preferentially dephosphorylates phosphoinositides at the D3 position of the inositol ring (Maehama et al. (1999) Trends Cell Biol., Maehama et al. (1998) J. Biol. Chem.). PTEN is the product of the tumor suppressor gene PTEN/MMAC, mutations in which have been correlated with a number of different tumor types, including those of the brain, prostate, endometrium, breast, and lung. (see, for example, U.S. Pat. Publ. 2012-0253020).

Representative human PTEN cDNA and protein sequences are well-known in the art and are publicly available from the National Center for Biotechnology Information (NCBI). For example, PTEN sequences are available under accession numbers NM_000314.4 and NP_000305.3. Nucleic acid and polypeptide sequences of PTEN orthologs in organisms other than humans are well known and include, for example, chimpanzee PTEN (XM_521544.4 and XP_521544.3), monkey PTEN (NM_001260965.1 and NP_001247894.1), dog PTEN (NM_001003192.1 and NP_001003192.1), mouse PTEN (NM_008960.2 and NP_032986.1), rat PTEN (NM_031606.1 and NP_113794.1), chicken PTEN (XM_421555.4 and XP_421555.2), and zebrafish PTEN (NM_001001822.2 and NP_001001822.1). Representative PTEN sequences are presented below in Table 1. It is to be noted that the term can further be used to refer to any combination of features described herein regarding PTEN molecules. For example, any combination of sequence composition, percentage identify, sequence length, domain structure, functional activity, etc can be used to describe a PTEN molecule of the present invention.

The term "inhibiting PTEN mutation" includes any one or more mutations in the PTEN gene that reduce or eliminate PTEN tumor suppressor activity. Examples of LKB1 mutations include, but are not limited to, missense, nonsense, frameshift, deletion, addition, a kinase domain mutation, and combinations thereof. In another embodiment, the deletion, insertion or mutation of PTEN is in the catalytic kinase domain.

An "over-expression" or "significantly higher level of expression" of a biomarker refers to an expression level in a test sample that is greater than the standard error of the assay employed to assess expression, and is preferably at least twice, and more preferably 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher than the expression activity or level of the biomarker in a control sample (e.g., sample from a healthy subject not having the biomarker associated disease) and preferably, the average expression level of the biomarker in several control samples. A "significantly lower level of expression" of a biomarker refers to an expression level in a test sample that is at least twice, and more preferably 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more lower than the expression level of the biomarker in a control sample (e.g., sample from a healthy subject not having the biomarker associated disease) and preferably, the average expression level of the biomarker in several control samples.

The term "predictive" includes the use of a biomarker nucleic acid, protein, and/or metabolite status, e.g., over- or under-activity, emergence, expression, growth, remission, recurrence or resistance of tumors before, during or after therapy, for determining the likelihood of response of a cancer to anti-immune checkpoint inhibitor treatment (e.g., therapeutic antibodies against PD-1, PD-L1, and/or CTLA-4). Such predictive use of the biomarker may be confirmed by, e.g., (1) increased or decreased copy number (e.g., by FISH, FISH plus SKY, single-molecule sequencing, e.g., as described in the art at least at J. Biotechnol., 86:289-301, or qPCR), overexpression or underexpression of a biomarker nucleic acid (e.g., by ISH, Northern Blot, or qPCR), increased or decreased biomarker protein (e.g., by IHC) and/or biomarker metabolite, or increased or decreased activity (determined by, for example, modulation of oncogene biomarkers (e.g., activating mutations in oncogene biomarkers) and tumor suppressor biomarkers (e.g., inhibiting mutations in tumor suppressors)), e.g., in more than about 5%, 6%, 7%, 8%, 9%, 10%, 11%, 12%, 13%, 14%, 15%, 20%, 25%, 30%, 40%, 50%, 60%, 70%, 80%, 90%, 95%, 100%, or more of assayed human cancers types or cancer samples; (2) its absolute or relatively modulated presence or absence in a biological sample, e.g., a sample containing tissue, whole blood, serum, plasma, buccal scrape, saliva, cerebrospinal fluid, urine, stool, or bone marrow, from a subject, e.g. a human, afflicted with cancer; (3) its absolute or relatively modulated presence or absence in clinical subset of patients with cancer (e.g., those responding to a particular anti-immune checkpoint inhibitor therapy or those developing resistance thereto).

The terms "prevent," "preventing," "prevention," "prophylactic treatment," and the like refer to reducing the probability of developing a disease, disorder, or condition in a subject, who does not have, but is at risk of or susceptible to developing a disease, disorder, or condition.

The term "probe" refers to any molecule which is capable of selectively binding to a specifically intended target molecule, for example, a nucleotide transcript or protein encoded by or corresponding to a biomarker nucleic acid. Probes can be either synthesized by one skilled in the art, or derived from appropriate biological preparations. For purposes of detection of the target molecule, probes may be specifically designed to be labeled, as described herein. Examples of molecules that can be utilized as probes include, but are not limited to, RNA, DNA, proteins, antibodies, and organic molecules.

The term "prognosis" includes a prediction of the probable course and outcome of cancer or the likelihood of recovery from the disease. In some embodiments, the use of statistical algorithms provides a prognosis of cancer in an individual. For example, the prognosis can be surgery, development of a clinical subtype of cancer (e.g., solid tumors, such as lung cancer, melanoma, and renal cell carcinoma), development of one or more clinical factors, development of intestinal cancer, or recovery from the disease.

The term "response to anti-immune checkpoint inhibitor therapy" relates to any response of the hyperproliferative disorder (e.g., cancer) to an anti-immune checkpoint inhibitor therapy, such as anti-immune checkpoint inhibitor therapy, preferably to a change in tumor mass and/or volume after initiation of neoadjuvant or adjuvant chemotherapy. Hyperproliferative disorder response may be assessed, for example for efficacy or in a neoadjuvant or adjuvant situation, where the size of a tumor after systemic intervention can be compared to the initial size and dimensions as measured by CT, PET, mammogram, ultrasound or palpation. Responses may also be assessed by caliper measurement or pathological examination of the tumor after biopsy or surgical resection. Response may be recorded in a quantitative fashion like percentage change in tumor volume or in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of hyperproliferative disorder response may be done early after the onset of neoadjuvant or adjuvant therapy, e.g., after a few hours, days, weeks or preferably after a few months. A typical endpoint for response assessment is upon termination of neoadjuvant chemotherapy or upon surgical removal of residual tumor cells and/or the tumor bed. This is typically three months after initiation of neoadjuvant therapy. In some embodiments, clinical efficacy of the therapeutic treatments described herein may be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD over 6 months. In some embodiments, the CBR for a particular cancer therapeutic regimen is at least 25%, 30%, 35%, 40%, 45%, 50%, 55%, 60%, 65%, 70%, 75%, 80%, 85%, or more. Additional criteria for evaluating the response to cancer therapies are related to "survival," which includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment can be expanded to include response to chemotherapy, probability of survival, probability of metastasis within a given time period, and probability of tumor recurrence. For example, in order to determine appropriate threshold values, a particular cancer therapeutic regimen can be administered to a population of subjects and the outcome can be correlated to biomarker measurements that were determined prior to administration of any cancer therapy. The outcome measurement may be pathologic response to therapy given in the neoadjuvant setting. Alternatively, outcome measures, such as overall survival and disease-free survival can be monitored over a period of time for subjects following cancer therapy for whom biomarker measurement values are known. In certain embodiments, the doses administered are standard doses known in the art for cancer therapeutic agents. The period of time for which subjects are monitored can vary. For example, subjects may be monitored for at least 2, 4, 6, 8, 10, 12, 14, 16, 18, 20, 25, 30, 35, 40, 45, 50, 55, or 60 months. Biomarker measurement threshold values that correlate to outcome of a cancer therapy can be determined using well-known methods in the art, such as those described in the Examples section.

The term "resistance" refers to an acquired or natural resistance of a cancer sample or a mammal to a cancer therapy (i.e., being nonresponsive to or having reduced or limited response to the therapeutic treatment), such as having a reduced response to a therapeutic treatment by 25% or more, for example, 30%, 40%, 50%, 60%, 70%, 80%, or more, to 2-fold, 3-fold, 4-fold, 5-fold, 10-fold, 15-fold, 20-fold or more. The reduction in response can be measured by comparing with the same cancer sample or mammal before the resistance is acquired, or by comparing with a different cancer sample or a mammal who is known to have no resistance to the therapeutic treatment. A typical acquired resistance to chemotherapy is called "multidrug resistance." The multidrug resistance can be mediated by P-glycoprotein or can be mediated by other mechanisms, or it can occur when a mammal is infected with a multi-drug-resistant microorganism or a combination of microorganisms. The determination of resistance to a therapeutic treatment is routine in the art and within the skill of an ordinarily skilled clinician, for example, can be measured by cell proliferative assays and cell death assays as described herein as "sensitizing." In some embodiments, the term "reverses resistance" means that the use of a second agent in combination with a primary cancer therapy (e.g., chemotherapeutic or radiation therapy) is able to produce a significant decrease in tumor volume at a level of statistical significance (e.g., p<0.05) when compared to tumor volume of untreated tumor in the circumstance where the primary cancer therapy (e.g., chemotherapeutic or radiation therapy) alone is unable to produce a statistically significant decrease in tumor volume compared to tumor volume of untreated tumor. This generally applies to tumor volume measurements made at a time when the untreated tumor is growing log rhythmically.

The terms "response" or "responsiveness" refers to an anti-cancer response, e.g. in the sense of reduction of tumor size or inhibiting tumor growth. The terms can also refer to an improved prognosis, for example, as reflected by an increased time to recurrence, which is the period to first recurrence censoring for second primary cancer as a first event or death without evidence of recurrence, or an increased overall survival, which is the period from treatment to death from any cause. To respond or to have a response means there is a beneficial endpoint attained when exposed to a stimulus. Alternatively, a negative or detrimental symptom is minimized, mitigated or attenuated on exposure to a stimulus. It will be appreciated that evaluating the likelihood that a tumor or subject will exhibit a favorable response is equivalent to evaluating the likelihood that the tumor or subject will not exhibit favorable response (i.e., will exhibit a lack of response or be non-responsive).

An "RNA interfering agent" as used herein, is defined as any agent which interferes with or inhibits expression of a target biomarker gene by RNA interference (RNAi). Such RNA interfering agents include, but are not limited to, nucleic acid molecules including RNA molecules which are homologous to the target biomarker gene of the invention, or a fragment thereof, short interfering RNA (siRNA), and small molecules which interfere with or inhibit expression of a target biomarker nucleic acid by RNA interference (RNAi).

"RNA interference (RNAi)" is an evolutionarily conserved process whereby the expression or introduction of RNA of a sequence that is identical or highly similar to a target biomarker nucleic acid results in the sequence specific degradation or specific post-transcriptional gene silencing (PTGS) of messenger RNA (mRNA) transcribed from that targeted gene (see Coburn, G. and Cullen, B. (2002) *J. of Virology* 76(18):9225), thereby inhibiting expression of the target biomarker nucleic acid. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex that recognizes and cleaves target mRNAs. RNAi can also be initiated by introducing nucleic acid molecules, e.g., synthetic siRNAs or RNA interfering agents, to inhibit or silence the expression of target biomarker nucleic acids. As used herein, "inhibition of target biomarker nucleic acid expression" or "inhibition of marker gene expression" includes any decrease in expression or protein activity or level of the target biomarker nucleic acid or protein encoded by the target biomarker nucleic acid. The decrease may be of at least 30%, 40%, 50%, 60%, 70%, 80%, 90%, 95% or 99% or more as compared to the expression of a target biomarker nucleic acid or the activity or level of the protein encoded by a target biomarker nucleic acid which has not been targeted by an RNA interfering agent.

The term "sample" used for detecting or determining the presence or level of at least one biomarker is typically whole blood, plasma, serum, saliva, urine, stool (e.g., feces), tears, and any other bodily fluid (e.g., as described above under the definition of "body fluids"), or a tissue sample (e.g., biopsy) such as a small intestine, colon sample, or surgical resection tissue. In certain instances, the method of the present invention further comprises obtaining the sample from the individual prior to detecting or determining the presence or level of at least one marker in the sample.

The term "sensitize" means to alter cancer cells or tumor cells in a way that allows for more effective treatment of the associated cancer with a cancer therapy (e.g., anti-immune checkpoint inhibitor, chemotherapeutic, and/or radiation therapy). In some embodiments, normal cells are not affected to an extent that causes the normal cells to be unduly injured by the anti-immune checkpoint inhibitor therapy. An increased sensitivity or a reduced sensitivity to a therapeutic treatment is measured according to a known method in the art for the particular treatment and methods described herein below, including, but not limited to, cell proliferative assays (Tanigawa N, Kern D H, Kikasa Y, Morton D L, Cancer Res 1982; 42: 2159-2164), cell death assays (Weisenthal L M, Shoemaker R H, Marsden J A, Dill P L. Baker J A, Moran E M, Cancer Res 1984; 94: 161-173; Weisenthal L M, Lippman M E, Cancer Treat Rep 1985; 69: 615-632; Weisenthal L M, In: Kaspers G J L, Pieters R, Twentyman P R, Weisenthal L M, Veerman A J P, eds. Drug Resistance in Leukemia and Lymphoma. Langhorne, P A: Harwood Academic Publishers, 1993: 415-432; Weisenthal L M, Contrib Gynecol Obstet 1994; 19: 82-90). The sensitivity or resistance may also be measured in animal by measuring the tumor size reduction over a period of time, for example, 6 month for human and 4-6 weeks for mouse. A composition or a method sensitizes response to a therapeutic treatment if the increase in treatment sensitivity or the reduction in resistance is 25% or more, for example, 30%, 40%, 50%, 60%, 70%, 80%, or more, to 2-fold, 3-fold, 4-fold, 5-fold, 10-fold, 15-fold, 20-fold or more, compared to treatment sensitivity or resistance in the absence of such composition or method. The determination of sensitivity or resistance to a therapeutic treatment is routine in the art and within the skill of an ordinarily skilled clinician. It is to be understood that any method described herein for enhancing the efficacy of a cancer therapy can be equally applied to methods for sensitizing hyperproliferative or otherwise cancerous cells (e.g., resistant cells) to the cancer therapy.

The term "synergistic effect" refers to the combined effect of two or more anti-immune checkpoint inhibitor agents can be greater than the sum of the separate effects of the anticancer agents alone.

"Short interfering RNA" (siRNA), also referred to herein as "small interfering RNA" is defined as an agent which functions to inhibit expression of a target biomarker nucleic acid, e.g., by RNAi. An siRNA may be chemically synthesized, may be produced by in vitro transcription, or may be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, or 22 nucleotides in length, and may contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

In another embodiment, an siRNA is a small hairpin (also called stem loop) RNA (shRNA). In one embodiment, these shRNAs are composed of a short (e.g., 19-25 nucleotide) antisense strand, followed by a 5-9 nucleotide loop, and the analogous sense strand. Alternatively, the sense strand may precede the nucleotide loop structure and the antisense strand may follow. These shRNAs may be contained in plasmids, retroviruses, and lentiviruses and expressed from, for example, the pol III U6 promoter, or another promoter (see, e.g., Stewart, et al. (2003) *RNA* April; 9(4):493-501 incorporated by reference herein).

RNA interfering agents, e.g., siRNA molecules, may be administered to a patient having or at risk for having cancer, to inhibit expression of a biomarker gene which is overexpressed in cancer and thereby treat, prevent, or inhibit cancer in the subject.

The term "subject" refers to any healthy animal, mammal or human, or any animal, mammal or human afflicted with a cancer, e.g., lung, ovarian, pancreatic, liver, breast, prostate, and colon carcinomas, as well as melanoma and multiple myeloma. The term "subject" is interchangeable with "patient."

The term "survival" includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g. time of diagnosis or start of treatment) and end point (e.g. death, recurrence or metastasis). In addition, criteria for efficacy of treatment can be expanded to include response to chemotherapy, probability of survival, probability of metastasis within a given time period, and probability of tumor recurrence.

The term "therapeutic effect" refers to a local or systemic effect in animals, particularly mammals, and more particularly humans, caused by a pharmacologically active substance. The term thus means any substance intended for use in the diagnosis, cure, mitigation, treatment or prevention of disease or in the enhancement of desirable physical or mental development and conditions in an animal or human. The phrase "therapeutically-effective amount" means that amount of such a substance that produces some desired local or systemic effect at a reasonable benefit/risk ratio applicable to any treatment. In certain embodiments, a therapeutically effective amount of a compound will depend on its therapeutic index, solubility, and the like. For example, certain compounds discovered by the methods of the present invention may be administered in a sufficient amount to produce a reasonable benefit/risk ratio applicable to such treatment.

The terms "therapeutically-effective amount" and "effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment. Toxicity and therapeutic efficacy of subject compounds may be determined by standard pharmaceutical procedures in cell cultures or experimental animals, e.g., for determining the $LD_{50}$ and the $ED_{50}$. Compositions that exhibit large therapeutic indices are preferred. In some embodiments, the $LD_{50}$ (lethal dosage) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more reduced for the agent relative to no administration of the agent. Similarly, the $ED_{50}$ (i.e., the concentration which achieves a half-maximal inhibition of symptoms) can be measured and can be, for example, at least 10%, 20%, 30%, 40%, 50%, 60%, 70%, 80%, 90%, 10%, 200%, 300%, 400%, 500%, 600%, 700%, 800%, 900%, 1000% or more increased for the agent relative to no administration of the agent. Also, Similarly, the $IC_{50}$ (i.e., the concentration which achieves half-maximal cytotoxic or cytostatic effect on cancer cells) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more increased for the agent relative to no administration of the agent. In some embodiments, cancer cell growth in an assay can be inhibited by at least about 10%, 15%, 20%, 25%, 30%, 35%, 40%, 45%, 50%, 55%, 60%, 65%, 70%, 75%, 80%, 85%, 90%, 95%, or even 100%. In another embodiment, at least about a 10%, 15%, 20%, 25%, 30%, 35%, 40%, 45%, 50%, 55%, 60%, 65%, 70%, 75%, 80%, 85%, 90%, 95%, or even 100% decrease in a solid malignancy can be achieved.

A "transcribed polynucleotide" or "nucleotide transcript" is a polynucleotide (e.g. an mRNA, hnRNA, a cDNA, or an analog of such RNA or cDNA) which is complementary to or homologous with all or a portion of a mature mRNA made by transcription of a biomarker nucleic acid and normal post-transcriptional processing (e.g. splicing), if any, of the RNA transcript, and reverse transcription of the RNA transcript.

There is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid and the amino acid sequence encoded by that nucleic acid, as defined by the genetic code.

| GENETIC CODE | |
|---|---|
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartie acid (Asp, D) | GAC, GAT |
| Cysteine (Cys, C) | TGC, TGT |
| Glutamie acid (Glu, E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe, F) | TTC, TTT |
| Proline (Pro, P) | CCA, CCC, CCG, CCT |
| Salm (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Wine (Val, V) | GTA, GTC, GTG, GTT |
| Termination signal (end) | TAA, TAG, TGA |

An important and well known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In view of the foregoing, the nucleotide sequence of a DNA or RNA encoding a biomarker nucleic acid (or any portion thereof) can be used to derive the polypeptide amino acid sequence, using the genetic code to translate the DNA or RNA into an amino acid sequence. Likewise, for polypeptide amino acid sequence, corresponding nucleotide sequences that can encode the polypeptide can be deduced from the genetic code (which, because of its redundancy, will produce multiple nucleic acid sequences for any given amino acid sequence). Thus, description and/or disclosure herein of a nucleotide sequence which encodes a polypeptide should be considered to also include description and/or disclosure of the amino acid sequence encoded by the nucleotide sequence. Similarly, description and/or disclosure of a polypeptide amino acid sequence herein should be considered to also include description and/or disclosure of all possible nucleotide sequences that can encode the amino acid sequence.

Finally, nucleic acid and amino acid sequence information for the loci and biomarkers of the present invention (e.g., biomarkers listed in Table 1) are well known in the art and readily available on publicly available databases, such as the National Center for Biotechnology Information (NCBI). For example, exemplary nucleic acid and amino acid sequences derived from publicly available sequence databases are provided below.

TABLE 1

SEQ ID No: 1 Human ARG1 cDNA sequence (transcript variant 1)
```
  1 atgagcgcca agtccagaac catagggatt attggagctc ctttctcaaa gggacagcca
 61 cgaggagggg tggaagaagg ccctacagta ttgagaaagg ctggtctgct tgagaaactt
121 aaagaacaag taactcaaaa cttttttaatt ttagagtgtg atgtgaagga ttatgggac
181 ctgcccttg ctgacatccc taatgacagt ccctttcaaa ttgtgaagaa tccaaggtct
```

TABLE 1-continued

```
241 gtgggaaaag caagcgagca gctggctggc aagtggcag aagtcaagaa gaacggaaga
301 atcagcctgg tgctgggcgg agaccacagt ttggcaattg gaagcatctc tggccatgcc
361 agggtccacc ctgatcttgg agtcatctg gtggatgctc acactgatat caacactcca
421 ctgacaacca caagtggaaa cttgcatgga caacctgtat cttcctcct gaaggaacta
481 aaaggaaaga ttccgatgt gccaggattc tcctgggtga ctccctgtat atctgccaag
541 gatattgtgt atattggctt gagagacgtg gaccctgggg aacactacat tttgaaaact
601 ctaggcatta aatactttc aatgactgaa gtggacagac taggaattgg caaggtgatg
661 gaagaaacac tcagctatct actaggaaga aagaaaaggc caattcatct aagttttgat
721 gttgacggac tggacccatc tttcacacca gctactggca caccagtcgt ggggggtctg
781 acatacagag aaggtctcta catcacagaa gaaatctaca aaacagggct actctcagga
841 ttagatataa tggaagtgaa cccatccctg ggaagacac cagaagaagt aactcgaaca
901 gtgaacacag cagttgcaat aaccttggct tgtttcggac ttgctcggga gggtaatcac
961 aagcctattg actaccttaa ccccacctaag taa
```

SEQ ID No: 2 Human ARG1 amino acid sequence (isoform 1)
```
  1 msaksrtigi igapfskgqp rggveegptv lrkagllekl keqvtqnfli lecdvkdygd
 61 lpfadipnds pfqivknprs vgkaseqlag kvaevkkngr islvlggdhs laigsisqha
121 rvhpdlgviw vdahtdintp ltttsgnlhg qpvsfllkel kgkipdvpgf swvtpcisak
181 divyiglrdv dpgehyilkt lgikyfsmte vdrlgikvm eetlsyllgr kkrpihlsfd
241 vdgldpsftp atgtpvvggl tyreglyite eiyktgllsg ldimevnpsl gktpeevtrt
301 vntavaitla cfglaregnh kpidylnppk
```

SEQ ID No: 3 Human ARG1 cDNA sequence (transcript variant 2)
```
  1 atgagcgcca agtccagaac catagggatt attggagctc ctttctcaaa gggacagcca
 61 cgaggagggg tggaagaagg ccctacagta ttgagaaagg ctggtctgct tgagaaactt
121 aaagaacaag agtgtgatgt gaaggattat ggggacctgc cctttgctga catccctaat
181 gacagtccct tcaaattgt gaagaatcca aggtctgtgg aaaagcaag cgagcagctg
241 gctggcaagt ggcagaagt caagaagaac ggaagaatca gcctggtgct gggcggagac
301 cacagtttgg caattggaag catctctggc catgccaggg tccaccctg tcttggagtc
361 atctgggtgg atgctcacac tgatatcaac actccactga caaccacag tggaaacttg
421 catggacaac ctgtatcttt cctcctgaag gaactaaaag gaaagattcc cgatgtgcca
481 ggattctcct gggtgactcc ctgtatatct gccaaggata ttgtgtatat ggcttgaga
541 gacgtggacc ctggggaaca ctacattttg aaaactctag gcattaaata cttttcaatg
601 actgaagtgg acagactagg aattggcaag gtgatgaag aaacactcag ctatctacta
661 ggaagaaaga aaaggccaat tcatctaagt tttgatgttg acggactgga cccatctttc
721 acaccagcta ctggcacacc agtcgtggga ggtctgacat acagagaagg tctctacatc
781 acagaagaaa tctacaaaac agggctactc tcaggattga tataatgga agtgaaccca
841 tccctgggga gacaccagga agaagtaact cgaacagtga cacagcagt tgcaataacc
901 ttggcttgtt tcggacttgc tcgggagggt aatcacaage ctattgacta ccttaaccca
961 cctaagtaa
```

SEQ ID No: 4 Human ARG1 amino acid sequence (isoform 2)
```
  1 msaksrtigi igapfskgqp rggveegptv lrkagllekl keqecdvkdy gdlpfadipn
 61 dspfqivknp rsvgkaseql agkvaevkkn grislvlggd hslaigsisq harvhpdlgv
121 iwvdahtdin tplttsgnl hgqpvsfllk elkgkipdvp gfswvtpcis akdivyiglr
181 dvdpgehyil ktlgikyfsm tevdrlgigk vmeetlsyll grkkrpihls fdvdgldpsf
241 tpatgtpvvg gltyreglyi teeiyktgll sgldimevnp slgktpeevt rtvntavait
301 lacfglareg nhkpidylnp pk
```

SEQ ID No: 5 Human KRAS cDNA sequence (transcript variant 1)
```
  1 atgactgaat ataaacttgt ggtagttgga gctggtggcg taggcaagag tgccttgacg
 61 atacagctaa ttcagaatca ttttgtggac gaatatgatc caacaataga ggattcctac
121 aggaagcaag tagtaattga tggagaaacc tgtctcttgg atattctcga cacagcaggt
181 caagaggagt acagtgcaat gagggaccag tacatgagga ctggggaggg ctttctttgt
241 gtatttgcca taaataatac taaatcattt gaagatattc accattatag agaacaaatt
301 aaaagagtta aggactctga agatgtacct atggtcctag taggaaataa atgtgatttg
361 ccttctagaa cagtagacac aaaacaggct caggacttag caagaagtta tggaattcct
421 tttattgaaa catcagcaaa gacaagacag agtggaggat gcttttta tacattggtg
481 agggagatcc gacaatacag attgaaaaaa atcagcaaag aagaaagac tcctggctgt
541 gtgaaaatta aaaaatgcat tataatgtaa
```

SEQ ID No: 6 Human KRAS amino acid sequence (isoform 1)
```
  1 mteyklvvvg aggvgksalt iqliqnhfvd eydptiedsy rkqvvidget clldildtag
 61 qeeysamrdq ymrtgegflc vfainntksf edihhyreqi krvkdsedvp mvlvgnkcdl
121 psrtvdtkqa qdlarsygip fietsaktrq rvedafytlv reirqyrlkk iskeektpgc
181 vkikkcim
```

SEQ ID No: 7 Human KRAS cDNA sequence (transcript variant 2)
```
  1 atgactgaat ataaacttgt ggtagttgga gctggtggcg taggcaagag tgccttgacg
 61 atacagctaa ttcagaatca ttttgtggac gaatatgatc caacaataga ggattcctac
121 aggaagcaag tagtaattga tggagaaacc tgtctcttgg atattctcga cacagcaggt
181 caagaggagt acagtgcaat gagggaccag tacatgagga ctggggaggg ctttctttgt
241 gtatttgcca taaataatac taaatcattt gaagatattc accattatag agaacaaatt
301 aaaagagtta aggactctga agatgtacct atggtcctag taggaaataa atgtgatttg
361 ccttctagaa cagtagacac aaaacaggct caggacttag caagaagtta tggaattcct
421 tttattgaaa catcagcaaa gacaagacag ggtgttgatg atgccttcta tacattagtt
481 cgagaaattc gaaaacataa agaaaagatg agcaaagatg taaaagaa gaaaagaag
541 tcaaagacaa agtgtgtaat tatgtaa
```

TABLE 1-continued

```
SEQ ID No: 8 Human KRAS amino acid sequence (isoform 2)
    1 mteyklvvvg aggvgksalt iqliqnhfvd eydptiedsy rkqvvidget clldildtag
   61 qeeysamrdq ymrtgegflc vfainntksf edihhyreqi krvkdsedvp mvlvgnkcdl
  121 psrtvdtkqa qdlarsygip fietsaktrq gvddafytlv reirkhkekm skdgkkkkkk
  181 sktkkcvim SEQ ID No: 9 Human NRAS cDNA sequence
    1 atgactgagt acaaactggt ggtggttgga gcaggtggtg ttgggaaaag cgcactgaca
   61 atccagctaa tccagaacca cttttgtagat gaatatgatc ccaccataga ggattcttac
  121 agaaaacaag tggttataga tggtgaaacc tgtttgttgg acatactgga tacagctgga
  181 caagaagagt acagtgccat gagagaccaa tacatgagga caggcaaagg cttcctctgt
  241 gtatttgcca tcaataatag caagtcattt gcggatatta acctctacag ggagcagatt
  301 aagcgagtaa aagactcgga tgatgtacct atggtgtacc tgggaaacaa gtgtgatttg
  361 ccaacaagga cagttgatac aaaacaagcc cacgaactgg ccaagagtta cgggattcca
  421 ttcattgaaa cctcagccaa gaccagacag ggtgttgaag atgctttta cacactggta
  481 agagaaatac gccagtaccg aatgaaaaaa ctcaacagca gtgatgatgg gactcagggt
  541 tgtatgggat tgccatgtgt ggtgatgtaa SEQ ID No: 10 Human NRAS amino acid sequence
    1 mteyklvvvg aggvgksalt iqliqnhfvd eydptiedsy rkqvvidget clldildtag
   61 qeeysamrdq ymrtgegflc vfainntksf edihhyreqi krvkdsedvp mvlvgnkcdl
  121 psrtvdtkqa helaksygip fietsaktrq gvedafytlv reirqyrmkk lnssddgtqg
  181 cmglpcvvm SEQ ID No: 11 Human HRAS cDNA sequence (transcript variant 1)
    1 atgacggaat ataagctggt ggtggtgggc gccggcggtg tgggcaagag tgcgctgacc
   61 atccagctga tccagaacca ttttgtggac gaatacgacc ccactataga ggattcctac
  121 cggaagcagg tggtcattga tggggagacg tgcctgttgg acatcctgga taccgccggc
  181 caggaggagt acagcgccat gcgggaccag tacatgcgca ccgggagg cttcctgtgt
  241 gtgtttgcca tcaacaacac caagtctttt gaggacatcc accagtacag ggagcagatc
  301 aaacgggtga aggactcgga tgacgtgccc atggtgctgg tgggaacaa gtgtgacctg
  361 gctgcacgca ctgtggaatc tcggcaggct caggacctcg cccgaagcta cggcatcccc
  421 tacatcgaga cctcggccaa gacccggcag ggagtggagg atgccttcta cacgttggtg
  481 cgtgagatcc ggcagcacaa gctgcggaag ctgaaccctc ctgatgagag tggccccggc
  541 tgcatgagct gcaagtgtgt gctctcctga SEQ ID No: 12 Human NRAS cDNA sequence (transcript variant 3)
    1 atgacggaat ataagctggt ggtggtgggc gccggcggtg tgggcaagag tgcgctgacc
   61 atccagctga tccagaacca ttttgtggac gaatacgacc ccactataga ggattcctac
  121 cggaagcagg tggtcattga tggggagacg tgcctgttgg acatcctgga taccgccggc
  181 caggaggagt acagcgccat gcgggaccag tacatgcgca ccgggagg cttcctgtgt
  241 gtgtttgcca tcaacaacac caagtctttt gaggacatcc accagtacag ggagcagatc
  301 aaacgggtga aggactcgga tgacgtgccc atggtgctgg tgggaacaa gtgtgacctg
  361 gctgcacgca ctgtggaatc tcggcaggct caggacctcg cccgaagcta cggcatcccc
  421 tacatcgaga cctcggccaa gacccggcag ggagtggagg atgccttcta cacgttggtg
  481 cgtgagatcc ggcagcacaa gctgcggaag ctgaaccctc ctgatgagag tggccccggc
  541 tgcatgagct gcaagtgtgt gctctcctga SEQ ID No: 13 Human NRAS amino acid sequence (isoform 1)
    1 mteyklvvvg aggvgksalt iqliqnhfvd eydptiedsy rkqvvidget clldildtag
   61 qeeysamrdq ymrtgegflc vfainntksf edihhyreqi krvkdsedvp mvlvgnkcdl
  121 aartvesrqa qdlarsygip yietsaktrq gvedafytlv reirqhklrk lnppdesgpg
  181 cnscjcvls SEQ ID No: 14 Human NRAS cDNA sequence (transcript variant 2)
    1 atgacggaat ataagctggt ggtggtgggc gccggcggtg tgggcaagag tgcgctgacc
   61 atccagctga tccagaacca ttttgtggac gaatacgacc ccactataga ggattcctac
  121 cggaagcagg tggtcattga tggggagacg tgcctgttgg acatcctgga taccgccggc
  181 caggaggagt acagcgccat gcgggaccag tacatgcgca ccgggagg cttcctgtgt
  241 gtgtttgcca tcaacaacac caagtctttt gaggacatcc accagtacag ggagcagatc
  301 aaacgggtga aggactcgga tgacgtgccc atggtgctgg tgggaacaa gtgtgacctg
  361 gctgcacgca ctgtggaatc tcggcaggct caggacctcg cccgaagcta cggcatcccc
  421 tacatcgaga cctcggccaa gacccggcag ggcagccgct ctggctctag ctccagctcc
  481 gggaccctct gggaccccc gggacccatg tga SEQ ID No: 15 Human NRAS amino acid sequence (isoform 2)
    1 mteyklvvvg aggvgksalt iqliqnhfvd eydptiedsy rkqvvidget clldildtag
   61 qeeysamrdq ymrtgegflc vfainntksf edihhyreqi krvkdsedvp mvlvgnkcdl
  121 aartvesrqa qdlarsygip yietsaktrq gsrsgsssss gtlwdppgpm SEQ ID No: 16 Human LKB1 cDNA sequence
    1 atggaggtgg tggacccgca gcagctgggc atgttcacgg agggcgagct gatgtcggtg
   61 ggtatggaca cgttcatcca ccgcatcgac tccaccgagg tcatctacca gccgcgccgc
  121 aagcgggcca agctcatcgg caagtacctg atggggacc tgctggggga aggctcttac
  181 gcaaggtga aggaggtgct ggactcggag agcgtgca caagggccgt caagatcctc
  241 aagaagaaga agttgcgaag gatccccaac ggggaggcca acgtgaagga ggaaattcaa
  301 ctactgagga ggttacggca caaaaatgtc atccagctgg tggatgtgtt atacaacgaa
  361 gagaagcaga aaatgtatat ggtgatggag tactgcgtgt gtggcatgca ggaaatgctg
  421 gacagcgtgc cggagaagcg tttcccagtg tgccaggccc acgggtactt ctgtcagctg
  481 attgacggcc tggagtacct gcatagccag ggcattgtgc acaaggacat caagcgcgg
```

TABLE 1-continued

```
 541 aacctgctgc tcaccaccgg tggcaccctc aaaatctccg acctgggcgt ggccgaggca
 601 ctgcacccgt tcgcggcgga cgacacctgc cggaccagcc agggctcccc ggctttccag
 661 ccgcccgaga ttgccaacgg cctggacacc ttctccggct tcaaggtgga catctggtcg
 721 gctggggtca ccctctacaa catcaccacg ggtctgtacc ccttcgaagg ggacaacatc
 781 tacaagttgt ttgagaacat cgggaagggg agctacgcca tcccgggcga ctgtggcccc
 841 ccgctctctg acctgctgaa agggatgctt gagtacgaac cggccaagag gttctccatc
 901 cggcagatcc ggcagcacag ctggttccgg aagaaacatc ctccggctga agcaccagtg
 961 cccatcccac cgagcccaga caccaaggac cggtggcgca gcatgactgt ggtgccgtac
1021 ttggaggacc tgcacggcgc ggacgaggac gaggacctct tcgacatcga ggatgacatc
1081 atctacactc aggacttcac ggtgcccgga caggtcccag aagaggaggc cagtcacaat
1141 ggacagcgcc ggggcctccc caaggccgtg tgtatgaacg gcacagaggc ggcgcagctg
1201 agcaccaaat ccagggcgga gggccgggcc cccaaccctg cccgcaaggc ctgctccgcc
1261 agcagcaaga tccgccggct gtcggcctgc aagcagcagt ga SEQ ID No: 17 Human LKB1 amino acid sequence
    1 mevvdpqqlg mftegelmsv gmdtfihrid steviyqprr krakligkyl mgdllgegsy
   61 gkvkevldse tlcrravkil kkkklrripn geanvkkeiq llrrlrhknv iqlvdvlyne
  121 ekqkmymvme ycvcgmqeml dsvpekrfpv cqahgyfcql idgleylhsq givhkdikpg
  181 nlllttggtl kisdlgvaea lhpfaaddtc rtsqgspafq ppeiangldt fsgfkvdiws
  241 agvtlynitt glypfegdni yklfenigkg syaipgdcgp plsdllkgml eyepakrfsi
  301 rqirqhswfr kkhppaeapv pippspdtkd rwrsmtvvpy ledlhgaded edlfdieddi
  361 iytqdftvpg qvpeeeashn gqrrglpkav cmngteaaql stksraegra pnparkacsa
  421 sskirrlsac kqq SEQ ID No: 18 Human PTEN cDNA sequence
    1 mtaiikeivs rnkrryqedg fdldltyiyp niiamgfpae rlegvyrnni ddvvrfldsk
   61 hknhykiynl caerhydtak fncrvaqypf edhnppqlel ikpfcedldq wlseddnhva
  121 aihckagkgr tgvmicayll hrgkflkaqe aldfygevrt rdkkgvtips qrryvyyysy
  181 llknnldyrp vallfhkmmf etipmfsggt cnpqfvvcql kvkiyssnsg ptrredkfmy
  241 fefpqplpvc gdikveffhk qnkmlkkdkm fhfwvntffi pgpeetsekv engslcdqel
  301 dsicsierad ndkeylvltl tkndldkank dkanryfspn fkvklyftkt veepsnpeas
  361 sstsvtpdvs dnepdhyrys dttdsdpene pfdedqhtqi tkv SEQ ID No: 19 Human PTEN amino acid sequence
    1 mtaiikeivs rnkrryqedg fdldltyiyp niiamgfpae rlegvyrnni ddvvrfldsk
   61 hknhykiynl caerhydtak fncrvaqypf edhnppqlel ikpfcedldq wlseddnhva
  121 aihckagkgr tgvmicayll hrgkflkaqe aldfygevrt rdkkgvtips qrryvyyysy
  181 llknnldyrp vallfhkmmf etipmfsggt cnpqfvvcql kvkiyssnsg ptrredkfmy
  241 fefpqplpvc gdikveffhk qnkmlkkdkm fhfwvntffi pgpeetsekv engslcdqel
  301 dsicsierad ndkeylvltl tkndldkank dkanryfspn fkvklyftkt veepsnpeas
  361 sstsvtpdvs dnepdhyrys dttdsdpene pfdedqhtqi tkv
```

* Included in Table 1 are RNA nucleic acid molecules (e.g., thymines replaced with uredines), nucleic acid molecules encoding orthologs of the encoded proteins, as well as DNA or RNA nucleic acid sequences comprising a nucleic acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with the nucleic acid sequence of any SEQ ID NO listed in Table 1, or a portion thereof. Such nucleic acid molecules can have a function of the full-length nucleic acid as described further herein, but harbor one or more activating oncogene mutations or one or more inhibiting tumor suppressor mutations to thereby active oncogenes or inhibed tumor suppressors.
* Included in Table 1 are orthologs of the proteins, as well as polypeptidc molecules comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99_5%, or more identity across their full length with an amino acid sequence of any SEQ ID NO listed in Table 1, or a portion thereof. Such polypeptides can have a function of the full-length polypeptide as described further herein, but harbor one or more activating oncogene mutations or one or more inhibiting tumor suppressor mutations to thereby active oncogenes or inhibed tumor suppressors.
* Included in Table 1 are arginase 1 metabolites and reactants, such as arginine (e.g., L-arginine), creatine, ornithine, and urea.

II. SUBJECTS

In one embodiment, the subject for whom predicted likelihood of efficacy of an anti-immune checkpoint inhibitor therapy is determined, is a mammal (e.g., mouse, rat, primate, non-human mammal, domestic animal such as dog, cat, cow, horse), and is preferably a human.

In another embodiment of the methods of the invention, the subject has not undergone treatment, such as chemotherapy, radiation therapy, targeted therapy, and/or anti-immune checkpoint inhibitor therapy. In still another embodiment, the subject has undergone treatment, such as chemotherapy, radiation therapy, targeted therapy, and/or anti-immune checkpoint inhibitor therapy.

In certain embodiments, the subject has had surgery to remove cancerous or precancerous tissue. In other embodiments, the cancerous tissue has not been removed, e.g., the cancerous tissue may be located in an inoperable region of the body, such as in a tissue that is essential for life, or in a region where a surgical procedure would cause considerable risk of harm to the patient.

The methods of the invention can be used to determine the responsiveness to anti-immune checkpoint inhibitor therapies of many different cancers in subjects such as those described above. In one embodiment, the cancers are solid tumors, such as lung cancer or lung cancer subtypes (e.g., squamous cell carcinoma), melanoma, and/or renal cell carcinoma. In another embodiment, the cancer is an epithelial cancer such as, but not limited to, brain cancer (e.g., glioblastomas) bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In still other embodiments, the cancer is breast cancer, prostate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers may be characterized in various other ways including, but not limited to, serous, endometrioid, mucinous, clear cell, brenner, or undifferentiated.

III. SAMPLE COLLECTION, PREPARATION AND SEPARATION

In some embodiments, biomarker amount and/or activity measurement(s) in a sample from a subject is compared to a predetermined control (standard) sample. The sample from the subject is typically from a diseased tissue, such as cancer cells or tissues. The control sample can be from the same subject or from a different subject. The control sample is typically a normal, non-diseased sample. However, in some embodiments, such as for staging of disease or for evaluating the efficacy of treatment, the control sample can be from a diseased tissue. The control sample can be a combination of samples from several different subjects. In some embodiments, the biomarker amount and/or activity measurement(s) from a subject is compared to a pre-determined level. This pre-determined level is typically obtained from normal samples. As described herein, a "pre-determined" biomarker amount and/or activity measurement(s) may be a biomarker amount and/or activity measurement(s) used to, by way of example only, evaluate a subject that may be selected for treatment, evaluate a response to an anti-immune checkpoint inhibitor therapy, and/or evaluate a response to a combination anti-immune checkpoint inhibitor therapy. A pre-determined biomarker amount and/or activity measurement(s) may be determined in populations of patients with or without cancer. The pro-determined biomarker amount and/or activity measurement(s) can be a single number, equally applicable to every patient, or the pre-determined biomarker amount and/or activity measurement(s) can vary according to specific subpopulations of patients. Age, weight, height, and other factors of a subject may affect the pre-determined biomarker amount and/or activity measurement(s) of the individual. Furthermore, the pre-determined biomarker amount and/or activity can be determined for each subject individually. In one embodiment, the amounts determined and/or compared in a method described herein are based on absolute measurements. In another embodiment, the amounts determined and/or compared in a method described herein are based on relative measurements, such as ratios (e.g., expression and/or activity of activating oncogene biomarkers to that of wild type oncogene biomarkers, expression and/or activity of inhibiting tumor suppressor biomarkers to that of wild type tumor suppressor biomarkers, and expression and/or activity of a biomarker of interest normalized to that of a housekeeping gene).

The pre-determined biomarker amount and/or activity measurement(s) can be any suitable standard. For example, the pre-determined biomarker amount and/or activity measurement(s) can be obtained from the same or a different human for whom a patient selection is being assessed. In one embodiment, the pre-determined biomarker amount and/or activity measurement(s) can be obtained from a previous assessment of the same patient. In such a manner, the progress of the selection of the patient can be monitored over time. In addition, the control can be obtained from an assessment of another human or multiple humans, e.g., selected groups of humans, if the subject is a human. In such a manner, the extent of the selection of the human for whom selection is being assessed can be compared to suitable other humans, e.g., other humans who are in a similar situation to the human of interest, such as those suffering from similar or the same condition(s) and/or of the same ethnic group.

In some embodiments of the present invention the change of biomarker amount and/or activity measurement(s) from the pre-determined level is about 0.5 fold, about 1.0 fold, about 1.5 fold, about 2.0 fold, about 2.5 fold, about 3.0 fold, about 3.5 fold, about 4.0 fold, about 4.5 fold, or about 5.0 fold or greater. In some embodiments, the fold change is less than about 1, less than about 5, less than about 10, less than about 20, less than about 30, less than about 40, or less than about 50. In other embodiments, the fold change in biomarker amount and/or activity measurement(s) compared to a predetermined level is more than about 1, more than about 5, more than about 10, more than about 20, more than about 30, more than about 40, or more than about 50.

Biological samples can be collected from a variety of sources from a patient including a body fluid sample, cell sample, or a tissue sample comprising nucleic acids and/or proteins. "Body fluids" refer to fluids that are excreted or secreted from the body as well as fluids that are normally not (e.g., bronchoalveolar lavage fluid, amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, vomit). In a preferred embodiment, the subject and/or control sample is selected from the group consisting of cells, cell lines, histological slides, paraffin embedded tissues, biopsies, whole blood, nipple aspirate, serum, plasma, buccal scrape, saliva, cerebrospinal fluid, urine, stool, and bone marrow. In one embodiment, the sample is serum, plasma, or urine. IN another embodiment, the sample is serum.

The samples can be collected from individuals repeatedly over a longitudinal period of time (e.g., once or more on the order of days, weeks, months, annually, biannually, etc.). Obtaining numerous samples from an individual over a period of time can be used to verify results from earlier detections and/or to identify an alteration in biological pattern as a result of, for example, disease progression, drug treatment, etc. For example, subject samples can be taken and monitored every month, every two months, or combinations of one, two, or three month intervals according to the invention. In addition, the biomarker amount and/or activity measurements of the subject obtained over time can be conveniently compared with each other, as well as with those of normal controls during the monitoring period, thereby providing the subject's own values, as an internal, or personal, control for long-term monitoring.

Sample preparation and separation can involve any of the procedures, depending on the type of sample collected and/or analysis of biomarker measurement(s). Such procedures include, by way of example only, concentration, dilution, adjustment of pH, removal of high abundance polypeptides (e.g., albumin, gamma globulin, and transferrin, etc.), addition of preservatives and calibrants, addition of protease inhibitors, addition of denaturants, desalting of samples, concentration of sample proteins, extraction and purification of lipids.

The sample preparation can also isolate molecules that are bound in non-covalent complexes to other protein (e.g., carrier proteins). This process may isolate those molecules bound to a specific carrier protein (e.g., albumin), or use a more general process, such as the release of bound molecules from all carrier proteins via protein denaturation, for example using an acid, followed by removal of the carrier proteins.

Removal of undesired proteins (e.g., high abundance, uninformative, or undetectable proteins) from a sample can be achieved using high affinity reagents, high molecular weight filters, ultracentrifugation and/or electrodialysis. High affinity reagents include antibodies or other reagents (e.g., aptamers) that selectively bind to high abundance proteins. Sample preparation could also include ion exchange chromatography, metal ion affinity chromatography, gel filtration, hydrophobic chromatography, chromatofocusing, adsorption chromatography, isoelectric focusing and related techniques. Molecular weight filters include membranes that separate molecules on the basis of size and molecular weight. Such filters may further employ reverse osmosis, nanofiltration, ultrafiltration and microfiltration.

Ultracentrifugation is a method for removing undesired polypeptides from a sample. Ultracentrifugation is the centrifugation of a sample at about 15,000-60,000 rpm while monitoring with an optical system the sedimentation (or lack thereof) of particles. Electrodialysis is a procedure which uses an electromembrane or semipermeable membrane in a process in which ions are transported through semi-permeable membranes from one solution to another under the influence of a potential gradient. Since the membranes used in electrodialysis may have the ability to selectively transport ions having positive or negative charge, reject ions of the opposite charge, or to allow species to migrate through a semipermable membrane based on size and charge, it renders electrodialysis useful for concentration, removal, or separation of electrolytes.

Separation and purification in the present invention may include any procedure known in the art, such as capillary electrophoresis (e.g., in capillary or on-chip) or chromatography (e.g., in capillary, column or on a chip). Electrophoresis is a method which can be used to separate ionic molecules under the influence of an electric field. Electrophoresis can be conducted in a gel, capillary, or in a microchannel on a chip. Examples of gels used for electrophoresis include starch, acrylamide, polyethylene oxides, agarose, or combinations thereof. A gel can be modified by its cross-linking, addition of detergents, or denaturants, immobilization of enzymes or antibodies (affinity electrophoresis) or substrates (zymography) and incorporation of a pH gradient. Examples of capillaries used for electrophoresis include capillaries that interface with an electrospray.

Capillary electrophoresis (CE) is preferred for separating complex hydrophilic molecules and highly charged solutes. CE technology can also be implemented on microfluidic chips. Depending on the types of capillary and buffers used, CE can be further segmented into separation techniques such as capillary zone electrophoresis (CZE), capillary isoelectric focusing (CIEF), capillary isotachophoresis (cITP) and capillary electrochromatography (CEC). An embodiment to couple CE techniques to electrospray ionization involves the use of volatile solutions, for example, aqueous mixtures containing a volatile acid and/or base and an organic such as an alcohol or acetonitrile.

Capillary isotachophoresis (cITP) is a technique in which the analytes move through the capillary at a constant speed but are nevertheless separated by their respective mobilities. Capillary zone electrophoresis (CZE), also known as free-solution CE (FSCE), is based on differences in the electrophoretic mobility of the species, determined by the charge on the molecule, and the frictional resistance the molecule encounters during migration which is often directly proportional to the size of the molecule. Capillary isoelectric focusing (CIEF) allows weakly-ionizable amphoteric molecules, to be separated by electrophoresis in a pH gradient. CEC is a hybrid technique between traditional high performance liquid chromatography (HPLC) and CE.

Separation and purification techniques used in the present invention include any chromatography procedures known in the art. Chromatography can be based on the differential adsorption and elution of certain analytes or partitioning of analytes between mobile and stationary phases. Different examples of chromatography include, but not limited to, liquid chromatography (LC), gas chromatography (GC), high performance liquid chromatography (HPLC), etc.

IV. BIOMARKER NUCLEIC ACIDS AND POLYPEPTIDES

One aspect of the invention pertains to the use of isolated nucleic acid molecules that correspond to biomarker nucleic acids that encode a biomarker polypeptide or a portion of such a polypeptide. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid molecule. Preferably, an "isolated" nucleic acid molecule is free of sequences (preferably protein-encoding sequences) which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kB, 4 kB, 3 kB, 2 kB, 1 kB, 0.5 kB or 0.1 kB of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques, or substantially free of chemical precursors or other chemicals when chemically synthesized.

A biomarker nucleic acid molecule of the present invention can be isolated using standard molecular biology techniques and the sequence information in the database records described herein. Using all or a portion of such nucleic acid sequences, nucleic acid molecules of the invention can be isolated using standard hybridization and cloning techniques (e.g., as described in Sambrook et al., ed., *Molecular Cloning: A Laboratory Manual, 2nd ed.*, Cold Spring Harbor Laboratory Press, Cold Spring Harbor, N.Y., 1989).

A nucleic acid molecule of the invention can be amplified using cDNA, mRNA, or genomic DNA as a template and appropriate oligonucleotide primers according to standard PCR amplification techniques. The nucleic acid molecules so amplified can be cloned into an appropriate vector and characterized by DNA sequence analysis. Furthermore, oligonucleotides corresponding to all or a portion of a nucleic acid molecule of the invention can be prepared by standard synthetic techniques, e.g., using an automated DNA synthesizer.

Moreover, a nucleic acid molecule of the invention can comprise only a portion of a nucleic acid sequence, wherein the full length nucleic acid sequence comprises a marker of the invention or which encodes a polypeptide corresponding to a marker of the invention. Such nucleic acid molecules can be used, for example, as a probe or primer. The probe/primer typically is used as one or more substantially purified oligonucleotides. The oligonucleotide typically comprises a region of nucleotide sequence that hybridizes under stringent conditions to at least about 7, preferably about 15, more preferably about 25, 50, 75, 100, 125, 150, 175, 200, 250, 300, 350, or 400 or more consecutive nucleotides of a biomarker nucleic acid sequence. Probes based on the sequence of a biomarker nucleic acid molecule can be used to detect transcripts or genomic sequences corresponding to one or more markers of the invention. The probe comprises a label group attached thereto, e.g., a radioisotope, a fluorescent compound, an enzyme, or an enzyme co-factor.

A biomarker nucleic acid molecules that differ, due to degeneracy of the genetic code, from the nucleotide sequence of nucleic acid molecules encoding a protein which corresponds to the biomarker, and thus encode the same protein, are also contemplated.

In addition, it will be appreciated by those skilled in the art that DNA sequence polymorphisms that lead to changes in the amino acid sequence can exist within a population (e.g., the human population). Such genetic polymorphisms can exist among individuals within a population due to natural allelic variation. An allele is one of a group of genes which occur alternatively at a given genetic locus. In addition, it will be appreciated that DNA polymorphisms that affect RNA expression levels can also exist that may affect the overall expression level of that gene (e.g., by affecting regulation or degradation).

The term "allele," which is used interchangeably herein with "allelic variant," refers to alternative forms of a gene or portions thereof. Alleles occupy the same locus or position on homologous chromosomes. When a subject has two identical alleles of a gene, the subject is said to be homozygous for the gene or allele. When a subject has two different alleles of a gene, the subject is said to be heterozygous for the gene or allele. For example, biomarker alleles can differ from each other in a single nucleotide, or several nucleotides, and can include substitutions, deletions, and insertions of nucleotides. An allele of a gene can also be a form of a gene containing one or more mutations.

The term "allelic variant of a polymorphic region of gene" or "allelic variant", used interchangeably herein, refers to an alternative form of a gene having one of several possible nucleotide sequences found in that region of the gene in the population. As used herein, allelic variant is meant to encompass functional allelic variants, non-functional allelic variants, SNPs, mutations and polymorphisms.

The term "single nucleotide polymorphism" (SNP) refers to a polymorphic site occupied by a single nucleotide, which is the site of variation between allelic sequences. The site is usually preceded by and followed by highly conserved sequences of the allele (e.g., sequences that vary in less than $\frac{1}{100}$ or $\frac{1}{1000}$ members of a population). A SNP usually arises due to substitution of one nucleotide for another at the polymorphic site. SNPs can also arise from a deletion of a nucleotide or an insertion of a nucleotide relative to a reference allele. Typically the polymorphic site is occupied by a base other than the reference base. For example, where the reference allele contains the base "T" (thymidine) at the polymorphic site, the altered allele can contain a "C" (cytidine), "G" (guanine), or "A" (adenine) at the polymorphic site. SNP's may occur in protein-coding nucleic acid sequences, in which case they may give rise to a defective or otherwise variant protein, or genetic disease. Such a SNP may alter the coding sequence of the gene and therefore specify another amino acid (a "missense" SNP) or a SNP may introduce a stop codon (a "nonsense" SNP). When a SNP does not alter the amino acid sequence of a protein, the SNP is called "silent." SNP's may also occur in noncoding regions of the nucleotide sequence. This may result in defective protein expression, e.g., as a result of alternative spicing, or it may have no effect on the function of the protein.

As used herein, the terms "gene" and "recombinant gene" refer to nucleic acid molecules comprising an open reading frame encoding a polypeptide corresponding to a marker of the invention. Such natural allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the invention.

In another embodiment, a biomarker nucleic acid molecule is at least 7, 15, 20, 25, 30, 40, 60, 80, 100, 150, 200, 250, 300, 350, 400, 450, 550, 650, 700, 800, 900, 1000, 1100, 1200, 1300, 1400, 1500, 1600, 1700, 1800, 1900, 2000, 2200, 2400, 2600, 2800, 3000, 3500, 4000, 4500, or more nucleotides in length and hybridizes under stringent conditions to a nucleic acid molecule corresponding to a marker of the invention or to a nucleic acid molecule encoding a protein corresponding to a marker of the invention. As used herein, the term "hybridizes under stringent conditions" is intended to describe conditions for hybridization and washing under which nucleotide sequences at least 60% (65%, 70%, 75%, 80%, preferably 85%) identical to each other typically remain hybridized to each other. Such stringent conditions are known to those skilled in the art and can be found in sections 6.3.1-6.3.6 of *Current Protocols in Molecular Biology*, John Wiley & Sons, N.Y. (1989). A preferred, non-limiting example of stringent hybridization conditions are hybridization in 6× sodium chloride/sodium citrate (SSC) at about 45° C., followed by one or more washes in 0.2×SSC, 0.1% SDS at 50-65° C.

In addition to naturally-occurring allelic variants of a nucleic acid molecule of the invention that can exist in the population, the skilled artisan will further appreciate that sequence changes can be introduced by mutation thereby leading to changes in the amino acid sequence of the encoded protein, without altering the biological activity of the protein encoded thereby. For example, one can make nucleotide substitutions leading to amino acid substitutions at "non-essential" amino acid residues. A "non-essential" amino acid residue is a residue that can be altered from the wild-type sequence without altering the biological activity, whereas an "essential" amino acid residue is required for biological activity. For example, amino acid residues that are not conserved or only semi-conserved among homologs of various species may be non-essential for activity and thus would be likely targets for alteration. Alternatively, amino acid residues that are conserved among the homologs of various species (e.g., murine and human) may be essential for activity and thus would not be likely targets for alteration.

Accordingly, another aspect of the invention pertains to nucleic acid molecules encoding a polypeptide of the invention that contain changes in amino acid residues that are not essential for activity. Such polypeptides differ in amino acid sequence from the naturally-occurring proteins which correspond to the markers of the invention, yet retain biological activity. In one embodiment, a biomarker protein has an amino acid sequence that is at least about 40% identical, 50%, 60%, 70%, 75%, 80%, 83%, 85%, 87.5%, 90%, 91%, 92%, 93%, 94%, 95%, 96%, 97%, 98%, 99% or identical to the amino acid sequence or a biomarker protein described herein.

An isolated nucleic acid molecule encoding a variant protein can be created by introducing one or more nucleotide substitutions, additions or deletions into the nucleotide sequence of nucleic acids of the invention, such that one or more amino acid residue substitutions, additions, or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed recombinantly and the activity of the protein can be determined.

In some embodiments, the present invention further contemplates the use of anti-biomarker antisense nucleic acid molecules, i.e., molecules which are complementary to a sense nucleic acid of the invention, e.g., complementary to the coding strand of a double-stranded cDNA molecule corresponding to a marker of the invention or complementary to an mRNA sequence corresponding to a marker of the invention. Accordingly, an antisense nucleic acid molecule of the invention can hydrogen bond to (i.e. anneal with) a sense nucleic acid of the invention. The antisense nucleic acid can be complementary to an entire coding strand, or to only a portion thereof, e.g., all or part of the protein coding region (or open reading frame). An antisense nucleic acid molecule can also be antisense to all or part of a non-coding region of the coding strand of a nucleotide sequence encoding a polypeptide of the invention. The non-coding regions ("5' and 3' untranslated regions") are the 5' and 3' sequences which flank the coding region and are not translated into amino acids.

An antisense oligonucleotide can be, for example, about 5, 10, 15, 20, 25, 30, 35, 40, 45, or 50 or more nucleotides in length. An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been sub-cloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a polypeptide corresponding to a selected marker of the invention to thereby inhibit expression of the marker, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. Examples of a route of administration of antisense nucleic acid molecules of the invention includes direct injection at a tissue site or infusion of the antisense nucleic acid into a blood- or bone marrow-associated body fluid. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an α-anomeric nucleic acid molecule. An α-anomeric nucleic acid molecule forms specific double-stranded hybrids with complementary RNA in which, contrary to the usual α-units, the strands run parallel to each other (Gaultier et al., 1987, *Nucleic Acids Res.* 15:6625-6641). The antisense nucleic acid molecule can also comprise a 2'-o-methylribonucleotide (Inoue et al., 1987, *Nucleic Acids Res.* 15:6131-6148) or a chimeric RNA-DNA analogue (Inoue e al., 1987, *FEBS Lett.* 215:327-330).

The present invention also encompasses ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes as described in Haselhoff and Gerlach, 1988, *Nature* 334:585-591) can be used to catalytically cleave mRNA transcripts to thereby inhibit translation of the protein encoded by the mRNA. A ribozyme having specificity for a nucleic acid molecule encoding a polypeptide corresponding to a marker of the invention can be designed based upon the nucleotide sequence of a cDNA corresponding to the marker. For example, a derivative of a Tetrahymena L-19 IVS RNA can be constructed in which the nucleotide sequence of the active site is complementary to the nucleotide sequence to be cleaved (see Cech et al. U.S. Pat. No. 4,987,071; and Cech et al. U.S. Pat. No. 5,116,742). Alternatively, an mRNA encoding a polypeptide of the invention can be used to select a catalytic RNA having a specific ribonuclease activity from a pool of RNA molecules (see, e.g., Bartel and Szostak, 1993, *Science* 261:1411-1418).

The present invention also encompasses nucleic acid molecules which form triple helical structures. For example, expression of a biomarker protein can be inhibited by targeting nucleotide sequences complementary to the regulatory region of the gene encoding the polypeptide (e.g., the promoter and/or enhancer) to form triple helical structures that prevent transcription of the gene in target cells. See generally Helene (1991) *Anticancer Drug Des.* 6(6):569-84; Helene (1992) *Ann. N.Y. Acad. Sci.* 660:27-36; and Maher (1992) *Bioassays* 14(12):807-15.

In various embodiments, the nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acid molecules (see Hyrup et al., 1996, *Bioorganic & Medicinal Chemistry* 4(1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra: Perry-O'Keefe et al. (1996) *Proc. Natl. Acad. Sci. USA* 93:14670-675.

PNAs can be used in therapeutic and diagnostic applications. For example, PNAs can be used as antisense or antigene agents for sequence-specific modulation of gene expression by, e.g., inducing transcription or translation arrest or inhibiting replication. PNAs can also be used, e.g., in the analysis of single base pair mutations in a gene by, e.g., PNA directed PCR clamping; as artificial restriction enzymes when used in combination with other enzymes, e.g., S1 nucleases (Hyrup (1996), supra; or as probes or primers for DNA sequence and hybridization (Hyrup, 1996, supra; Perry-O'Keefe et al., 1996, *Proc. Natl. Acad. Sci. USA* 93:14670-675).

In another embodiment, PNAs can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which can combine the advantageous properties of PNA and DNA. Such chimeras allow DNA recognition enzymes, e.g., RNASE H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup, 1996, supra). The synthesis of PNA-DNA chimeras can be performed as described in Hyrup (1996), supra, and Finn et al. (199) *Nucleic Acids Res.* 24(17):3357-63. For example, a DNA chain can be synthesized on a solid support using standard phosphoramidite coupling chemistry and modified nucleoside analogs. Compounds such as 5'-(4-methoxytrityl)amino-5'-deoxy-thymidine phosphoramidite can be used as a link between the PNA and the 5' end of DNA (Mag et al., 1989, *Nucleic Acids Res.* 17:5973-88). PNA monomers are then coupled in a step-wise manner to produce a chimeric molecule with a 5' PNA segment and a 3' DNA segment (Finn et al., 1996, *Nucleic Acids Res.* 24(17):3357-63). Alternatively, chimeric molecules can be synthesized with a 5' DNA segment and a 3' PNA segment (Peterser et al., 1975, *Bioorganic Med. Chem. Lett.* 5:1119-11124).

In other embodiments, the oligonucleotide can include other appended groups such as peptides (e.g., for targeting host cell receptors in vivo), or agents facilitating transport across the cell membrane (see, e.g., Letsinger et al., 1989, *Proc. Natl. Acad. Sci. USA* 86:6553-6556; Lemaitre et al., 1987, *Proc. Natl. Acad. Sci. USA* 84:648-652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al., 1988, *Bio/Techniques* 6:958-976) or intercalating agents (see, e.g., Zon, 1988, *Pharm. Res.* 5:539-549). To this end, the oligonucleotide can be conjugated to another molecule, e.g., a peptide, hybridization triggered cross-linking agent, transport agent, hybridization-triggered cleavage agent, etc.

Another aspect of the invention pertains to the use of biomarker proteins and biologically active portions thereof. In one embodiment, the native polypeptide corresponding to a marker can be isolated from cells or tissue sources by an appropriate purification scheme using standard protein purification techniques. In another embodiment, polypeptides corresponding to a marker of the invention are produced by recombinant DNA techniques. Alternative to recombinant expression, a polypeptide corresponding to a marker of the invention can be synthesized chemically using standard peptide synthesis techniques.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest.

Biologically active portions of a biomarker polypeptide include polypeptides comprising amino acid sequences sufficiently identical to or derived from a biomarker protein amino acid sequence described herein, but which includes fewer amino acids than the full length protein, and exhibit at least one activity of the corresponding full-length protein. Typically, biologically active portions comprise a domain or motif with at least one activity of the corresponding protein. A biologically active portion of a protein of the invention can be a polypeptide which is, for example, 10, 25, 50, 100 or more amino acids in length. Moreover, other biologically active portions, in which other regions of the protein are deleted, can be prepared by recombinant techniques and evaluated for one or more of the functional activities of the native form of a polypeptide of the invention.

Preferred polypeptides have an amino acid sequence of a biomarker protein encoded by a nucleic acid molecule described herein. Other useful proteins are substantially identical (e.g., at least about 40%, preferably 50%, 60%, 70%, 75%, 80%, 83%, 85%, 88%, 90%, 91%, 92%, 93%, 94%, 95%, 96%, 97%, 98%, or 99%) to one of these sequences and retain the functional activity of the protein of the corresponding naturally-occurring protein yet differ in amino acid sequence due to natural allelic variation or mutagenesis.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment the two sequences are the same length.

The determination of percent identity between two sequences can be accomplished using a mathematical algorithm. A preferred, non-limiting example of a mathematical algorithm utilized for the comparison of two sequences is the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the NBLAST and XBLAST programs of Altschul, et al. (1990) *J. Mol. Biol.* 215:403-410. BLAST nucleotide searches can be performed with the NBLAST program, score=100, wordlength=12 to obtain nucleotide sequences homologous to a nucleic acid molecules of the invention. BLAST protein searches can be performed with the XBLAST program, score=50, wordlength=3 to obtain amino acid sequences homologous to a protein molecules of the invention. To obtain gapped alignments for comparison purposes, Gapped BLAST can be utilized as described in Altschul et al. (1997) *Nucleic Acids Res.* 25:3389-3402. Alternatively, PSI-Blast can be used to perform an iterated search which detects distant relationships between molecules. When utilizing BLAST, Gapped BLAST, and PSI-Blast programs, the default parameters of the respective programs (e.g., XBLAST and NBLAST) can be used. See http://www.ncbi.nlm.nih.gov. Another preferred, non-limiting example of a mathematical algorithm utilized for the comparison of sequences is the algorithm of Myers and Miller, (1988) *Comput Appl Biosci,* 4:11-7. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson and Lipman (1988) *Proc. Natl. Acad. Sci. USA* 85:2444-2448. When using the FASTA algorithm for comparing nucleotide or amino acid sequences, a PAM120 weight residue table can, for example, be used with a k-tuple value of 2.

The percent identity between two sequences can be determined using techniques similar to those described above, with or without allowing gaps. In calculating percent identity, only exact matches are counted.

The invention also provides chimeric or fusion proteins corresponding to a biomarker protein. As used herein, a "chimeric protein" or "fusion protein" comprises all or part (preferably a biologically active part) of a polypeptide corresponding to a marker of the invention operably linked to a heterologous polypeptide (i.e., a polypeptide other than the polypeptide corresponding to the marker). Within the fusion protein, the term "operably linked" is intended to indicate that the polypeptide of the invention and the heterologous polypeptide are fused in-frame to each other. The heterologous polypeptide can be fused to the amino-terminus or the carboxyl-terminus of the polypeptide of the invention.

One useful fusion protein is a GST fusion protein in which a polypeptide corresponding to a marker of the invention is fused to the carboxyl terminus of GST sequences. Such fusion proteins can facilitate the purification of a recombinant polypeptide of the invention.

In another embodiment, the fusion protein contains a heterologous signal sequence, immunoglobulin fusion protein, toxin, or other useful protein sequence. Chimeric and fusion proteins of the invention can be produced by standard recombinant DNA techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see, e.g., Ausubel et al., supra). Moreover, many expression vectors are commercially available that already encode a fusion moiety (e.g., a GST polypeptide). A nucleic acid encoding a polypeptide of the invention can be cloned into such an expression vector such that the fusion moiety is linked in-frame to the polypeptide of the invention.

A signal sequence can be used to facilitate secretion and isolation of the secreted protein or other proteins of interest. Signal sequences are typically characterized by a core of hydrophobic amino acids which are generally cleaved from the mature protein during secretion in one or more cleavage events. Such signal peptides contain processing sites that allow cleavage of the signal sequence from the mature proteins as they pass through the secretory pathway. Thus, the invention pertains to the described polypeptides having a signal sequence, as well as to polypeptides from which the signal sequence has been proteolytically cleaved (i.e., the cleavage products). In one embodiment, a nucleic acid sequence encoding a signal sequence can be operably linked in an expression vector to a protein of interest, such as a protein which is ordinarily not secreted or is otherwise difficult to isolate. The signal sequence directs secretion of the protein, such as from a eukaryotic host into which the expression vector is transformed, and the signal sequence is subsequently or concurrently cleaved. The protein can then be readily purified from the extracellular medium by art recognized methods. Alternatively, the signal sequence can be linked to the protein of interest using a sequence which facilitates purification, such as with a GST domain.

The present invention also pertains to variants of the biomarker polypeptides described herein. Such variants have an altered amino acid sequence which can function as either agonists (mimetics) or as antagonists. Variants can be generated by mutagenesis, e.g., discrete point mutation or truncation. An agonist can retain substantially the same, or a subset, of the biological activities of the naturally occurring form of the protein. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein.

Variants of a biomarker protein which function as either agonists (mimetics) or as antagonists can be identified by screening combinatorial libraries of mutants, e.g., truncation mutants, of the protein of the invention for agonist or antagonist activity. In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g., for phage display). There are a variety of methods which can be used to produce libraries of potential variants of the polypeptides of the invention from a degenerate oligonucleotide sequence. Methods for synthesizing degenerate oligonucleotides are known in the art (see, e.g., Narang, 1983, *Tetrahedron* 39:3; Itakura et al., 1984, *Annu. Rev. Biochem.* 53:323; Itakura et al., 1984, *Science* 198: 1056; Ike et al., 1983 *Nucleic Acid Res.* 11:477).

In addition, libraries of fragments of the coding sequence of a polypeptide corresponding to a marker of the invention can be used to generate a variegated population of polypeptides for screening and subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes amino terminal and internal fragments of various sizes of the protein of interest.

Several techniques are known in the art for screening gene products of combinatorial libraries made by point mutations or truncation, and for screening cDNA libraries for gene products having a selected property. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the invention (Arkin and Yourvan, 1992, *Proc. Natl. Acad. Sci. USA* 89:7811-7815; Delgrave et al., 1993, *Protein Engineering* 6(3):327-331).

The production and use of biomarker nucleic acid and/or biomarker polypeptide molecules described herein can be facilitated by using standard recombinant techniques. In some embodiments, such techniques use vectors, preferably expression vectors, containing a nucleic acid encoding a biomarker polypeptide or a portion of such a polypeptide. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, namely expression vectors, are capable of directing the expression of genes to which they are operably linked. In general, expression vectors of utility in recombinant DNA techniques are often in the form of plasmids (vectors). However, the present invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, *Methods in Enzymology: Gene Expression Technology* vol. 185, Academic Press, San Diego, Calif. (1991). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein.

The recombinant expression vectors for use in the invention can be designed for expression of a polypeptide corresponding to a marker of the invention in prokaryotic (e.g., *E. coli*) or eukaryotic cells (e.g., insect cells (using baculovirus expression vectors), yeast cells or mammalian cells). Suitable host cells are discussed further in Goeddel, supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988, *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al., 1988, *Gene* 69:301-315) and pET 11d (Studier et al., p. 60-89, In *Gene Expression Technology: Methods in Enzymology* vol. 185, Academic Press, San Diego, Calif., 1991). Target biomarker nucleic acid expression from the pTrc vector relies on host RNA polymerase transcription from a hybrid trp-lac fusion promoter. Target biomarker nucleic acid expression from the pET 11d vector relies on transcription from a T7 gn10-lac fusion promoter mediated by a co-expressed viral RNA polymerase (T7 gn1). This viral polymerase is supplied by host strains BL21 (DE3) or HMS174 (DE3) from a resident prophage harboring a T7 gn1 gene under the transcriptional control of the lacUV 5 promoter.

One strategy to maximize recombinant protein expression in *E. coli* is to express the protein in a host bacterium with an impaired capacity to proteolytically cleave the recombinant protein (Gottesman, p. 119-128, In *Gene Expression Technology: Methods in Enzymology* vol. 185, Academic Press, San Diego, Calif., 1990. Another strategy is to alter the nucleic acid sequence of the nucleic acid to be inserted into an expression vector so that the individual codons for each amino acid are those preferentially utilized in *E. coli* (Wada et al., 1992, *Nucleic Acids Res.* 20:2111-2118). Such alteration of nucleic acid sequences of the invention can be carried out by standard DNA synthesis techniques.

In another embodiment, the expression vector is a yeast expression vector. Examples of vectors for expression in yeast *S. cerevisiae* include pYepSec1 (Baldari et al., 1987, *EMBO J.* 6:229-234), pMFa (Kurjan and Herskowitz, 1982, *Cell* 30:933-943), pJRY88 (Schultz t al., 1987, *Gene* 54:113-123), pYES2 (Invitrogen Corporation, San Diego, Calif.), and pPicZ (Invitrogen Corp, San Diego, Calif.).

Alternatively, the expression vector is a baculovirus expression vector. Baculovirus vectors available for expression of proteins in cultured insect cells (e.g., Sf9 cells) include the pAc series (Smith et al., 1983, *Mol. Cell Biol.* 3:2156-2165) and the pVL series (Lucklow and Summers, 1989, *Virology* 170:31-39).

In yet another embodiment, a nucleic acid of the invention is expressed in mammalian cells using a mammalian expression vector. Examples of mammalian expression vectors include pCDM8 (Seed, 1987, *Nature* 329:840) and pMT2PC (Kaufman et al., 1987, *EMBO J.* 6:187-195). When used in mammalian cells, the expression vector's control functions are often provided by viral regulatory elements. For example, commonly used promoters are derived from polyoma. Adenovirus 2, cytomegalovirus and Simian Virus 40. For other suitable expression systems for both prokaryotic and eukaryotic cells see chapters 16 and 17 of Sambrook et al., supra.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., 1987, *Genes Dev.* 1:268-277), lymphoid-specific promoters (Calame and Eaton, 1988, *Adv. Immunol.* 43:235-275), in particular promoters of T cell receptors (Winoto and Baltimore, 1989, *EMBO J.* 8:729-733) and immunoglobulins (Banerji et al., 1983, *Cell* 33:729-740; Queen and Baltimore, 1983, *Cell* 33:741-748), neuron-specific promoters (e.g., the neurofilament promoter, Byrne and Ruddle, 1989, *Proc. Natl. Acad. Sci. USA* 86:5473-5477), pancreas-specific promoters (Edlund et al., 1985, *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine box promoters (Kessel and Gruss, 1990, *Science* 249:374-379) and the α-fetoprotein promoter (Camper and Tilghman, 1989, *Genes Dev.* 3:537-546).

The invention further provides a recombinant expression vector comprising a DNA molecule cloned into the expression vector in an antisense orientation. That is, the DNA molecule is operably linked to a regulatory sequence in a manner which allows for expression (by transcription of the DNA molecule) of an RNA molecule which is antisense to the mRNA encoding a polypeptide of the invention. Regulatory sequences operably linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue-specific or cell type specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes (see Weintraub et al., 1986, *Trends in Genetics*, Vol. 1(1)).

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic (e.g., *E. coli*) or eukaryotic cell (e.g., insect cells, yeast or mammalian cells).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die).

V. ANALYZING BIOMARKER NUCLEIC ACIDS AND POLYPEPTIDES

Biomarker nucleic acids and/or biomarker polypeptides can be analyzed according to the methods described herein and techniques known to the skilled artisan to identify such genetic or expression alterations useful for the present invention including, but not limited to, 1) an alteration in the level of a biomarker transcript or polypeptide, 2) a deletion or addition of one or more nucleotides from a biomarker gene, 4) a substitution of one or more nucleotides of a biomarker gene, 5) aberrant modification of a biomarker gene, such as an expression regulatory region, and the like.

a. Methods for Detection of Copy Number

Methods of evaluating the copy number of a biomarker nucleic acid are well known to those of skill in the art. The presence or absence of chromosomal gain or loss can be evaluated simply by a determination of copy number of the regions or markers identified herein.

In one embodiment, a biological sample is tested for the presence of copy number changes in genomic loci containing the genomic marker. A copy number of at least 3, 4, 5, 6, 7, 8, 9, or 10 is predictive of poorer outcome of anti-immune checkpoint inhibitor treatment.

Methods of evaluating the copy number of a biomarker locus include, but are not limited to, hybridization-based assays. Hybridization-based assays include, but are not limited to, traditional "direct probe" methods, such as Southern blots, in situ hybridization (e.g., FISH and FISH plus SKY) methods, and "comparative probe" methods, such as comparative genomic hybridization (CGH), e.g., cDNA-based or oligonucleotide-based CGH. The methods can be used in a wide variety of formats including, but not limited to, substrate (e.g. membrane or glass) bound methods or array-based approaches.

In one embodiment, evaluating the biomarker gene copy number in a sample involves a Southern Blot. In a Southern Blot, the genomic DNA (typically fragmented and separated on an electrophoretic gel) is hybridized to a probe specific for the target region. Comparison of the intensity of the hybridization signal from the probe for the target region with control probe signal from analysis of normal genomic DNA (e.g., a non-amplified portion of the same or related cell, tissue, organ, etc.) provides an estimate of the relative copy number of the target nucleic acid. Alternatively, a Northern blot may be utilized for evaluating the copy number of encoding nucleic acid in a sample. In a Northern blot, mRNA is hybridized to a probe specific for the target region. Comparison of the intensity of the hybridization signal from the probe for the target region with control probe signal from analysis of normal RNA (e.g., a non-amplified portion of the same or related cell, tissue, organ, etc.) provides an estimate of the relative copy number of the target nucleic acid. Alternatively, other methods well known in the art to detect RNA can be used, such that higher or lower expression relative to an appropriate control (e.g., a non-amplified portion of the same or related cell tissue, organ, etc.) provides an estimate of the relative copy number of the target nucleic acid.

An alternative means for determining genomic copy number is in situ hybridization (e.g., Angerer (1987) *Meth. Enzymol* 152: 649). Generally, in situ hybridization comprises the following steps: (1) fixation of tissue or biological structure to be analyzed; (2) prehybridization treatment of the biological structure to increase accessibility of target DNA, and to reduce nonspecific binding; (3) hybridization of the mixture of nucleic acids to the nucleic acid in the biological structure or tissue; (4) post-hybridization washes to remove nucleic acid fragments not bound in the hybridization and (5) detection of the hybridized nucleic acid fragments. The reagent used in each of these steps and the conditions for use vary depending on the particular application. In a typical in situ hybridization assay, cells are fixed to a solid support, typically a glass slide. If a nucleic acid is to be probed, the cells are typically denatured with heat or alkali. The cells are then contacted with a hybridization solution at a moderate temperature to permit annealing of labeled probes specific to the nucleic acid sequence encoding the protein. The targets (e.g., cells) are then typically washed at a predetermined stringency or at an increasing stringency until an appropriate signal to noise ratio is obtained. The probes are typically labeled, e.g., with radioisotopes or fluorescent reporters. In one embodiment, probes are sufficiently long so as to specifically hybridize with the target nucleic acid(s) under stringent conditions. Probes generally range in length from about 200 bases to about 1000 bases. In some applications it is necessary to block the hybridization capacity of repetitive sequences. Thus, in some embodiments, tRNA, human genomic DNA, or Cot-I DNA is used to block non-specific hybridization.

An alternative means for determining genomic copy number is comparative genomic hybridization. In general, genomic DNA is isolated from normal reference cells, as well as from test cells (e.g., tumor cells) and amplified, if necessary. The two nucleic acids are differentially labeled and then hybridized in situ to metaphase chromosomes of a reference cell. The repetitive sequences in both the reference and test DNAs are either removed or their hybridization capacity is reduced by some means, for example by prehybridization with appropriate blocking nucleic acids and/or including such blocking nucleic acid sequences for said repetitive sequences during said hybridization. The bound, labeled DNA sequences are then rendered in a visualizable form, if necessary. Chromosomal regions in the test cells which are at increased or decreased copy number can be identified by detecting regions where the ratio of signal from the two DNAs is altered. For example, those regions that have decreased in copy number in the test cells will show relatively lower signal from the test DNA than the reference compared to other regions of the genome. Regions that have been increased in copy number in the test cells will show relatively higher signal from the test DNA. Where there are chromosomal deletions or multiplications, differences in the ratio of the signals from the two labels will be detected and the ratio will provide a measure of the copy number. In another embodiment of CGH, array CGH (aCGH), the immobilized chromosome element is replaced with a collection of solid support bound target nucleic acids on an array, allowing for a large or complete percentage of the genome to be represented in the collection of solid support bound targets. Target nucleic acids may comprise cDNAs, genomic DNAs, oligonucleotides (e.g., to detect single nucleotide polymorphisms) and the like. Array-based CGH may also be performed with single-color labeling (as opposed to labeling the control and the possible tumor sample with two different dyes and mixing them prior to hybridization, which will yield a ratio due to competitive hybridization of probes on the arrays). In single color CGH, the control is labeled and hybridized to one array and absolute signals are read, and the possible tumor sample is labeled and hybridized to a second array (with identical content) and absolute signals are read. Copy number difference is calculated based on absolute signals from the two arrays. Methods of preparing immobilized chromosomes or arrays and performing comparative genomic hybridization are well known in the art (see, e.g., U.S. Pat. Nos. 6,335,167; 6,197,501; 5,830,645; and 5,665,549 and Albertson (1984) *EMBO J.* 3: 1227-1234: Pinkel (1988) *Proc. Natl. Acad. Sci. USA* 85: 9138-9142; EPO Pub. No. 430,402; *Methods in Molecular Biology*, Vol. 33: In situ Hybridization Protocols, Choo, ed., Humana Press, Totowa, N.J. (1994), etc.) In another embodiment, the hybridization protocol of Pinkel, et al. (1998) *Nature Genetics* 20: 207-211, or of Kallioniemi (1992) *Proc. Natl Acad Sci USA* 89:5321-5325 (1992) is used.

In still another embodiment, amplification-based assays can be used to measure copy number. In such amplification-based assays, the nucleic acid sequences act as a template in an amplification reaction (e.g., Polymerase Chain Reaction (PCR). In a quantitative amplification, the amount of amplification product will be proportional to the amount of template in the original sample. Comparison to appropriate controls, e.g. healthy tissue, provides a measure of the copy number.

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided in Innis, et al. (1990) PCR Protocols. *A Guide to Methods and Applications*, Academic Press, Inc. N.Y.). Measurement of DNA copy number at microsatellite loci using quantitative PCR analysis is described in Ginzonger, et al. (2000) *Cancer Research* 60:5405-5409. The known nucleic acid sequence for the genes is sufficient to enable one of skill in the art to routinely select primers to amplify any portion of the gene. Fluorogenic quantitative PCR may also be used in the methods of the invention. In fluorogenic quantitative PCR, quantitation is based on amount of fluorescence signals, e.g., TaqMan and SYBR green.

Other suitable amplification methods include, but are not limited to, ligase chain reaction (LCR) (see Wu and Wallace (1989) *Genomics* 4: 560, Landegren, et al. (1988) *Science* 241:1077, and Barringer et al. (1990) *Gene* 89: 117), transcription amplification (Kwoh, et al. (1989) *Proc. Natl. Acad. Sci. USA* 86: 1173), self-sustained sequence replication (Guatelli, et al. (1990) *Proc. Nat. Acad. Sci. USA* 87: 1874), dot PCR, and linker adapter PCR, etc.

Loss of heterozygosity (LOH) and major copy proportion (MCP) mapping (Wang, Z. C., et al. (2004) *Cancer Res* 64(1):64-71; Seymour, A. B., et al. (1994) *Cancer Res* 54, 2761-4; Hahn. S. A., et al. (1995) *Cancer Res* 55, 4670-5; Kimura, M., et al. (1996) *Genes Chromosomes Cancer* 17, 88-93; Li et al., (2008) *MBC Bioinform.* 9, 204-219) may also be used to identify regions of amplification or deletion.

b. Methods for Detection of Biomarker Nucleic Acid Expression

Biomarker expression may be assessed by any of a wide variety of well known methods for detecting expression of a transcribed molecule or protein. Non-limiting examples of such methods include immunological methods for detection of secreted, cell-surface, cytoplasmic, or nuclear proteins, protein purification methods, protein function or activity assays, nucleic acid hybridization methods, nucleic acid reverse transcription methods, and nucleic acid amplification methods.

In preferred embodiments, activity of a particular gene is characterized by a measure of gene transcript (e.g. mRNA), by a measure of the quantity of translated protein, or by a measure of gene product activity. Marker expression can be monitored in a variety of ways, including by detecting mRNA levels, protein levels, or protein activity, any of which can be measured using standard techniques. Detection can involve quantification of the level of gene expression (e.g., genomic DNA, cDNA, mRNA, protein, or enzyme activity), or, alternatively, can be a qualitative assessment of the level of gene expression, in particular in comparison with a control level. The type of level being detected will be clear from the context.

In another embodiment, detecting or determining expression levels of a biomarker and functionally similar homologs thereof, including a fragment or genetic alteration thereof (e.g., in regulatory or promoter regions thereof) comprises detecting or determining RNA levels for the marker of interest. In one embodiment, one or more cells from the subject to be tested are obtained and RNA is isolated from the cells. In a preferred embodiment, a sample of breast tissue cells is obtained from the subject.

In one embodiment, RNA is obtained from a single cell. For example, a cell can be isolated from a tissue sample by laser capture microdissection (LCM). Using this technique, a cell can be isolated from a tissue section, including a stained tissue section, thereby assuring that the desired cell is isolated (see, e.g., Bonner et al. (1997) Science 278: 1481; Emmert-Buck et al. (1996) Science 274:998; Fend et al. (1999) Am. J. Path. 154: 61 and Murakami et al. (2000) Kidney Int. 58:1346). For example, Murakami et al., supra, describe isolation of a cell from a previously immunostained tissue section.

It is also be possible to obtain cells from a subject and culture the cells in vitro, such as to obtain a larger population of cells from which RNA can be extracted. Methods for establishing cultures of non-transformed cells, i.e., primary cell cultures, are known in the art.

When isolating RNA from tissue samples or cells from individuals, it may be important to prevent any further changes in gene expression after the tissue or cells has been removed from the subject. Changes in expression levels are known to change rapidly following perturbations, e.g., heat shock or activation with lipopolysaccharide (LPS) or other reagents. In addition, the RNA in the tissue and cells may quickly become degraded. Accordingly, in a preferred embodiment, the tissue or cells obtained from a subject is snap frozen as soon as possible.

RNA can be extracted from the tissue sample by a variety of methods, e.g., the guanidium thiocyanate lysis followed by CsCl centrifugation (Chirgwin et al., 1979, Biochemistry 18:5294-5299). RNA from single cells can be obtained as described in methods for preparing cDNA libraries from single cells, such as those described in Dulac, C. (1998) Curr. Top. Dev. Biol. 36, 245 and Jena et al. (1996) J. Immunol. Methods 190:199. Care to avoid RNA degradation must be taken, e.g., by inclusion of RNAsin.

The RNA sample can then be enriched in particular species. In one embodiment, poly(A)+ RNA is isolated from the RNA sample. In general, such purification takes advantage of the poly-A tails on mRNA. In particular and as noted above, poly-T oligonucleotides may be immobilized within on a solid support to serve as affinity ligands for mRNA. Kits for this purpose are commercially available, e.g., the MessageMaker kit (Life Technologies, Grand Island, N.Y.).

In a preferred embodiment, the RNA population is enriched in marker sequences. Enrichment can be undertaken, e.g., by primer-specific cDNA synthesis, or multiple rounds of linear amplification based on cDNA synthesis and template-directed in vitro transcription (see, e.g., Wang et al. (1989) PNAS 86, 9717; Dulac et al., supra, and Jena et al., supra).

The population of RNA, enriched or not in particular species or sequences, can further be amplified. As defined herein, an "amplification process" is designed to strengthen, increase, or augment a molecule within the RNA. For example, where RNA is mRNA, an amplification process such as RT-PCR can be utilized to amplify the mRNA, such that a signal is detectable or detection is enhanced. Such an amplification process is beneficial particularly when the biological, tissue, or tumor sample is of a small size or volume.

Various amplification and detection methods can be used. For example, it is within the scope of the present invention to reverse transcribe mRNA into cDNA followed by polymerase chain reaction (RT-PCR); or, to use a single enzyme for both steps as described in U.S. Pat. No. 5,322,770, or reverse transcribe mRNA into cDNA followed by symmetric gap ligase chain reaction (RT-AGLCR) as described by R. L. Marshall, et al., PCR Methods and Applications 4: 80-84 (1994). Real time PCR may also be used.

Other known amplification methods which can be utilized herein include but are not limited to the so-called "NASBA" or "3SR" technique described in PNAS USA 87: 1874-1878 (1990) and also described in Nature 350 (No. 6313): 91-92 (1991); Q-beta amplification as described in published European Patent Application (EPA) No. 4544610; strand displacement amplification (as described in G. T. Walker et al., Clin. Chem. 42: 9-13 (1996) and European Patent Application No. 684315; target mediated amplification, as described by PCT Publication WO9322461; PCR; ligase chain reaction (LCR) (see, e.g., Wu and Wallace, Genomics 4, 560 (1989), Landegren et al., Science 241, 1077 (1988)); self-sustained sequence replication (SSR) (see, e.g., Guatelli et al., Proc. Nat. Acad. Sci. USA, 87, 1874 (1990)); and transcription amplification (see. e.g., Kwoh et al., Proc. Natl. Acad. Sci. USA 86, 1173 (1989)).

Many techniques are known in the state of the art for determining absolute and relative levels of gene expression, commonly used techniques suitable for use in the present invention include Northern analysis, RNase protection assays (RPA), microarrays and PCR-based techniques, such as quantitative PCR and differential display PCR. For example, Northern blotting involves running a preparation of RNA on a denaturing agarose gel, and transferring it to a suitable support, such as activated cellulose, nitrocellulose or glass or nylon membranes. Radiolabeled cDNA or RNA is then hybridized to the preparation, washed and analyzed by autoradiography.

In situ hybridization visualization may also be employed, wherein a radioactively labeled antisense RNA probe is hybridized with a thin section of a biopsy sample, washed, cleaved with RNase and exposed to a sensitive emulsion for autoradiography. The samples may be stained with hematoxylin to demonstrate the histological composition of the sample, and dark field imaging with a suitable light filter shows the developed emulsion. Non-radioactive labels such as digoxigenin may also be used.

Alternatively, mRNA expression can be detected on a DNA array, chip or a microarray. Labeled nucleic acids of a test sample obtained from a subject may be hybridized to a solid surface comprising biomarker DNA. Positive hybridization signal is obtained with the sample containing biomarker transcripts. Methods of preparing DNA arrays and their use are well known in the art (see, e.g., U.S. Pat. Nos. 6,618,6796; 6,379,897; 6,664,377; 6,451,536; 548,257; U.S. 20030157485 and Schena et al. (1995) *Science* 20, 467-470; Gerhold et al. (1999) *Trends In Biochem. Sci.* 24, 168-173; and Lennon et al. (2000) *Drug Discovery Today* 5, 59-65, which are herein incorporated by reference in their entirety). Serial Analysis of Gene Expression (SAGE) can also be performed (See for example U.S. Patent Application 20030215858).

To monitor mRNA levels, for example, mRNA is extracted from the biological sample to be tested, reverse transcribed, and fluorescently-labeled cDNA probes are generated. The microarrays capable of hybridizing to marker cDNA are then probed with the labeled cDNA probes, the slides scanned and fluorescence intensity measured. This intensity correlates with the hybridization intensity and expression levels.

Types of probes that can be used in the methods described herein include cDNA, riboprobes, synthetic oligonucleotides and genomic probes. The type of probe used will generally be dictated by the particular situation, such as riboprobes for in situ hybridization, and cDNA for Northern blotting, for example. In one embodiment, the probe is directed to nucleotide regions unique to the RNA. The probes may be as short as is required to differentially recognize marker mRNA transcripts, and may be as short as, for example, 15 bases; however, probes of at least 17, 18, 19 or 20 or more bases can be used. In one embodiment, the primers and probes hybridize specifically under stringent conditions to a DNA fragment having the nucleotide sequence corresponding to the marker. As herein used, the term "stringent conditions" means hybridization will occur only if there is at least 95% identity in nucleotide sequences.

In another embodiment, hybridization under "stringent conditions" occurs when there is at least 97% identity between the sequences.

The form of labeling of the probes may be any that is appropriate, such as the use of radioisotopes, for example, $^{32}$P and $^{35}$S. Labeling with radioisotopes may be achieved, whether the probe is synthesized chemically or biologically, by the use of suitably labeled bases.

In one embodiment, the biological sample contains polypeptide molecules from the test subject. Alternatively, the biological sample can contain mRNA molecules from the test subject or genomic DNA molecules from the test subject.

In another embodiment, the methods further involve obtaining a control biological sample from a control subject, contacting the control sample with a compound or agent capable of detecting marker polypeptide, mRNA, genomic DNA, or fragments thereof, such that the presence of the marker polypeptide, mRNA, genomic DNA, or fragments thereof, is detected in the biological sample, and comparing the presence of the marker polypeptide, mRNA, genomic DNA, or fragments thereof, in the control sample with the presence of the marker polypeptide, mRNA, genomic DNA, or fragments thereof in the test sample.

c. Methods for Detection of Biomarker Protein Expression

The activity or level of a biomarker protein can be detected and/or quantified by detecting or quantifying the expressed polypeptide. The polypeptide can be detected and quantified by any of a number of means well known to those of skill in the art. Aberrant levels of polypeptide expression of the polypeptides encoded by a biomarker nucleic acid and functionally similar homologs thereof, including a fragment or genetic alteration thereof (e.g., in regulatory or promoter regions thereof) are associated with the likelihood of response of a cancer to an anti-immune checkpoint inhibitor therapy. Any method known in the art for detecting polypeptides can be used. Such methods include, but are not limited to, immunodiffusion, immunoelectrophoresis, radioimmunoassay (RIA), enzyme-linked immunosorbant assays (ELISAs), immunofluorescent assays, Western blotting, binder-ligand assays, immunohistochemical techniques, agglutination, complement assays, high performance liquid chromatography (HPLC), thin layer chromatography (TLC), hyperdiffusion chromatography, and the like (e.g., Basic and Clinical Immunology. Sites and Terr, eds., Appleton and Lange, Norwalk, Conn. pp 217-262, 1991 which is incorporated by reference). Preferred are binder-ligand immunoassay methods including reacting antibodies with an epitope or epitopes and competitively displacing a labeled polypeptide or derivative thereof.

For example, ELISA and RIA procedures may be conducted such that a desired biomarker protein standard is labeled (with a radioisotope such as $^{125}$I or $^{35}$S, or an assayable enzyme, such as horseradish peroxidase or alkaline phosphatase), and, together with the unlabelled sample, brought into contact with the corresponding antibody, whereon a second antibody is used to bind the first, and radioactivity or the immobilized enzyme assayed (competitive assay). Alternatively, the biomarker protein in the sample is allowed to react with the corresponding immobilized antibody, radioisotope- or enzyme-labeled anti-biomarker proteinantibody as allowed to react with the system, and radioactivity or the enzyme assayed (ELISA-sandwich assay). Other conventional methods may also be employed as suitable.

The above techniques may be conducted essentially as a "one-step" or "two-step" assay. A "one-step" assay involves contacting antigen with immobilized antibody and, without washing, contacting the mixture with labeled antibody. A "two-step" assay involves washing before contacting, the mixture with labeled antibody. Other conventional methods may also be employed as suitable.

In one embodiment, a method for measuring biomarker protein levels comprises the steps of: contacting a biological specimen with an antibody or variant (e.g., fragment) thereof which selectively binds the biomarker protein, and detecting whether said antibody or variant thereof is bound to said sample and thereby measuring the levels of the biomarker protein.

Enzymatic and radiolabeling of biomarker protein and/or the antibodies may be effected by conventional means. Such means will generally include covalent linking of the enzyme to the antigen or the antibody in question, such as by glutaraldehyde, specifically so as not to adversely affect the activity of the enzyme, by which is meant that the enzyme must still be capable of interacting with its substrate, although it is not necessary for all of the enzyme to be active, provided that enough remains active to permit the assay to be effected. Indeed, some techniques for binding enzyme are non-specific (such as using formaldehyde), and will only yield a proportion of active enzyme.

It is usually desirable to immobilize one component of the assay system on a support, thereby allowing other components of the system to be brought into contact with the component and readily removed without laborious and time-consuming labor. It is possible for a second phase to be immobilized away from the first, but one phase is usually sufficient.

It is possible to immobilize the enzyme itself on a support, but if solid-phase enzyme is required, then this is generally best achieved by binding to antibody and affixing the antibody to a support, models and systems for which are well-known in the art. Simple polyethylene may provide a suitable support.

Enzymes employable for labeling are not particularly limited, but may be selected from the members of the oxidase group, for example. These catalyze production of hydrogen peroxide by reaction with their substrates, and glucose oxidase is often used for its good stability, ease of availability and cheapness, as well as the ready availability of its substrate (glucose). Activity of the oxidase may be assayed by measuring the concentration of hydrogen peroxide formed after reaction of the enzyme-labeled antibody with the substrate under controlled conditions well-known in the art.

Other techniques may be used to detect biomarker protein according to a practitioner's preference based upon the present disclosure. One such technique is Western blotting (Towbin et al., Proc. Nat. Acad. Sci. 76:4350 (1979)), wherein a suitably treated sample is run on an SDS-PAGE gel before being transferred to a solid support, such as a nitrocellulose filter. Anti-biomarker protein antibodies (unlabeled) are then brought into contact with the support and assayed by a secondary immunological reagent, such as labeled protein A or anti-immunoglobulin (suitable labels including $^{125}$I, horseradish peroxidase and alkaline phosphatase). Chromatographic detection may also be used.

Immunohistochemistry may be used to detect expression of biomarker protein, e.g., in a biopsy sample. A suitable antibody is brought into contact with, for example, a thin layer of cells, washed, and then contacted with a second, labeled antibody. Labeling may be by fluorescent markers, enzymes, such as peroxidase, avidin, or radiolabelling. The assay is scored visually, using microscopy.

Anti-biomarker protein antibodies, such as intrabodies, may also be used for imaging purposes, for example, to detect the presence of biomarker protein in cells and tissues of a subject. Suitable labels include radioisotopes, iodine ($^{125}$I, $^{121}$I), carbon ($^{14}$C), sulphur ($^{35}$S), tritium ($^{3}$H), indium ($^{112}$In), and technetium ($^{99}$mTc), fluorescent labels, such as fluorescein and rhodamine, and biotin.

For in vivo imaging purposes, antibodies are not detectable, as such, from outside the body, and so must be labeled, or otherwise modified, to permit detection. Markers for this purpose may be any that do not substantially interfere with the antibody binding, but which allow external detection. Suitable markers may include those that may be detected by X-radiography, NMR or MRI. For X-radiographic techniques, suitable markers include any radioisotope that emits detectable radiation but that is not overtly harmful to the subject, such as barium or cesium, for example. Suitable markers for NMR and MRI generally include those with a detectable characteristic spin, such as deuterium, which may be incorporated into the antibody by suitable labeling of nutrients for the relevant hybridoma, for example.

The size of the subject, and the imaging system used, will determine the quantity of imaging moiety needed to produce diagnostic images. In the case of a radioisotope moiety, for a human subject, the quantity of radioactivity injected will normally range from about 5 to 20 millicuries of technetium-99. The labeled antibody or antibody fragment will then preferentially accumulate at the location of cells which contain biomarker protein. The labeled antibody or antibody fragment can then be detected using known techniques.

Antibodies that may be used to detect biomarker protein include any antibody, whether natural or synthetic, full length or a fragment thereof, monoclonal or polyclonal, that binds sufficiently strongly and specifically to the biomarker protein to be detected. An antibody may have a $K_d$ of at most about $10^{-6}$M, $10^{-7}$M, $10^{-8}$M, $10_{-9}$M, $10^{-10}$M, $10^{-11}$M, $10^{-12}$M. The phrase "specifically binds" refers to binding of, for example, an antibody to an epitope or antigen or antigenic determinant in such a manner that binding can be displaced or competed with a second preparation of identical or similar epitope, antigen or antigenic determinant. An antibody may bind preferentially to the biomarker protein relative to other proteins, such as related proteins.

Antibodies are commercially available or may be prepared according to methods known in the art.

Antibodies and derivatives thereof that may be used encompass polyclonal or monoclonal antibodies, chimeric, human, humanized, primatized (CDR-grafted), veneered or single-chain antibodies as well as functional fragments, i.e., biomarker protein binding fragments, of antibodies. For example, antibody fragments capable of binding to a biomarker protein or portions thereof, including, but not limited to, Fv, Fab, Fab' and F(ab') 2 fragments can be used. Such fragments can be produced by enzymatic cleavage or by recombinant techniques. For example, papain or pepsin cleavage can generate Fab or F(ab') 2 fragments, respectively. Other proteases with the requisite substrate specificity can also be used to generate Fab or F(ab') 2 fragments. Antibodies can also be produced in a variety of truncated forms using antibody genes in which one or more stop codons have been introduced upstream of the natural stop site. For example, a chimeric gene encoding a F(ab') 2 heavy chain portion can be designed to include DNA sequences encoding the CH, domain and hinge region of the heavy chain.

Synthetic and engineered antibodies are described in, e.g., Cabilly et al., U.S. Pat. No. 4,816,567 Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Queen et al., European Patent No. 0451216 B1; and Padlan, E. A. et al., EP 0519596 A1. See also. Newman, R. et al., BioTechnology, 10: 1455-1460 (1992), regarding primatized antibody, and Ladner et al., U.S. Pat. No. 4,946,778 and Bird, R. E. et al., Science, 242: 423-426 (1988)) regarding single-chain antibodies. Antibodies produced from a library, e.g., phage display library, may also be used.

In some embodiments, agents that specifically bind to a biomarker protein other than antibodies are used, such as peptides. Peptides that specifically bind to a biomarker protein can be identified by any means known in the art. For example, specific peptide binders of a biomarker protein can be screened for using peptide phage display libraries.

d. Methods for Detection of Biomarker Metabolite Expression

Biomarker metabolites, such as those shown in Table 1 can be detected in numerous ways according to well-known techniques. For example, such metabolites, as well as biomarker proteins, can be detected using mass spectrometry methods, such as MALDI/TOF (time-of-flight), SELDI/TOF, liquid chromatography-mass spectrometry (LC-MS), gas chromatography-mass spectrometry (GC-MS), high performance liquid chromatography-mass spectrometry (HPLC-MS), capillary electrophoresis-mass spectrometry, nuclear magnetic resonance spectrometry, or tandem mass spectrometry (e.g., MS/MS, MS/MS/MS, ESI-MS/MS, etc.). See for example, U.S. Patent Application Nos: 20030199001, 20030134304, 20030077616, which are herein incorporated by reference.

Mass spectrometry methods are well known in the art and have been used to quantify and/or identify biomolecules, such as chemical metabolites and proteins (see, e.g., Li et al. (2000) Tibtech 18, 151-160; Rowley et al. (2000) Methods 20, 383-397; Kuster and Mann (1998) Curr. Opin. Structural Biol. 8, 393-400). Further, mass spectrometric techniques have been developed that permit at least partial de novo sequencing of isolated proteins (see, e.g., Chait et al. (1993) Science 262, 89-92; Keough et al. (1999) Proc. Natl. Acad. Sci. USA. 96, 7131-7136; reviewed in Bergman (2000) EXS 88, 133-44).

In certain embodiments, a gas phase ion spectrophotometer is used. In other embodiments, laser-desorption/ionization mass spectrometry is used to analyze the sample. Modern laser desorption/ionization mass spectrometry ("LDI-MS") can be practiced in two main variations: matrix assisted laser desorption/ionization ("MALDI") mass spectrometry and surface-enhanced laser desorption/ionization ("SELDI"). In MALDI, the analyte is mixed with a solution containing a matrix, and a drop of the liquid is placed on the surface of a substrate. The matrix solution then co-crystallizes with the biological molecules. The substrate is inserted into the mass spectrometer. Laser energy is directed to the substrate surface where it desorbs and ionizes the biological molecules without significantly fragmenting them. However, MALDI has limitations as an analytical tool. It does not provide means for fractionating the sample, and the matrix material can interfere with detection, especially for low molecular weight analytes (see, e.g., Hellenkamp et al., U.S. Pat. No. 5,118,937 and Beavis and Chait, U.S. Pat. No. 5,045,694).

In SELDI, the substrate surface is modified so that it is an active participant in the desorption process. In one variant, the surface is derivatized with adsorbent and/or capture reagents that selectively bind the protein of interest. In another variant, the surface is derivatized with energy absorbing molecules that are not desorbed when struck with the laser. In another variant, the surface is derivatized with molecules that bind the protein of interest and that contain a photolytic bond that is broken upon application of the laser. In each of these methods, the derivatizing agent generally is localized to a specific location on the substrate surface where the sample is applied (see, e.g., Hutchens and Yip, U.S. Pat. No. 5,719,060 and Hutchens and Yip, WO 98/59361). The two methods can be combined by, for example, using a SELDI affinity surface to capture an analyte and adding matrix-containing liquid to the captured analyte to provide the energy absorbing material.

For additional information regarding mass spectrometers, see, e.g., Principles of Instrumental Analysis, 3rd edition, Skoog, Saunders College Publishing, Philadelphia, 1985; and Kirk-Othmer Encyclopedia of Chemical Technology, 4.sup.th ed. Vol. 15 (John Wiley & Sons, New York 1995), pp. 1071-1094.

Detection of the presence of a marker or other substances will typically involve detection of signal intensity. For example, in certain embodiments, the signal strength of peak values from spectra of a first sample and a second sample can be compared (e.g., visually or by computer analysis) to determine the relative amounts of particular biomolecules. Software programs such as the Biomarker Wizard program (Ciphergen Biosystems, Inc., Fremont, Calif.) can be used to aid in analyzing mass spectra. The mass spectrometers and their techniques are well known to those of skill in the art.

Any person skilled in the art understands, any of the components of a mass spectrometer (e.g., desorption source, mass analyzer, detect, etc.) and varied sample preparations can be combined with other suitable components or preparations described herein, or to those known in the art. For example, in some embodiments a control sample may contain heavy atoms (e.g. $^{13}C$) thereby permitting the test sample to be mixed with the known control sample in the same mass spectrometry run. In some embodiments, internal controls, such as phenylalanine-d8 and/or valine-d8 can be run with the samples.

In one embodiment, a laser desorption time-of-flight (TOF) mass spectrometer is used. In laser desorption mass spectrometry, a substrate with a bound marker is introduced into an inlet system. The marker is desorbed and ionized into the gas phase by laser from the ionization source. The ions generated are collected by an ion optic assembly, and then in a time-of-flight mass analyzer, ions are accelerated through a short high voltage field and let drift into a high vacuum chamber. At the far end of the high vacuum chamber, the accelerated ions strike a sensitive detector surface at a different time. Since the time-of-flight is a function of the mass of the ions, the elapsed time between ion formation and ion detector impact can be used to identify the presence or absence of molecules of specific mass to charge ratio.

In some embodiments the relative amounts of one or more biomolecules present in a first or second sample is determined, in part, by executing an algorithm with a programmable digital computer. The algorithm identifies at least one peak value in the first mass spectrum and the second mass spectrum. The algorithm then compares the signal strength of the peak value of the first mass spectrum to the signal strength of the peak value of the second mass spectrum of the mass spectrum. The relative signal strengths are an indication of the amount of the biomolecule that is present in the first and second samples. A standard containing a known amount of a biomolecule can be analyzed as the second sample to provide better quantification of the amount of the biomolecule present in the first sample. In certain embodiments, the identity of the biomolecules in the first and second sample can also be determined.

e. Methods for Detection of Biomarker Structural Alterations

The following illustrative methods can be used to identify the presence of a structural alteration in a biomarker nucleic acid and/or biomarker polypeptide molecule in order to, for example, identify oncogene biomarkers (e.g., activating mutations in oncogene biomarkers) and tumor suppressor biomarkers (e.g., inhibiting mutations in tumor suppressors).

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077-1080; and Nakazawa et al. (1994) Proc. Natl. Acad. Sci. USA 91:360-364), the latter of which can be particularly useful for detecting point mutations in a biomarker nucleic acid such as a biomarker gene (see Abravaya et al. (1995) Nucleic Acids Res. 23:675-682). This method can include the steps of collecting a sample of cells from a subject, isolating nucleic acid (e.g., genomic, mRNA or both) from the cells of the sample, contacting the nucleic acid sample with one or more primers which specifically hybridize to a biomarker gene under conditions such that hybridization and amplification of the biomarker gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al. (1990) Proc. Natl. Acad. Sci. USA 87:1874-1878), transcriptional amplification system (Kwoh, D. Y. et al. (1989) Proc. Natl. Acad. Sci. USA 86:1173-1177), Q-Beta Replicase (Lizardi, P. M. et al. (1988) Bio-Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a biomarker nucleic acid from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in biomarker nucleic acid can be identified by hybridizing a sample and control nucleic acids, e.g., DNA or RNA, to high density arrays containing hundreds or thousands of oligonucleotide probes (Cronin, M. T. et al. (1996) Hum. Mutat. 7:244-255; Kozal, M. J. et al. (1996) Nat. Med. 2:753-759). For example, biomarker genetic mutations can be identified in two dimensional arrays containing light-generated DNA probes as described in Cronin et al. (1996) supra. Briefly, a first hybridization array of probes can be used to scan through long stretches of DNA in a sample and control to identify base changes between the sequences by making linear arrays of sequential, overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene. Such biomarker genetic mutations can be identified in a variety of contexts, including, for example, germline and somatic mutations.

In yet another embodiment, any of a variety of sequencing reactions known in the art can be used to directly sequence a biomarker gene and detect mutations by comparing the sequence of the sample biomarker with the corresponding wild-type (control) sequence. Examples of sequencing reactions include those based on techniques developed by Maxam and Gilbert (1977) *Proc. Natl. Acad. Sci. USA* 74:560 or Sanger (1977) *Proc. Natl. Acad Sci. USA* 74:5463. It is also contemplated that any of a variety of automated sequencing procedures can be utilized when performing the diagnostic assays (Naeve (1995) *Biotechniques* 19:448-53), including sequencing by mass spectrometry (see, e.g., PCT International Publication No. WO 94/16101; Cohen et al. (1996) *Adv. Chromatogr.* 36:127-162; and Griffin et al. (1993) *Appl. Biochem. Biotechnol.* 38:147-159).

Other methods for detecting mutations in a biomarker gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes formed by hybridizing (labeled) RNA or DNA containing the wild-type biomarker sequence with potentially mutant RNA or DNA obtained from a tissue sample. The double-stranded duplexes are treated with an agent which cleaves single-stranded regions of the duplex such as which will exist due to base pair mismatches between the control and sample strands. For instance, RNA/DNA duplexes can be treated with RNase and DNA/DNA hybrids treated with St nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) Proc. Natl. Acad. Sci. USA 85:4397 and Saleeba et al. (1992) Methods Enzymol. 217:286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in biomarker cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657-1662). According to an exemplary embodiment, a probe based on a biomarker sequence, e.g., a wild-type biomarker treated with a DNA mismatch repair enzyme, and the cleavage products, if any, can be detected from electrophoresis protocols or the like (e.g., U.S. Pat. No. 5,459,039.)

In other embodiments, alterations in electrophoretic mobility can be used to identify mutations in biomarker genes. For example, single strand conformation polymorphism (SSCP) may be used to detect differences in electrophoretic mobility between mutant and wild type nucleic acids (Orita et al. (1989) *Proc Natl. Acad. Sci USA* 86:2766 see also Cotton (1993) *Mutat. Res.* 285:125-144 and Hayashi (1992) *Genet. Anal. Tech. Appl.* 9:73-79). Single-stranded DNA fragments of sample and control biomarker nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet.* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to ensure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys. Chem.* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163; Saiki et al. (1989) *Proc. Natl. Acad. Sci. USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437-2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

3. Anti-Cancer Therapies and Combination Therapies

The efficacy of anti-immune checkpoint inhibitor therapy is predicted according to biomarker amount and/or activity associated with a cancer in a subject according to the methods described herein. In one embodiment, such anti-immune checkpoint inhibitor therapy or combinations of therapies (e.g., anti-PD-1, anti-PD-L1, anti-PD-L2, and anti-CTLA4 therapies) can be administered once a subject is indicated as being a likely responder to anti-immune checkpoint inhibitor therapy. In another embodiment, such anti-immune checkpoint inhibitor therapy can be avoided once a subject is indicated as not being a likely responder to anti-immune checkpoint inhibitor therapy and an alternative treatment regimen, such as targeted and/or untargeted anti-cancer therapies can be administered. Combination therapies are also contemplated and can comprise, for example, one or more chemotherapeutic agents and radiation, one or more chemotherapeutic agents and immunotherapy, or one or more chemotherapeutic agents, radiation and chemotherapy, each combination of which can be with or without anti-immune checkpoint inhibitor therapy.

The term "targeted therapy" refers to administration of agents that selectively interact with a chosen biomolecule to thereby treat cancer.

Immunotherapy is one form of targeted therapy that may comprise, for example, the use of cancer vaccines and/or sensitized antigen presenting cells. For example, an oncolytic virus is a virus that is able to infect and lyse cancer cells, while leaving normal cells unharmed, making them potentially useful in cancer therapy. Replication of oncolytic viruses both facilitates tumor cell destruction and also produces dose amplification at the tumor site. They may also act as vectors for anticancer genes, allowing them to be specifically delivered to the tumor site. The immunotherapy can involve passive immunity for short-term protection of a host, achieved by the administration of pre-formed antibody directed against a cancer antigen or disease antigen (e.g., administration of a monoclonal antibody, optionally linked to a chemotherapeutic agent or toxin, to a tumor antigen). For example, anti-VEGF and mTOR inhibitors are known to be effective in treating renal cell carcinoma. Immunotherapy can also focus on using the cytotoxic lymphocyte-recognized epitopes of cancer cell lines. Alternatively, antisense polynucleotides, ribozymes, RNA interference molecules, triple helix polynucleotides and the like, can be used to selectively modulate biomolecules that are linked to the initiation, progression, and/or pathology of a tumor or cancer.

The term "untargeted therapy" refers to administration of agents that do not selectively interact with a chosen biomolecule yet treat cancer. Representative examples of untargeted therapies include, without limitation, chemotherapy, gene therapy, and radiation therapy.

In one embodiment, chemotherapy is used. Chemotherapy includes the administration of a chemotherapeutic agent. Such a chemotherapeutic agent may be, but is not limited to, those selected from among the following groups of compounds: platinum compounds, cytotoxic antibiotics, antimetabolites, anti-mitotic agents, alkylating agents, arsenic compounds, DNA topoisomerase inhibitors, taxanes, nucleoside analogues, plant alkaloids, and toxins; and synthetic derivatives thereof. Exemplary compounds include, but are not limited to, alkylating agents: cisplatin, treosulfan, and trofosfamide; plant alkaloids: vinblastine, paclitaxel, docetaxol; DNA topoisomerase inhibitors: teniposide, crisnatol, and mitomycin; anti-folates: methotrexate, mycophenolic acid, and hydroxyurea; pyrimidine analogs: 5-fluorouracil, doxifluridine, and cytosine arabinoside; purine analogs: mercaptopurine and thioguanine: DNA antimetabolites: 2'-deoxy-5-fluorouridine, aphidicolin glycinate, and pyrazoloimidazole; and antimitotic agents: halichondrin, colchicine, and rhizoxin. Compositions comprising one or more chemotherapeutic agents (e.g., FLAG, CHOP) may also be used. FLAG comprises fludarabine, cytosine arabinoside (Ara-C) and G-CSF. CHOP comprises cyclophosphamide, vincristine, doxorubicin, and prednisone. In another embodiments, PARP (e.g., PARP-L and/or PARP-2) inhibitors are used and such inhibitors are well known in the art (e.g., Olaparib, ABT-888, BSI-201, BGP-15 (N-Gene Research Laboratories, Inc.); INO-1001 (Inotek Pharmaceuticals Inc.); PJ34 (Soriano et al., 2001; Pacher et al., 2002b); 3-aminobenzamide (Trevigen); 4-amino-1,8-naphthalimide; (Trevigen); 6(5H)-phenanthridinone (Trevigen); benzamide (U.S. Pat. Re. 36,397); and NU1025 (Bowman et al.). The mechanism of action is generally related to the ability of PARP inhibitors to bind PARP and decrease its activity. PARP catalyzes the conversion of .beta.-nicotinamide adenine dinucleotide (NAD+) into nicotinamide and poly-ADP-ribose (PAR). Both poly (ADP-ribose) and PARP have been linked to regulation of transcription, cell proliferation, genomic stability, and carcinogenesis (Bouchard V. J. et. al. Experimental Hematology, Volume 31, Number 6, June 2003, pp. 446-454(9); Herceg Z.; Wang Z.-Q. Mutation Research/Fundamental and Molecular Mechanisms of Mutagenesis, Volume 477, Number 1, 2 Jun. 2001, pp. 97-110(14)). Poly(ADP-ribose) polymerase 1 (PARP1) is a key molecule in the repair of DNA single-strand breaks (SSBs) (de Murcia J. et al. 1997. Proc Natl Acad Sci USA 94:7303-7307; Schreiber V, Dantzer F, Ame J C, de Murcia G (2006) Nat Rev Mol Cell Biol 7:517-528; Wang Z Q. et al. (1997) Genes Dev 11:2347-2358). Knockout of SSB repair by inhibition of PARP1 function induces DNA double-strand breaks (DSBs) that can trigger synthetic lethality in cancer cells with defective homology-directed DSB repair (Bryant H E, et al. (2005) Nature 434:913-917; Farmer H, et al. (2005) Nature 434:917-921). The foregoing examples of chemotherapeutic agents are illustrative, and are not intended to be limiting.

In another embodiment, radiation therapy is used. The radiation used in radiation therapy can be ionizing radiation. Radiation therapy can also be gamma rays, X-rays, or proton beams. Examples of radiation therapy include, but are not limited to, external-beam radiation therapy, interstitial implantation of radioisotopes (I-125 palladium, iridium), radioisotopes such as strontium-89, thoracic radiation therapy, intraperitoneal P-32 radiation therapy, and/or total abdominal and pelvic radiation therapy. For a general overview of radiation therapy, see Hellman, Chapter 16: Principles of Cancer Management: Radiation Therapy, 6th edition, 2001, DeVita et al., eds., J. B. Lippencott Company, Philadelphia. The radiation therapy can be administered as external beam radiation or teletherapy wherein the radiation is directed from a remote source. The radiation treatment can also be administered as internal therapy or brachytherapy wherein a radioactive source is placed inside the body close to cancer cells or a tumor mass. Also encompassed is the use of photodynamic therapy comprising the administration of photosensitizers, such as hematoporphyrin and its derivatives, Vertoporfin (BPD-MA), phthalocyanine, photosensitizer Pc4, demethoxy-hypocrellin A; and 2BA-2-DMHA.

In another embodiment, hormone therapy is used. Hormonal therapeutic treatments can comprise, for example, hormonal agonists, hormonal antagonists (e.g., flutamide, bicalutamide, tamoxifen, raloxifene, leuprolide acetate (LUPRON), LH-RH antagonists), inhibitors of hormone biosynthesis and processing, and steroids (e.g., dexamethasone, retinoids, deltoids, betamethasone, cortisol, cortisone, prednisone, dehydrotestosterone, glucocorticoids, mineralocorticoids, estrogen, testosterone, progestins), vitamin A derivatives (e.g., all-trans retinoic acid (ATRA)); vitamin D3 analogs; antigestagens (e.g., mifepristone, onapristone), or antiandrogens (e.g., cyproterone acetate).

In another embodiment, hyperthermia, a procedure in which body tissue is exposed to high temperatures (up to 106° F.) is used. Heat may help shrink tumors by damaging cells or depriving them of substances they need to live. Hyperthermia therapy can be local, regional, and whole-body hyperthermia, using external and internal heating devices. Hyperthermia is almost always used with other forms of therapy (e.g., radiation therapy, chemotherapy, and biological therapy) to try to increase their effectiveness. Local hyperthermia refers to heat that is applied to a very small area, such as a tumor. The area may be heated externally with high-frequency waves aimed at a tumor from a device outside the body. To achieve internal heating, one of several types of sterile probes may be used, including thin, heated wires or hollow tubes filled with warm water, implanted microwave antennae; and radiofrequency electrodes. In regional hyperthermia, an organ or a limb is heated. Magnets and devices that produce high energy are placed over the region to be heated. In another approach, called perfusion, some of the patient's blood is removed, heated, and then pumped (perfused) into the region that is to be heated internally. Whole-body heating is used to treat metastatic cancer that has spread throughout the body. It can be accomplished using warm-water blankets, hot wax, inductive coils (like those in electric blankets), or thermal chambers (similar to large incubators). Hyperthermia does not cause any marked increase in radiation side effects or complications. Heat applied directly to the skin, however, can cause discomfort or even significant local pain in about half the patients treated. It can also cause blisters, which generally heal rapidly.

In still another embodiment, photodynamic therapy (also called PDT, photoradiation therapy, phototherapy, or photochemotherapy) is used for the treatment of some types of cancer. It is based on the discovery that certain chemicals known as photosensitizing agents can kill one-celled organisms when the organisms are exposed to a particular type of light PDT destroys cancer cells through the use of a fixed-frequency laser light in combination with a photosensitizing agent. In PDT, the photosensitizing agent is injected into the bloodstream and absorbed by cells all over the body. The agent remains in cancer cells for a longer time than it does in normal cells. When the treated cancer cells are exposed to laser light, the photosensitizing agent absorbs the light and produces an active form of oxygen that destroys the treated cancer cells. Light exposure must be timed carefully so that it occurs when most of the photosensitizing agent has left healthy cells but is still present in the cancer cells. The laser light used in PDT can be directed through a fiber-optic (a very thin glass strand). The fiber-optic is placed close to the cancer to deliver the proper amount of light. The fiber-optic can be directed through a bronchoscope into the lungs for the treatment of lung cancer or through an endoscope into the esophagus for the treatment of esophageal cancer. An advantage of PDT is that it causes minimal damage to healthy tissue. However, because the laser light currently in use cannot pass through more than about 3 centimeters of tissue (a little more than one and an eighth inch), PDT is mainly used to treat tumors on or just under the skin or on the lining of internal organs. Photodynamic therapy makes the skin and eyes sensitive to light for 6 weeks or more after treatment. Patients are advised to avoid direct sunlight and bright indoor light for at least 6 weeks. If patients must go outdoors, they need to wear protective clothing, including sunglasses. Other temporary side effects of PDT are related to the treatment of specific areas and can include coughing, trouble swallowing, abdominal pain, and painful breathing or shortness of breath. In December 1995, the U.S. Food and Drug Administration (FDA) approved a photosensitizing agent called porfimer sodium, or Photofrin®, to relieve symptoms of esophageal cancer that is causing an obstruction and for esophageal cancer that cannot be satisfactorily treated with lasers alone. In January 1998, the FDA approved porfimer sodium for the treatment of early nonsmall cell lung cancer in patients for whom the usual treatments for lung cancer are not appropriate. The National Cancer Institute and other institutions are supporting clinical trials (research studies) to evaluate the use of photodynamic therapy for several types of cancer, including cancers of the bladder, brain, larynx, and oral cavity.

In yet another embodiment, laser therapy is used to harness high-intensity light to destroy cancer cells. This technique is often used to relieve symptoms of cancer such as bleeding or obstruction, especially when the cancer cannot be cured by other treatments. It may also be used to treat cancer by shrinking or destroying tumors. The term "laser" stands for light amplification by stimulated emission of radiation. Ordinary light, such as that from a light bulb, has many wavelengths and spreads in all directions. Laser light, on the other hand, has a specific wavelength and is focused in a narrow beam. This type of high-intensity light contains a lot of energy. Lasers are very powerful and may be used to cut through steel or to shape diamonds. Lasers also can be used for very precise surgical work, such as repairing a damaged retina in the eye or cutting through tissue (in place of a scalpel). Although there are several different kinds of lasers, only three kinds have gained wide use in medicine: Carbon dioxide ($CO_2$) laser—This type of laser can remove thin layers from the skin's surface without penetrating the deeper layers. This technique is particularly useful in treating tumors that have not spread deep into the skin and certain precancerous conditions. As an alternative to traditional scalpel surgery, the $CO_2$ laser is also able to cut the skin. The laser is used in this way to remove skin cancers. Neodymium:yttrium-aluminum-garnet (Nd:YAG) laser—Light from this laser can penetrate deeper into tissue than light from the other types of lasers, and it can cause blood to clot quickly. It can be carried through optical fibers to less accessible parts of the body. This type of laser is sometimes used to treat throat cancers. Argon laser—This laser can pass through only superficial layers of tissue and is therefore useful in dermatology and in eye surgery. It also is used with light-sensitive dyes to treat tumors in a procedure known as photodynamic therapy (PDT). Lasers have several advantages over standard surgical tools, including: Lasers are more precise than scalpels. Tissue near an incision is protected, since there is little contact with surrounding skin or other tissue. The heat produced by lasers sterilizes the surgery site, thus reducing the risk of infection. Less operating time may be needed because the precision of the laser allows for a smaller incision. Healing time is often shortened; since laser heat seals blood vessels, there is less bleeding, swelling, or scarring. Laser surgery may be less complicated. For example, with fiber optics, laser light can be directed to parts of the body without making a large incision. More procedures may be done on an outpatient basis. Lasers can be used in two ways to treat cancer; by shrinking or destroying a tumor with heat, or by activating a chemical—known as a photosensitizing agent—that destroys cancer cells. In PDT, a photosensitizing agent is retained in cancer cells and can be stimulated by light to cause a reaction that kills cancer cells. $CO_2$ and Nd:YAG lasers are used to shrink or destroy tumors. They may be used with endoscopes, tubes that allow physicians to see into certain areas of the body, such as the bladder. The light from some lasers can be transmitted through a flexible endoscope fitted with fiber optics. This allows physicians to see and work in parts of the body that could not otherwise be reached except by surgery and therefore allows very precise aiming of the laser beam. Lasers also may be used with low-power microscopes, giving the doctor a clear view of the site being treated. Used with other instruments, laser systems can produce a cutting area as small as 200 microns in diameter— less than the width of a very fine thread. Lasers are used to treat many types of cancer. Laser surgery is a standard treatment for certain stages of glottis (vocal cord), cervical, skin, lung, vaginal, vulvar, and penile cancers. In addition to its use to destroy the cancer, laser surgery is also used to help relieve symptoms caused by cancer (palliative care). For example, lasers may be used to shrink or destroy a tumor that is blocking a patient's trachea (windpipe), making it easier to breathe. It is also sometimes used for palliation in colorectal and anal cancer. Laser-induced interstitial thermotherapy (LITT) is one of the most recent developments in laser therapy. LITT uses the same idea as a cancer treatment called hyperthermia; that heat may help shrink tumors by damaging cells or depriving them of substances they need to live. In this treatment, lasers are directed to interstitial areas (areas between organs) in the body. The laser light then raises the temperature of the tumor, which damages or destroys cancer cells.

The duration and/or dose of treatment with anti-immune checkpoint inhibitor therapies may vary according to the particular anti-immune checkpoint inhibitor agent or combination thereof (e.g., anti-ARG1 agents like small molecule inhibitors in combination with inhibitors of PD-1, PD-L1, PD-L2, CTLA-4, and the like). An appropriate treatment time for a particular cancer therapeutic agent will be appreciated by the skilled artisan. The invention contemplates the continued assessment of optimal treatment schedules for each cancer therapeutic agent, where the phenotype of the cancer of the subject as determined by the methods of the invention is a factor in determining optimal treatment doses and schedules.

Any means for the introduction of a polynucleotide into mammals, human or non-human, or cells thereof may be adapted to the practice of this invention for the delivery of the various constructs of the invention into the intended recipient. In one embodiment of the invention, the DNA constructs are delivered to cells by transfection, i.e., by delivery of "naked" DNA or in a complex with a colloidal dispersion system. A colloidal system includes macromolecule complexes, nanocapsules, microspheres, beads, and lipid-based systems including oil-in-water emulsions, micelles, mixed micelles, and liposomes. The preferred colloidal system of this invention is a lipid-complexed or liposome-formulated DNA. In the former approach, prior to formulation of DNA, e.g., with lipid, a plasmid containing a transgene bearing the desired DNA constructs may first be experimentally optimized for expression (e.g., inclusion of an intron in the 5' untranslated region and elimination of unnecessary sequences (Felgner, et al., Ann NY Acad Sci 126-139, 1995). Formulation of DNA, e.g. with various lipid or liposome materials, may then be effected using known methods and materials and delivered to the recipient mammal. See. e.g., Canonico et al, Am J Respir Cell Mol Biol 10:24-29, 1994; Tsan et al, Am J Physiol 268; Alton et al., Nat Genet. 5:135-142, 1993 and U.S. Pat. No. 5,679,647 by Carson et al.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs, which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. Naked DNA or DNA associated with a delivery vehicle, e.g., liposomes, can be administered to several sites in a subject (see below).

Nucleic acids can be delivered in any desired vector. These include viral or non-viral vectors, including adenovirus vectors, adeno-associated virus vectors, retrovirus vectors, lentivirus vectors, and plasmid vectors. Exemplary types of viruses include HSV (herpes simplex virus), AAV (adeno associated virus), HIV (human immunodeficiency virus), BIV (bovine immunodeficiency virus), and MLV (murine leukemia virus). Nucleic acids can be administered in any desired format that provides sufficiently efficient delivery levels, including in virus particles, in liposomes, in nanoparticles, and complexed to polymers.

The nucleic acids encoding a protein or nucleic acid of interest may be in a plasmid or viral vector, or other vector as is known in the art. Such vectors are well known and any can be selected for a particular application. In one embodiment of the invention, the gene delivery vehicle comprises a promoter and a demethylase coding sequence. Preferred promoters are tissue-specific promoters and promoters which are activated by cellular proliferation, such as the thymidine kinase and thymidylate synthase promoters. Other preferred promoters include promoters which are activatable by infection with a virus, such as the α- and β-interferon promoters, and promoters which are activatable by a hormone, such as estrogen. Other promoters which can be used include the Moloney virus LTR, the CMV promoter, and the mouse albumin promoter. A promoter may be constitutive or inducible.

In another embodiment, naked polynucleotide molecules are used as gene delivery vehicles, as described in WO 90/11092 and U.S. Pat. No. 5,580,859. Such gene delivery vehicles can be either growth factor DNA or RNA and, in certain embodiments, are linked to killed adenovirus. Curiel et al., Hum. Gene. Ther. 3:147-154, 1992. Other vehicles which can optionally be used include DNA-ligand (Wu et al., J. Biol. Chem. 264:16985-16987, 1989), lipid-DNA combinations (Felgner et al., Proc. Natl. Acad. Sci. USA 84:7413 7417, 1989), liposomes (Wang et al., Proc. Natl. Acad. Sci. 84:7851-7855, 1987) and microprojectiles (Williams et al., Proc. Natl. Acad. Sci. 88:2726-2730, 1991).

A gene delivery vehicle can optionally comprise viral sequences such as a viral origin of replication or packaging signal. These viral sequences can be selected from viruses such as astrovirus, coronavirus, orthomyxovirus, papovavirus, paramyxovirus, parvovirus, picornavirus, poxvirus, retrovirus, togavirus or adenovirus. In a preferred embodiment, the growth factor gene delivery vehicle is a recombinant retroviral vector. Recombinant retroviruses and various uses thereof have been described in numerous references including, for example, Mann et al., Cell 33:153, 1983, Cane and Mulligan, Proc. Nat'l. Acad. Sci. USA 81:6349, 1984, Miller et al., *Human Gene Therapy* 1:5-14, 1990, U.S. Pat. Nos. 4,405,712, 4,861,719, and 4,980,289, and PCT Application Nos. WO 89/02,468, WO 89/05,349, and WO 90/02,806. Numerous retroviral gene delivery vehicles can be utilized in the present invention, including for example those described in EP 0,415,731; WO 90/07936; WO 94/03622; WO 93:25698; WO 93/25234; U.S. Pat. No. 5,219,740; WO 9311230; WO 9310218; Vile and Hart, Cancer Res. 53:3860-3864, 1993; Vile and Hart, Cancer Res. 53:962-967, 1993; Ram et al., Cancer Res. 53:83-88, 1993; Takamiya et al., J. Neurosci. Res. 33:493-503, 1992; Baba et al., J. Neurosurg. 79:729-735, 1993 (U.S. Pat. No. 4,777,127, GB 2,200,651, EP 0,345,242 and WO91/02805).

Other viral vector systems that can be used to deliver a polynucleotide of the invention have been derived from herpes virus, e.g., Herpes Simplex Virus (U.S. Pat. No. 5,631,236 by Woo et al., issued May 20, 1997 and WO 00/08191 by Neurovex), vaccinia virus (Ridgeway (1988) Ridgeway, "Mammalian expression vectors," In: Rodriguez R L, Denhardt D T, ed. Vectors: A survey of molecular cloning vectors and their uses. Stoneham: Butterworth; Baichwal and Sugden (1986) "Vectors for gene transfer derived from animal DNA viruses: Transient and stable expression of transferred genes," In: Kucherlapati R, ed. Gene transfer. New York: Plenum Press; Coupar et al. (1988) Gene, 68:1-10), and several RNA viruses. Preferred viruses include an alphavirus, a poxivirus, an arena virus, a vaccinia virus, a polio virus, and the like. They offer several attractive features for various mammalian cells (Friedmann (1989) Science, 244:1275-1281; Ridgeway, 1988, supra; Baichwal and Sugden, 1986, supra; Coupar et al., 1988; Horwich et al. (1990) J. Virol., 64:642-650).

In other embodiments, target DNA in the genome can be manipulated using well-known methods in the art. For example, the target DNA in the genome can be manipulated by deletion, insertion, and/or mutation are retroviral insertion, artificial chromosome techniques, gene insertion, random insertion with tissue specific promoters, gene targeting, transposable elements and/or any other method for introducing foreign DNA or producing modified DNA/modified nuclear DNA. Other modification techniques include deleting DNA sequences from a genome and/or altering nuclear DNA sequences. Nuclear DNA sequences, for example, may be altered by site-directed mutagenesis.

In other embodiments, recombinant biomarker polypeptides, and fragments thereof, can be administered to subjects. In some embodiments, fusion proteins can be constructed and administered which have enhanced biological properties. In addition, the biomarker polypeptides, and fragment thereof, can be modified according to well-known pharmacological methods in the art (e.g., pegylation, glycosylation, oligomerization, etc.) in order to further enhance desirable biological activities, such as increased bioavailability and decreased proteolytic degradation.

4. Clinical Efficacy

Clinical efficacy can be measured by any method known in the art. For example, the response to a therapy, such as anti-immune checkpoint inhibitor therapies, relates to any response of the cancer, e.g., a tumor, to the therapy, preferably to a change in tumor mass and/or volume after initiation of neoadjuvant or adjuvant chemotherapy. Tumor response may be assessed in a neoadjuvant or adjuvant situation where the size of a tumor after systemic intervention can be compared to the initial size and dimensions as measured by CT, PET, mammogram, ultrasound or palpation and the cellularity of a tumor can be estimated histologically and compared to the cellularity of a tumor biopsy taken before initiation of treatment. Response may also be assessed by caliper measurement or pathological examination of the tumor after biopsy or surgical resection. Response may be recorded in a quantitative fashion like percentage change in tumor volume or cellularity or using a semi-quantitative scoring system such as residual cancer burden (Symmans et al., *J. Clin. Oncol.* (2007) 25:4414-4422) or Miller-Payne score (Ogston et al., (2003) *Breast* (Edinburgh, Scotland) 12:320-327) in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of tumor response may be performed early after the onset of neoadjuvant or adjuvant therapy, e.g., after a few hours, days, weeks or preferably after a few months. A typical endpoint for response assessment is upon termination of neoadjuvant chemotherapy or upon surgical removal of residual tumor cells and/or the tumor bed.

In some embodiments, clinical efficacy of the therapeutic treatments described herein may be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD over 6 months. In some embodiments, the CBR for a particular anti-immune checkpoint inhibitor therapeutic regimen is at least 25%, 30%, 35%, 40%, 45%, 50%, 55%, 60%, 65%, 70%, 75%, 80%, 85%, or more.

Additional criteria for evaluating the response to anti-immune checkpoint inhibitor therapies are related to "survival," which includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment can be expanded to include response to chemotherapy, probability of survival, probability of metastasis within a given time period, and probability of tumor recurrence.

For example, in order to determine appropriate threshold values, a particular anti-immune checkpoint inhibitor therapeutic regimen can be administered to a population of subjects and the outcome can be correlated to biomarker measurements that were determined prior to administration of any anti-immune checkpoint inhibitor therapy. The outcome measurement may be pathologic response to therapy given in the neoadjuvant setting. Alternatively, outcome measures, such as overall survival and disease-free survival can be monitored over a period of time for subjects following anti-immune checkpoint inhibitor therapy for whom biomarker measurement values are known. In certain embodiments, the same doses of anti-immune checkpoint inhibitor agents are administered to each subject. In related embodiments, the doses administered are standard doses known in the art for anti-immune checkpoint inhibitor agents. The period of time for which subjects are monitored can vary. For example, subjects may be monitored for at least 2, 4, 6, 8, 10, 12, 14, 16, 18, 20, 25, 30, 35, 40, 45, 50, 55, or 60 months. Biomarker measurement threshold values that correlate to outcome of an anti-immune checkpoint inhibitor therapy can be determined using methods such as those described in the Examples section.

5. Further Uses and Methods of the Present Invention

The compositions described herein can be used in a variety of diagnostic, prognostic, and therapeutic applications.

a. Screening Methods

One aspect of the present invention relates to screening assays, including non-cell based assays. In one embodiment, the assays provide a method for identifying whether a cancer is likely to respond to anti-immune checkpoint inhibitor therapy and/or whether an agent can inhibit the growth of or kill a cancer cell that is unlikely to respond to anti-immune checkpoint inhibitor therapy.

In one embodiment, the invention relates to assays for screening test agents which bind to, or modulate the biological activity of, at least one biomarker listed in Table 1. In one embodiment, a method for identifying such an agent entails determining the ability of the agent to modulate, e.g. inhibit, the at least one biomarker listed in Table 1.

In one embodiment, an assay is a cell-free or cell-based assay, comprising contacting at least one biomarker listed in Table 1, with a test agent, and determining the ability of the test agent to modulate (e.g. inhibit) the enzymatic activity of the biomarker, such as by measuring direct binding of substrates or by measuring indirect parameters as described below.

In another embodiment, an assay is a cell-free or cell-based assay, comprising contacting at least one metabolite biomarker listed in Table 1, with a test agent, and determining the ability of the test agent to sequester the availability of the metabolite biomarker to signal or otherwise be sensed, such as by measuring direct binding of substrates or by measuring indirect parameters as described below.

For example, in a direct binding assay, biomarker protein (or their respective target polypeptides or molecules) can be coupled with a radioisotope or enzymatic label such that binding can be determined by detecting the labeled protein or molecule in a complex. For example, the targets can be labeled with $^{125}$I, $^{35}$S, $^{14}$C, or $^{3}$H, either directly or indirectly, and the radioisotope detected by direct counting of radioemission or by scintillation counting. Alternatively, the targets can be enzymatically labeled with, for example, horseradish peroxidase, alkaline phosphatase, or luciferase, and the enzymatic label detected by determination of conversion of an appropriate substrate to product. Determining the interaction between biomarker and substrate can also be accomplished using standard binding or enzymatic analysis assays. In one or more embodiments of the above described assay methods, it may be desirable to immobilize polypeptides or molecules to facilitate separation of complexed from uncomplexed forms of one or both of the proteins or molecules, as well as to accommodate automation of the assay.

Binding of a test agent to a target can be accomplished in any vessel suitable for containing the reactants. Non-limiting examples of such vessels include microtiter plates, test tubes, and micro-centrifuge tubes. Immobilized forms of the antibodies of the present invention can also include antibodies bound to a solid phase like a porous, microporous (with an average pore diameter less than about one micron) or macroporous (with an average pore diameter of more than about 10 microns) material, such as a membrane, cellulose, nitrocellulose, or glass fibers; a bead, such as that made of agarose or polyacrylamide or latex; or a surface of a dish, plate, or well, such as one made of polystyrene.

In an alternative embodiment, determining the ability of the agent to modulate the interaction between the biomarker and a substrate or a biomarker metabolite and its natural binding partner can be accomplished by determining the ability of the test agent to modulate the activity of a polypeptide or other product that functions downstream or upstream of its position within the pathway (e.g., feedback loops).

The present invention further pertains to novel agents identified by the above-described screening assays. Accordingly, it is within the scope of this invention to further use an agent identified as described herein in an appropriate animal model. For example, an agent identified as described herein can be used in an animal model to determine the efficacy, toxicity, or side effects of treatment with such an agent. Alternatively, an antibody identified as described herein can be used in an animal model to determine the mechanism of action of such an agent.

b. Predictive Medicine

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining the amount and/or activity level of a biomarker listed in Table 1 in the context of a biological sample (e.g., blood, serum, cells, or tissue) to thereby determine whether an individual afflicted with a cancer is likely to respond to anti-immune checkpoint inhibitor therapy, whether in an original or recurrent cancer. Such assays can be used for prognostic or predictive purpose to thereby prophylactically treat an individual prior to the onset or after recurrence of a disorder characterized by or associated with biomarker polypeptide, nucleic acid expression or activity. The skilled artisan will appreciate that any method can use one or more (e.g., combinations) of biomarkers listed in Table 1.

Another aspect of the present invention pertains to monitoring the influence of agents (e.g., drugs, compounds, and small nucleic acid-based molecules) on the expression or activity of a biomarker listed in Table 1. These and other agents are described in further detail in the following sections.

The skilled artisan will also appreciated that, in certain embodiments, the methods of the present invention implement a computer program and computer system. For example, a computer program can be used to perform the algorithms described herein. A computer system can also store and manipulate data generated by the methods of the present invention which comprises a plurality of biomarker signal changes/profiles which can be used by a computer system in implementing the methods of this invention. In certain embodiments, a computer system receives biomarker expression data; (ii) stores the data; and (iii) compares the data in any number of ways described herein (e.g., analysis relative to appropriate controls) to determine the state of informative biomarkers from cancerous or pre-cancerous tissue. In other embodiments, a computer system (i) compares the determined expression biomarker level to a threshold value; and (ii) outputs an indication of whether said biomarker level is significantly modulated (e.g., above or below) the threshold value, or a phenotype based on said indication.

In certain embodiments, such computer systems are also considered part of the present invention. Numerous types of computer systems can be used to implement the analytic methods of this invention according to knowledge possessed by a skilled artisan in the bioinformatics and/or computer arts. Several software components can be loaded into memory during operation of such a computer system. The software components can comprise both software components that are standard in the art and components that are special to the present invention (e.g., dCHIP software described in Lin et al. (2004) *Bioinformatics* 20, 1233-1240; radial basis machine learning algorithms (RBM) known in the art).

The methods of the invention can also be programmed or modeled in mathematical software packages that allow symbolic entry of equations and high-level specification of processing, including specific algorithms to be used, thereby freeing a user of the need to procedurally program individual equations and algorithms. Such packages include, e.g., Matlab from Mathworks (Natick, Mass.), Mathematica from Wolfram Research (Champaign, Ill.) or S-Plus from MathSoft (Seattle, Wash.).

In certain embodiments, the computer comprises a database for storage of biomarker data. Such stored profiles can be accessed and used to perform comparisons of interest at a later point in time. For example, biomarker expression profiles of a sample derived from the non-cancerous tissue of a subject and/or profiles generated from population-based distributions of informative loci of interest in relevant populations of the same species can be stored and later compared to that of a sample derived from the cancerous tissue of the subject or tissue suspected of being cancerous of the subject.

In addition to the exemplary program structures and computer systems described herein, other, alternative program structures and computer systems will be readily apparent to the skilled artisan. Such alternative systems, which do not depart from the above described computer system and programs structures either in spirit or in scope, are therefore intended to be comprehended within the accompanying claims.

c. Diagnostic Assays

The present invention provides, in part, methods, systems, and code for accurately classifying whether a biological sample is associated with a cancer that is likely to respond to anti-immune checkpoint inhibitor therapy. In some embodiments, the present invention is useful for classifying a sample (e.g., from a subject) as associated with or at risk for responding to or not responding to anti-immune checkpoint inhibitor therapy using a statistical algorithm and/or empirical data (e.g., the amount or activity of a biomarker listed in Table 1).

An exemplary method for detecting the amount or activity of a biomarker listed in Table 1, and thus useful for classifying whether a sample is likely or unlikely to respond to anti-immune checkpoint inhibitor therapy involves obtaining a biological sample from a test subject and contacting the biological sample with an agent, such as a protein-binding agent like an antibody or antigen-binding fragment thereof, or a nucleic acid-binding agent like an oligonucleotide, capable of detecting the amount or activity of the biomarker in the biological sample. In some embodiments, at least one antibody or antigen-binding fragment thereof is used, wherein two, three, four, five, six, seven, eight, nine, ten, or more such antibodies or antibody fragments can be used in combination (e.g., in sandwich ELISAs) or in serial. In certain instances, the statistical algorithm is a single learning statistical classifier system. For example, a single learning statistical classifier system can be used to classify a sample as a based upon a prediction or probability value and the presence or level of the biomarker. The use of a single learning statistical classifier system typically classifies the sample as, for example, a likely anti-immune checkpoint inhibitor therapy responder or progressor sample with a sensitivity, specificity, positive predictive value, negative predictive value, and/or overall accuracy of at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

Other suitable statistical algorithms are well known to those of skill in the art. For example, learning statistical classifier systems include a machine learning algorithmic technique capable of adapting to complex data sets (e.g., panel of markers of interest) and making decisions based upon such data sets. In some embodiments, a single learning statistical classifier system such as a classification tree (e.g., random forest) is used. In other embodiments, a combination of 2, 3, 4, 5, 6, 7, 8, 9, 10, or more learning statistical classifier systems are used, preferably in tandem. Examples of learning statistical classifier systems include, but are not limited to, those using inductive teaming (e.g., decision/classification trees such as random forests, classification and regression trees (C&RT), boosted trees, etc.), Probably Approximately Correct (PAC) learning, connectionist learning (e.g., neural networks (NN), artificial neural networks (ANN), neuro fuzzy networks (NFN), network structures, perceptrons such as multi-layer perceptrons, multi-layer feed-forward networks, applications of neural networks, Bayesian learning in belief networks, etc.), reinforcement learning (e.g., passive learning in a known environment such as naive learning, adaptive dynamic learning, and temporal difference learning, passive learning in an unknown environment, active learning in an unknown environment, learning action-value functions, applications of reinforcement learning, etc.), and genetic algorithms and evolutionary programming. Other learning statistical classifier systems include support vector machines (e.g., Kernel methods), multivariate adaptive regression splines (MARS), Levenberg-Marquardt algorithms, Gauss-Newton algorithms, mixtures of Gaussians, gradient descent algorithms, and learning vector quantization (LVQ). In certain embodiments, the method of the present invention further comprises sending the sample classification results to a clinician, e.g., an oncologist.

In another embodiment, the diagnosis of a subject is followed by administering to the individual a therapeutically effective amount of a defined treatment based upon the diagnosis.

In one embodiment, the methods further involve obtaining a control biological sample (e.g., biological sample from a subject who does not have a cancer or whose cancer is susceptible to anti-immune checkpoint inhibitor therapy), a biological sample from the subject during remission, or a biological sample from the subject during treatment for developing a cancer progressing despite anti-immune checkpoint inhibitor therapy.

d. Prognostic Assays

The diagnostic methods described herein can furthermore be utilized to identify subjects having or at risk of developing a cancer that is likely or unlikely to be responsive to anti-immune checkpoint inhibitor therapy. The assays described herein, such as the preceding diagnostic assays or the following assays, can be utilized to identify a subject having or at risk of developing a disorder associated with a misregulation of the amount or activity of at least one biomarker described in Table 1, such as in cancer. Alternatively, the prognostic assays can be utilized to identify a subject having or at risk for developing a disorder associated with a misregulation of the at least one biomarker described in Table 1, such as in cancer. Furthermore, the prognostic assays described herein can be used to determine whether a subject can be administered an agent (e.g., an agonist, antagonist, peptidomimetic, polypeptide, peptide, nucleic acid, small molecule, or other drug candidate) to treat a disease or disorder associated with the aberrant biomarker expression or activity.

e. Treatment Methods

The compositions described herein (including dual binding antibodies and derivatives and conjugates thereof) can be used in a variety of in vitro and in vivo therapeutic applications using the formulations and/or combinations described herein. In one embodiment, anti-immune checkpoint inhibitor agents can be used to treat cancers determined to be responsive thereto. For example, antibodies that block the interaction between PD-L1, PD-L2, and/or CTLA-4 and their receptors (e.g., PD-L1 binding to PD-1, PD-L2 binding to PD-1, and the like) can be used to treat cancer in subjects identified as likely responding thereto.

6. Pharmaceutical Compositions

In another aspect, the present invention provides pharmaceutically acceptable compositions which comprise a therapeutically-effective amount of an agent that modulates (e.g., decreases) biomarker expression and/or activity, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "therapeutically-effective amount" as used herein means that amount of an agent that modulates (e.g., inhibits) biomarker expression and/or activity, or expression and/or activity of the complex, or composition comprising an agent that modulates (e.g., inhibits) biomarker expression and/or activity, or expression and/or activity of the complex, which is effective for producing some desired therapeutic effect, e.g., cancer treatment, at a reasonable benefit/risk ratio.

The phrase "pharmaceutically acceptable" is employed herein to refer to those agents, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the subject. Some examples of materials which can serve as pharmaceutically-acceptable carriers include: (1) sugars, such as lactose, glucose and sucrose, (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar, (14) buffering agents, such as magnesium hydroxide and aluminum hydroxide; (15) alginic acid; (16) pyrogen-free water, (17) isotonic saline; (18) Ringer's solution; (19) ethyl alcohol; (20) phosphate buffer solutions; and (21) other non-toxic compatible substances employed in pharmaceutical formulations.

The term "pharmaceutically-acceptable salts" refers to the relatively non-toxic, inorganic and organic acid addition salts of the agents that modulates (e.g., inhibits) biomarker expression and/or activity, or expression and/or activity of the complex encompassed by the invention. These salts can be prepared in situ during the final isolation and purification of the agents, or by separately reacting a purified agent in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like (See, for example, Berge et al. (1977) "Pharmaceutical Salts", *J. Pharm. Sci.* 66:1-19).

In other cases, the agents useful in the methods of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of agents that modulates (e.g., inhibits) biomarker expression and/or activity, or expression and/or activity of the complex. These salts can likewise be prepared in situ during the final isolation and purification of the agents, or by separately reacting the purified agent in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like: (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations useful in the methods of the present invention include those suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient, which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an agent that modulates (e.g., inhibits) biomarker expression and/or activity, with the carrier and, optionally, one or more accessory ingredients. In general, the formulations are prepared by uniformly and intimately bringing into association a agent with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a agent as an active ingredient. A compound may also be administered as a bolus, electuary or paste.

In solid dosage forms for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia: (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent.

Tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions, which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions, which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active agent may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more agents with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Formulations which are suitable for vaginal administration also include pessaries, tampons, creams, gels, pastes, foams or spray formulations containing such carriers as are known in the art to be appropriate.

Dosage forms for the topical or transdermal administration of an agent that modulates (e.g., inhibits) biomarker expression and/or activity include powders, sprays, ointments, pastes, creams, lotions, gels, solutions, patches and inhalants. The active component may be mixed under sterile conditions with a pharmaceutically-acceptable carrier, and with any preservatives, buffers, or propellants which may be required.

The ointments, pastes, creams and gels may contain, in addition to a agent, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an agent that modulates (e.g., inhibits) biomarker expression and/or activity, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The agent that modulates (e.g., inhibits) biomarker expression and/or activity, can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a agent to the body. Such dosage forms can be made by dissolving or dispersing the agent in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this invention.

Pharmaceutical compositions of this invention suitable for parenteral administration comprise one or more agents in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of an agent that modulates (e.g., inhibits) biomarker expression and/or activity, in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

When the agents of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

Actual dosage levels of the active ingredients in the pharmaceutical compositions of this invention may be determined by the methods of the present invention so as to obtain an amount of the active ingredient, which is effective to achieve the desired therapeutic response for a particular subject, composition, and mode of administration, without being toxic to the subject.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054 3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The present invention also encompasses kits for detecting and/or modulating oncogene biomarkers (e.g., activating mutations in oncogene biomarkers) and tumor suppressor biomarkers (e.g., inhibiting mutations in tumor suppressors) described herein. A kit of the present invention may also include instructional materials disclosing or describing the use of the kit or an antibody of the disclosed invention in a method of the disclosed invention as provided herein. A kit may also include additional components to facilitate the particular application for which the kit is designed. For example, a kit may additionally contain means of detecting the label (e.g., enzyme substrates for enzymatic labels, filter sets to detect fluorescent labels, appropriate secondary labels such as a sheep anti-mouse-HRP, etc.) and reagents necessary for controls (e.g., control biological samples or metabolite standards). A kit may additionally include buffers and other reagents recognized for use in a method of the disclosed invention. Non-limiting examples include agents to reduce non-specific binding, such as a carrier protein or a detergent.

Other embodiments of the present invention are described in the following Examples. The present invention is further illustrated by the following examples which should not be construed as further limiting.

EXAMPLES

Example 1: Materials and Methods for Examples 2-7 a. Mouse Cohorts and Human Samples

Mouse cohorts of Lkb1$^{fl/fl}$;Pten$^{fl/fl}$, Lkb1$^{fl/fl}$;Pten$^{fl/fl}$;p53; LSL:Kras$^{G12D}$, LSL:Kras$^{G12D}$;p53$^{fl/fl}$, LSL:Kras$^{G12D}$; Lkb1$^{fl/fl}$, LSL:Kras$^{G12D}$;Pten$^{fl/fl}$ and LSL:Kras$^{G12D}$; LKB1$^{fl/fl}$;p53$^{fl/fl}$ were all maintained in virus-free conditions on a mixed 129/FVB background. Nu/Nu mice were purchased from Charles River Laboratories International Inc. All the mice were housed in a BL2 lab at Dana Farber Cancer Institute. All care and treatment of experimental animals were in accordance with Harvard Medical School/Dana-Farber Cancer Institute institutional animal care and use committee (IACUC) guidelines. Mice were given Ad-Cre via intranasal infections at 6-8 weeks old. Mice were monitored for signs of lung tumor onset and euthanized for gross and histological analysis and tumor isolation upon signs of distress. Patient slides were provided by the pathology department of Brigham and Women's Hospital. All human samples and clinical information were obtained under Institutional Review Board approved protocols (02-180 and 07-0120). Frozen PDX tissues were purchased from the Van Andel Institute (Grand Rapids, Mich.).

b. Flow Cytometry Analysis and Sorting

Tumors were dissected from the lungs of primary mice and tumor tissue was prepared as described in Curtis et al. (2010) *Cell Stem Cell* 7:127-133 and Akbay et al. (2013) *Cancer Discov.* 3:1355-1363. Single cell suspensions were stained using rat-anti-mouse antibodies. Detailed antibody information and gating strategy can be found in Akbay et al. (2013) *Cancer Discov.* 3:1355-1363 and as follows:

| Gating strategy and antibody list for flow cytometry | |
|---|---|
| Cells | Gating markers |
| Tumor Associated Macrophages (TAMs) | CD45$^+$CD11c$^+$CD11b$^-$ CD103$^-$ |
| Tumor Associated Neutrophils (TANs) | CD45$^+$ CD11b$^+$Ly6G$^+$ |
| T cells | CD45$^+$CD3$^+$ |
| Treg cells | CD45$^+$CD3$^+$FOXP3$^+$ |
| B cells | CD45$^+$CD19$^+$ |
| NK cells | CD45$^+$DX5$^+$NKp46$^+$CD3$^-$ |

| Anti-murine antibodies | | | |
|---|---|---|---|
| Antigen | Clone | Antigen | Clone |
| CD103 | 2E7 | F4/80 | BM8 |
| CD11b | M1/70 | FOXP3 | FJK-16s |
| CD11c | N418 | LAG-3 | 631501 |
| CD31 | MEC 13.3 | Ly6C | HK1.4 |
| CD3ε | 145-2C11 | Ly6G | 1A8 |
| CD4 | RM4-5 | NGFR | EP1039Y |
| CD44 | IM7 | PD-1 | 29F.1A12 |
| CD45 | 30-F11 | PD-L1 | 10F.9G2 |
| CD8 | 53-6.7 | SCA 1 | D7 |
| CTLA-4 | UC10-4B9 | TIM-3 | RMT3-23 |
| EpCAM | G8.8 | CD16/CD32 | 2.4G2 |

| Anti-human antibodies | |
|---|---|
| Antigen | Clone |
| CD31 | WM59 |
| CD45 | HI39 |
| EpCAM | EBA-1 |
| NGFR | ME20.4 |
| PD-L1 | MIH1 |

All antibodies were incubated for 15-20 minutes at 1:100 dilutions for primary antibodies and 1:200 for secondary antibodies. Cell sorting was performed with a BD FACS Aria II, and data were analyzed with FloJo software (Tree Star). For sorting NGFR and SCA1 fractions, cells were first gated on FSC/SCC and DAPI$^-$ cells, then on EpCAM-PECy7$^+$CD45-APC$^-$CD31-APC$^-$, and finally on SCA1-FITC and NGFR-PE fractions.

c. 3D Culture and Tumor Transplants

FACS-sorted mouse cells were resuspended in MTEC/Plus containing 20 ng/ml EGF and FGF2, mixed 1:1 with growth factor-reduced Matrigel (BD Biosciences), and pipetted into a 12-well 0.4 μm Transwell insert (Falcon). MTEC/Plus medium (700 μl) was added to the lower chamber and refreshed every other day. Intratracheal transplants were performed as described (Curtis et al. (2010) *Cell Stem Cell* 7:127-133). Intrathoracic injections were performed as described (Jongsma et al. (2008) *Cancer Cell* 13:261-271).

d. Gene Expression Profile Analysis

Arrays were performed in Dana-Farber Cancer Institute facility on Affymetrix mouse Gene1.0ST slides. Array quality was assessed using the R/Bioconductor package (available on the World Wide Web at bioconductor.org). Raw CEL files from U133A Affymetrix arrays were processed using the robust multiarray average (RMA) algorithm (Irizarry et al. (2003) *Nucleic Acids Res.* 31:e15). To identify genes correlating with the phenotypic groups, the limma and SAM algorithms (Smyth (2004) *Stat. Appl. Genet. Mol. Biol.* 3:Article3 (e-pub)) were used to fit a statistical linear model to the data. The data were then tested for differential gene expression in the three groups: Normal EpCAM$^+$, Kras tumor EpCAM$^+$ and LP tumor EpCAM$^+$. For the analysis of the EpCAM$^-$CD45$^+$ immune cell fractions, LP tumor EpCAM$^+$, Kras tumor CD45$^+$ and LP tumor CD45$^+$ were contrasted. The vennSelect function in R was used to contrast the differentially expressed genes for each cell type. Multiple hypothesis testing was corrected for using the Benjamini and Hochberg method (BH) (Benjamini and Hochberg (1995) *J. R. Statist. Soc. B* 57:289-300), and significantly differentially expressed genes are reported (Table 2). The array raw data and log 2 RMA signal were uploaded to GEO under GEO accession number: GSE54353. For the mouse and human comparative analysis fold changes of gene expression in the LP mice as compared to normal lung and human squamous cell cancers with PTEN or LKB1 abnormalities compared to normal lung (available on the World Wide Web at tcga-data.nci.nih.gov/tcga/) were analyzed using SAMR using the two class comparison function (available on the World Wide Web at stat.stanford.edu/~tibs/SAM/). For GSEA analysis (Subramanian et al. (2005) *Proc. Natl. Acad. Sci. U.S.A.* 102: 15545-15550) either the LP tumor EpCAM$^+$ vs Kras tumor EpCAM$^+$ rank ordered gene list, or the LP tumor CD45$^+$ vs Kras tumor CD45$^+$ rank ordered gene list was used.

e. Quantitative RT PCR

RNA-sorted tumor populations was isolated on Qiagen RNeasy kit. cDNA was made using the SuperScript II kit (Invitrogen). Relative gene expression was assayed with Taqman assays performed on the StepOnePlus™ Real-Time PCR System (Applied Biosystems).

f. Histology and Immunohistochemistry

Mice were sacrificed with $CO_2$ and the right lobe was dissected and snap-frozen for biochemical analysis. The remainder of the lungs was inflated with neutral buffered 10% formalin overnight at room temperature and then transferred to 70% ethanol, embedded in paraffin, and sectioned at 5 μm. Hematoxylin and eosin (H&E) stains were performed in the Department of Pathology in Brigham and Women's Hospital. PD-L1 immunohistochemistry was performed using an automated immunostainer (Ventana, Tucson, Ariz.) on patient slides and manually on the mouse slides at 10 mg/ml concentration using anti-PD-L1 antibody as described in Chen et al. (2013) *Clin. Cancer Res.* 19:3462-3473. Antibodies used for other markers are listed below:

| Antibodies | Companies | Cat. ID |
|---|---|---|
| p-AKT | Cell Signaling | 4060 |
| P-ERK1/2 | Cell Signaling | 4376 |
| MPO | Novus | R-1073 |
| F4/80 | eBioscience | 14-4801-82 |
| CD163 | Leica | NCL-CD163 |
| EpCAM | Protein Tech | 21050-1-AP |
| Cytokeratin 5 | Epitomics | 1988-1 |
| TTF1 | DAKO | M3575 |
| p63 | Abcam | ab53039 |
| SOX2 (C70B1) | Cell Signaling | 3728S |
| NGFR | Epitomics | 1812-1 |
| FOXP3 | eBioscience | 14-5773 |
| SPC | Millipore | AB3786 | g. BALF Collection and Cytokine Measurement

One milliliter of PBS was injected into the trachea to inflate the lungs, which were then aspirated and frozen. Cytokine concentrations in BALFs were measured with ELISA kits for mouse CXCL1, CXCL2, CCXL5, CXCL7, GCSF, TGF-β1 (R&D Systems) and IL6 (BD biosciences).

h. Metabolomics Profiles Analysis

Metabolite extraction and targeted mass spectrometry analysis for metabolomics profiles were conducted as described in Yuan et al. (2012) *Nat. Protoc.* 7:872-881. Briefly, the frozen tumors were smashed in cold 80% HPLC-grade methanol on dry ice twice, and then the extractions were Speed Vac/lyophilized to a pellet using no heat. The data were normalized and analyzed with MetaboAnalyst 2.0 (Xia et al. (2012) *Nucleic Acids Res.* 40:W127-W133). In hierarchical cluster analysis, each sample begins as a separate cluster and the algorithm proceeds to combine them until all samples belong to one cluster. Clustering result shown as a heat map (distance measure using Pearson and clustering algorithm using ward).

i. Statistical Analysis

Statistical analyses were carried out using GraphPad Prism. All numerical data are presented as mean±standard error of the mean (SEM). Grouped analysis was performed using two-way ANOVA. Column analysis was using one-way ANOVA or t-test. A p-value less than 0.05 was considered statistically significant.

j. Gene Expression Data

Expression data from wild type and EGFR transgenic mice were obtained from Weaver et al. (2012) *Cancer Res.* 72:921-933. Expression data from Kras mutant mice were obtained from Chen et al. (2010) *Cancer Res.* 70:9827-9836. The data were converted into log 2 values.

k. Mouse Husbandry and Breeding

All EGFR transgenic mice carrying tetracycline inducible human EGFR cDNA were previously generated, crossed with CC10-RTTA mice expressing reverse tetracycline activator from lung Clara cell CC10 promoter, and maintained in mixed background. Double positive progeny were fed with doxycycline diet starting at 5-6 weeks of age for the induction of tumors and maintained on doxycyline throughout the study. EGFR and KrasG12D mice were maintained in mixed (C57Bl/6, FVB, and S129) background and given adeno virus expressing Cre recombinase ($5\times10^6$ titer) intranasally at 5 weeks of age for induction of recombination and tumor formation. All breedings and in vivo experiments were performed with the approval of the DFC1 Animal Care and Use Committee.

n. Arginase Inhibitor Compounds and Treatment

The arginase inhibitor (R)-2-Amino-6-borono-2-(2-(piperidin-1-yl)ethyl)hexanoic acid, also known as compound HY-15775/compound 9, was obtained from MedChem Express and is well known in the art (see, for example, Van Zandt et al. (2013) *J. Med. Chem.* 56:2568-2580). The compound was administered to mice at 30 mg/kg in phosphate-buffered saline (PBS) via oral gavage once daily.

m. Immune Cell Analysis

Total lung cell and tumor infiltrating immune cell characterization was performed as described in Akbay et al. (2013) *Cancer Discov.* 3:1355-1363.

n. MRI Tumor Volume Quantification

Animals were anesthetized with 1.5-2% isoflurane (Iso-Flo; Abbott) in 100% oxygen. Both cardiac and respiratory gating was applied to minimize motion effects. Acquisition of the magnetic resonance signal was synchronized with the cardiac and respiratory cycles. MRI protocols optimized for assessing pulmonary parenchyma and vessels in normal mice were adapted for operation at 7 Tesla (BioSpec; Broker BioSpin). Tumor volume quantifications were performed using 3D-Slicer software as described in Weaver et al. (2012) *Cancer Res.* 72:921-933.

Example 2: Lkb1$^{fl/fl}$;Pten$^{fl/fl}$ Mice Develop Lung Squamous Cell Carcinomas that Recapitulate the Human Disease In order to examine the possibility that Lkb1 and Pten loss would lead to lung SCC formation, 6-8 week-old Lkb1$^{fl/fl}$, Pten$^{fl/fl}$ (Lkb1,Pten or LP) mice were administered Adenovirus-Crec (Ad-Cre) via intranasal instillation (FIG. 1A). In contrast to other lung-specific genetic mouse models described to date, including Kras$^{G12D}$ (Kras), Kras$^{G12D}$: p53$^{fl/fl}$ (Kras;p53), Kras$^{G12D}$;Lkb1$^{fl/fl}$ (Kras;Lkb1) and Kras$^{G12D}$;p53$^{fl/fl}$;Lkb1$^{fl/fl}$ (Kras;p53;Lkb1), in which the predominant phenotypes are adenocarcinoma or mixed adenosquamous cell carcinoma, 100% of the LP mice developed typical lung squamous cell carcinomas (SCC) with a 40-50 week latency (FIGS. 1B and 2A-2B). Small malignant nodules with squamous characteristics were evident at different time-points after Ad-Cre infection ranging from 30 to 40 weeks. Both Lkb1 and Pten were confirmed to be homozygously deleted by PCR on genomic DNA from sorted tumor cells (FIG. 2C). The LP tumors were verified as recapitulating human SCC pathology: within the tumor nodules, mature squamous cells growing in a solid configuration with aberrant nuclear morphology (FIG. 1Ca), large infiltrates of neutrophils (FIG. 1Cb), and keratinized cells or individual cells with markedly dense eosinophilic cytoplasm were all observed (FIG. 1Cc). Tumors showed hallmarks of well-differentiated SCC, including invading fibrous stroma with prominent keratinization (keratin pearls) (FIG. 1Cd). In some cases, SCC nodules were visible in airways (FIG. 1Ce), and at later time points showed lymphovascular invasion (FIG. 1Cf). Tumors arose in both the proximal (FIG. 2D, top arrow) and distal lung (FIG. 2D-2E, bottom arrows), though many nodules appeared to be surrounded completely by alveolar epithelium. Low frequency metastatic lesions were visible in the chest wall of these mice (3/78) (FIG. 2F).

To confirm the phenotype of the LP tumors, immunohistochemistry was performed for markers used clinically to distinguish human lung ADC from lung SCC. TTF1 (also known as NKX2-1) and SOX2 are genomically amplified in lung adenocarcinomas and squamous cell carcinomas, respectively, and routinely used as histologic markers (Bass et al. (2009) *Nat. Genet.* 41:1238-1242; Weir et al. (2007) *Nature* 450:893-898). In addition, positive staining for the markers p63 and keratin-5/6 (KRT5/6) appear to robustly classify SCCs from ADCs (Fatima et al. (2012) *Diagn. Cytopathol.* 40:943-948). Similar to the human SCC samples, the LP tumor nodules displayed high expression of p63, KRT5 and SOX2, while TTF1 staining was negative (FIG. 3A). The expression patterns of p63, KRT5 and SOX2 in SCC co-localized with the expression of epithelial cell adhesion molecule (EpCAM) (FIG. 3A). In contrast, Kras$^{G12D}$-driven murine ADC and human ADC tissues were p63-, KRT5- and SOX2-negative, while TTF1 staining was strongly positive, confirming their ADC phenotype (FIG. 3A). Together these data indicate that LP tumors strongly resemble human SCC by their expression of the classic squamous markers p63, KRT5/6 and SOX2, and hallmarks of squamous differentiation such as keratin deposition.

Figure 3:
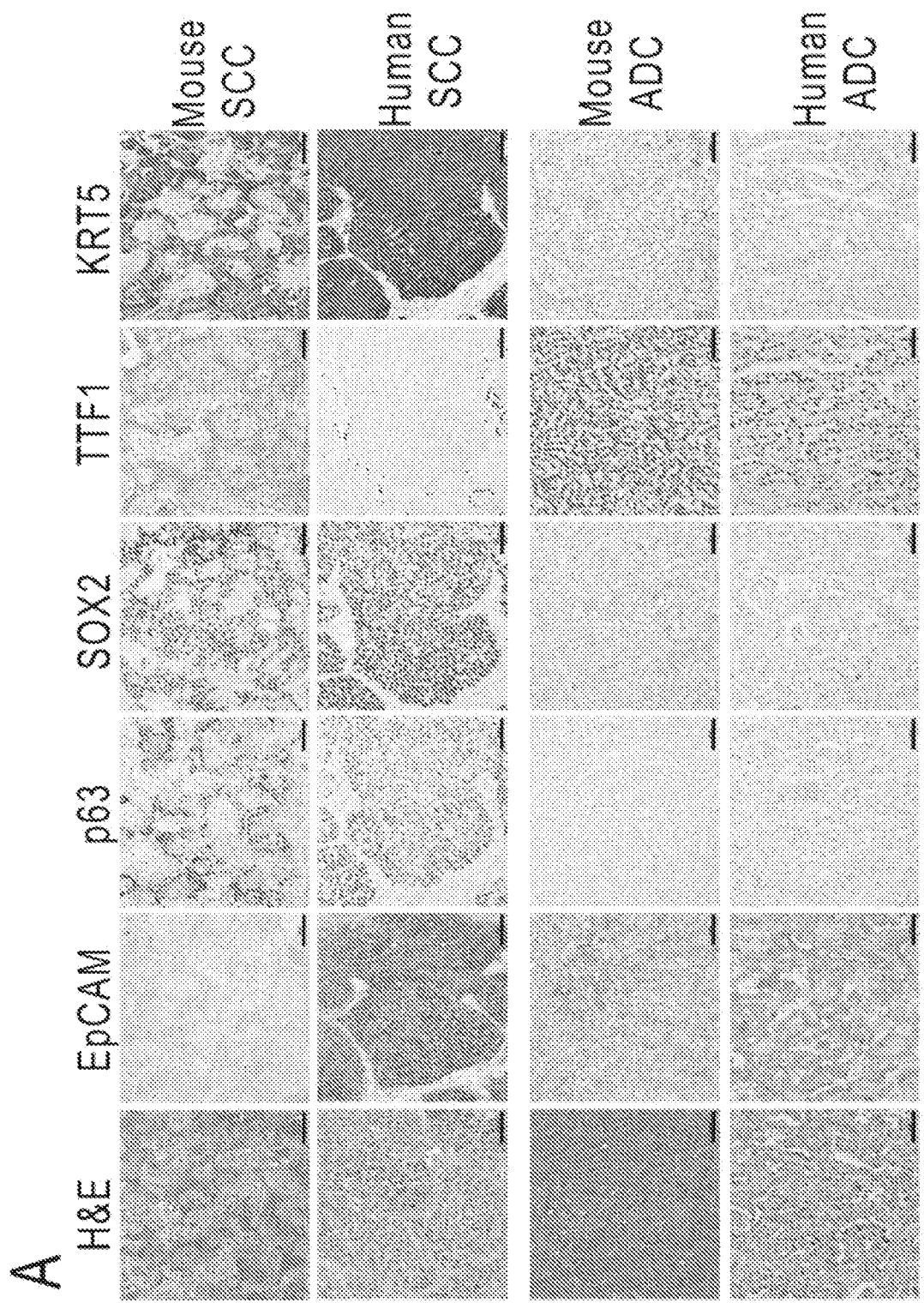
FIG. 3 includes 3 panels, identified as panels A, B, and C, which show that lung SCCs in $Lkb1^{fl/fl}$;$Pten^{fl/fl}$ mice closely recapitulate the human disease. Panel A shows the results of immunohistochemically stained human and mouse ADC and SCC tumors. The SCC canonical markers KRT5, SOX2 and p63, and the ADC canonical marker TTF1, were used to distinguish the tumor types. EpCAM is an epithelial cell marker, and the expression patterns of p63, KRT5 and SOX2 in SCC co-localized with EpCAM expression. Scale bar=100 µm for all panels. Panel B shows microarray expression profiling results of normal lung and SCC tumors from mouse and human. Up-regulated genes in both mouse and human SCC were enriched for a squamous differentiation signature. Panel C shows that down-regulated genes from the analysis in Panel B were enriched for a normal lung terminal respiratory unit signature.
Figure 3:
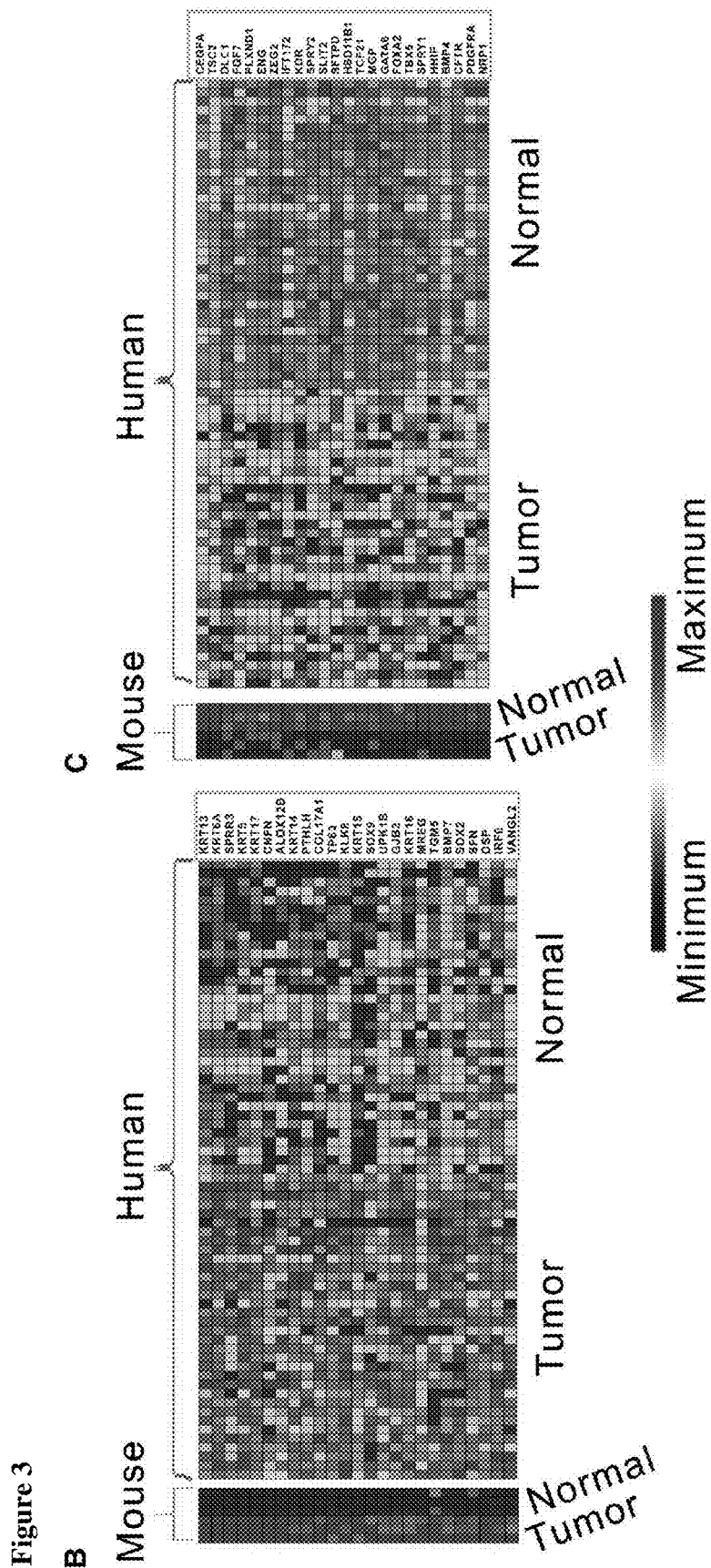
Figure 4:
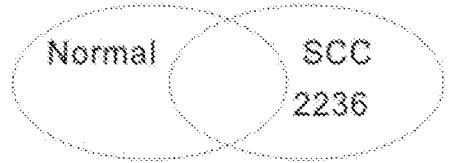
FIG. 4 includes 2 panels, identified as panels A and B, which further show that lung SCCs in $Lkb1^{fl/fl}$;$Pten^{fl/fl}$ mice closely recapitulate the human disease. Panel A shows a schematic of a gene expression profile comparison of 34 human SCC tumors with either LKB1 or PTEN alterations to 35 normal human lung tissues samples, and three tumor bearing Lkb1;Pten mouse SCC to lungs from age-matched LP mice that never received Ad-Cre. There were 489 up-regulated genes and 404 down-regulated genes shared by the human and mouse contrasts. Panel B shows that the results of the 893 shared differentially expressed genes in human and mouse SCC clustered and displayed by heat map.
Figure 4:
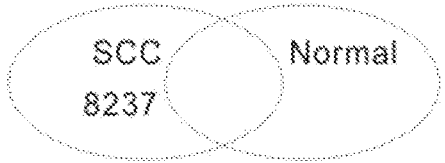
Figure 4:
Figure 4:
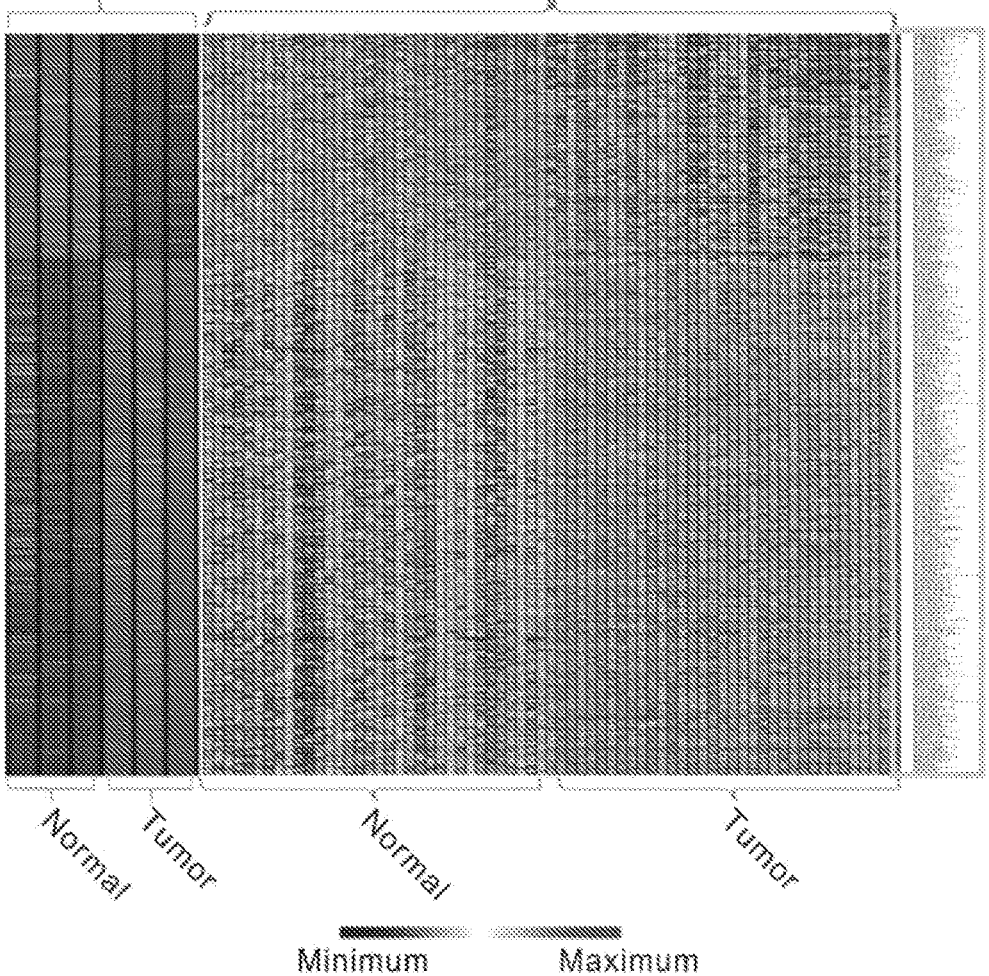

Next, the transcriptional landscapes of the LP tumors to those found in primary human tumors were compared. To do this, the gene expression profile of 34 human SCC tumors with either LKB1 or PTEN alterations from the Cancer Genome Atlas (Cancer Genome Atlas Research (2012) *Nature* 489:519-525) was compared to 35 normal human lung tissues samples to generate a list of genotype-specific SCC genes. In parallel, the gene expression profiles of LP tumors from three independent mice were compared to profiles of normal lung from three age-matched LP mice that never received Ad-Cre. In the human comparison, 8237 genes were significantly differentially expressed in the SCCs versus normal human lung with a corrected p value (90$^{th}$ percentile FDR) of zero. Compared to normal, 3658 genes were up-regulated in tumors and 4579 down-regulated. In the smaller mouse dataset, 2236 genes were differentially expressed with 916 up-regulated and 1320 down-regulated (FIG. 4A). Comparison of the mouse and human gene sets yielded 893 genes that were significantly differentially expressed in both human tumors with LKB1 and/or PTEN alterations and LP mouse SCCs (FIG. 4B). Among the shared up-regulated genes were several known squamous-associated genes, including SOX2, P63, NOTCH3. HRAS and several keratins (KRT5/KRT6). Gene ontogeny analysis demonstrated enrichment for genes implicated in squamous differentiation (p=3.62×10$^{-10}$; FIG. 3B). In contrast, the shared down-regulated genes were enriched for terminal respiratory unit differentiation, consistent with the idea that SCC more closely resembles proximal lung cells than distal epithelia (p=4.07×10$^{-7}$; FIG. 3C).

Figure 5:
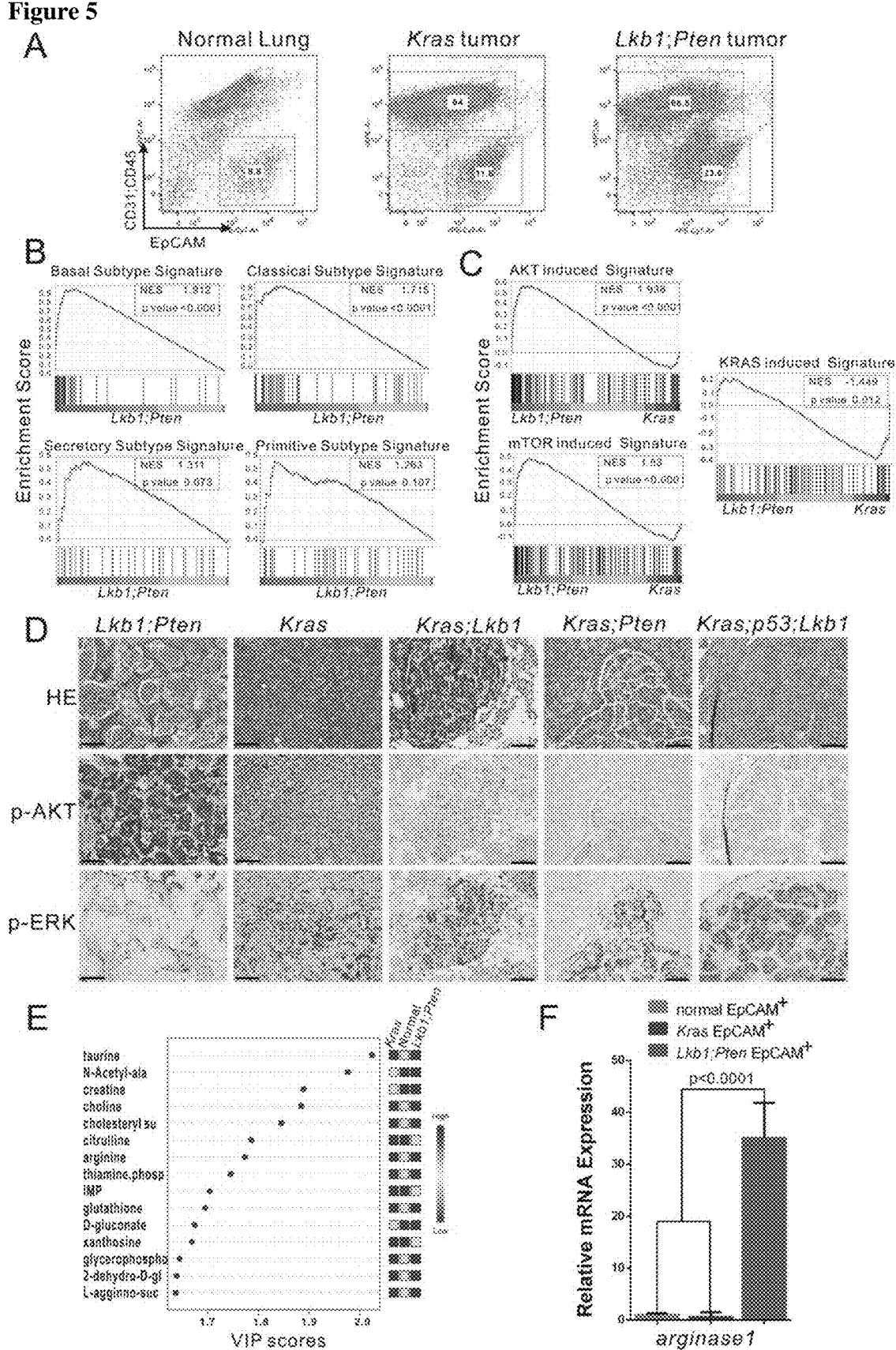
FIG. 5 includes 6 panels, identified as panels A, B, C, D, E, and F, which show that $Lkb1^{fl/fl}$;$Pten^{fl/fl}$ lung SCCs display unique gene expression, metabolism, and downstream signaling pathways. Panel A shows representative flow cytometric plots for sorting the epithelial fractions (CD45⁻CD31⁻EpCAM⁺) from LP tumor nodules, Kras tumor nodules and normal lung. The RNA from purified epithelial cells was extracted for gene expression profile analysis. Panel B shows the results of gene set enrichment analysis (GSEA) (Subramanian et al. (2007) *Bioinformatics* 23:3251-3253) used to compare the gene expression profile of Lkb1;Pten tumor cells to transcriptionally well-defined subclasses of human lung SCC (Wilkerson et al. (2010) *Clin. Cancer Res.* 16:4864-4875). GSEA was performed using the Java GSEA desktop application on pre-ranked gene lists constructed from RMA normalized expression data. The Lkb1;Pten model very closely recapitulates the expression pattern found in the basal subtype of human SCC. Panel C shows the results of GSEA analysis used to discover the molecular pathways altered in Lkb1;Pten and Kras tumors. All gene sets were downloaded from the World Wide Web at broadinstitute.org/gsea/msigdb/genesets.jsp. AKT and mTOR gene sets were both derived from Majumder et al. (2004) *Nat. Med.* 10:594-601. The lung-specific KRAS mutation gene set was derived from Barbie et al. (2009) *Nature* 462:108-112. Compared to Kras tumors, AKT and mTOR gene sets are both more significantly enriched in the Lkb1;Pten model. Panel D shows the results of immunohistochemical staining for H&E, p-AKT and p-ERK on Lkb1; Pten, Kras, Kras;Lkb1, Kras;Pten and Kras;p53;Lkb1 tumor nodules with low magnification (×200). Scale bar=100 µm for all panels. Panel E shows a graph of top metabolites used to cluster normal lung from Kras tumor and Lkb1;Pten tumor. L-arginine (reduced) and creatine (increased), two byproducts of L-arginine metabolism, show that the arginine metabolism pathway is skewed towards the function of the enzyme arginase1 in the Lkb1;Pten tumors. Panel F shows the results of real-time RT-PCR for arginase1 mRNA expression in the indicated EpCAM⁺CD45⁻CD31⁻ purified populations from normal lung, Kras, and Lkb1;Pten tumors. Comparing with normal lung and Kras, arginase1 is highly expressed in Lkb1;Pten EpCAM⁺CD45⁻CD31⁻ tumors cells (n=5 for normal EpCAM⁺ cells; n=4 for Kras EpCAM⁺ cells; n=5 for Lkb1;Pten EpCAM⁺ cells; data are presented as mean+/−SEM; p<0.0001).
Figure 6:
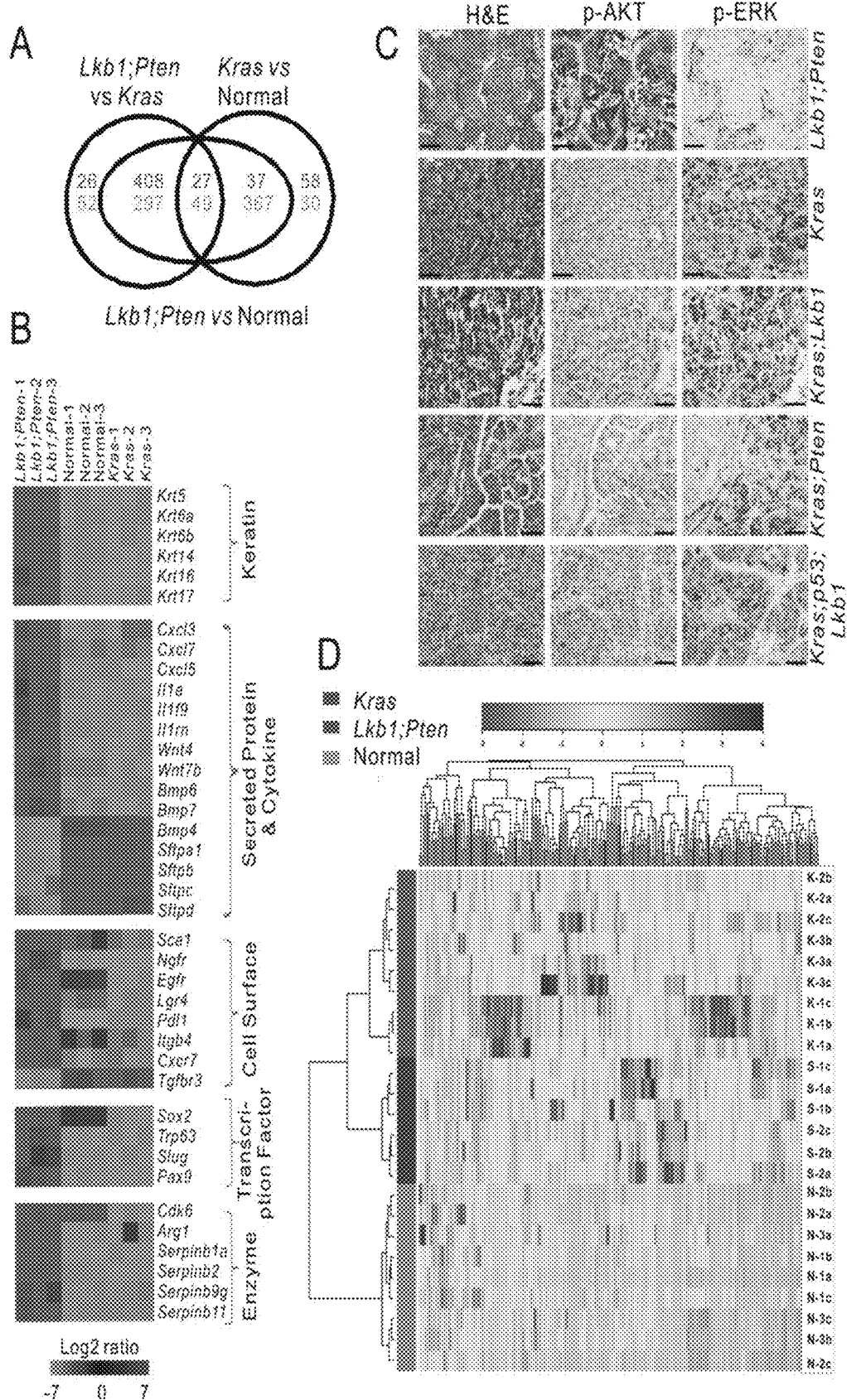
FIG. 6 includes 4 panels, identified as panels A, B, C, and D, which further show that $Lkb1^{fl/fl}$;$Pten^{fl/fl}$ lung SCCs display unique gene expression, metabolism, and downstream signaling pathways. Panel A shows the results of EpCAM$^+$CD31$^-$CD45$^-$ cells isolated by FACS and subjected to microarray expression analysis (top line=number of up-regulated genes; bottom line-number of down-regulated genes). An Euler diagram illustrating the gene expression profiles of epithelial cells from LP SCCs, Kras ADCs, and normal lung tissues, is shown. Panel B shows a heat map depicting differential expression of selected genes in LP SCCs, Kras ADCs and normal lung tissues as determined by microarray expression profiling. Red indicates up-regulation and green indicates down-regulation. Panel C shows the results of immunohistochemical staining for p-AKT and p-ERK on LP, Kras, Kras;Lkb1, Kras;Pten and Kras;p53; Lkb1 tumor nodules. Scale bar=50 µm for all panels. Panel D shows the results of hierarchical clustering by Ward Method of quantitative metabolomic profiling for LP SCC tumors (S). Kras ADC (K) tumors and normal lung tissues (N).

Example 3: Lkb1$^{fl/fl}$;Pten$^{fl/fl}$ Lung SCCs Display Unique Gene Expression, Metabolism and Downstream Signaling Pathways In order to characterize the gene expression profiles specific to the tumor cells within the mouse Lkb1;Pten SCCs, fluorescence activated cell sorting (FACS) was used to enrich for the epithelial cells (CD45$^-$CD31$^-$EpCAM$^+$) from LP SCC tumor nodules, Kras driven tumor nodules and normal lung (FIG. 5A). The gene expression profiles of these three epithelial cell fractions were then contrasted (FIG. 6A; p<0.001). Remarkably, all of the genes differentially expressed between normal epithelial and LP tumor cells are likewise differentially expressed when comparing Kras tumor to LP tumor cells. This result indicates that Kras tumors retain some gene expression reminiscent of the normal distal lung epithelial cell, from which they likely arise. In contrast, LP tumor cells do not resemble ADC or normal distal lung cells, and instead have markers expressed by tracheal basal cells as discussed below.

The genes that were differentially expressed in the LP tumor cells when compared to both Kras tumor cells and normal lung were then focused on. In this comparison, 408 genes were up-regulated and 297 genes were down-regulated with a log fold change >1.8 and an adjusted p value <0.001 (Table 2). Selected genes that can be organized by function/family are illustrated by a heat map (FIG. 6B). Gene sets that were up-regulated in LP tumors include the keratin family members, including Krt5, which were observed by IHC, and other squamous keratins, such as Krt6a, Krt6b and Krt14. Also highly up-regulated in LP tumors were the transcription factors Sox2 and p63, consistent with the IHC results, and Slug and Pax9. Among the secreted proteins and cytokines produced by these tumors were several Cxcl family members, including Cxcl3, Cxcl7 and Cxcl5, and members of the Wnt, Bmp and interleukin super-families. Several enzymes that were highly expressed in LP cells included Serpin family members and arginase1. Lastly, genes for proteins and receptors known to be localized to the cell membrane that were highly expressed in LP cells included Sca1, Ngfr, Egfr and Pdl1. Ngfr in particular was of interest because it is known to be a stem cell marker in the tracheal epithelium, and Pdl1 expression suggested a mechanism of immune evasion for LP tumor cells. Genes down-regulated in LP tumors included Tgfrb3 and surfactants.

Gene set enrichment analysis (GSEA) was then used to query the pathways and molecular phenotypes specific to the LP tumors (Subramanian et al. (2007) *Bioinformatics* 23:3251-3253). To do this, a rank-ordered gene list derived from the contrast of LP EpCAM$^+$ cells to Kras EpCAM$^+$ cells was used. The gene list was first queried for enrichment of the four known transcriptionally defined sub-classes of human lung SCC (Wilkerson et al. (2010) *Clin. Cancer Res.* 16:4864-4875). It was found that the LP model very closely recapitulates the expression pattern found in the basal subtype of human SCC (FIG. 5B; p<0.0001; NES=1.9). Gene sets enriched in the LP tumor cells compared to Kras tumor cells included those positively regulated by AKT1 and mTOR, while a lung specific KRAS-associated gene set was enriched in the Kras cells (FIG. 5C; p<0.0001 for AKT1 and mTOR; p=0.012 for KRAS). In addition, compared to tumors driven by Kras, Kras;Lkb1. Kras;Pten and Kras;p53; Lkb1, the LP tumors have much stronger p-AKT but weaker p-ERK staining (FIGS. 6C-6D). Together these data indicate that the oncogenic signaling pathways activated in the Lkb1;Pten tumors predominantly involve AKT and mTOR, while those in Kras tumors involve downstream mediators of RAS signaling such as MEK and ERK.

To address potential metabolic differences between SCC, ADC and normal lung, the metabolites in each tissue were profiled. In addition to the transcriptional differences observed among the samples, metabolic profiles of LP tumors, Kras tumors and normal murine lungs were unique. The metabolic profiles of both Kras and LP tumors clustered completely separately from normal lung. Furthermore, metabolites in Kras tumors and LP tumors segregated the tumor types into two distinct clusters (FIG. 6D and Table 3). Among the metabolites most significantly changed in LP cells relative to normal lung were L-arginine (reduced) and creatine (increased) (FIG. 5E), which were expected due to the increased expression of arginase1 in these cells, which was confirmed by real-time RT-PCR (FIG. 5F; p<0.001).

Example 4: Lkb1$^{fl/fl}$;Pten$^{fl/fl}$ Lung SCCs are Enriched for Tumor-Associated Neutrophils (TANs)

Figure 7:
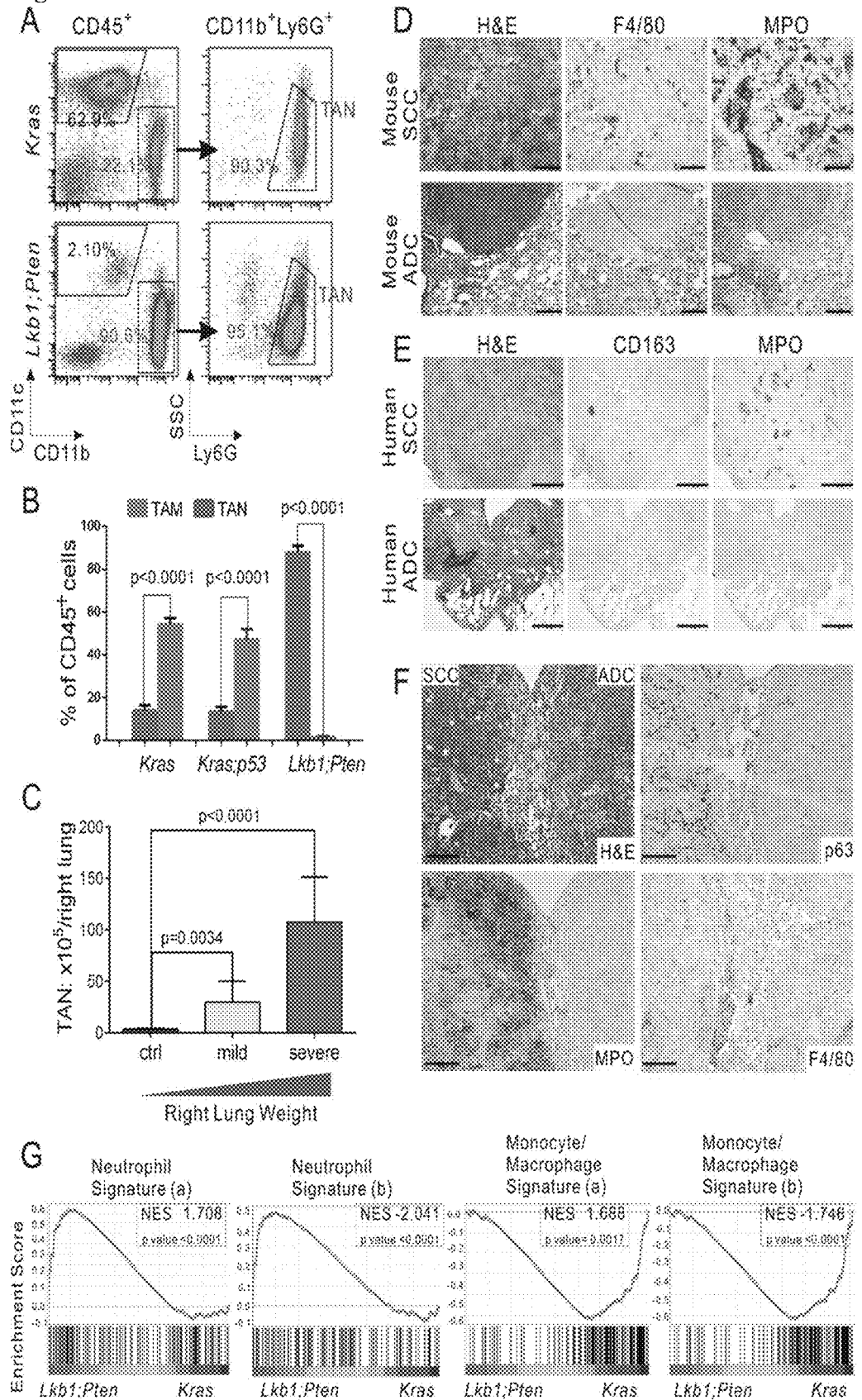
FIG. 7 includes 7 panels, identified as panels A, B, C, D, E, F, and G, which show that tumor-associated neutrophils (TANs) were the predominant inflammatory cell population in Lkb1$^{fl/fl}$;Pten$^{fl/fl}$ SCC tumors. Panel A shows representative flow cytometry plots for Kras ADC and LP SCC dissociated tumors. Plots are gated on live single CD45$^+$ cells. Gating was performed as described in the Examples. In Kras tumors, tumor TAMs (CD45$^+$CD11c$^+$CD11b$^-$CD103$^-$) comprised the majority of CD45$^+$ cells, while in LP tumors, TANs (CD45$^+$CD11b$^+$Ly6G$^+$) were predominant. Panel B shows quantification of inflammatory cell populations in Kras tumors (n=7), Kras;p53 tumors (n=8) and Lkb1;Pten tumors (n=7) by flow cytometry (mean+/−SEM; p<0.0001). Panel C shows quantification of TANs within right lung lobes from samples with progressively increasing weights (shown in Panel A of FIG. 8), indicating different tumor burdens. N=8 for normal lung control; n=5 for mild disease group (tumor plus surrounding tissue weight less than 750 mg); n=5 for severe disease group (tumor plus surrounding tissue weight greater than 750 mg); mean+/−SEM; mild vs. control p=0.0034; severe vs. control p<0.0001. Panels D and E show representative immunohistochemical staining for MPO, F4/80, and CD163 in SCCs and ADCs. The mouse slides were LP SCC and Kras driven ADCs. MPO staining indicating neutrophils was only positive in SCC nodules. F4/80 marks macrophages in mice, while CD163 marks macrophages in humans. Scale bar=200 µm for all sub-panels of Panel D; scale bar=800 µm for all sub-panels of Panel E. Panel F shows representative immunohistochemical staining on Lkb1;Pten;p53 tumors where distinct areas of ADC and SCC were adjacently located. p63 and MPO staining were restricted to the SCC area. Scale bar=200 µm for all panels. Panel G shows the results of GSEA analysis used to confirm the major immune cell types within Lkb1;Pten SCCs and Kras ADCs (Abbas et al. (2005) *Genes Immun.* 6:319-331; Konuma et al. (2011) *Exp. Hematol.* 39:697-709).

As noted histologically, the LP SCC lesions contained large neutrophilic infiltrates, suggesting that the immune microenvironment was distinct from the typical tumor associated macrophage (TAM)-rich microenvironments observed in most mouse Kras and Kras;p53 driven ADC models. To better understand the role of the inflammatory microenvironment in lung SCC versus Kras ADC, immune cells (CD45$^+$) from LP SCCs and Kras or Kras;p53 ADCs were compared by flow cytometry. In Kras and Kras;p53 tumors TAMs (alveolar macrophages, CD45$^+$CD11c$^+$CD11b$^-$CD103$^-$) predominated; however, within the LP tumors, the CD45$^+$ population contained significantly fewer macrophages and more TANs (CD45$^+$CD11b$^+$Ly6G$^+$) (FIGS. 7A-7B; p<0.0001). TANs may promote tumorigenesis by stimulating angiogenesis and immunosuppression in the tumor microenvironment (Dumitru et al. (2013) *Semin. Cancer Biol.* 23:141-148). Interestingly, the prevalence of TANs increased with tumor burden, as lung lobes with higher weight (indicative of higher tumor burden) showed substantially more TANs (FIG. 7C; p<0.0001). In contrast, the absolute counts of T cells. B cells, NK cells and TAMs decreased with increasing lobe weight (FIG. 8A), suggesting a selective recruitment and/or proliferation of TANs during SCC tumor progression.

Figure 8:
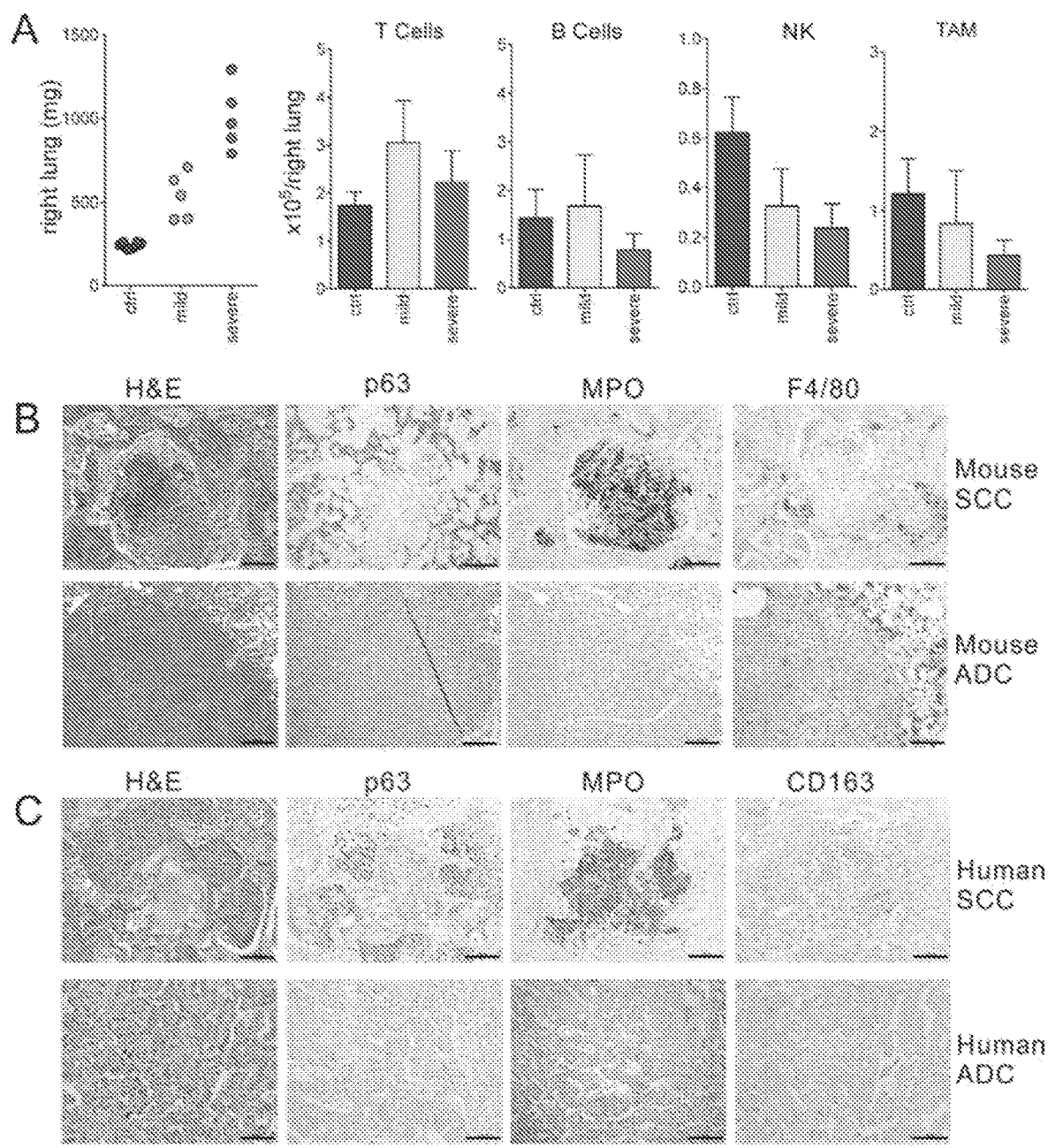
FIG. 8 includes 6 panels, identified as panels A, B, C, D, E, and F, which further show that TANs were the predominant inflammatory cell population in Lkb1$^{fl/fl}$;Pten$^{fl/fl}$ SCC tumors. Panel A shows quantification of inflammatory cells by flow cytometry from samples with progressively increasing weights, indicating different tumor burdens: normal lung control (n=8); mild disease group (tumor plus surrounding tissue weight less than 750 mg), n=5; severe disease group (tumor plus surrounding tissue weight greater than 750 mg), n=5. The immune cell populations were gated as described in the Examples. Macrophages (TAM), T cells, B cells, and NK cells within the tumors decreased with increasing tumor burden. Panels B and C correspond to Panels D and E of FIG. 7 and show representative immunohistochemical staining at high magnification of mouse and human SCC and ADC for MPO, p63 and F4/80 (mouse)/CD163 (human). Within the SCC nodule, MPO$^+$ TANs are specifically surrounded by p63$^+$ squamous epithelial cells. Scale bar=100 µm for all panels. Panel D shows representative immunohistochemical staining for p63, MPO and F4/80. Distinct areas of ADC and SCC are observed in close proximity to each other in the lung of Kras;Lkb1 mouse. Magnifications are indicated on the images. Scale bar for the top panels=100 µm; scale bar for the middle and bottom panels=1,000 µm. Panel E shows the results of real-time RT-PCR for Mpo, Arg1 and Cxcr2 mRNA expression in the indicated CD45$^+$ purified populations. Compared with Kras and Kras;p53, Mpo, Arg1 and Cxcr2 expression level in Lkb1;Pten tumor CD45$^+$ cells were significantly elevated; p values are indicated on each panel. Panel F shows that CXCL1, CXCL2, CXCL5, CXCL7 and GCSF levels in BAL fluid from Lkb1;Pten tumor-bearing mice were detected by ELISA. Compared to levels in normal BAL fluid, the levels of each of these cytokines were significant increased. N=9 for normal control lung BALF; n=7 for LP tumor-bearing BALF; p value is indicated on each panel. Data shown in Panels A, E, and F are presented as mean+/−SEM.
Figure 8:
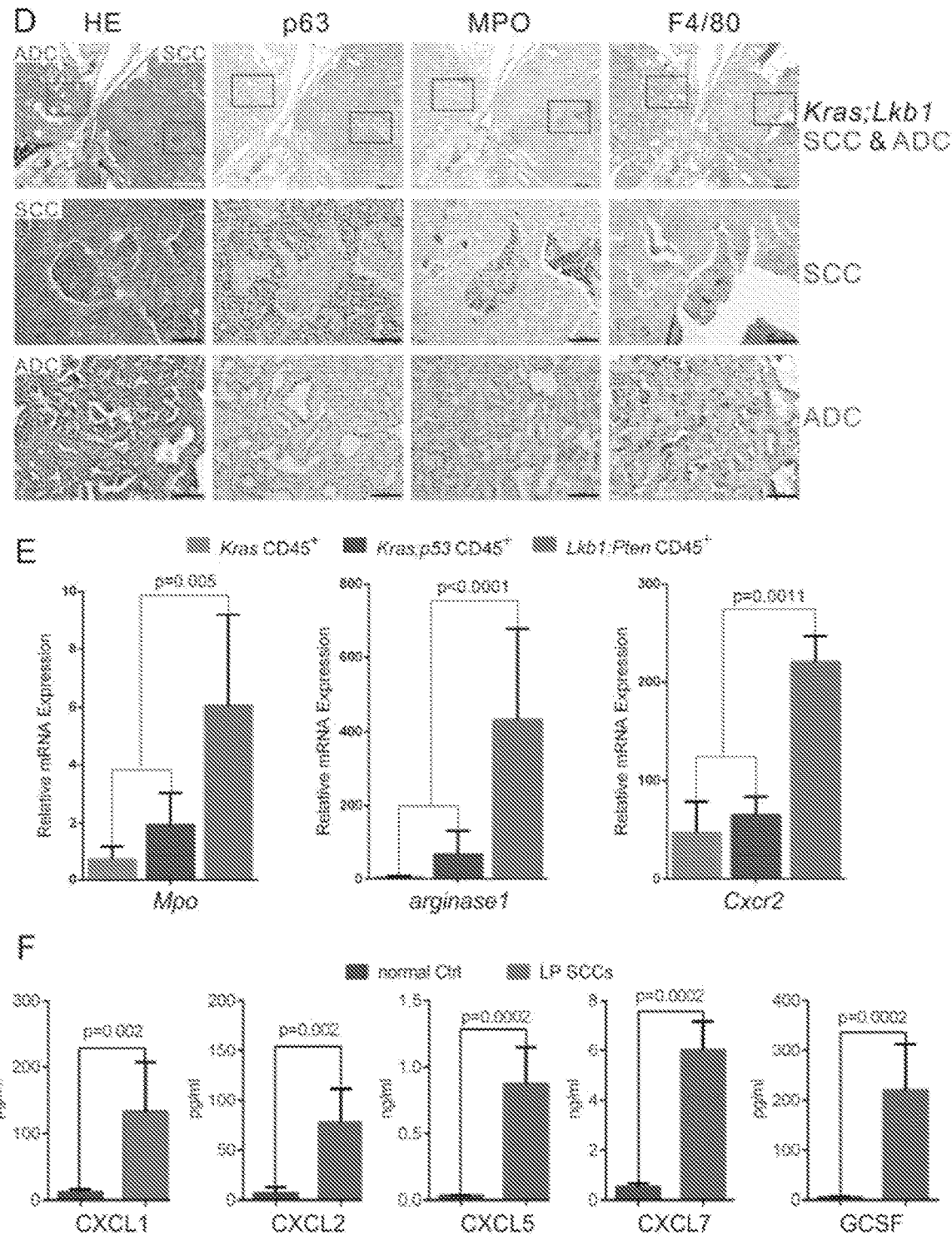

To further confirm the presence of TANs in LP tumor nodules in situ, staining for myeloperoxidase (Mpo), a marker that is highly expressed by TANs in tumor bearing mice (Youn et al. (2012) *J. Leukoc. Biol.* 91:167-181), was performed. Within the LP SCCs, MPO$^+$ TANs appeared to be specifically localized to squamous lesions surrounded by p63$^+$ epithelial cells (FIGS. 7D and 8B). Conversely, macrophages, identified by F4/80$^+$ staining in mouse tissue were distributed widely within or around SCC and ADC lesions (FIGS. 7D and 8B). Similar patterns were observed in human samples. MPO staining was strongly positive in 13/15 human primary SCC samples examined, while only 4/12 human primary ADC showed staining (Table 4; p=0.007). Macrophages (CD163$^+$ in human tissue) were scattered in both human ADCs and SCCs (FIGS. 7E and 8C). These differences in cell infiltrates between adenocarcinoma and squamous cell carcinoma lesions were clearly evident in tumors obtained from the mixed histology p53$^{fl/fl}$;Pten$^{fl/fl}$;Lkb1$^{fl/fl}$ (p53;Lkb1;Pten or PLP) mouse model. In this model, distinct areas of ADC and SCC were sometimes observed in close proximity to each other in the lung. Confirming their histologic identity, the squamous areas in PLP mice expressed high levels of p63, while the acinar areas were negative. Importantly, staining for MPO was specific to the SCC area of the tumor, suggesting that TANs are specifically recruited to SCC lesions (FIG. 7F). Similarly, the enrichment for TANs specifically in the areas of SCC tumors, but not in the adjacent ADC tumors, was also observed in the Kras;Lkb1 mouse model, which also has the mixed ADC and SCC histology (FIG. 8D).

To further explore the differences between CD45$^+$ fractions within SCC and ADC lung tumors, CD45$^+$EpCAM$^-$ cells were isolated from LP and Kras tumors, and microarray analysis was performed. By contrasting the gene expression profiles of LP CD45$^+$ cells against LP EpCAM$^+$ cells and Kras CD45$^+$ cells, a list of 156 genes significantly enriched in LP CD45$^+$ cells (Table 5; adjusted p<0.025) was constructed. Among the genes highly expressed by these cells was Ly6G, further confirming the TAN phenotype (Youn et al. (2012) *J. Leukoc. Biol.* 91:167-181). By qPCR, it was also confirmed that Mpo, arginase1 and Cxcr2 are enriched in SCC lesions from LP mice, while their expression was negligible in Kras- and Kras;p53-tumor derived CD45$^+$ cells (p=0.005, p<0.001 and p=0.0011 respectively: FIG. 8E). Immunologic signatures that were enriched in the ranked ordered list of LP vs Kras CD45$^+$ genes were also queried. By using two sets of independently derived signatures comparing monocyte/macrophages to neutrophils (Abbas et al. (2005) *Genes Inmun.* 6:319-331; Konuma et al. (2011) *Exp. Hematol.* 39:697-709), a clear enrichment for neutrophil signatures in the LP CD45$^+$ cells was found, while macrophage signatures were significantly enriched in the Kras CD45$^+$ cells (FIG. 7G) (p<0.001).

From expression profiling of sorted mouse lung cancer cells, it has been demonstrated that lung cancers driven by Kras have higher level of arginase, thereby also providing an means to stratify lung cancer patient for arginase inhibitors. Similarly, it is believed based on both experimental evidence and theory that arginase expression is upregulated in cancers having an activating NRAS mutation and/or an activating HRAS mutation.

Elevated expression of the chemokine receptor Cxcr2 suggests one mechanism through which the LP EpCAM$^+$ cells are able to specifically recruit TANs. Many of the CXC-Ligand family members have neutrophil chemoattractant activity (De Filippo et al. (2013) *Blood* 121.4930-4937), and appeared to be up-regulated at the transcriptional level in the EpCAM microarray. Therefore, the protein concentrations of these cytokines, including CXCL1, CXCL2, CXCL5 and CXCL7, were assessed in bronchoalveolar lavage (BAL) fluid from Lkb1;Pten tumor-bearing mice. Compared with levels observed BAL fluid isolated from normal mice, all these chemokines were significantly elevated in BAL, fluid from LP tumor-bearing mice (FIG. 8F; p<0.002), suggesting a mechanism through which TANs are recruited and stimulated by these tumors. In addition, GCSF, another essential regulator of neutrophil trafficking (Semerad et al. (2002) *Immunity* 17:413-423), was also elevated in LP BAL fluid (FIG. 8F; p=0.0002). Together, these data confirm that in contrast to murine Kras and Kras;p53 ADC models that contain predominantly macrophages, lung SCCs show accumulation of TANs, indicating that distinct oncogenic drivers in NSCLC sculpt the immune microenvironment in different ways.

Figure 9:
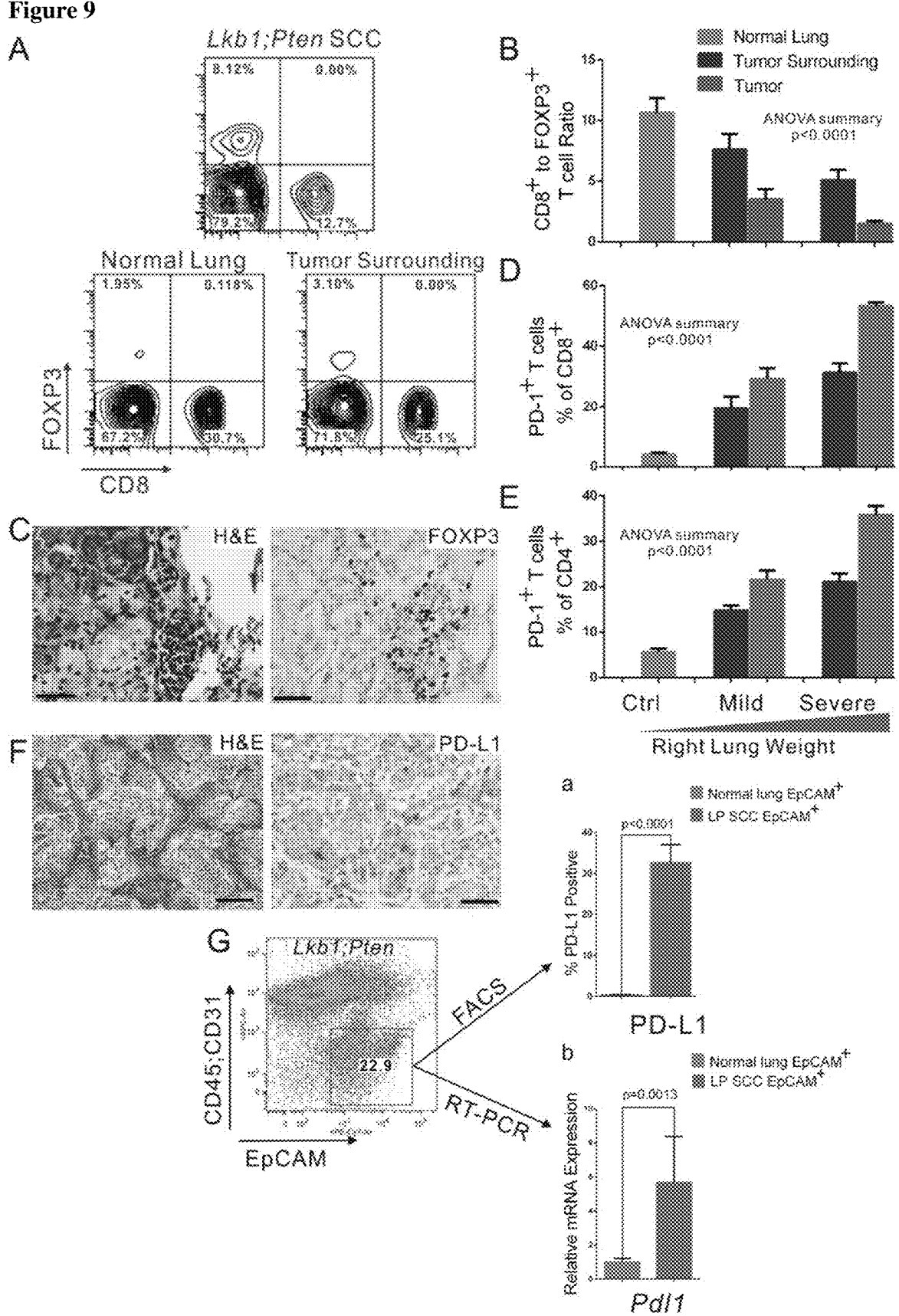
FIG. 9 includes 7 panels, identified as panels A, B, C, D, E, F, and G, which show that Lkb1$^{fl/fl}$;Pten$^{fl/fl}$ lung SCCs display hallmarks of immune suppression. Panel A shows representative flow cytometry plots for FOXP3 and CD8 in total CD3$^+$ T cells within LP SCC tumor, uninduced normal lung and lung surrounding LP SCC tumors. Panel B shows ratios of CD8$^+$ T cells to FOXP3$^+$ Tregs as determined with flow cytometry; n=8 for control lung; n=5 for mild disease group: n=5 for severe disease group; p<0.0001. Panel C shows the results of immunohistochemical staining for FOXP3 and confirms the presence of Tregs in LP SCC nodules. Scale bar=50 µm for both panels. Panels D and E show quantification the percentage of PD-1-positive cells within the CD8$^+$ and CD4$^+$ T cell populations; n=8 for control lung; n=5 for mild disease group; n=5 for severe disease group; p<0.0001. Panel F shows representative immunohistochemical staining for PD-L1 on LP SCC nodules. Scale bar=100 µm for both panels. Panel G(a) shows the percentage of PD-L1 positive cells within the EpCAM$^+$CD45$^-$CD31$^-$ fraction from LP SCC as measured by flow cytometry; n=7 for LP tumors, n=5 for normal lung; p<0.0001. Panel G(b) shows the results of real-time RT PCR for Pdl1 mRNA levels in the indicated EpCAM$^+$ purified cells from SCC tumors and normal lung tissue; n=6 for normal lung; n=5 for LP SCC tumors; p=0.0013. Data in Panels B, D, E, and G are presented as mean+/−SEM.
Figure 10:
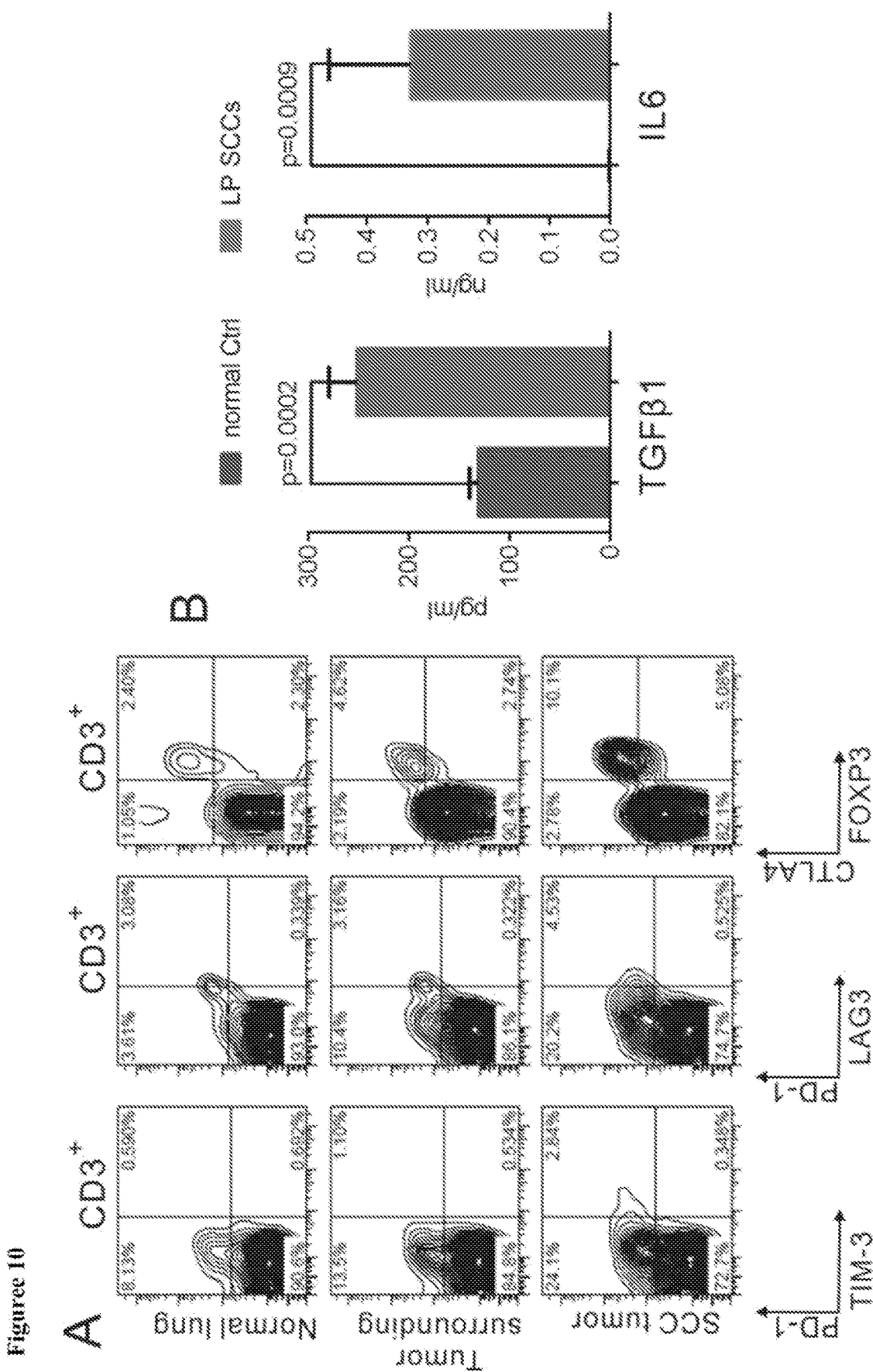
FIG. 10 includes 2 panels, identified as panels A and B, which further show that Lkb1$^{fl/fl}$;Pten$^{fl/fl}$ lung SCCs display hallmarks of immune suppression. Panel A shows representative flow cytometric plots for T cell and associated immunoregulatory markers within Lkb1;Pten SCC tumors, adjacent tissue and normal lung without Ad-Cre inhalation. Panel B shows that TGFβ1 and IL6 levels in BAL fluid from Lkb1;Pten tumor-bearing mice were detected by ELISA. Compared with those in BAL fluids from normal mice, TGFβ and IL6 levels were significant increased; n=9 for normal control lung; n=7 for LP tumor-bearing mice. Data are presented as mean+/−SEM. P-values are indicated on each panel.

Example 5: Lkb1$^{fl/fl}$;Pten$^{fl/fl}$ Lung SCCs Display Hallmarks of Immune Suppression The types of T cells present in LP SCC tumors were evaluated by flow cytometry. Compared to T cell populations isolated from normal lung and peri-tumoral areas, the T cells within LP tumors were significantly enriched for Tregs as determined by FOXP3 staining (FIG. 9A). The ratio of CD8$^+$ T cells to FOXP3$^+$ Tregs within the tumor and surrounding tissues decreased with increasing tumor burden, indicating that the levels of immunosuppression rose with disease progression (FIG. 9B; p<0.0001). The accumulation of Tregs in LP tumors was further confirmed by immunohistochemical staining for FOXP3 in LP nodules (FIG. 9C). In addition, T cells in LP tumors highly expressed the negative T cell co-stimulatory molecule programmed cell death protein 1 (PD-1) and increased percentages of PD-1 positive T cells (both CD4$^+$ and CD8$^+$) correlated with increased tumor burden (FIGS. 9D-9E; p<0.0001). In contrast to the increased PD-1 expression on T cells, lymphocyte-activation gene 3 (LAG3) and T-cell immunoglobulin domain and mucin domain 3 (TIM3), two other known immune-modulating proteins, showed modestly increased expression (FIG. 10A). Cytokines in BAL fluids, including TGFβ and IL6, were further evaluated. Compared to levels in normal lung, these cytokines were significantly increased in BAL fluids from LP tumor-bearing mice (FIG. 10B; p<0.0009). Previous reports have shown that TGFβ and IL6 promote tumor growth, regulate Treg cell development and cause immunosuppression (Flavell et al. (2010) *Nat. Rev. Immunol.* 10:554-567).

Figure 2:
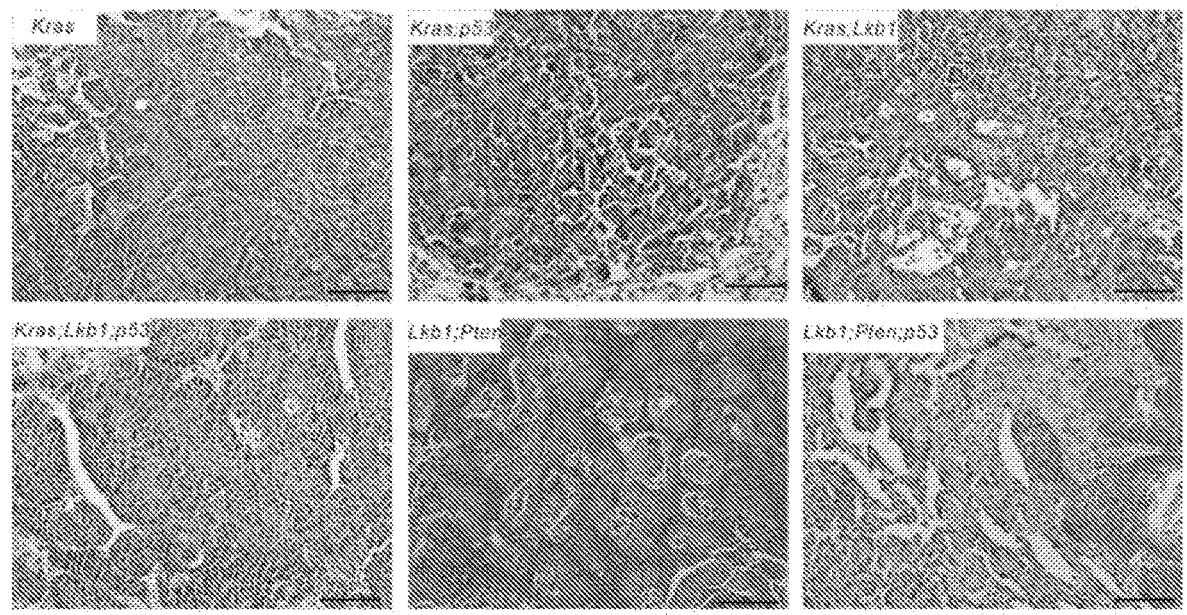
FIG. 2 includes 6 panels, identified as panels A, B, C, D, E, and F, which further show that bi-allelic inactivation of both Lkb1 and Pten in the mouse lung leads to squamous cell carcinoma. Panel A shows representative histology of hematoxylin and eosin (H&E)-stained genetically engineered mouse models of the indicated genotypes. Genotype indicated on images; scale bar=100 µm for all panels. Panel B shows the results of Kaplan-Meyer survival analysis of Lkb1;Pten mice following intra-nasal Ad-Cre instillation. Median survival=45.71 weeks. Panel C shows the results of end-point PCR for LoxP recombination in the Lkb1 and Pten alleles in the indicated sorted or total tumor cell populations. Panels D and E show images of total lungs from Lkb1;Pten mice stained with H&E to show both tumor location and tumor burden at 40-50 week time-points. Note that while some tumors appear to arise in the proximal lung at the branch point from trachea into the lobe (Panel D(a), top arrow), other tumors arise appear to be isolated in the distal lung and completely surrounded by alveolar epithelium (Panels D(a) and E(a), bottom arrows). Panel E(a) corresponds to 45-50 weeks, while Panel E(b) corresponds to 40-45 weeks post Ad-Cre. Scale bar in Panels D(b), F(a), and F(b)=500 µm; scale bar in Panels D(a), E(a), and E(b)=5,000 µm. Panel F shows H&E stained chest wall metastasis of the Lkb1;Pten primary tumor cells. Scale bar=100 µm on both panels.
Figure 2:
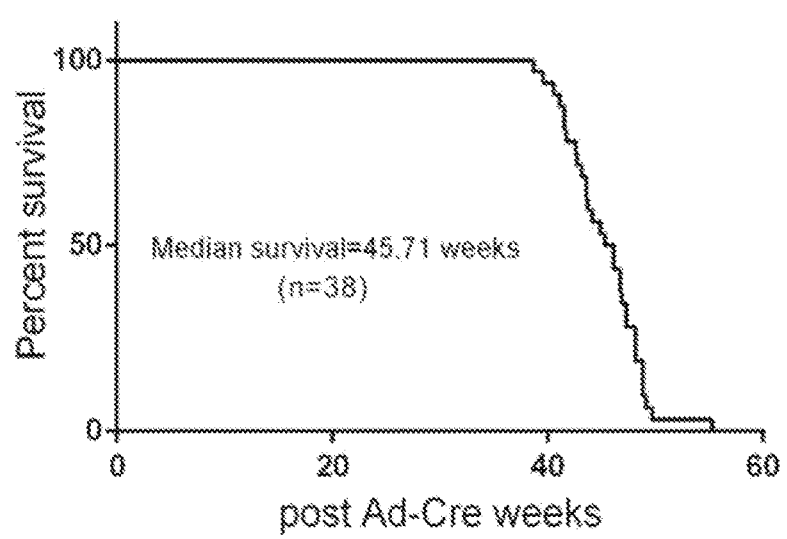
Figure 2:
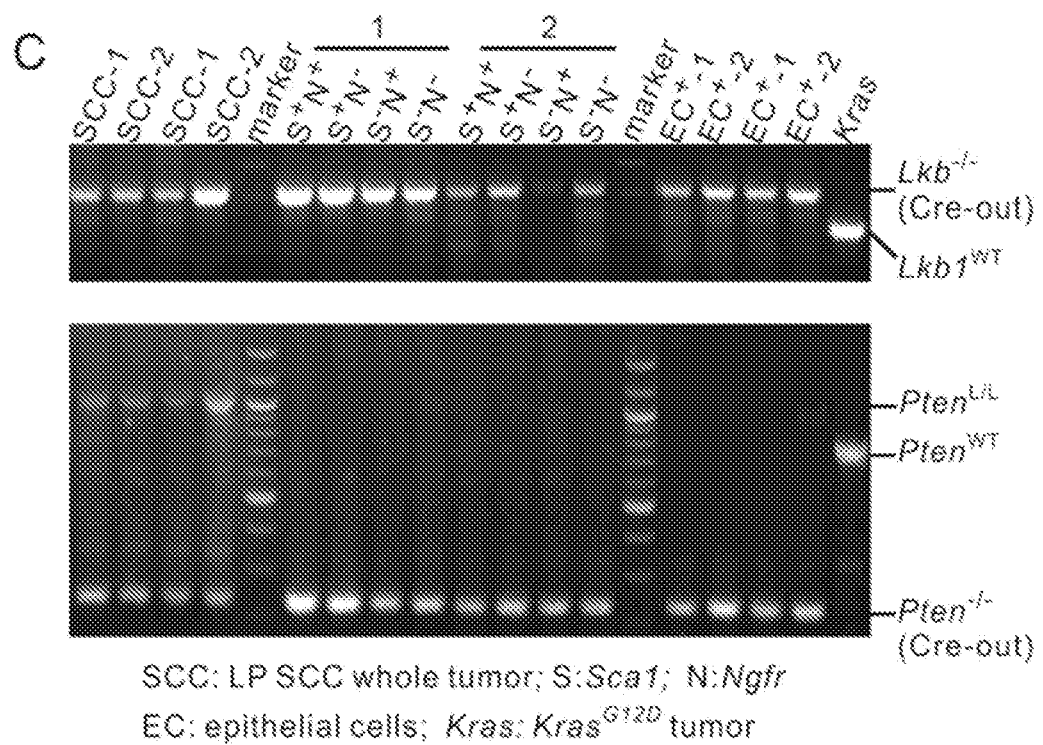
Figure 2:
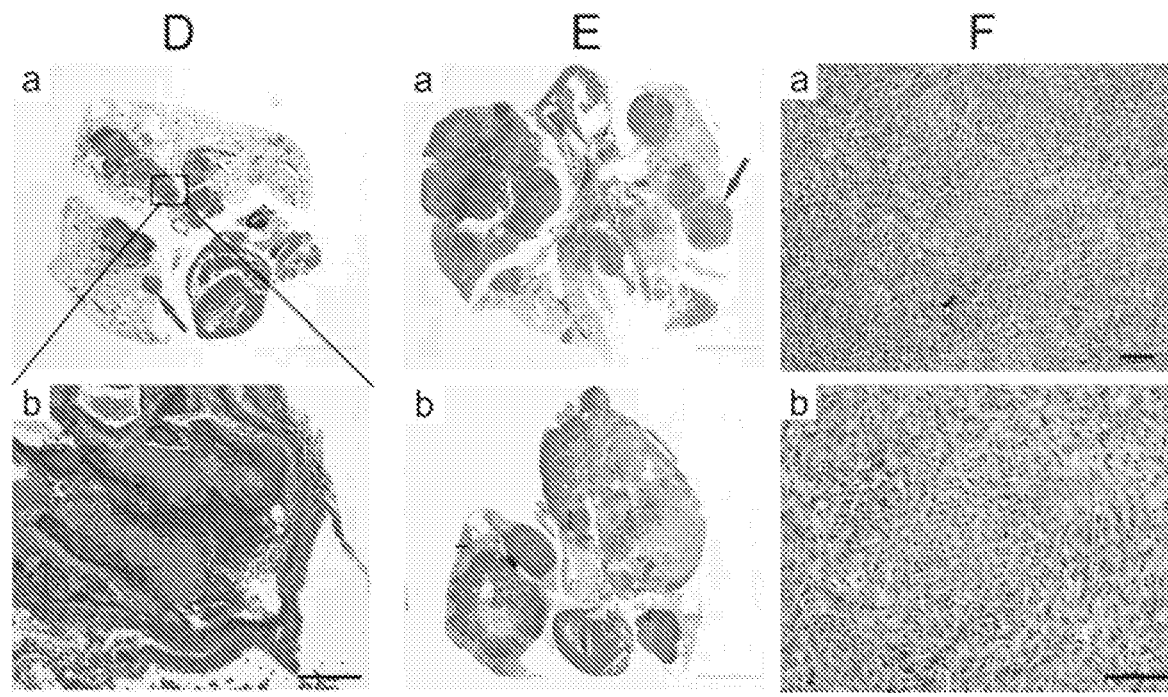

Since high levels of Pdl1 were observed in the LP EpCAM$^+$ cells by microarray, and published work suggests that PD-L1 can induce Tregs (Francisco et al. (2009) *J. Exp. Med.* 206:3015-3029), the expression of this immunomodulating protein was further explored. PD-L1 expression was first observed on LP tumor cells by immunohistochemistry (FIG. 9F). High cell surface expression of PD-L1 on EpCAM$^+$CD45$^-$ cells from LP tumors was confirmed by flow cytometry (FIG. 9G1; p<0.000). Pdl1 expression was further confirmed with real-time PCR on EpCAM$^+$CD45$^-$ cells from normal lung and LP tumors, and 6-fold more Pdl1 mRNA was observed in the LP tumor cells when compared to levels in normal distal lung epithelium (FIG. 9G2, p=0.0013). The increased numbers of Tregs, together with the high levels of PD-1 and PD-L1 on immune and tumor cells, respectively, indicated that immune suppression plays an important role during lung SCC tumorigenesis.

Example 6: A SCA1$^+$NGFR$^+$ Phenotype is Enriched in Lkb1$^{fl/fl}$;Pten$^{fl/fl}$ Lung SCC Tumor Propagating Cells (TPCs)

Figure 11:
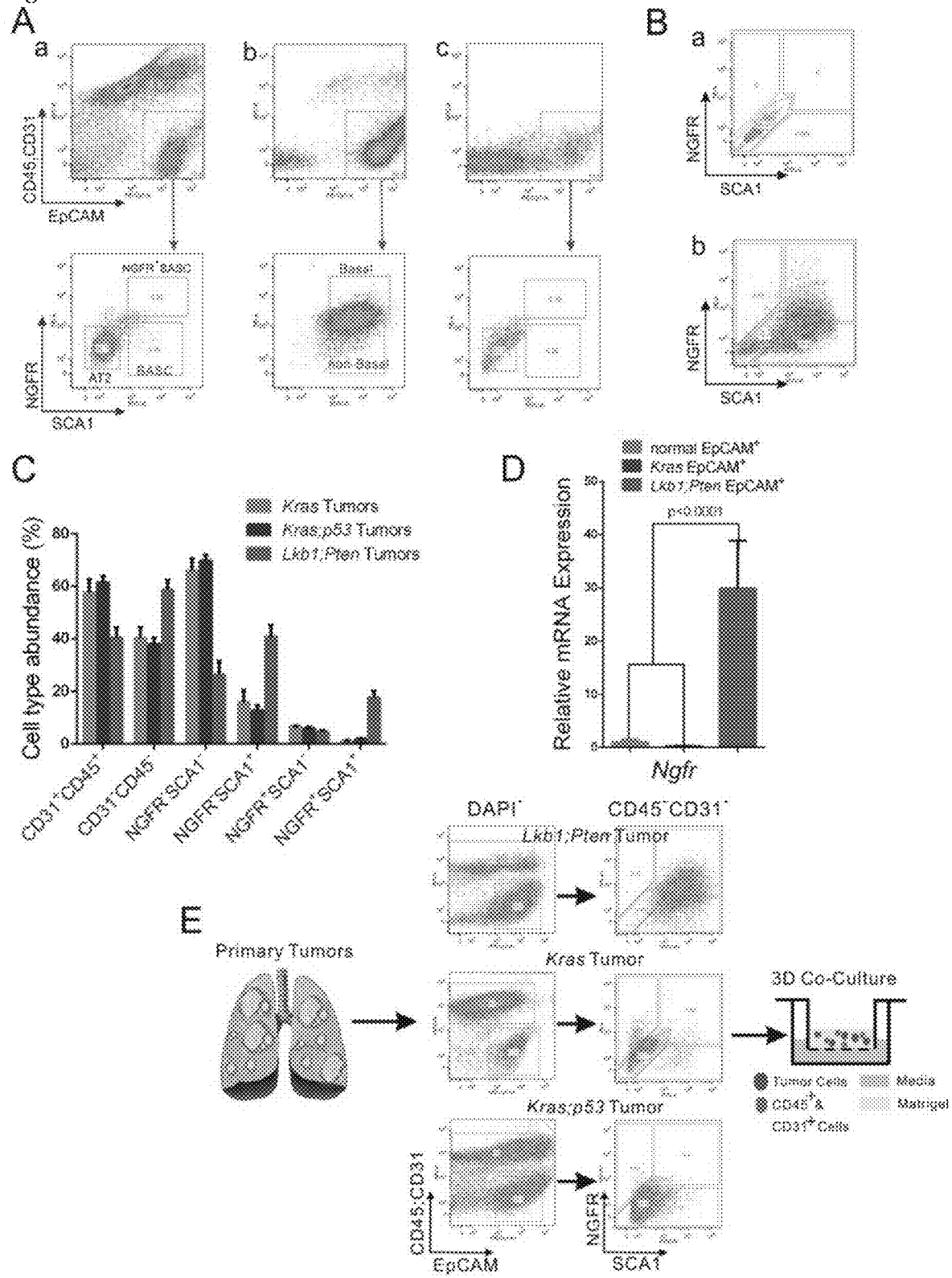
FIG. 11 includes 8 panels, identified as panels A, B, C, D, E, F, G, and H, which show that Lkb1$^{fl/fl}$;Pten$^{fl/fl}$ lung SCC contain SCA1$^+$NGFR$^+$ tumor propagating cells that can serially transplant squamous disease. Panel A shows NGFR and SCA1 expression in distal lung and trachea as measured by flow cytometry: a. Lung; b. Tracheas; c. Lung EpCAM single stained gating control. Dissociated total distal lung, and dissociated tracheal epithelium were stained for DAPI, CD45, CD31, EpCAM, SCA1, and NGFR. When gated on the DAPI$^-$CD31$^-$CD45$^-$EpCAM$^+$ epithelial cells, only a small fraction (~1%) of the distal lung epithelium expressed SCA1 and NGFR, while ~20% of the tracheal epithelium is SCA1$^+$NGFR$^+$. Panel B shows NGFR and SCA1 expression in the Lkb1;Pten tumors. Dissociated tumors were again stained for DAPI, CD45, CD31, EpCAM, SCA1 and NGFR. When gated on the DAPI$^-$CD31$^-$CD45$^-$EpCAM$^+$ epithelial cells, a large portion of the cells express SCA1, and of those ~17% also express NGFR. a. unstained tumor gated on FSC/SCC and DAPI-negative; b. stained Lkb1;Pten SCC. Panel C shows the results of flow cytometry for the various indicated cell populations within dissociated Kras, Kras;p53 and Lkb1;Pten tumors; data are presented as mean+/−SEM. Panel D shows the results of real-time RT-PCR for Ngfr mRNA expression in the indicated EpCAM$^+$ purified populations. Compared with normal lung EpCAM$^+$ cells and Kras tumor EpCAM$^+$ cells, Ngfr in Lkb1;Pten SCC EpCAM$^+$ cells was significantly increased; n=5 for normal EpCAM$^+$ cells; n=4 for Kras EpCAM: cells; n=5 for Lkb1; Pten EpCAM$^+$ cells; data are presented as mean+/−SEM; p<0.0001. Panel E shows a schematic for the FACS procedure using NGFR and SCA1 makers and in vitro 3D culture. The digested tumor cells were initially gated on epithelial cells (CD45$^-$CD31$^-$EpCAM$^+$) and were secondarily gated by NGFR and SCA1 expression. Four fractions with different markers (SCA1$^+$NGFR$^+$, SCA1$^-$NGFR$^+$, SCA1$^+$NGFR$^-$ and SCA1$^-$NGFR$^-$) were collected and co-cultured in Matrigel with equal amounts of CD45$^+$CD31$^+$ 'support' cells that were isolated from the same primary tumors. Representative flow cytometric plots from Lkb1;Pten, Kras and Kras;p53 tumors are shown. Panel F shows characterization of tumorspheres in 3D cultures. Representative bright field images of 3D culture colonies derived from primary mouse tumors of the indicated genotypes (top), H&E (middle) and IF (bottom). Fixed and sectioned tumorspheres were stained with anti-p63 (green), anti-SPC (red) and DAPI (blue) to show squamous and adeno differentiation; scale bar=100 μm for all panels. Imaging was performed with a Nikon 90i camera and NIS-Elements software and processed with NIS-Elements™ and Adobe Photoshop™. Panel G shows a schematic of the in vivo serial transplantation procedure. Panel H shows representative H&E stained sections and flow cytometric plots of primary, secondary and tertiary Lkb1;Pten lung tumors. Scale bar=100 μm for all panels.
Figure 11:
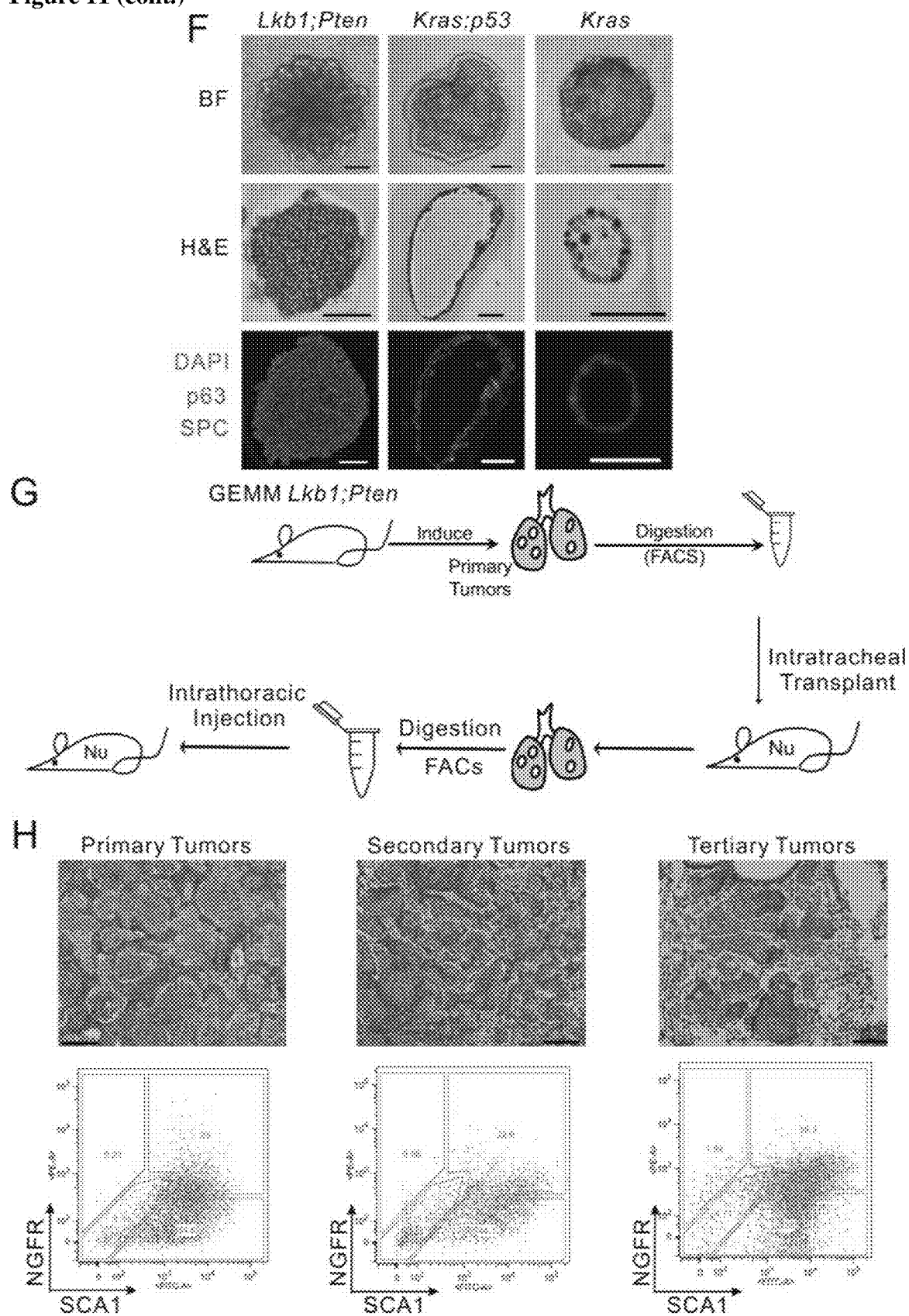
Figure 12:
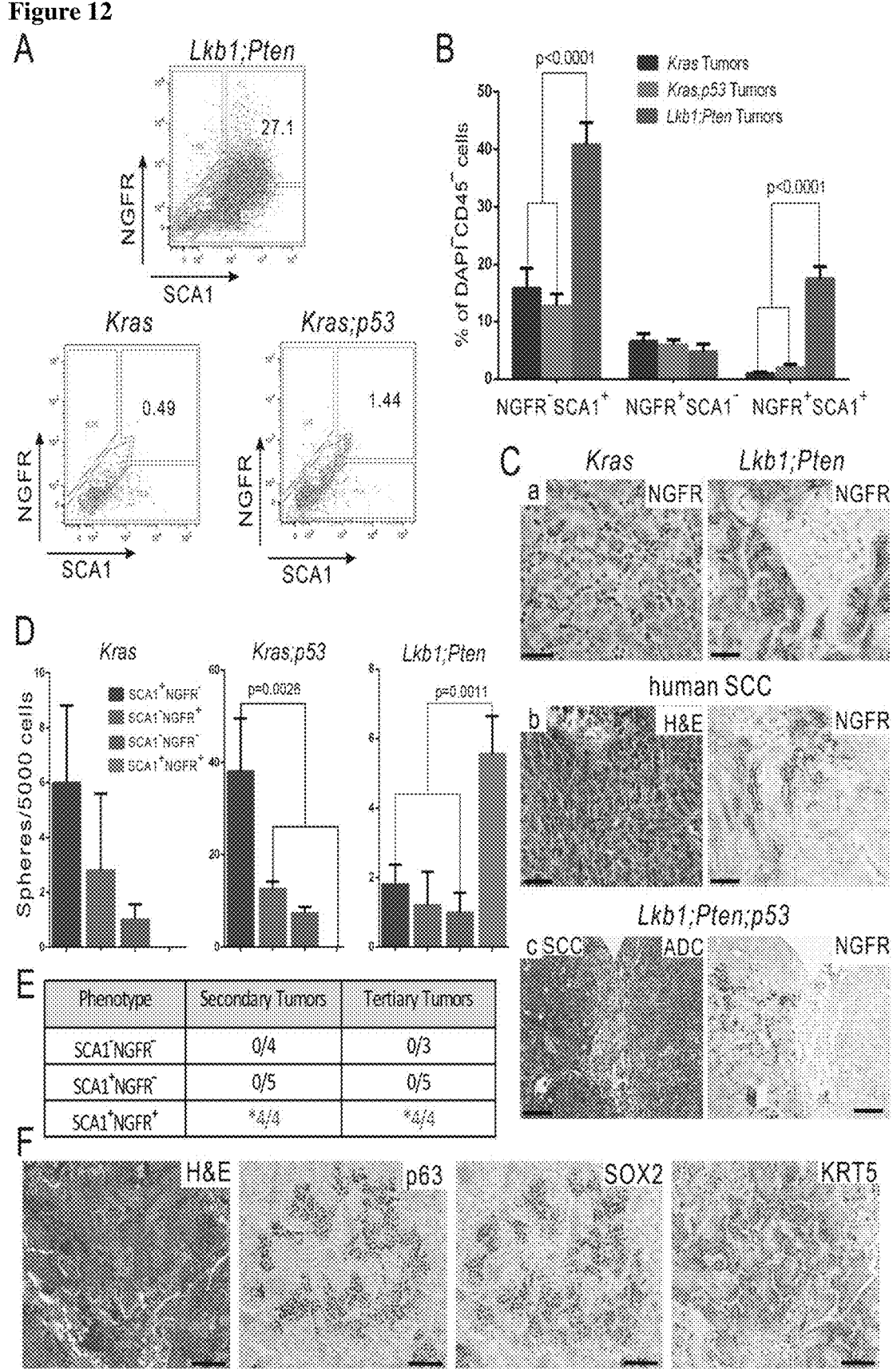
FIG. 12 includes 6 panels, identified as panels A, B, C, D, E, and F, which further show that Lkb1$^{fl/fl}$;Pten$^{fl/fl}$ lung SCC contain SCA1$^+$NGFR$^+$ tumor propagating cells that can serially transplant squamous disease. Panel A shows representative flow cytometry plots for NGFR and SCA1 expression within the indicated EpCAM$^+$CD45$^-$CD31$^-$ dissociated tumor cell populations. LP tumor cells showed much higher expression of both SCA1 and NGFR than either the Kras or Kras;p53 tumors. Panel B shows quantification of SCA1- and NGFR-expressing cells with the EpCAM$^+$CD45$^-$CD31$^-$ population as assessed by flow cytometry. The percentage of SCA1$^+$NGFR$^+$ in LP tumors is much higher than in Kras or Kras;p53 tumors; n=23 for Kras tumors; n=25 for Kras;p53 tumors; n=34 for Lkb1;Pten tumors; p<0.0001. Panel C shows representative immunohistochemical staining for NGFR on mouse SCC and ADC (a) and human SCC nodules (b). NGFR staining is strongly positive on SCC tumors but negative on ADC tumors. In the Lkb1;Pten;p53 tumors, distinct areas of ADC and SCC were adjacently located. NGFR staining was restricted to the SCC area (c). Scale bar=50 μm for panels of FIGS. 12(B)a and 12(B)b; scale bar=200 μm for sub-panels of Panel (B)c. Panel D shows quantification of tumorspheres derived from SCA1$^+$NGFR$^+$, SCA1$^-$NGFR$^+$, SCA1$^+$NGFR$^-$ and SCA1$^-$NGFR$^-$ FACS purified cells that were co-cultured in Matrigel with equal amounts of CD45$^+$CD31$^+$ cells from the same primary tumors. Each fraction was seeded at 5,000 tumor cells/well. The colony propagating ability of the SCA1$^+$NGFR$^+$ fraction in LP tumors is higher than that of the other fractions; p=0.0011. Panel E shows quantification of tumor propagation ability of FACS isolated SCA1$^+$NGFR$^+$, SCA1$^+$NGFR$^+$, and SCA1$^+$NGFR$^+$ LP tumor cells. The secondary tumors were derived from intra-tracheal transplant, with tumor formation latency of ~30-40 weeks. The tertiary tumors were derived from intra-thoracic injection, with the tumor formation latency of ~20-30 weeks. 10,000 sorted cells from each fraction were injected for each fraction and each experiment. Only SCA1$^+$NGFR$^+$ populations could form tumors and be serially transplanted; p=0.001 for secondary tumors; p=0.002 for tertiary tumors; Fisher's Exact Test. Panel F shows representative immunohistochemical staining on tertiary tumors derived from SCA1$^+$NGFR$^+$ LP tumor cells after intra-thoracic injection. The tumors retained a squamous histology and were positive for all of the squamous markers examined. Scale bar=100 μm for all panels. Data are presented as mean+/−SEM in Panels B and D.

It was determined if LP SCCs contained distinct tumor propagating cell (TPC) populations. The analysis was begun with two known stem cell makers, SCA1 and NGFR, which mark BASCs and tracheal basal cells, respectively. NGFR expression was examined on BASCs and SCA1 expression on basal cells. It was found that while nearly 100% of NGFR$^+$ basal cells expressed SCA1, only ~25% of SCA1$^+$ BASCs express NGFR (FIG. 11A). Within the EpCAM$^+$ CD45$^-$ cell populations, LP tumor cells showed high expression of SCA1 and NGFR, and LP tumors harbored a unique population of SCA1$^+$NGFR$^+$ cells that comprised an average of 17.5% of the LP EpCAM$^+$ cells. Interestingly, this population was nearly absent in both Kras and Kras;p53 ADC models (FIGS. 12A-12B (p<0.0001) and 11B-11C). Ngfr transcript was 30-fold more abundant in LP tumor cells than in normal lung or Kras epithelial fractions (FIG. 11D; p<0.0001). NGFR also specifically stained the LP SCC tumor lesions but was not detectable in Kras tumor lesions by IHC (FIG. 12C1). Likewise, in human primary lung SCCs, NGFR staining was observed in 11/13 samples examined, while only 2/12 human primary ADC sections had detectable NGFR staining (FIG. 12C2 and Table 4; p=0.001). In p53;Pten;Lkb1 (PLP) tumors where the ADC and SCC lesions were juxtaposed, NGFR staining was specific to the SCC side of the tissue section (FIG. 12C3).

FACS was used to fractionate LP EpCAM$^+$CD31$^-$CD45$^-$ tumor cells according to SCA1 and NGFR expression for functional comparison of TPC capacity. First, a surrogate in vitro assay for tumor propagation was used. Four distinct populations, SCA1$^+$NGFR$^+$, SCA1$^-$NGFR$^+$, SCA1$^+$NGFR$^-$ and SCA1$^-$NGFR$^-$ cells, were collected and co-cultured in Matrigel with CD45$^+$CD31$^+$ 'support' cells isolated from the primary tumors. The tumor colony forming ability of Kras and Kras;p53 sorted tumor fractions was also evaluated in the 3D Matrigel system (FIG. 11E). In agreement with previous in vivo results described in Curtis et al. (2010) *Cell Stem Cell* 7:127-133 and validating this assay for TPC capacity, SCA1$^+$ cells from Kras;p53 tumors were enriched for tumor colony formation ability (p=0.0026), but the same was not true for Kras tumors. SCA1$^+$NGFR$^+$ cells from LP tumors formed the most tumor colonies in 3D cultures, suggesting that they are the fraction enriched for tumor propagation (FIG. 12D, p=0.0011). The morphology and histology of the LP tumor colonies were distinct from those found in Kras or Kras;p53 tumor cultures (FIG. 11F). By immunofluorescence, the Lkb1;Pten tumor colonies expressed the squamous marker p63, but not the adenocarcinoma associated Surfactant protein C (SPC), while both the Kras and Kras;p53 derived colonies expressed SPC (FIG. 11F).

To determine if SCA1$^+$NGFR$^+$ cells from LP tumors were enriched for tumor propagating cell characteristics in vivo, three major fractions of the EpCAM$^+$ cells from primary LP tumors. SCA1$^+$NGFR$^+$, SCA1$^+$NGFR$^-$ and SCA1$^-$NGFR$^-$ were transplanted orthotopically into immuno-compromised mouse recipients immediately following FACS purification (FIG. 11G). The fraction of SCA1$^-$NGFR$^+$ was not tested due to its reproducibly small abundance. Of the four mice that received SCA1$^+$NGFR$^+$ cells, all developed typical SCC with p63$^+$, SOX2$^+$ and KRT5$^+$ staining within 30-40 weeks (FIGS. 12E-12F). To assess the presence of self-renewing TPCs within these tumors, the secondary tumors were dissected, dissociated, sorted for NGFR and SCA1 and the three major fractions were transplanted for tertiary tumor formation. All mice transplanted with SCA1$^+$NGFR$^+$ developed tertiary SCC within 11-27 weeks (FIG. 12E; p=0.001 for secondary; p=0.002 for tertiary; Fisher's Exact Test). All primary, secondary and tertiary tumors shared the same histological and FACS characteristics (FIG. 11H).

Together these data demonstrate that LP tumors contained a distinct population of SCA1$^+$NGFR$^+$ tumor propagating cells that could transplant disease retaining squamous characteristics.

Example 7: Tumor Propagating Cells Express High Levels of PD-L1

Figure 13:
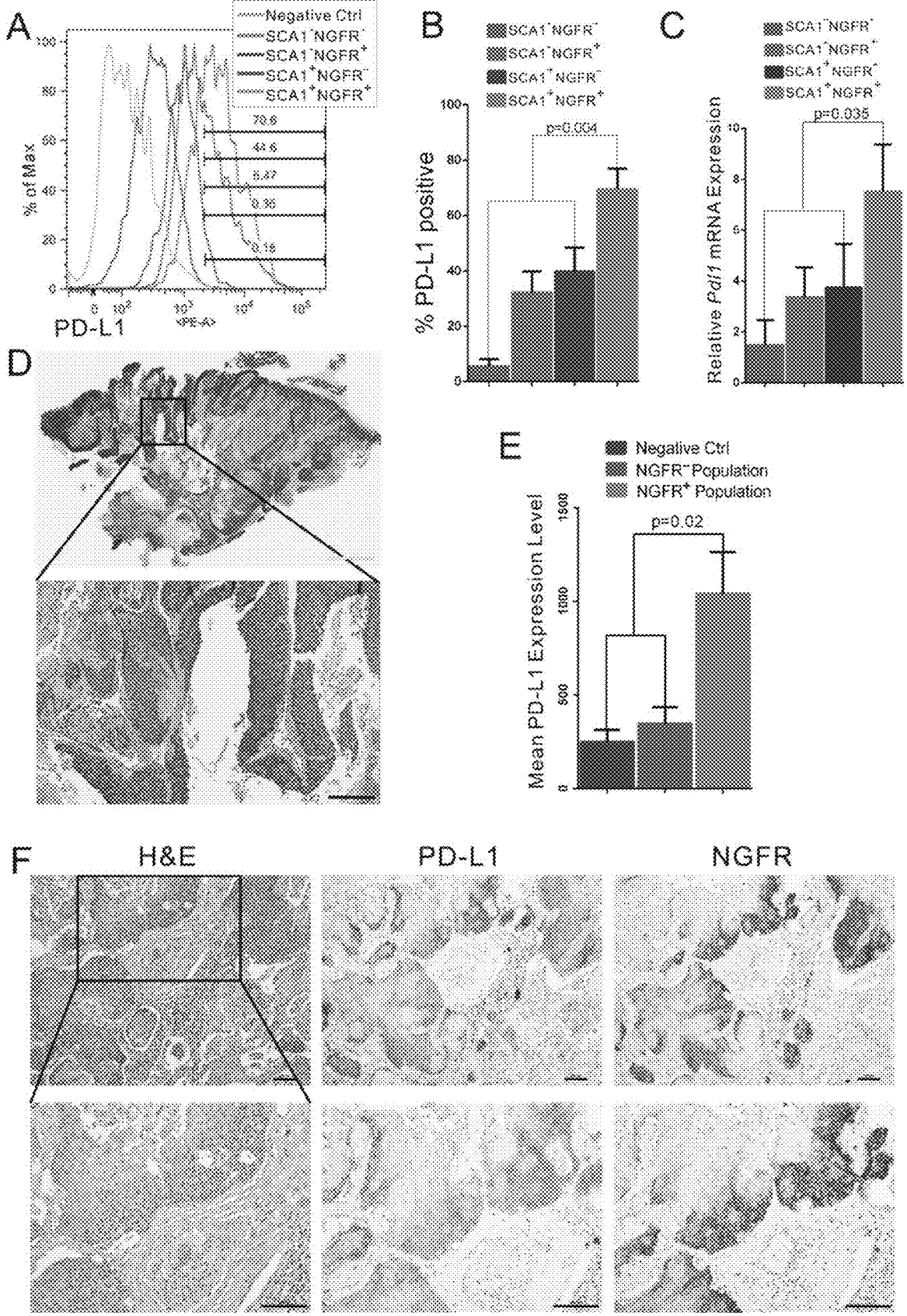
FIG. 13 includes 6 panels, identified as panels A, B, C, D, E, and F, which show that SCA1$^+$NGFR$^+$ tumor propagating cells in Lkb1$^{fl/fl}$;Pten$^{fl/fl}$ lung SCC tumor express high levels of PD-L1. Panel A shows a representative histogram of PD-L1 expressing cells from a dissociated LP tumor gated on DAPI$^-$EpCAM$^+$CD45$^-$CD31$^-$ cells and then for the 4 indicated fractions of SCA1;NGFR expressing cells. The unstained control trace in gray is shown for gating. Panel B shows quantification of PD-L1 expression level by flow cytometric analysis. PD-L1 expression is higher in SCA1$^+$NGFR$^+$ population than any other population; n=7 tumors; p=0.004. Panel C shows the results of real-time RT-PCR quantification of Pdl1 mRNA expression in SCA1$^+$NGFR$^+$, SCA1$^-$NGFR$^+$, SCA1$^+$NGFR$^-$, and SCA1$^-$NGFR$^-$ sorted populations; n=7 tumors; p=0.035. Panel D shows the results of representative H&E staining confirming that PDX tumors retained squamous histology; scale bar for bottom panel=200 μm; scale bar for top panel=2,000 μm. Panel E shows quantification of PD-L1 expression level by flow cytometric analysis of PDX samples. Mean fluorescence intensities for PD-L1 antibody on EpCAM$^+$NGFR$^+$ fractions are higher than those for EpCAM$^+$NGFR$^-$ fractions. The control is unstained dissociated PDX cells; n=6 tumors; p=0.02. Panel F shows serial sections of formalin fixed human SCC tumors stained with H&E, PD-L1 or NGFR. PD-L1 is co-localized to the NGFR$^+$ cells within these tumors. Scale bar=100 μm for all panels. Data are presented as mean+/−SEM in Panels B, C, and E.

Little is known about how tumor propagating cells escape immunologic clearance and clonally expand to form malignant tumor nodules. To address this question, the PD-L1 level on LP tumor cell fractions was further quantified. By gating the four SCA1;NGFR fractions and analyzing the percentage of PD-L1$^+$ cells in each fraction, a clear enrichment for PD-L1$^+$ cells was found within the SCA1$^+$NGFR$^+$ fraction (FIG. 13A). Within a group of 7 mice, an average of 69% of SCA1$^+$NGFR$^+$ cells expressed PD-L1 on their cell surface, while only 39% of SCA1$^+$NGFR$^-$ or 32% of SCA1$^-$NGFR$^+$ cells were PD-L1$^+$ (FIG. 13B; p=0.004). Likewise, by real-time RT PCR for Pdl1 within the sorted LP tumor fractions, SCA1$^+$NGFR$^+$ cells had 7-fold more Pdl1 mRNA than SCA1$^-$NGFR$^-$ cells and about 2-fold more than SCA1$^+$NGFR$^-$ or SCA1$^-$NGFR$^+$ cells (FIG. 13C; p=0.035). Flow cytometry and real time RT-PCR were also used to assess PD-L1 levels in BASCs and basal cells. NGFR$^+$ BASCs expressed the most PD-L1 in the distal lung, while PD-L1 expression was uniformly high by flow cytometry in the trachea (FIGS. 14A-14B).

Figure 14:
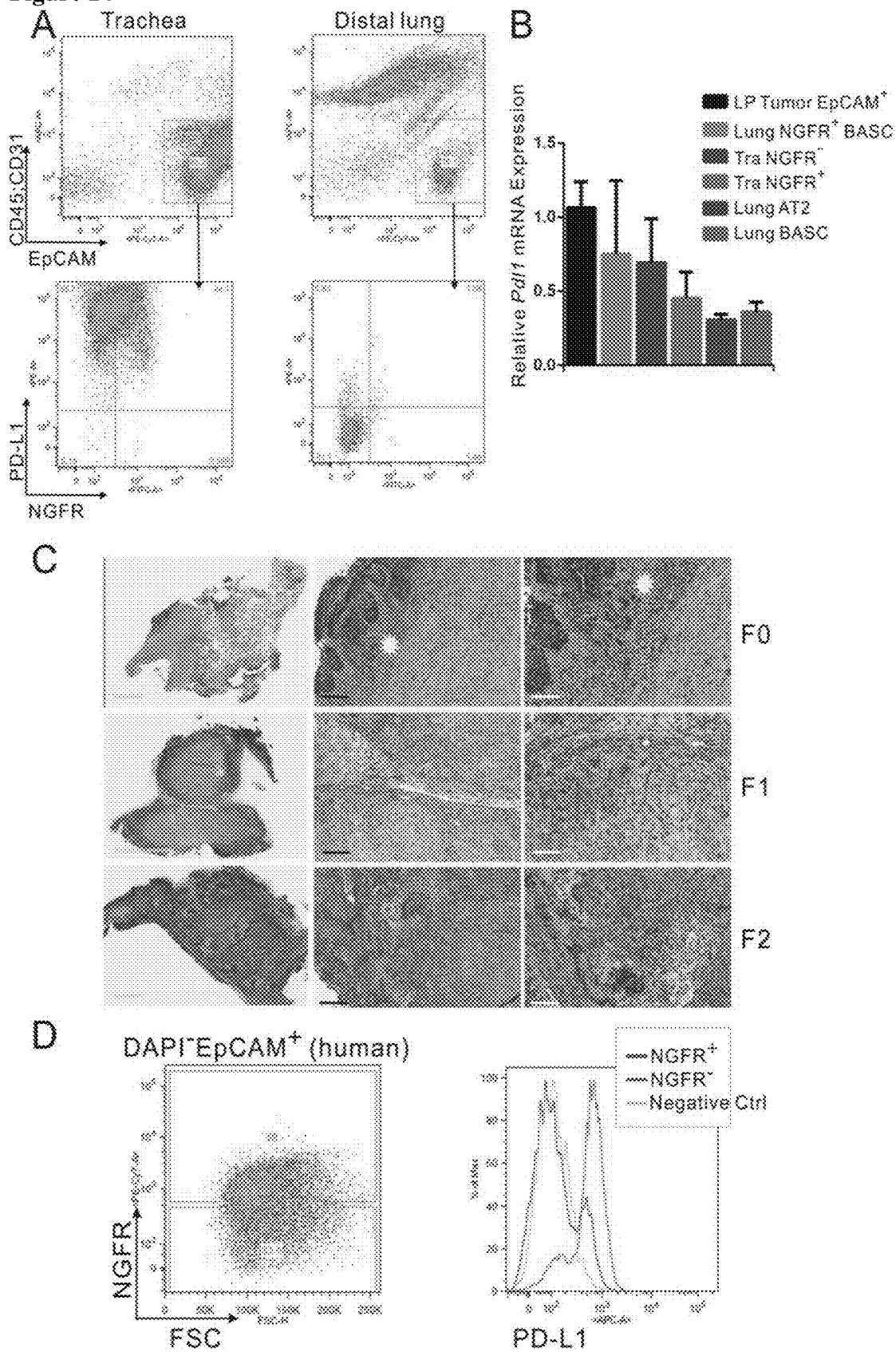
FIG. 14 includes 4 panels, identified as panels A, B, C, and D, which further show that SCA1$^+$NGFR$^+$ tumor propagating cells in Lkb1$^{fl/fl}$;Pten$^{fl/fl}$ lung SCCs tumor express high levels of PD-L1. Panel A shows PD-L1 expression in distal lung and trachea, as measured by flow cytometry. Dissociated total distal lung, and dissociated tracheal epithelium were stained for DAPI, CD45, CD31, EpCAM, PD-L1, and NGFR. When gated on the DAPI$^-$CD31$^-$CD45$^-$ EpCAM+ epithelial cells, only a small fraction (~2%) of the distal lung epithelium expressed PD-L1 and NGFR, while ~40% of the tracheal epithelium is PD-L1+NGFR+. Panel B shows the results of real time RT-PCR for Pdl1 transcript from the various sorted cell populations indicated; data are presented as mean+/−SEM. Panel C shows representative H&E stained sections of primary patient SCC tumors (F0) and first-(F1) and second-generation PDX tumor samples (F2), showing that squamous morphology is maintained. Scale bar for left column panels=2,000 µm; scale bar for middle column panels=200 µm: scale bar for right column panels=100 µm. Panel D shows representative flow cytometry plots of PDX tumor analysis. EpCAM+ human cells were gated for NGFR+ and NGFR− fractions, and PD-L1 expression on both fractions was assessed by mean fluorescence intensity as depicted in the histogram.

In order to explore the relationship between NGFR and PD-L1 expression in patient tissue, human lung SCC tissues that were passaged in immunocompromised mice as Patient-Derived Xenografts (PDXs) were used (FIG. 14C). Hematoxylin and eosin (H&E)-stained sections from the PDX samples showed that the squamous histology of the tumors was retained in the xenograft model (FIG. 13D). PDX samples were dissociated and stained with antibodies directed against human CD31, CD45, EpCAM, NGFR and PD-L1 (FIG. 14D). The amount of PD-L1 staining on both EpCAM$^+$NGFR$^+$ and EpCAM$^+$NGFR$^-$ fractions was analyzed. Using 6 different PDX samples, PD-L1 staining was 4.2-fold higher in the NGFR$^+$ fraction relative to the NGFR$^-$ fraction of the human EpCAM$^+$ tumor cells (FIG. 13E; p=0.02). This trend was further confirmed with independent human lung SCC tumor samples by staining serial sections for NGFR and PD-L1. Clearly, PD-L1 is co-localized to the NGFR$^+$ cells within these tumors, indicating that the majority of NGFR$^+$ cells co-express PD-L1 (FIG. 13F). Therefore, in lung SCC, PD-L1 is most abundantly expressed on tumor cells that express NGFR, and if these cells are analogous to the NGFR$^+$ cells in mouse tumors, they will also be enriched for TPC activity.

Figure 15:
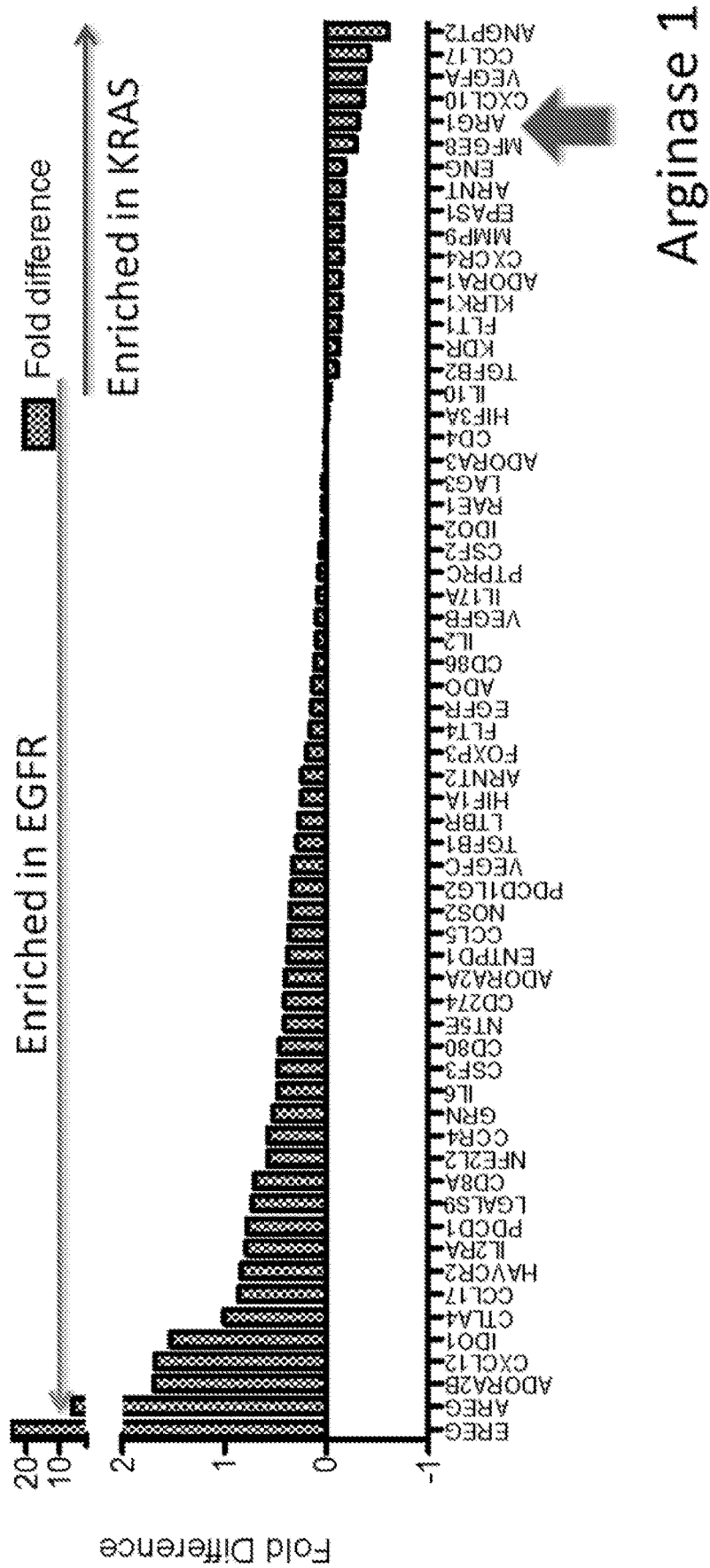
FIG. 15 shows a comparison of microarray expression data with a focus on immune-related genes in EGFR (T790M and L858R) mutant mouse tumors and Kras (G12D) mutant mouse tumors, both normalized to normal lungs.
Figure 16:
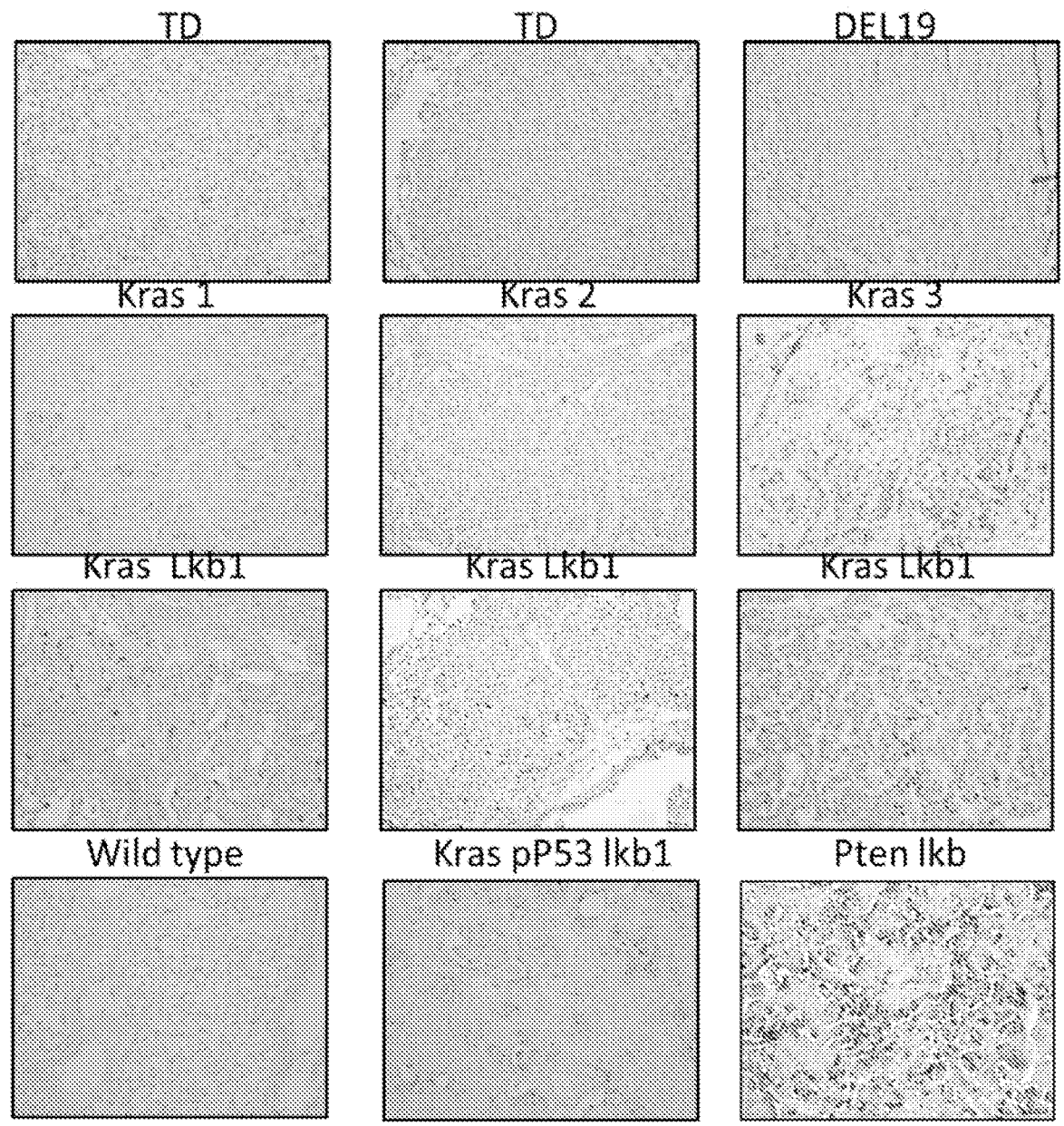
FIG. 16 shows representative images from arginase 1 immunohistochemistry on EGFR T790M and Del19 (i.e., TD) mutant mouse tumors, EGFR Del19 (i.e., DEL19) mutant mouse tumors, and the indicated Kras mutant mouse tumors. Such mutant mice are well known in the art (see, for example, Ohashi et al. (2013) *J. Clin. Oncol.* 31:1070-1080; Ji et al. (2006) *Cancer Cell* 9:485-495; Li et al. (2007) *Cancer Cell* 12:81-93; Zhou et al. (2009) *Nature* 462:1070-1074).

Example 8: Arginase Inhibitors Modulate Immune Cell Populations and Function to Treat Cancer in a Variety of Tumor Models As described above, arginase 1 expression is significantly increased in LP tumor cells. Similarly, arginase 1 expression is enriched in Kras G12D mutant mice, as opposed to EGFR mutant mice, as measured by both gene expression and immunohistochemical analyses (FIGS. 15-16). The Kras1, Kras2, and Kras3 images shown in FIG. 16 are from different tumors obtained from different Kras G12D mutant mice. In general, Kras mutant tumors (e.g., obtained from Kras G12D mutants, Kras G12D+Lkb1 mutants, and Kras G12D+p53+Lkb1 mutants) express arginase 1 at a higher level than EGFR mutant tumors. Pten, Lkb1, and p53 tumors also express high levels of arginase 1 (see, for example, Xu et al. (2014) *Cancer Cell* 25:590-604).

Figure 17:
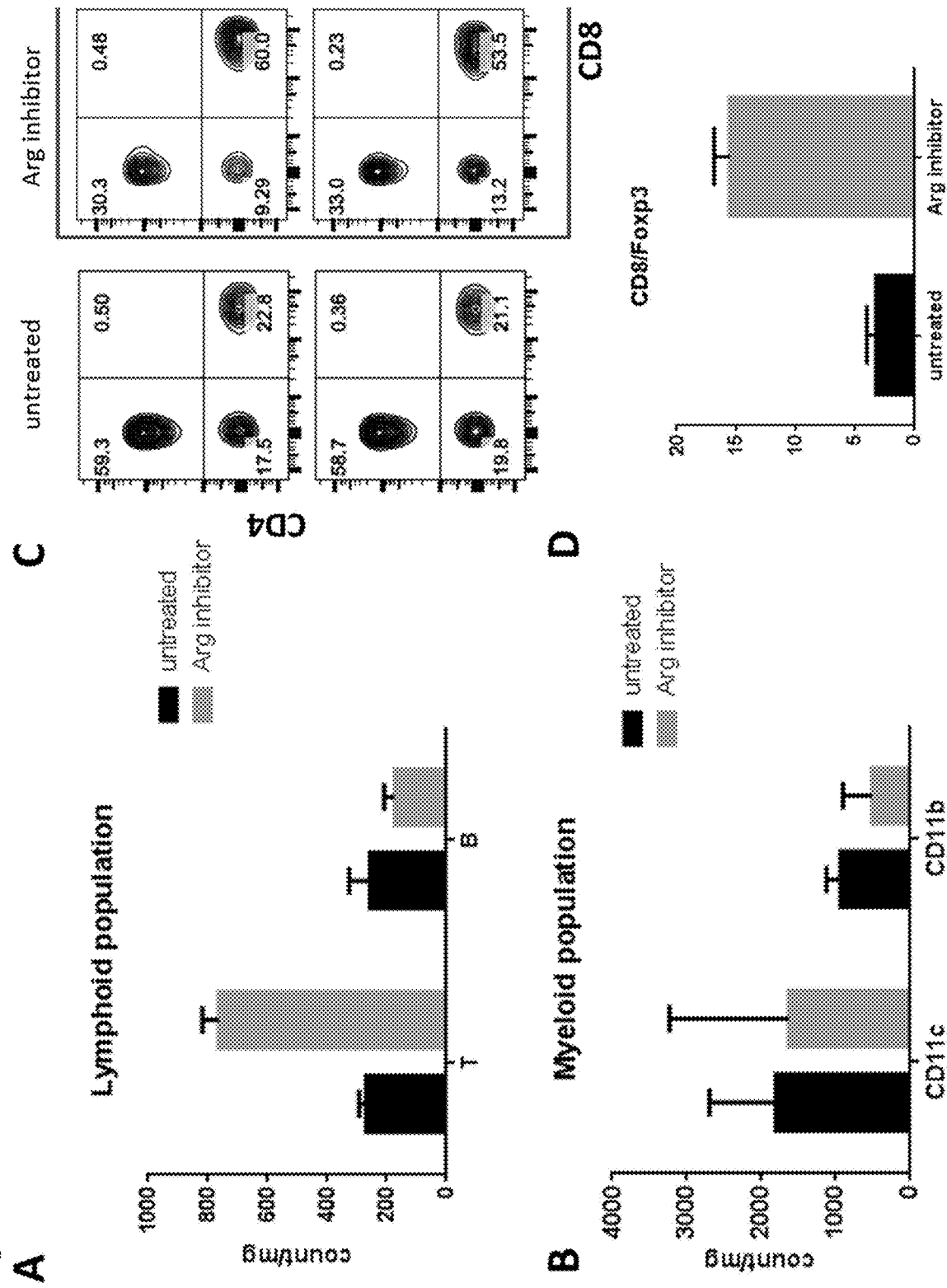
FIG. 17 includes 4 panels, identified as panels A, B, C, and D, which show the results of treating Kras mutant mice with the arginase inhibitor, compound 9/HY-15775. After 1 week of short-term treatment with the arginase inhibitor compound at 30 mg/kg through once daily gavage, an increase in total T cell counts (Panel A), no change in CD11c and CD11b myeloid populations (Panel B), a decrease in the ratio of CD4 T cells and an increase in CD8 T cells in the total T cell population (Panel C), and an increase in the ratio of CD8 to FoxP3 cells (i.e., the ratio of cytotoxic T cells to regulatory T cells) (Panel D) was determined.
Figure 18:
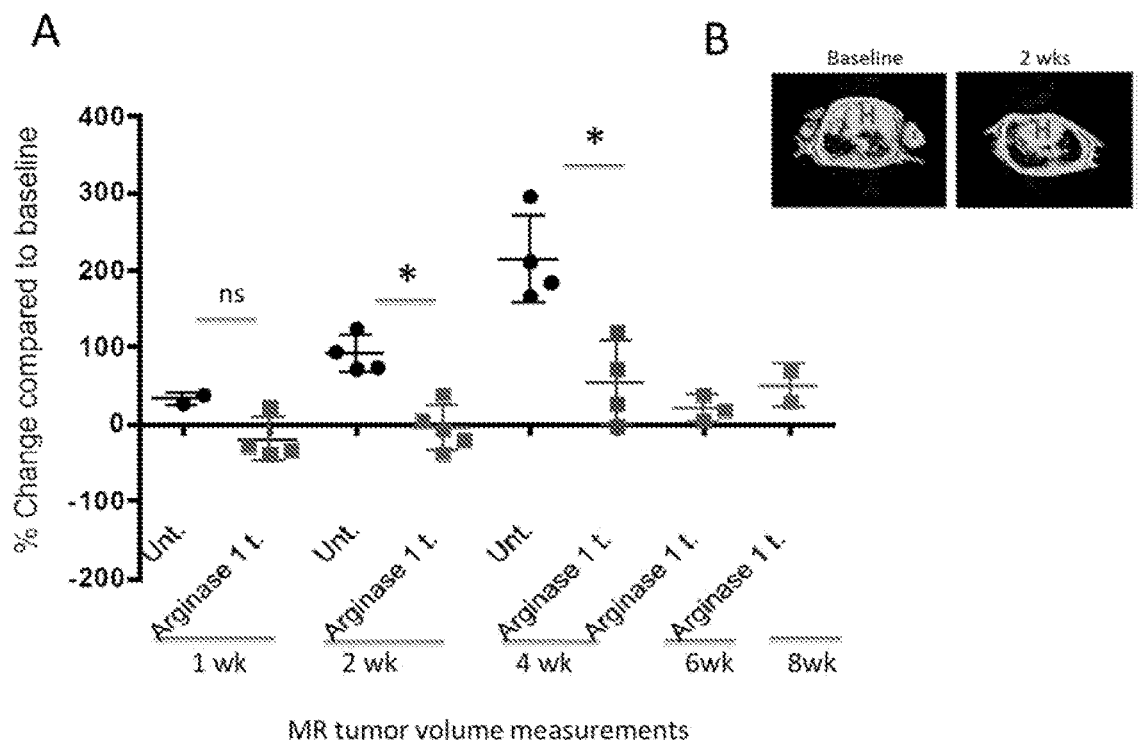
FIG. 18 includes 2 panels, identified as panels A and B, which show the results of treating $Kras^{G12D}$ mice with the arginase inhibitor, compound 9/HY-15775. Treatment with the arginase inhibitor compound at 30 mg/kg through once daily gavage resulted in decrease in lung tumor volumes in $Kras^{G12D}$ mice in 1 week (Panel A). The graph represents the percentage tumor volume change compared to baseline tumor levels. Unt.=untreated mice; arginase t=arginase inhibitor-treated mice. Panel B shows a representative lung MRI image; Unt.=untreated and t=compound9-treated.
Figure 19:
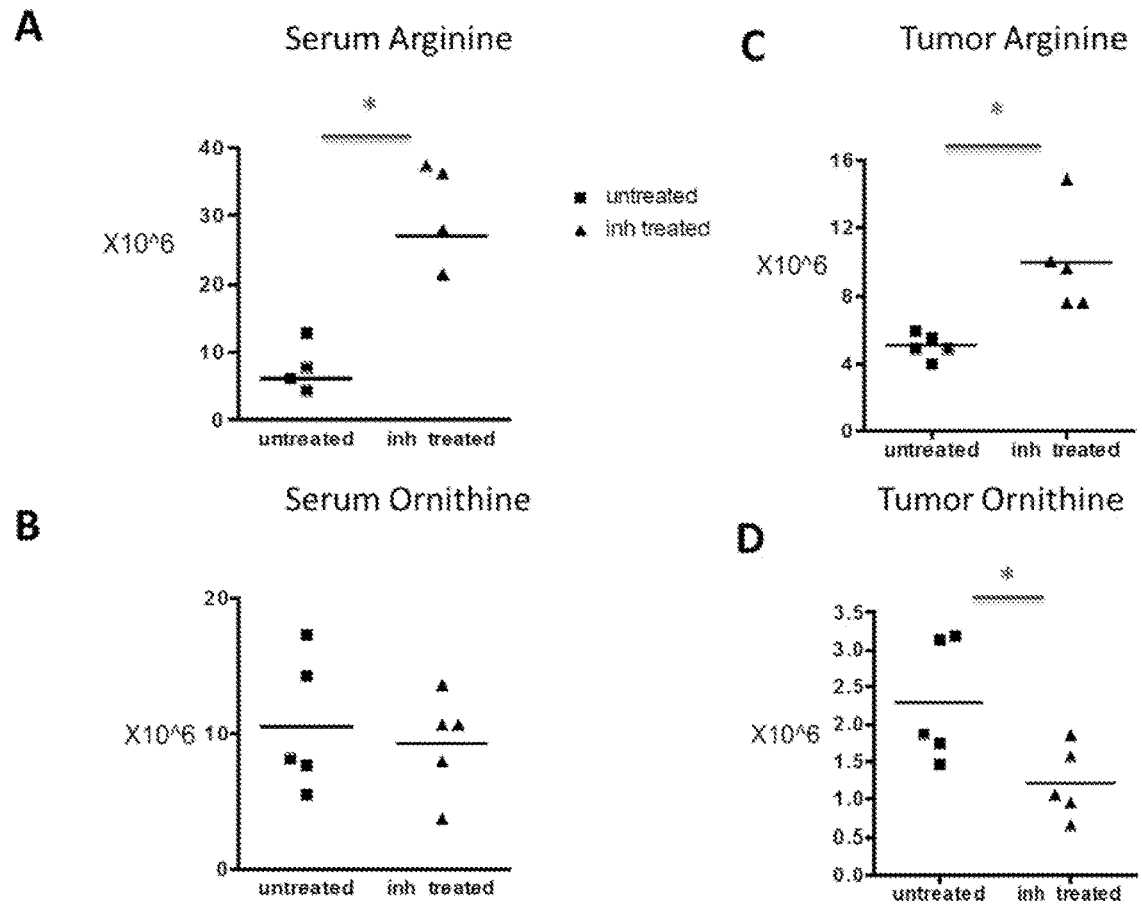
FIG. 19 includes 4 panels, identified as panels A, B, C, and D, which show target engagement of the arginase inhibitor (compound 9). Levels of serum and tumor ornithine and arginine levels in the mice from metabolomics profiling-untreated versus compound 9-treated for 3 days at 100 mg/kg are shown in each of Panels A, B, C, and D.

Treatment of the Kras mutant mice with the arginase inhibitor, compound 9/HY-15775, altered immune cell populations and function. For example, after 1 week of short-term treatment with the arginase inhibitor compound at 30 mg/kg through once daily gavage, an increase in total T cell counts (FIG. 17A), no change in CD11c and CD11b myeloid populations (FIG. 17B), a decrease in the ratio for CD4 T cells and an increase in CD8 T cells in the total T cell population (FIG. 17C), and an increase in the ratio of CD8 to FoxP3 cells (i.e., the ratio of cytotoxic T cells to regulatory T cells) (FIG. 17D) was determined. Moreover, treatment of Kras$^{G12D}$ mice with compound 9/HY-15775 resulted in decreases in lung tumor volumes in the mice within 1 week (FIG. 18).

Thus, bi-allelic inactivation of both Lkb1 and Pten in the mouse lung leads to fully penetrant squamous cell carcinoma. When compared to lung Kras driven ADC models, the immune microenvironment of these SCCs was enriched for TANs. Furthermore, it was demonstrated that SCA1$^+$NGFR$^+$ tumor cells are enriched for tumor propagating ability and express high levels of the immune-evasion molecule PD-L1. These tumors very closely recapitulate the gene expression profiles of the basal subtype of human lung SCC, indicating that these mice can serve as a valuable model for understanding progression and maintenance of basal lung SCCs. This SCC model are useful for the investigation of the molecular mechanisms of human SCC carcinogenesis and allow for further pre-clinical and co-clinical investigation of novel therapies aimed at eradicating lung tumors.

Despite the fact that lung adenocarcinoma (ADC) and squamous cell carcinoma (SCC) occur at relatively equal frequencies world-wide, developing a genetic model of lung SCC has been challenging. The Ad-Cre inhalation method may specifically target more distal lung progenitors, thus selecting for tumor cells-of-origin that predispose towards an ADC phenotype. Several studies have targeted deletion of squamous tumor suppressors, such as Pten, or activation of squamous oncogenes, such as Sox2. Despite these efforts, only partial SCC differentiation was observed in either model (Lu et al. (2010) *PLoS One* 5:e11022; Malkoski et al. (2013) *Mol. Carcinog.* (e-pub) doi:10.1002/mc/22030). By contrast, it is demonstrated herein that deletion of both Pten and Lkb1, via the traditional Ad-Cre inhalation system, is able to produce lung tumors of purely squamous phenotype. Lkb1;Pten tumor lesions appeared to grow into the distal lung, suggesting that if basal cells are the cells-of-origin, they are able to migrate more distally to propagate disease. When the expression of stem cell markers in normal lung tissue was examined, 100% of basal cells were SCA1$^+$, while ~25% of BASCs were NGFR$^+$. These data suggest an alternate possibility that a rare subset of NGFR$^+$ BASCs could serve as distal cells-of-origin for these tumors. SPC-CreER and CCSP-CreER both failed to produce tumors when used with the Lkb1;Pten alleles, indicating that distal lung cells may not be the primary targets of oncogenic transformation in this model. Further examination of the cells of origin for these tumors, including the use of basal-cell specific Cre strains or repetitive injury that targets particular cell populations, will help elucidate which lung cells can serve as precursors for these squamous tumors.

As expected, the loss of both Lkb1 and Pten in these tumors activated the AKT and mTOR pathways, likely driving cellular proliferation and tumorigenesis. The deletion of these genes was also associated with the up-regulation of specific cytokines and other immune modulating proteins, leading to a unique tumor microenvironment. Compared to Kras tumor cells, the LP EpCAM$^+$ cells expressed very high levels of the chemokines CXCL3 and CXCL5, the BAL fluid contained elevated CXCL1, CXCL2, CXCL5 and CXCL7. The CXC chemokine family controls the migration and adhesion of monocytes and neutrophils, mediating its effects on target cells by interacting with CXCR2 (Pold et al. (2004) *Cancer Res.* 64:1853-1860). CXCL5, is also known as epithelial-derived neutrophil-activating peptide 78 (ENA-78), and its expression is associated with PI3K/AKT and Raf/MEK/ERK activation (Hsu et al. (2012) *Oncogene* 32:4436-4447). Recent findings in tumor bearing mice and cancer patients indicate that the increased metabolism of L-arginine by TANs producing arginase1 can inhibit T cell lymphocyte responses (Raber et al. (2012) *Immunol. Invest.* 41:614-634), and it is likely that this mechanism is in play in the LP tumors. Furthermore, strong MPO staining in patient SCC tissues was observed, suggesting that activated TANs are a key component of SCC in both mouse and human.

In addition to expression of the TAN-attracting cytokines, the LP EpCAM$^+$ cells expressed high levels of the immune evasion molecule PD-L1. Recently, there has been much excitement surrounding the potential of targeting molecules such as PD-L1 to 'reawaken' the immune system and cause tumor destruction. In the phase I study of nivolumab, a fully humanized monoclonal antibody to PD-1, PD-L1 expression was determined by IHC in pre-treatment tumor biopsies of various tumor types (n=42). 36% of patients whose tumors showed PD-L1 expression achieved objective response to nivolumab treatment (9/25), while none of the patients with PD-L1 negative tumors showed any objective response (0/17), although some achieved prolonged stable disease (Topalian et al. (2012) *N. Engl. J. Med.* 366:2443-2454). These data indicate that PD-L1 expression influences response to anti-PD-1 antibody therapy. With the accumulation of clinical data, the actual correlation between PD-L1 expression and response to anti-PD-1 therapy should become clearer.

Intriguingly, the TPCs within the SCC model showed enrichment for PD-L1 expression, suggesting that TPCs have unique immune evasion properties. Strikingly, it was found that the SCA1$^+$NGFR1$^+$ cell population had enhanced tumor-propagating activity compared to other tumor cell populations. The studies described herein compared three tumor cell populations from murine SCC, and the SCA1$^-$NGFR$^+$ population could not be assessed due to low abundance. Thus, there could be additional TPCs to characterize in Lkb1;Pten SCCs. Furthermore, while PDX analyses showed that NGFR$^+$ human SCC cells are enriched for PD-L1, the identity of TPCs in human SCC has not been established with a functional assay. SCA1 as a TPC marker is not useful for human cell studies, and markers in addition to NGFR may be required to enrich for propagating activity from primary patient SCCs. It may be possible to first debulk tumors with a more generally targeted inhibitor or surgery, and then prevent tumor recurrence and/or metastasis through administration of anti-PD-1 therapy to target TPCs. Together these data demonstrate the potential of immunotherapy for the treatment of lung SCC and lay the groundwork for further investigation into the response of both cancer cells and the immune microenvironment to such treatments.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) on the world wide web and/or the National Center for Biotechnology Information (NCBI) on the world wide web.

EQUIVALENTS

Those skilled in the art will recognize, or be able to ascertain using no more than routine experimentation, many equivalents to the specific embodiments of the invention described herein. Such equivalents are intended to be encompassed by the following claims.

TABLE 2

Genes with significantly altered expression in EpCam+ cells: LP tumor vs Kras tumor vs Normal lung EpCam+ cells (log2 fold >1; or log2 fold <1)

| Symbol | Description | GenBank | p-value | log2 fold change for LKB1PTEN - Normal | log2 fold change for LKB1PTEN - Kras |
|---|---|---|---|---|---|
| 10530986 | Tmprss11g | transmembrane protease, serine 11g | 5.24E−08 | 7.299 | 7.039 |
| 10484520 | 4833423E24Rik | RIKEN cDNA 4833423E24 gene | 4.55E−08 | 7.001 | 7.176 |
| 10349138 | Serpinb11 | serine (or cysteine) peptidase inhibitor, clade B (ovalbumin), member 11 | 1.45E−07 | 6.994 | 7.051 |

TABLE 2-continued

Genes with significantly altered expression in EpCam+ cells: LP tumor vs Kras tumor vs Normal lung EpCam+ cells
(log2 fold >1; or log2 fold <1)

| Symbol | Description | GenBank | p-value | log2 fold change for LKB1PTEN - Normal | log2 fold change for LKB1PTEN - Kras |
|---|---|---|---|---|---|
| 10432774 | Krt6b | keratin 6B | 4.71E−07 | 6.78 | 6.036 |
| 10454154 | Dsg3 | desmoglein 3 | 1.46E−08 | 6.747 | 6.636 |
| 10424662 | Psca | prostate stem cell antigen | 2.09E−04 | 6.699 | 5.414 |
| 10531009 | Tmprss11bnl | transmembrane protease, serine 11b N terminal like | 3.97E−08 | 6.698 | 6.784 |
| 10407435 | Akr1c18 | aldo-keto reductase family 1, member C18 | 1.21E−05 | 6.589 | 5.117 |
| 10502575 | Clca4 | chloride channel calcium activated 4 | 3.93E−05 | 6.37 | 6.261 |
| 10475517 | AA467197 | expressed sequence AA467197 | 2.97E−06 | 6.339 | 5.841 |
| 10530974 | Tmprss11a | transmembrane protease, serine 11a | 4.10E−08 | 6.315 | 6.078 |
| 10432780 | Krt6a | keratin 6A | 1.75E−06 | 6.255 | 5.885 |
| 10499896 | Sprr3 | small proline-rich protein 3 | 3.97E−08 | 6.164 | 5.819 |
| 10472235 | Dapl1 | death associated protein-like 1 | 4.10E−08 | 6.106 | 6.259 |
| 10432785 | Krt5 | keratin 5 | 2.28E−07 | 6.056 | 5.997 |
| 10499952 | Crct1 | cysteine-rich C-terminal 1 | 1.23E−06 | 5.961 | 5.719 |
| 10493870 | Sprr2f | small proline-rich protein 2F | 1.40E−06 | 5.891 | 5.866 |
| 10552488 | Klk10 | kallikrein related-peptidase 10 | 1.72E−07 | 5.731 | 5.533 |
| 10530960 | Tmprss11d | transmembrane protease, serine 11d | 3.97E−08 | 5.692 | 5.68 |
| 10493864 | Sprr2d | small proline-rich protein 2D | 2.11E−07 | 5.674 | 5.528 |
| 10589703 | Ltf | lactotransferrin | 4.12E−05 | 5.582 | 5.786 |
| 10493850 | Sprr2a1 | small proline-rich protein 2A1 | 4.07E−07 | 5.562 | 5.102 |
| 10391052 | Krt14 | keratin 14 | 4.16E−08 | 5.532 | 5.177 |
| 10523120 | Cxcl5 (ENA78) | chemokine (C-X-C motif) ligand 5 | 1.25E−06 | 5.467 | 5.105 |
| 10584604 | Trim29 | tripartite motif-containing 29 | 1.46E−08 | 5.456 | 5.228 |
| 10493858 | Sprr2a1 | small proline-rich protein 2A1 | 1.58E−07 | 5.432 | 5.015 |
| 10349157 | Serpinb2 | serine (or cysteine) peptidase inhibitor, clade B, member 2 | 5.23E−08 | 5.411 | 5.033 |
| 10567366 | Gp2 | glycoprotein 2 (zymogen granule membrane) | 4.50E−06 | 5.383 | 5.415 |
| 10450525 | Gm9573 | predicted gene 9573 | 6.49E−07 | 5.366 | 5.161 |
| 10523128 | Ppbp (Cxcl7) | pro-platelet basic protein | 7.62E−05 | 5.338 | 6.538 |
| 10523138 | Cxcl3 | chemokine (C-X-C motif) ligand 3 | 3.67E−05 | 5.317 | 4.067 |
| 10391066 | Krt17 | keratin 17 | 9.92E−08 | 5.286 | 5.182 |
| 10407416 | Calml3 | calmodulin-like 3 | 3.97E−08 | 5.257 | 5.936 |
| 10550980 | Lypd3 | Ly6/Plaur domain containing 3 | 4.55E−08 | 5.157 | 4.745 |
| 10522411 | Cwh43 | cell wall biogenesis 43 C-terminal homolog (S. cerevisiae) | 9.47E−08 | 5.114 | 4.832 |
| 10368343 | Arg1 | arginase, liver | 4.29E−04 | 5.028 | 3.967 |
| 10502638 | Clca5 | chloride channel calcium activated 5 | 1.52E−07 | 5.017 | 4.904 |
| 10360398 | Ifi202b | interferon activated gene 202B | 6.13E−08 | 5.006 | 4.906 |
| 10417568 | Oit1 | oncoprotein induced transcript 1 | 2.33E−06 | 4.978 | 4.582 |
| 10476042 | Tgm3 | transglutaminase 3, E polypeptide | 2.89E−07 | 4.943 | 4.766 |
| 10408557 | Serpinb1a | serine (or cysteine) peptidase inhibitor, clade B, member 1a | 4.99E−08 | 4.917 | 5.076 |
| 10531724 | Plac8 | placenta-specific 8 | 9.61E−06 | 4.871 | 5.093 |
| 10399407 | Vsnl1 | visinin-like 1 | 8.26E−08 | 4.722 | 5.217 |
| 10531022 | Tmprss11e | transmembrane protease, serine 11e | 4.08E−06 | 4.709 | 4.731 |

TABLE 2-continued

Genes with significantly altered expression in EpCam+ cells: LP tumor vs Kras tumor vs Normal lung EpCam+ cells
(log2 fold >1; or log2 fold <1)

| Symbol | Description | GenBank | p-value | log2 fold change for LKB1PTEN - Normal | log2 fold change for LKB1PTEN - Kras |
|---|---|---|---|---|---|
| 10415431 | Mcpt1 | mast cell protease 1 | 3.80E−05 | 4.67 | 3.99 |
| 10457669 | Dsc3 | desmocollin 3 | 1.55E−07 | 4.662 | 4.452 |
| 10530998 | Tmprss11f | transmembrane protease, serine 11f | 1.28E−07 | 4.646 | 4.438 |
| 10577641 | 1810011O10 Rik | RIKEN cDNA 1810011O10 gene | 3.72E−05 | 4.635 | 3.587 |
| 10358124 | Pkp1 | plakophilin 1 | 3.87E−07 | 4.579 | 4.337 |
| 10542129 | Clec2g | C-type lectin domain family 2, member g | 4.45E−07 | 4.547 | 4.518 |
| 10445251 | Gpr110 | G protein-coupled receptor 110 | 2.04E−04 | 4.539 | 4.458 |
| 10419034 | 2610528A11 Rik | RIKEN cDNA 2610528A11 gene | 3.54E−07 | 4.516 | 4.323 |
| 10472538 | Dhrs9 | dehydrogenase/reductase (SDR family) member 9 | 3.82E−04 | 4.509 | 3.928 |
| 10439282 | Csta | cystatin A | 1.88E−06 | 4.498 | 4.388 |
| 10395365 | Agr2 | anterior gradient 2 (*Xenopus laevis*) | 1.64E−06 | 4.465 | 4.888 |
| 10434808 | Tprg | transformation related protein 63 regulated | 2.28E−07 | 4.461 | 4.017 |
| 10570434 | Ifitm1 | interferon induced transmembrane protein 1 | 1.28E−07 | 4.455 | 5.479 |
| 10552475 | Klk12 | kallikrein related-peptidase 12 | 1.48E−05 | 4.435 | 4.36 |
| 10469786 | Il1f 9 | interleukin 1 family, member 9 | 2.30E−06 | 4.426 | 5.283 |
| 10449807 | Ephx3 | epoxide hydrolase 3 | 2.73E−06 | 4.422 | 4.162 |
| 10552064 | Krtdap | keratinocyte differentiation associated protein | 4.80E−06 | 4.392 | 3.919 |
| 10347925 | Gm7609 | predicted pseudogene 7609 | 3.17E−04 | 4.368 | 3.391 |
| 10499899 | Sprr1a | small proline-rich protein 1A | 9.91E−04 | 4.364 | 4.02 |
| 10561025 | Cnfn | cornifelin | 3.13E−07 | 4.352 | 4.147 |
| 10493834 | Pglyrp4 | peptidoglycan recognition protein 4 | 4.13E−05 | 4.302 | 4.147 |
| 10390748 | Tns4 | tensin 4 | 1.60E−06 | 4.302 | 3.896 |
| 10575833 | Hsd17b2 | hydroxysteroid (17-beta) dehydrogenase 2 | 1.04E−05 | 4.273 | 3.874 |
| 10498361 | Gpr87 | G protein-coupled receptor 87 | 8.26E−08 | 4.243 | 4.197 |
| 10517401 | Grhl3 | grainyhead-like 3 (*Drosophila*) | 9.61E−06 | 4.227 | 3.892 |
| 10466521 | Gcnt1 | glucosaminyl (N-acetyl) transferase 1, core 2 | 3.91E−04 | 4.208 | 2.871 |
| 10493873 | Sprr2g | small proline-rich protein 2G | 2.59E−06 | 4.196 | 4.057 |
| 10517609 | Cda | cytidine deaminase | 1.30E−07 | 4.192 | 4.054 |
| 10439500 | Upk1b | uroplakin 1B | 5.25E−06 | 4.168 | 6.159 |
| 10569102 | Irf7 | interferon regulatory factor 7 | 1.40E−05 | 4.158 | 4.331 |
| 10558769 | Ifitm1 | interferon induced transmembrane protein 1 | 8.51E−08 | 4.146 | 5.055 |
| 10554034 | Lass3 | LAG1 homolog, ceramide synthase 3 | 7.30E−08 | 4.119 | 3.793 |
| 10575034 | Cdh3 | cadherin 3 | 2.61E−07 | 4.1 | 3.831 |
| 10368317 | Enpp3 | ectonucleotide pyrophosphatase/phosphodiesterase 3 | 1.39E−07 | 4.083 | 5.651 |
| 10500204 | Ecm1 | extracellular matrix protein 1 | 5.00E−05 | 4.063 | 3.996 |
| 10524631 | Oasl1 | 2′-5′ oligoadenylate synthetase-like 1 | 1.15E−06 | 4.041 | 3.937 |
| 10387838 | Alox12e | arachidonate lipoxygenase, epidermal | 1.06E−06 | 4.03 | 4.877 |
| 10606609 | Tspan6 | tetraspanin 6 | 6.36E−05 | 4.027 | 4.805 |
| 10574560 | Ces2f | carboxylesterase 2F | 5.05E−07 | 4.017 | 3.949 |

TABLE 2-continued

Genes with significantly altered expression in EpCam+ cells: LP tumor vs
Kras tumor vs Normal lung EpCam+ cells
(log2 fold >1; or log2 fold <1)

| Symbol | Description | GenBank | p-value | log2 fold change for LKB1PTEN - Normal | log2 fold change for LKB1PTEN - Kras |
|---|---|---|---|---|---|
| 10462623 | Ifit1 | interferon-induced protein with tetratricopeptide repeats 1 | 1.95E−06 | 4.016 | 4.226 |
| 10515115 | Slc5a9 | solute carrier family 5 (sodium/glucose cotransporter), member 9 | 1.67E−07 | 4.008 | 4.18 |
| 10569020 | Ifitm6 | interferon induced transmembrane protein 6 | 7.30E−08 | 3.989 | 4.204 |
| 10552462 | Klk14 | kallikrein related-peptidase 14 | 5.27E−06 | 3.984 | 3.486 |
| 10394119 | Zfp750 | zinc finger protein 750 | 2.45E−06 | 3.955 | 3.667 |
| 10360391 | Ifi203 | interferon activated gene 203 | 1.65E−05 | 3.952 | 3.739 |
| 10408798 | Tfap2a | transcription factor AP-2, alpha | 1.26E−07 | 3.95 | 3.593 |
| 10350742 | Rnasel | ribonuclease L (2',5'-oligoisoadenylate synthetase-dependent) | 6.15E−05 | 3.944 | 3.734 |
| 10377490 | Alox12b | arachidonate 12-lipoxygenase, 12Rtype | 1.45E−07 | 3.935 | 3.933 |
| 10547056 | Tmem40 | transmembrane protein 40 | 6.31E−06 | 3.927 | 3.44 |
| 10494016 | Them5 | thioesterase superfamily member 5 | 1.19E−04 | 3.905 | 3.43 |
| 10564417 | Aldh1a3 | aldehyde dehydrogenase family 1, subfamily A3 | 1.64E−06 | 3.895 | 3.639 |
| 10582879 | Csprs | component of Sp100-rs | 1.29E−04 | 3.865 | 2.879 |
| 10459633 | | | 3.63E−05 | 3.856 | 3.694 |
| 10375265 | Atp10b | ATPase, class V, type 10B | 6.40E−06 | 3.843 | 3.85 |
| 10587331 | Gsta1 | glutathione S-transferase, alpha 1 (Ya) | 4.37E−05 | 3.817 | 3.846 |
| 10379731 | Expi | extracellular proteinase inhibitor | 1.91E−04 | 3.813 | 3.601 |
| 10486988 | Duoxa1 | dual oxidase maturation factor 1 | 2.48E−07 | 3.799 | 3.663 |
| 10502791 | Ifi44 | interferon-induced protein 44 | 2.80E−05 | 3.797 | 3.808 |
| 10486197 | Rhov | ras homolog gene family, member V | 4.64E−07 | 3.787 | 3.915 |
| 10499891 | Sprr1b | small proline-rich protein 1B | 1.32E−06 | 3.781 | 3.65 |
| 10409551 | Pitx1 | paired-like homeodomain transcription factor 1 | 3.83E−07 | 3.778 | 3.43 |
| 10440019 | Tmem45a | transmembrane protein 45a | 1.73E−05 | 3.767 | 4.427 |
| 10556616 | Tmc5 | transmembrane channel-like gene family 5 | 3.46E−05 | 3.739 | 3.884 |
| 10592044 | Tmem45b | transmembrane protein 45b | 1.85E−05 | 3.739 | 3.567 |
| 10442381 | Prss27 | protease, serine, 27 | 5.70E−06 | 3.713 | 3.629 |
| 10552480 | Klk11 | kallikrein related-peptidase 11 | 4.10E−08 | 3.697 | 4.238 |
| 10469984 | Lrrc26 | leucine rich repeat containing 26 | 2.40E−05 | 3.681 | 4.406 |
| 10391061 | Krt16 | keratin 16 | 1.80E−05 | 3.681 | 3.437 |
| 10517825 | Padi1 | peptidyl arginine deiminase, type 1 | 4.85E−07 | 3.675 | 3.521 |
| 10540298 | Chl1 | cell adhesion molecule with homology to L1CAM | 4.45E−07 | 3.667 | 3.222 |
| 10600024 | Gpr50 | G-protein-coupled receptor 50 | 1.45E−05 | 3.663 | 3.52 |
| 10587383 | Cd109 | CD109 antigen | 5.38E−06 | 3.635 | 3.6 |
| 10404783 | Edn1 | endothelin 1 | 5.08E−04 | 3.612 | 2.499 |
| 10562223 | Fxyd3 | FXYD domain-containing ion transport regulator 3 | 2.57E−05 | 3.603 | 3.037 |
| 10570855 | Plat | plasminogen activator, tissue | 1.78E−04 | 3.59 | 3.652 |
| 10557862 | Itgam | integrin alpha M | 8.24E−05 | 3.581 | 3.374 |
| 10533720 | Niacr1 | niacin receptor 1 | 2.82E−06 | 3.58 | 3.513 |

TABLE 2-continued

Genes with significantly altered expression in EpCam+ cells: LP tumor vs Kras tumor vs Normal lung EpCam+ cells
(log2 fold >1; or log2 fold <1)

| Symbol | Description | GenBank | p-value | log2 fold change for LKB1PTEN - Normal | log2 fold change for LKB1PTEN - Kras |
|---|---|---|---|---|---|
| 10527158 | Fscn1 | fascin homolog 1, actin bundling protein (*Strongylocentrotus purpuratus*) | 1.76E−05 | 3.572 | 3.272 |
| 10493824 | S100a7a | S100 calcium binding protein A7A | 1.16E−04 | 3.569 | 3.153 |
| 10469816 | Il1rn | interleukin 1 receptor antagonist | 1.12E−06 | 3.548 | 3.409 |
| 10352798 | Kcnh1 | potassium voltage-gated channel, subfamily H (eag-related), member 1 | 1.64E−06 | 3.547 | 3.136 |
| 10395849 | Pax9 | paired box gene 9 | 4.71E−06 | 3.517 | 3.442 |
| 10534395 | Cldn4 | claudin 4 | 4.35E−04 | 3.517 | 2.714 |
| 10486681 | Tgm5 | transglutaminase 5 | 2.22E−05 | 3.51 | 3.088 |
| 10494761 | Vtcn1 | V-set domain containing T cell activation inhibitor 1 | 3.59E−06 | 3.464 | 4.052 |
| 10570741 | Defb1 | defensin beta 1 | 1.16E−07 | 3.455 | 3.552 |
| 10387855 | Alox15 | arachidonate 15-lipoxygenase | 3.41E−07 | 3.45 | 3.725 |
| 10347915 | Gm7609 | predicted pseudogene 7609 | 7.05E−05 | 3.435 | 2.456 |
| 10487588 | Il1a | interleukin 1 alpha | 4.46E−04 | 3.434 | 3.17 |
| 10441244 | Fam3b | family with sequence similarity 3, member B | 6.33E−05 | 3.422 | 2.806 |
| 10578904 | Cpe | carboxypeptidase E | 7.62E−06 | 3.418 | 3.668 |
| 10463836 | Gsto1 | glutathione S-transferase omega 1 | 3.96E−04 | 3.399 | 3.585 |
| 10379636 | Slfn4 | schlafen 4 | 2.21E−06 | 3.394 | 3.325 |
| 10396402 | Prkch | protein kinase C, eta | 1.54E−05 | 3.359 | 3.475 |
| 10493979 | Rptn | repetin | 7.82E−06 | 3.355 | 3.608 |
| 10448409 | Prss22 | protease, serine, 22 | 8.15E−05 | 3.355 | 2.838 |
| 10458534 | Pcdh1 | protocadherin 1 | 2.60E−05 | 3.353 | 2.835 |
| 10403229 | Itgb8 | integrin beta 8 | 6.22E−07 | 3.345 | 3.956 |
| 10531987 | Gbp4 | guanylate binding protein 4 | 3.87E−05 | 3.345 | 3.682 |
| 10450800 | Trim15 | tripartite motif-containing 15 | 5.83E−05 | 3.33 | 3.754 |
| 10507152 | Cyp4a12b | cytochrome P450, family 4, subfamily a, polypeptide 12B | 5.63E−04 | 3.326 | 4.992 |
| 10547621 | Apobec1 | apolipoprotein B mRNA editing enzyme, catalytic polypeptide 1 | 1.18E−07 | 3.291 | 3.617 |
| 10514338 | Mir31 | microRNA 31 | 1.69E−05 | 3.291 | 2.937 |
| 10530772 | Nmu | neuromedin U | 2.37E−05 | 3.289 | 2.858 |
| 10416273 | Phyhip | phytanoyl-CoA hydroxylase interacting protein | 1.85E−05 | 3.286 | 3.137 |
| 10582985 | Casp1 | caspase 1 | 9.71E−06 | 3.273 | 3.265 |
| 10482500 | Rnd3 | Rho family GTPase 3 | 3.75E−07 | 3.239 | 4.415 |
| 10487447 | Mall | mal, T cell differentiation protein-like | 3.64E−04 | 3.232 | 3.267 |
| 10578203 | Cldn23 | claudin 23 | 8.46E−07 | 3.229 | 3.677 |
| 10595392 | Elovl4 | elongation of very long chain fatty acids (FEN1/Elo2, SUR4/Elo3, yeast)-like 4 | 1.67E−07 | 3.213 | 3.143 |
| 10495993 | Elovl6 | ELOVL family member 6, elongation of long chain fatty acids (yeast) | 2.38E−06 | 3.168 | 3.384 |
| 10437210 | Bace2 | beta-site APP-cleaving enzyme 2 | 6.93E−06 | 3.149 | 3.967 |
| 10494500 | Ankrd35 | ankyrin repeat domain 35 | 1.69E−06 | 3.122 | 3.015 |
| 10422272 | Sox21 | SRY-box containing gene 21 | 5.09E−07 | 3.121 | 3.136 |
| 10574572 | Ces2g | carboxylesterase 2G | 1.07E−06 | 3.116 | 4.127 |
| 10498653 | 1110032A04Rik | RIKEN cDNA 1110032A04 gene | 2.09E−07 | 3.112 | 5.301 |
| 10607183 | Lhfpl1 | lipoma HMGIC fusion partner-like 1 | 1.02E−05 | 3.112 | 3.132 |

TABLE 2-continued

Genes with significantly altered expression in EpCam+ cells: LP tumor vs Kras tumor vs Normal lung EpCam+ cells
(log2 fold >1; or log2 fold <1)

| Symbol | Description | GenBank | p-value | log2 fold change for LKB1PTEN - Normal | log2 fold change for LKB1PTEN - Kras |
|---|---|---|---|---|---|
| 10349953 | Chit1 | chitinase 1 (chitotriosidase) | 6.21E−05 | 3.11 | 3.102 |
| 10602896 | Gpr64 | G protein-coupled receptor 64 | 8.77E−05 | 3.1 | 3.465 |
| 10507177 | Cyp4a32 | cytochrome P450, family 4, subfamily a, polypeptide 32 | 2.30E−06 | 3.093 | 3.001 |
| 10605034 | Xlr4c | X-linked lymphocyte-regulated 4C | 2.70E−06 | 3.092 | 3.205 |
| 10360382 | Ifi204 | interferon activated gene 204 | 2.37E−05 | 3.088 | 3.174 |
| 10456184 | Apcdd1 | adenomatosis polyposis coli down-regulated 1 | 1.29E−04 | 3.086 | 3.04 |
| 10593260 | Ankk1 | ankyrin repeat and kinase domain containing 1 | 3.44E−07 | 3.079 | 3.41 |
| 10521459 | Psapl1 | prosaposin-like 1 | 1.35E−05 | 3.064 | 3.051 |
| 10475456 | Duox1 | dual oxidase 1 | 6.60E−07 | 3.045 | 2.833 |
| 10384223 | Igfbp3 | insulin-like growth factor binding protein 3 | 3.73E−04 | 3.034 | 3.117 |
| 10504763 | Galnt12 | UDP-N-acetyl-alpha-D-galactosamine:polypeptide N-acetylgalactosaminyl-transferase 12 | 6.51E−06 | 3.027 | 2.896 |
| 10585803 | Stra6 | stimulated by retinoic acid gene 6 | 5.56E−07 | 3.022 | 3.091 |
| 10562480 | Nudt19 | nudix (nucleoside diphosphate linked moiety X)-type motif 19 | 1.07E−05 | 3.009 | 2.405 |
| 10493867 | Sprr2e | small proline-rich protein 2E | 8.89E−07 | 2.992 | 2.757 |
| 10534945 | Cyp3a13 | cytochrome P450, family 3, subfamily a, polypeptide 13 | 1.40E−05 | 2.991 | 2.843 |
| 10430174 | Apol9a | apolipoprotein L 9a | 2.28E−04 | 2.957 | 2.623 |
| 10561478 | Nccrp1 | non-specific cytotoxic cell receptor protein 1 homolog (zebrafish) | 1.08E−04 | 2.952 | 2.856 |
| 10549041 | Sico1a5 | solute carrier organic anion transporter family, member 1a5 | 1.32E−05 | 2.949 | 3.352 |
| 10351368 | Gpa33 | glycoprotein A33 (transmembrane) | 8.64E−04 | 2.923 | 2.488 |
| 10368970 | Prdm1 | PR domain containing 1, with ZNF domain | 4.32E−06 | 2.912 | 3.38 |
| 10430166 | Apol7a | apolipoprotein L 7a | 5.48E−05 | 2.912 | 2.808 |
| 10466127 | AW112010 | expressed sequence AW112010 | 3.61E−04 | 2.91 | 4.58 |
| 10356274 | Csprs | component of Sp100-rs | 7.98E−04 | 2.89 | 2.117 |
| 10456357 | Pmaip1 | phorbol-12-myristate-13-acetate-induced protein 1 | 6.35E−04 | 2.877 | 2.696 |
| 10429564 | Ly6a (Sca1) | lymphocyte antigen 6 complex, locus A | 2.58E−04 | 2.876 | 4.402 |
| 10597575 | Plcd1 | phospholipase C, delta 1 | 3.83E−07 | 2.875 | 3.419 |
| 10457614 | Aqp4 | aquaporin 4 | 1.21E−05 | 2.874 | 3.608 |
| 10374236 | Upp1 | uridine phosphorylase 1 | 5.48E−07 | 2.868 | 2.653 |
| 10513739 | Tnc | tenascin C | 1.85E−04 | 2.856 | 2.673 |
| 10482059 | Ggta1 | glycoprotein galactosyltransferase alpha 1, 3 | 2.35E−06 | 2.854 | 2.536 |
| 10466659 | Gda | guanine deaminase | 1.26E−07 | 2.853 | 3.359 |
| 10502156 | Ccdc109b | coiled-coil domain containing 109B | 5.80E−07 | 2.85 | 3.199 |
| 10455299 | Sh3rf2 | SH3 domain containing ring finger 2 | 4.14E−04 | 2.82 | 1.842 |
| 10434815 | Trp63 | transformation related protein 63 | 7.13E−06 | 2.801 | 2.895 |
| 10570606 | Defb14 | defensin beta 14 | 3.96E−05 | 2.786 | 2.758 |
| 10477406 | Bpifb3 | BPI fold containing family B, member 3 | 2.22E−05 | 2.783 | 2.554 |

TABLE 2-continued

Genes with significantly altered expression in EpCam+ cells: LP tumor vs Kras tumor vs Normal lung EpCam+ cells
(log2 fold >1; or log2 fold <1)

| Symbol | Description | GenBank | p-value | log2 fold change for LKB1PTEN - Normal | log2 fold change for LKB1PTEN - Kras |
|---|---|---|---|---|---|
| 10571984 | Ddx60 | DEAD (Asp-Glu-Ala-Asp) box polypeptide 60 | 2.18E−06 | 2.781 | 3.215 |
| 10545014 | Vopp1 | vesicular, overexpressed in cancer, prosurvival protein 1 | 1.00E−04 | 2.78 | 2.201 |
| 10584124 | Arhgap32 | Rho GTPase activating protein 32 | 2.78E−06 | 2.779 | 3.746 |
| 10460251 | 1700055N04Rik | RIKEN cDNA 1700055N04 gene | 6.33E−04 | 2.777 | 2.138 |
| 10402347 | Ifi27l2a | interferon, alpha-inducible protein 27 like 2A | 6.27E−04 | 2.772 | 2.748 |
| 10467508 | Blnk | B cell linker | 4.62E−06 | 2.771 | 3.277 |
| 10428943 | Gsdmc | gasdermin C | 2.61E−07 | 2.766 | 2.51 |
| 10395155 | Fam110c | family with sequence similarity 110, member C | 4.56E−06 | 2.761 | 2.513 |
| 10474419 | Lgr4 | leucine-rich repeat-containing G protein-coupled receptor 4 | 2.13E−05 | 2.755 | 3.811 |
| 10594758 | Gcnt3 | glucosaminyl (N-acetyl) transferase 3, mucin type | 8.66E−04 | 2.754 | 2.778 |
| 10462621 | I830012O16Rik | RIKEN cDNA I830012O16 gene | 7.37E−07 | 2.753 | 3.031 |
| 10387821 | Alox12 | arachidonate 12-lipoxygenase | 4.39E−04 | 2.729 | 1.896 |
| 10588043 | Rbp2 | retinol binding protein 2, cellular | 5.80E−06 | 2.714 | 2.707 |
| 10450982 | Gpr115 | G protein-coupled receptor 115 | 1.78E−06 | 2.711 | 2.629 |
| 10450501 | Tnf | tumor necrosis factor | 7.88E−05 | 2.703 | 2.94 |
| 10488938 | Fam83c | family with sequence similarity 83, member C | 4.19E−06 | 2.701 | 2.563 |
| 10437191 | B3galt5 | UDP-Gal:betaGlcNAc beta 1,3-galactosyltransferase, polypeptide 5 | 1.08E−04 | 2.7 | 2.397 |
| 10560862 | 2310033E01Rik | RIKEN cDNA 2310033E01 gene | 2.56E−05 | 2.689 | 2.459 |
| 10524621 | Oasl2 | 2'-5' oligoadenylate synthetase-like 2 | 1.08E−05 | 2.686 | 3.62 |
| 10587051 | Wdr72 | WD repeat domain 72 | 5.38E−07 | 2.685 | 3.046 |
| 10521038 | Slc5a1 | solute carrier family 5 (sodium/glucose cotransporter), member 1 | 5.68E−05 | 2.683 | 3.098 |
| 10555297 | Kcne3 | potassium voltage-gated channel, Isk-related subfamily, gene 3 | 4.62E−06 | 2.674 | 2.247 |
| 10434778 | Rtp4 | receptor transporter protein 4 | 7.40E−05 | 2.67 | 3.338 |
| 10404686 | Bmp6 | bone morphogenetic protein 6 | 3.24E−07 | 2.653 | 2.751 |
| 10556297 | Adm | adrenomedullin | 1.93E−05 | 2.65 | 3.237 |
| 10460259 | Aldh3b2 | aldehyde dehydrogenase 3 family, member B2 | 2.64E−06 | 2.643 | 2.185 |
| 10590365 | Vipr1 | vasoactive intestinal peptide receptor 1 | 5.01E−06 | 2.638 | 2.653 |
| 10536908 | Tspan33 | tetraspanin 33 | 2.58E−07 | 2.637 | 2.811 |
| 10584835 | Mpzl3 | myelin protein zero-like 3 | 1.28E−05 | 2.637 | 2.324 |
| 10368092 | Hebp2 | heme binding protein 2 | 1.67E−07 | 2.634 | 2.457 |
| 10462390 | Cd274 | CD274 antigen | 7.16E−04 | 2.632 | 2.507 |
| 10602840 | Sh3kbp1 | SH3-domain kinase binding protein 1 | 1.97E−07 | 2.617 | 2.977 |
| 10575993 | 6430548M08Rik | RIKEN cDNA 6430548M08 gene | 6.99E−05 | 2.615 | 2.072 |
| 10399465 | Fam84a | family with sequence similarity 84, member A | 9.88E−05 | 2.604 | 3.206 |
| 10443854 | Cyp4f39 | cytochrome P450, family 4, subfamily f, polypeptide 39 | 5.54E−06 | 2.596 | 3.179 |
| 10434934 | Bdh1 | 3-hydroxybutyrate dehydrogenase, type 1 | 9.28E−07 | 2.595 | 2.555 |

TABLE 2-continued

Genes with significantly altered expression in EpCam+ cells: LP tumor vs Kras tumor vs Normal lung EpCam+ cells
(log2 fold >1; or log2 fold <1)

| Symbol | Description | GenBank | p-value | log2 fold change for LKB1PTEN - Normal | log2 fold change for LKB1PTEN - Kras |
|---|---|---|---|---|---|
| 10468344 | Col17a1 | collagen, type XVII, alpha 1 | 3.53E−06 | 2.593 | 2.662 |
| 10588731 | Mst1r | macrophage stimulating 1 receptor (c-met-related tyrosine kinase) | 6.64E−05 | 2.591 | 2.362 |
| 10405566 | Slc25a48 | solute carrier family 25, member 48 | 1.74E−04 | 2.575 | 2.558 |
| 10566026 | Folr2 | folate receptor 2 (fetal) | 4.72E−06 | 2.569 | 2.658 |
| 10349872 | | | 1.97E−04 | 2.569 | 2.166 |
| 10375608 | Scgb3a1 | secretoglobin, family 3A, member 1 | 1.08E−04 | 2.566 | 4.409 |
| 10506583 | Ttc22 | tetratricopeptide repeat domain 22 | 5.44E−05 | 2.564 | 2.287 |
| 10397351 | Jdp2 | Jun dimerization protein 2 | 3.09E−05 | 2.558 | 2.708 |
| 10385504 | Gm5431 | predicted gene 5431 | 3.10E−06 | 2.557 | 2.751 |
| 10533198 | Oas2 | 2'-5' oligoadenylate synthetase 2 | 5.20E−06 | 2.552 | 2.401 |
| 10491477 | Sox2 | SRY-box containing gene 2 | 7.81E−07 | 2.547 | 5.077 |
| 10599120 | Dock11 | dedicator of cytokinesis 11 | 1.67E−07 | 2.544 | 3.108 |
| 10474526 | Lpcat4 | lysophosphatidylcholine acyltransferase 4 | 1.07E−05 | 2.541 | 2.79 |
| 10533246 | Oas1g | 2'-5' oligoadenylate synthetase 1G | 7.52E−05 | 2.54 | 1.858 |
| 10463997 | Pdcd4 | programmed cell death 4 | 1.91E−04 | 2.528 | 1.92 |
| 10462618 | Ifit3 | interferon-induced protein with tetratricopeptide repeats 3 | 1.30E−04 | 2.524 | 3.876 |
| 10509267 | Wnt4 | wingless-related MMTV integration site 4 | 8.73E−07 | 2.521 | 2.884 |
| 10421143 | Adam28 | a disintegrin and metallopeptidase domain 28 | 8.02E−04 | 2.519 | 3.299 |
| 10360040 | Fcgr3 | Fc receptor, IgG, low affinity III | 9.35E−05 | 2.507 | 2.047 |
| 10390211 | Igf2bp1 | insulin-like growth factor 2 mRNA binding protein 1 | 3.56E−06 | 2.496 | 2.477 |
| 10395389 | Sostdc1 | sclerostin domain containing 1 | 7.88E−04 | 2.492 | 2.365 |
| 10349661 | 5430435G22Rik | RIKEN cDNA 5430435G22 gene | 4.66E−05 | 2.471 | 2.268 |
| 10600093 | Zfp185 | zinc finger protein 185 | 5.38E−06 | 2.47 | 3.301 |
| 10492335 | Rap2b | RAP2B, member of RAS oncogene family | 2.56E−05 | 2.465 | 2.755 |
| 10396840 | Rdh12 | retinol dehydrogenase 12 | 5.15E−04 | 2.459 | 1.811 |
| 10445678 | 1700001C19Rik | RIKEN cDNA 1700001C19 gene | 7.88E−04 | 2.457 | 2.39 |
| 10462554 | Lipk | lipase, family member K | 1.69E−05 | 2.449 | 2.318 |
| 10444886 | 2300002M23Rik | RIKEN cDNA 2300002M23 gene | 6.03E−06 | 2.443 | 2.33 |
| 10454015 | Ttc39c | tetratricopeptide repeat domain 39C | 9.67E−05 | 2.439 | 2.156 |
| 10349166 | Serpinb10-ps | serine (or cysteine) peptidase inhibitor, clade B (ovalbumin), member 10, pseudogene | 4.00E−07 | 2.434 | 2.712 |
| 10420935 | Ephx2 | epoxide hydrolase 2, cytoplasmic | 8.96E−05 | 2.43 | 2.003 |
| 10552494 | Klk9 | kallikrein related-peptidase 9 | 1.35E−05 | 2.427 | 2.238 |
| 10361887 | Perp | PERP, TP53 apoptosis effector | 4.62E−05 | 2.423 | 2.052 |
| 10350473 | B3galt2 | UDP-Gal:betaGlcNAc beta 1,3-galactosyltransferase, polypeptide 2 | 1.37E−04 | 2.422 | 2.217 |
| 10404472 | Serpinb9g | serine (or cysteine) peptidase inhibitor, clade B, member 9g | 1.56E−04 | 2.422 | 1.815 |

TABLE 2-continued

Genes with significantly altered expression in EpCam+ cells: LP tumor vs Kras tumor vs Normal lung EpCam+ cells
(log2 fold >1; or log2 fold <1)

| Symbol | Description | GenBank | p-value | log2 fold change for LKB1PTEN - Normal | log2 fold change for LKB1PTEN - Kras |
|---|---|---|---|---|---|
| 10381049 | Rapgef11 | Rap guanine nucleotide exchange factor (GEF)-like 1 | 2.80E−05 | 2.412 | 2.244 |
| 10359034 | Qsox1 | quiescin Q6 sulfhydryl oxidase 1 | 9.89E−04 | 2.394 | 2.005 |
| 10503523 | Ggh | gamma-glutamyl hydrolase | 5.70E−06 | 2.389 | 2.213 |
| 10457872 | Slc39a6 | solute carrier family 39 (metal ion transporter), member 6 | 1.01E−06 | 2.383 | 2.165 |
| 10420362 | Gjb2 | gap junction protein, beta 2 | 6.57E−05 | 2.382 | 1.87 |
| 10394954 | Grhl1 | grainyhead-like 1 (*Drosophila*) | 2.56E−05 | 2.378 | 1.889 |
| 10367673 | Plekhg1 | pleckstrin homology domain containing, family G (with RhoGef domain) member 1 | 3.41E−07 | 2.353 | 2.543 |
| 10597182 | Nbeal2 | neurobeachin-like 2 | 2.70E−05 | 2.351 | 2.426 |
| 10409713 | Slc28a3 | solute carrier family 28 (sodium-coupled nucleoside transporter), member 3 | 6.52E−04 | 2.343 | 3.099 |
| 10608638 | Klra33 | killer cell lectin-like receptor subfamily A member 33 | 4.60E−06 | 2.337 | 2.203 |
| 10405783 | Mir24-1 | microRNA 24-1 | 3.05E−05 | 2.333 | 2.348 |
| 10502565 | Clca2 | chloride channel calcium activated 2 | 3.18E−04 | 2.333 | 2.117 |
| 10398665 | Tnfaip2 | tumor necrosis factor, alpha-induced protein 2 | 3.04E−05 | 2.322 | 2.823 |
| 10404649 | Dsp | desmoplakin | 2.82E−05 | 2.315 | 2.153 |
| 10404479 | Serpinb9g | serine (or cysteine) peptidase inhibitor, clade B, member 9g | 6.87E−04 | 2.31 | 2.187 |
| 10425354 | Mgat3 | mannoside acetylglucosaminyltransferase 3 | 5.92E−05 | 2.308 | 1.968 |
| 10384044 | Myl7 | myosin, light polypeptide 7, regulatory | 2.68E−06 | 2.305 | 2.812 |
| 10369835 | Phyhipl | phytanoyl-CoA hydroxylase interacting protein-like | 1.64E−06 | 2.297 | 2.461 |
| 10490903 | Car13 | carbonic anhydrase 13 | 2.46E−05 | 2.288 | 2.352 |
| 10379630 | Slfn2 | schlafen 2 | 7.82E−06 | 2.279 | 2.365 |
| 10386033 | Fat2 | FAT tumor suppressor homolog 2 (*Drosophila*) | 2.12E−04 | 2.272 | 1.932 |
| 10432682 | Krt80 | keratin 80 | 7.57E−04 | 2.263 | 2.388 |
| 10511870 | Fut9 | fucosyltransferase 9 | 4.71E−06 | 2.262 | 2.466 |
| 10366951 | Ndufa4l2 | NADH dehydrogenase (ubiquinone) 1 alpha subcomplex, 4-like 2 | 3.66E−04 | 2.258 | 1.966 |
| 10596747 | Sema3f | sema domain, immunoglobulin domain (Ig), short basic domain, secreted, (semaphorin) 3F | 1.03E−04 | 2.23 | 1.916 |
| 10410388 | | | 4.80E−04 | 2.222 | 2.641 |
| 10568873 | Adam8 | a disintegrin and metallopeptidase domain 8 | 1.27E−06 | 2.221 | 3.723 |
| 10355456 | Mreg | melanoregulin | 4.05E−07 | 2.22 | 2.38 |
| 10355343 | Abca12 | ATP-binding cassette, sub-family A (ABC1), member 12 | 6.04E−05 | 2.213 | 2.007 |
| 10394060 | Sectm1b | secreted and transmembrane 1B | 1.17E−04 | 2.211 | 2.7 |
| 10571657 | Acsl1 | acyl-CoA synthetase long-chain family member 1 | 1.26E−06 | 2.191 | 3.375 |

TABLE 2-continued

Genes with significantly altered expression in EpCam+ cells: LP tumor vs Kras tumor vs Normal lung EpCam+ cells
(log2 fold >1; or log2 fold <1)

| Symbol | Description | GenBank | p-value | log2 fold change for LKB1PTEN - Normal | log2 fold change for LKB1PTEN - Kras |
|---|---|---|---|---|---|
| 10374197 | Ramp3 | receptor (calcitonin) activity modifying protein 3 | 3.25E−04 | 2.19 | 2.193 |
| 10428707 | Has2 | hyaluronan synthase 2 | 2.59E−06 | 2.177 | 2.64 |
| 10385052 | Ranbp17 | RAN binding protein 17 | 2.65E−07 | 2.174 | 2.672 |
| 10474919 | Gm14137 | predicted gene 14137 | 9.41E−06 | 2.166 | 2.005 |
| 10357594 | Rassf5 | Ras association (RalGDS/AF-6) domain family member 5 | 1.79E−04 | 2.157 | 1.842 |
| 10595148 | Gsta2 | glutathione S-transferase, alpha 2 (Yc2) | 1.12E−05 | 2.149 | 2.308 |
| 10445061 | Rnf39 | ring finger protein 39 | 4.54E−05 | 2.133 | 1.957 |
| 10499329 | Rhbg | Rhesus blood group-associated B glycoprotein | 5.25E−06 | 2.131 | 2.933 |
| 10390175 | Ngfr | nerve growth factor receptor (TNFR superfamily, member 16) | 5.09E−05 | 2.131 | 1.974 |
| 10478997 | Tfap2c | transcription factor AP-2, gamma | 2.05E−05 | 2.128 | 1.853 |
| 10451287 | Isg15 | ISG15 ubiquitin-like modifier | 3.85E−04 | 2.127 | 1.885 |
| 10378754 | Fam57a | family with sequence similarity 57, member A | 6.28E−05 | 2.125 | 2.209 |
| 10507163 | Cyp4a10 | cytochrome P450, family 4, subfamily a, polypeptide 10 | 4.28E−04 | 2.107 | 2.069 |
| 10347481 | Cyp27a1 | cytochrome P450, family 27, subfamily a, polypeptide 1 | 4.72E−06 | 2.092 | 2.94 |
| 10415388 | Ltb4r2 | leukotriene B4 receptor 2 | 2.26E−05 | 2.087 | 1.97 |
| 10433776 | Snai2 | snail homolog 2 (Drosophila) | 9.53E−04 | 2.074 | 2.584 |
| 10492586 | Arl14 | ADP-ribosylation factor-like 14 | 1.98E−04 | 2.073 | 1.863 |
| 10545921 | Mxd1 | MAX dimerization protein 1 | 2.70E−05 | 2.07 | 2.273 |
| 10385083 | Gabrp | gamma-aminobutyric acid (GABA) A receptor, pi | 8.46E−07 | 2.068 | 6.019 |
| 10509273 | | | 2.23E−05 | 2.064 | 2.316 |
| 10501319 | Celsr2 | cadherin, EGF LAG seven-pass G-type receptor 2 (flamingo homolog, Drosophila) | 4.72E−06 | 2.062 | 2.341 |
| 10455015 | Vaultrc5 | vault RNA component 5 | 2.90E−05 | 2.062 | 2.081 |
| 10353102 | Cpa6 | carboxypeptidase A6 | 1.95E−05 | 2.062 | 2.075 |
| 10458663 | Dpysl3 | dihydropyrimidinase-like 3 | 6.36E−05 | 2.05 | 3.218 |
| 10480649 | 2310002J15Rik | RIKEN cDNA 2310002J15 gene | 1.98E−04 | 2.05 | 1.832 |
| 10580608 | | | 3.43E−05 | 2.043 | 2.174 |
| 10571567 | Sorbs2 | sorbin and SH3 domain containing 2 | 8.94E−04 | 2.042 | 2.916 |
| 10487405 | Prom2 | prominin 2 | 4.93E−06 | 2.023 | 2.227 |
| 10410776 | | | 3.66E−06 | 2.005 | 2.122 |
| 10511309 | 9930005F22Rik | RIKEN cDNA 9930005F22 gene | 2.63E−04 | 2.002 | 1.945 |
| 10549222 | Bcat1 | branched chain aminotransferase 1, cytosolic | 3.02E−05 | 1.999 | 1.853 |
| 10541799 | Lpar5 | lysophosphatidic acid receptor 5 | 1.04E−05 | 1.997 | 1.991 |
| 10542156 | Clec2d | C-type lectin domain family 2, member d | 7.99E−04 | 1.996 | 2.34 |
| 10440738 | Tiam1 | T cell lymphoma invasion and metastasis 1 | 1.16E−06 | 1.986 | 3.259 |
| 10474361 | Mpped2 | metallophosphoesterase domain containing 2 | 8.11E−05 | 1.979 | 2.173 |
| 10341807 | | | 1.01E−04 | 1.959 | 2.224 |
| 10469066 | Ccdc3 | coiled-coil domain containing 3 | 1.48E−04 | 1.935 | 1.834 |

TABLE 2-continued

Genes with significantly altered expression in EpCam+ cells: LP tumor vs Kras tumor vs Normal lung EpCam+ cells
(log2 fold >1; or log2 fold <1)

| Symbol | Description | GenBank | p-value | log2 fold change for LKB1PTEN - Normal | log2 fold change for LKB1PTEN - Kras |
|---|---|---|---|---|---|
| 10533729 | Vps37b | vacuolar protein sorting 37B (yeast) | 1.67E−05 | 1.923 | 2.251 |
| 10386197 | 2210407C18 Rik | RIKEN cDNA 2210407C18 gene | 3.35E−06 | 1.92 | 1.843 |
| 10405355 | Unc5a | unc-5 homolog A (*C. elegans*) | 3.06E−04 | 1.909 | 1.964 |
| 10489391 | Ada | adenosine deaminase | 7.06E−05 | 1.892 | 1.88 |
| 10564467 | Lrrc28 | leucine rich repeat containing 28 | 5.03E−05 | 1.888 | 1.814 |
| 10355312 | Ikzf2 | IKAROS family zinc finger 2 | 1.60E−04 | 1.876 | 2.546 |
| 10490129 | Bmp7 | bone morphogenetic protein 7 | 5.12E−05 | 1.869 | 2.215 |
| 10547553 | Mical3 | microtubule associated monoxygenase, calponin and LIM domain containing 3 | 2.31E−06 | 1.868 | 2.801 |
| 10532857 | Gltp | glycolipid transfer protein | 1.69E−06 | 1.855 | 1.835 |
| 10530100 | Arap2 | ArfGAP with RhoGAP domain, ankyrin repeat and PH domain 2 | 1.32E−05 | 1.845 | 2.569 |
| 10374727 | Bcl11a | B cell CLL/lymphoma 11A (zinc finger protein) | 1.26E−04 | 1.841 | 1.819 |
| 10431210 | Wnt7b | wingless-related MMTV integration site 7B | 1.33E−05 | 1.838 | 2.377 |
| 10417579 | 4930452B06 Rik | RIKEN cDNA 4930452B06 gene | 2.91E−05 | 1.833 | 2.552 |
| 10365428 | Btbd11 | BTB (POZ) domain containing 11 | 9.15E−05 | 1.832 | 2.137 |
| 10422244 | Slitrk6 | SLIT and NTRK-like family, member 6 | 1.10E−05 | 1.826 | 1.976 |
| 10587854 | Slc9a9 | solute carrier family 9 (sodium/hydrogen exchanger), member 9 | 5.38E−06 | 1.825 | 2.854 |
| 10413419 | Arhgef | Rho guanine nucleotide exchange factor (GEF) 3 | 4.44E−05 | 1.812 | 2.213 |
| 10414065 | Anxa8 | annexin A8 | 2.39E−04 | 1.797 | 4.253 |
| 10519324 | Cdk6 | cyclin-dependent kinase 6 | 1.41E−06 | 1.771 | 3.068 |
| 10367734 | Ust | uronyl-2-sulfotransferase | 4.00E−07 | 1.771 | 2.796 |
| 10476545 | Sptlc3 | serine palmitoyltransferase, long chain base subunit 3 | 7.13E−07 | 1.768 | 3.492 |
| 10591494 | S1pr5 | sphingosine-1-phosphate receptor 5 | 1.50E−05 | 1.765 | 1.869 |
| 10607116 | Ammecr1 | Alport syndrome, mental retardation, midface hypoplasia and elliptocytosis chromosomal region gene 1 homolog (human) | 3.23E−05 | 1.763 | 2.76 |
| 10456904 | Pstpip2 | proline-serine-threonine phosphatase-interacting protein 2 | 2.51E−05 | 1.761 | 3.023 |
| 10476538 | Btbd3 | BTB (POZ) domain containing 3 | 7.55E−05 | 1.739 | 2.146 |
| 10495416 | Vav3 | vav 3 oncogene | 4.57E−04 | 1.732 | 1.892 |
| 10508879 | Fam46b | family with sequence similarity 46, member B | 4.76E−04 | 1.72 | 1.836 |
| 10558150 | Htra1 | HtrA serine peptidase 1 | 2.31E−06 | 1.717 | 3.069 |
| 10566723 | Lmo1 | LIM domain only 1 | 3.19E−05 | 1.717 | 1.88 |
| 10578952 | BC030870 | cDNA sequence BC030870 | 1.75E−04 | 1.704 | 2.986 |
| 10507137 | Pdzk1ip1 | PDZK1 interacting protein 1 | 2.36E−04 | 1.697 | 1.889 |
| 10521602 | Cpeb2 | cytoplasmic polyadenylation element binding protein 2 | 1.38E−04 | 1.678 | 1.852 |
| 10500736 | Vangl1 | vang-like 1 (van gogh, *Drosophila*) | 5.88E−05 | 1.655 | 2.116 |
| 10492682 | Fam198b | family with sequence similarity 198, member B | 8.34E−04 | 1.63 | 2.669 |

TABLE 2-continued

Genes with significantly altered expression in EpCam+ cells: LP tumor vs Kras tumor vs Normal lung EpCam+ cells
(log2 fold >1; or log2 fold <1)

| Symbol | Description | GenBank | p-value | log2 fold change for LKB1PTEN - Normal | log2 fold change for LKB1PTEN - Kras |
|---|---|---|---|---|---|
| 10496425 | Adh7 | alcohol dehydrogenase 7 (class IV), mu or sigma polypeptide | 6.33E−04 | 1.63 | 1.877 |
| 10348451 | Cxcr7 | chemokine (C-X-C motif) receptor 7 | 1.20E−04 | 1.624 | 1.85 |
| 10405781 | Mir27b | microRNA 27b | 6.31E−05 | 1.57 | 1.967 |
| 10452419 | Efna5 | ephrin A5 | 1.85E−05 | 1.563 | 2.022 |
| 10452485 | Rab31 | RAB31, member RAS oncogene family | 7.85E−04 | 1.549 | 2.092 |
| 10522009 | Pgm1 | phosphoglucomutase 1 | 8.15E−05 | 1.519 | 2.11 |
| 10389238 | Dusp14 | dual specificity phosphatase 14 | 2.30E−05 | 1.518 | 2.673 |
| 10374366 | Egfr | epidermal growth factor receptor | 9.92E−07 | 1.507 | 4.181 |
| 10458731 | Mcc | mutated in colorectal cancers | 3.81E−05 | 1.504 | 2.286 |
| 10581992 | Maf | avian musculoaponeurotic fibrosarcoma (v-maf) AS42 oncogene homolog | 1.71E−06 | 1.503 | 2.184 |
| 10594988 | Mapk6 | mitogen-activated protein kinase 6 | 1.17E−04 | 1.492 | 2.036 |
| 10604076 | Snora69 | small nucleolar RNA, H/ACA box 69 | 7.28E−04 | 1.48 | 1.816 |
| 10428536 | Trps1 | trichorhinophalangeal syndrome 1 (human) | 1.73E−06 | 1.471 | 2.795 |
| 10396671 | Plekhg3 | pleckstrin homology domain containing, family G (with RhoGef domain) member 3 | 3.53E−06 | 1.469 | 2.285 |
| 10606235 | Zdhhc15 | zinc finger, DHHC domain containing 15 | 1.38E−04 | 1.469 | 2.094 |
| 10388591 | Cpd | carboxypeptidase D | 1.64E−06 | 1.467 | 2.233 |
| 10592106 | Tirap | toll-interleukin 1 receptor (TIR) domain-containing adaptor protein | 2.19E−05 | 1.455 | 1.845 |
| 10428534 | Trps1 | trichorhinophalangeal syndrome 1 (human) | 8.66E−05 | 1.44 | 3.085 |
| 10420957 | Ptk2b | PTK2 protein tyrosine kinase 2 beta | 4.38E−04 | 1.434 | 1.904 |
| 10382713 | Itgb4 | integrin beta 4 | 7.64E−04 | 1.412 | 2.21 |
| 10584615 | Pvrl1 | poliovirus receptor-related 1 | 1.93E−05 | 1.401 | 1.943 |
| 10585186 | 1600029D21Rik | RIKEN cDNA 1600029D21 gene | 2.70E−05 | 1.394 | 1.938 |
| 10345404 | C230030N03Rik | RIKEN cDNA C230030N03 gene | 1.51E−05 | 1.39 | 2.137 |
| 10538590 | Herc6 | hect domain and RLD 6 | 3.64E−04 | 1.336 | 1.9 |
| 10606495 | Pof1b | premature ovarian failure 1B | 4.16E−05 | 1.321 | 1.848 |
| 10344981 | Pi15 | peptidase inhibitor 15 | 7.85E−04 | 1.291 | 2.674 |
| 10422059 | Kctd12 | potassium channel tetramerisation domain containing 12 | 3.09E−06 | 1.272 | 2 |
| 10425945 | Fbln1 | fibulin 1 | 1.57E−06 | 1.271 | 3.51 |
| 10366746 | Lrig3 | leucine-rich repeats and immunoglobulin-like domains 3 | 1.31E−05 | 1.266 | 3.356 |
| 10479379 | Slco4a1 | solute carrier organic anion transporter family, member 4a1 | 1.03E−05 | 1.256 | 2.062 |
| 10500183 | Adamtsl4 | ADAMTS-like 4 | 3.95E−04 | 1.247 | 1.986 |
| 10514520 | Cyp2j9 | cytochrome P450, family 2, subfamily j, polypeptide 9 | 1.77E−04 | 1.228 | 1.893 |
| 10410408 | Adcy2 | adenylate cyclase 2 | 1.07E−04 | 1.215 | 1.864 |
| 10436519 | Robo1 | roundabout homolog 1 (*Drosophila*) | 1.08E−04 | 1.189 | 2.497 |
| 10599008 | Slc6a14 | solute carrier family 6 (neurotransmitter transporter), member 14 | 3.16E−04 | 1.168 | 2.849 |

TABLE 2-continued

Genes with significantly altered expression in EpCam+ cells: LP tumor vs Kras tumor vs Normal lung EpCam+ cells
(log2 fold >1; or log2 fold <1)

| Symbol | | Description | GenBank | p-value | log2 fold change for LKB1PTEN - Normal | log2 fold change for LKB1PTEN - Kras |
|---|---|---|---|---|---|---|
| 10384504 | Meis1 | Meis homeobox 1 | | 7.08E−04 | 1.118 | 1.975 |
| 10575926 | Atp2c2 | ATPase, Ca++ transporting, type 2C, member 2 | | 3.68E−04 | 1.116 | 1.938 |
| 10578045 | Nrg1 | neuregulin 1 | | 4.21E−05 | 1.037 | 3.204 |
| 10545812 | Sfxn5 | sideroflexin 5 | | 2.64E−04 | −1.021 | −2.012 |
| 10357239 | Tmem37 | transmembrane protein 37 | | 8.64E−04 | −1.058 | −1.853 |
| 10595298 | Filip1 | filamin A interacting protein 1 | | 8.37E−06 | −1.072 | −3.282 |
| 10493494 | Efna3 | ephrin A3 | | 9.54E−05 | −1.095 | −2.377 |
| 10471247 | Aif1l | allograft inflammatory factor 1-like | | 1.13E−05 | −1.151 | −2.433 |
| 10549473 | Caprin2 | caprin family member 2 | | 0,001 | −1.155 | −2.336 |
| 10485117 | Creb3l1 | cAMP responsive element binding protein 3-like 1 | | 9.20E−04 | −1.195 | −2.417 |
| 10544036 | Atp6v0a4 | ATPase, H+ transporting, lysosomal V0 subunit A4 | | 7.21E−05 | −1.204 | −3.675 |
| 10538253 | Mpp6 | membrane protein, palmitoylated 6 (MAGUK p55 subfamily member 6) | | 3.07E−05 | −1.235 | −2.421 |
| 10505187 | Ugcg | UDP-glucose ceramide glucosyltransferase | | 6.67E−05 | −1.272 | −1.897 |
| 10387100 | Shisa6 | shisa homolog 6 (*Xenopus laevis*) | | 1.22E−05 | −1.299 | −2.229 |
| 10420165 | Cideb | cell death-inducing DNA fragmentation factor, alpha subunit-like effector B | | 5.62E−06 | −1.313 | −2.681 |
| 10396094 | Klhdc2 | kelch domain containing 2 | | 3.28E−04 | −1.318 | −1.843 |
| 10444236 | H2-DMb2 | histocompatibility 2, class II, locus Mb2 | | 5.36E−05 | −1.34 | −2.163 |
| 10479794 | Prpf18 | PRP18 pre-mRNA processing factor 18 homolog (yeast) | | 6.91E−06 | −1.345 | −1.874 |
| 10424584 | Dennd3 | DENN/MADD domain containing 3 | | 0,001 | −1.348 | −1.954 |
| 10412298 | Itga1 | integrin alpha 1 | | 2.32E−04 | −1.357 | −2.385 |
| 10342964 | | | | 8.53E−04 | −1.364 | −2.392 |
| 10509410 | Rap1gap | Rap1 GTPase-activating protein | | 8.35E−05 | −1.371 | −2.108 |
| 10399046 | Vipr2 | vasoactive intestinal peptide receptor 2 | | 6.53E−05 | −1.374 | −2.895 |
| 10513722 | Tnfsf15 | tumor necrosis factor (ligand) superfamily, member 15 | | 4.65E−04 | −1.392 | −1.913 |
| 10523182 | Areg | amphiregulin | | 0.001 | −1.392 | −2.132 |
| 10447264 | Slc3a1 | solute carrier family 3, member 1 | | 6.69E−04 | −1.395 | −1.9 |
| 10607841 | Tceanc | transcription elongation factor A (SII) N-terminal and central domain containing | | 7.88E−05 | −1.399 | −2.786 |
| 10411459 | Tmem171 | transmembrane protein 171 | | 5.16E−04 | −1.401 | −1.934 |
| 10445875 | Btg3 | B cell translocation gene 3 | | 1.50E−05 | −1.426 | −2.14 |
| 10399505 | Greb1 | gene regulated by estrogen in breast cancer protein | | 6.95E−04 | −1.439 | −2.062 |
| 10422512 | A2ld1 | AIG2-like domain 1 | | 3.54E−04 | −1.439 | −2.42 |
| 10414262 | Ear2 | eosinophil-associated, ribonuclease A family, member 2 | | 2.56E−04 | −1.444 | −2.249 |
| 10359561 | Fmo4 | flavin containing monooxygenase 4 | | 9.39E−04 | −1.459 | −3.664 |
| 10379866 | Car4 | carbonic anhydrase 4 | | 1.69E−05 | −1.503 | −2.964 |
| 10381474 | Arl4d | ADP-ribosylation factor-like 4D | | 2.60E−05 | −1.51 | −2.353 |
| 10433597 | Snx29 | sorting nexin 29 | | 0.001 | −1.516 | −2.198 |

TABLE 2-continued

Genes with significantly altered expression in EpCam+ cells: LP tumor vs Kras tumor vs Normal lung EpCam+ cells
(log2 fold >1; or log2 fold <1)

| Symbol | Description | GenBank | p-value | log2 fold change for LKB1PTEN - Normal | log2 fold change for LKB1PTEN - Kras |
|---|---|---|---|---|---|
| 10546891 | Camk1 | calcium/calmodulin-dependent protein kinase I | 3.27E−06 | −1.527 | −2.387 |
| 10542880 | 4833442J19 Rik | RIKEN cDNA 4833442J19 gene | 5.23E−04 | −1.528 | −2.107 |
| 10531610 | Rasgef1b | RasGEF domain family, member 1B | 8.72E−04 | −1.53 | −1.815 |
| 10401968 | Galc | galactosylceramidase | 2.98E−05 | −1.546 | −1.961 |
| 10538214 | D330028D13 Rik | RIKEN cDNA D330028D13 gene | 3.04E−05 | −1.582 | −1.893 |
| 10444459 | Tnxb | tenascin XB | 6.49E−05 | −1.602 | −2.059 |
| 10486112 | Bmf | BCL2 modifying factor | 3.49E−05 | −1.623 | −2.015 |
| 10497222 | Zfp704 | zinc finger protein 704 | 2.81E−05 | −1.632 | −2.012 |
| 10546434 | Adamts9 | a disintegrin-like and metallopeptidase (reprolysin type) with thrombospondin type 1 motif, 9 | 5.79E−06 | −1.652 | −3.093 |
| 10445574 | Cul7 | cullin 7 | 2.56E−05 | −1.653 | −2.364 |
| 10344291 | | | 1.06E−04 | −1.658 | −2.234 |
| 10463704 | As3mt | arsenic (+3 oxidation state) methyltransferase | 1.35E−04 | −1.672 | −1.836 |
| 10355785 | Glb1l | galactosidase, beta 1-like | 2.00E−04 | −1.689 | −2.236 |
| 10355403 | Fn1 | fibronectin 1 | 0,001 | −1.69 | −2.689 |
| 10429160 | St3gal1 | ST3 beta-galactoside alpha-2,3-sialyltransferase 1 | 3.00E−05 | −1.695 | −1.818 |
| 10585214 | Cryab | crystallin, alpha B | 0.001 | −1.696 | −2.241 |
| 10530841 | Igfbp7 | insulin-like growth factor binding protein 7 | 1.71E−05 | −1.72 | −2.037 |
| 10546430 | Adamts9 | a disintegrin-like and metallopeptidase (reprolysin type) with thrombospondin type 1 motif, 9 | 5.50E−05 | −1.742 | −3.125 |
| 10359480 | Dnm3 | dynamin 3 | 4.62E−06 | −1.749 | −2.578 |
| 10505224 | Snx30 | sorting nexin family member 30 | 5.86E−05 | −1.768 | −1.9 |
| 10435345 | Mylk | myosin, light polypeptide kinase | 2.58E−06 | −1.783 | −2.089 |
| 10532085 | Tgfbr3 | transforming growth factor, beta receptor III | 9.35E−05 | −1.787 | −1.961 |
| 10541683 | C1rb | complement component 1, r subcomponent B | 5.08E−05 | −1.802 | −1.992 |
| 10455873 | Slc12a2 | solute carrier family 12, member 2 | 5.65E−07 | −1.802 | −2.052 |
| 10444291 | H2-Ab1 | histocompatibility 2, class II antigen A, beta 1 | 4.03E−06 | −1.803 | −2.246 |
| 10413152 | 1700112E06 Rik | RIKEN cDNA 1700112E06 gene | 2.10E−04 | −1.805 | −2.1 |
| 10572928 | Rasd2 | RASD family, member 2 | 0,001 | −1.81 | −2.604 |
| 10581434 | Dpep2 | dipeptidase 2 | 8.96E−05 | −1.818 | −3.456 |
| 10392142 | Cd79b | CD79B antigen | 6.62E−05 | −1.83 | −2.096 |
| 10467153 | Slc16a12 | solute carrier family 16 (monocarboxylic acid transporters), member 12 | 8.57E−07 | −1.853 | −2.99 |
| 10509596 | Rnf186 | ring finger protein 186 | 3.44E−05 | −1.855 | −1.853 |
| 10574676 | Nol3 | nucleolar protein 3 (apoptosis repressor with CARD domain) | 2.89E−04 | −1.857 | −2.515 |
| 10599696 | Ddx26b | DEAD/H (Asp-Glu-Ala-Asp/His) box polypeptide 26B | 1.61E−04 | −1.878 | −2.107 |
| 10424979 | Gpt | glutamic pyruvic transaminase, soluble | 1.73E−05 | −1.906 | −1.864 |
| 10476893 | Gzf1 | GDNF-inducible zinc finger protein 1 | 1.42E−04 | −1.908 | −1.929 |
| 10395925 | Mia2 | melanoma inhibitory activity 2 | 1.87E−04 | −1.935 | −2.672 |

TABLE 2-continued

Genes with significantly altered expression in EpCam+ cells: LP tumor vs Kras tumor vs Normal lung EpCam+ cells
(log2 fold >1; or log2 fold <1)

| Symbol | Description | GenBank | p-value | log2 fold change for LKB1PTEN - Normal | log2 fold change for LKB1PTEN - Kras |
|---|---|---|---|---|---|
| 10556413 | Micalcl | MICAL C-terminal like | 6.77E−06 | −1.942 | −1.888 |
| 10445268 | Gpr116 | G protein-coupled receptor 116 | 3.44E−05 | −1.949 | −1.886 |
| 10355974 | Wdfy1 | WD repeat and FYVE domain containing 1 | 1.75E−04 | −1.954 | −2.103 |
| 10576506 | Gnpat | glyceronephosphate 0-acyltransferase | 2.51E−04 | −1.973 | −2.178 |
| 10436983 | Dopey2 | dopey family member 2 | 1.21E−06 | −1.984 | −1.832 |
| 10422227 | Spry2 | sprouty homolog 2 (Drosophila) | 1.02E−04 | −1.992 | −2.319 |
| 10543319 | Fam3c | family with sequence similarity 3, member C | 0,001 | −1.992 | −2.587 |
| 10350630 | Fam129a | family with sequence similarity 129, member A | 9.06E−04 | −2.006 | −1.907 |
| 10559276 | Kcnq1 | potassium voltage-gated channel, subfamily Q, member 1 | 2.04E−04 | −2.017 | −1.894 |
| 10515733 | Szt2 | seizure threshold 2 | 1.04E−05 | −2.023 | −2.18 |
| 10397507 | Gstz1 | glutathione transferase zeta 1 (maleylacetoacetate isomerase) | 1.43E−04 | −2.025 | −2.183 |
| 10574259 | Gpr56 | G protein-coupled receptor 56 | 3.82E−06 | −2.025 | −2.187 |
| 10401519 | Npc2 | Niemann Pick type C2 | 7.00E−06 | −2.029 | −2.195 |
| 10471464 | St6galnac6 | ST6 (alpha-N-acetyl-neuraminyl-2,3-beta-galactosyl-1,3)-N-acetylgalactosaminide alpha-2,6-sialyltransferase 6 | 2.37E−05 | −2.029 | −2.268 |
| 10564805 | Pex11a | peroxisomal biogenesis factor 11 alpha | 3.09E−05 | −2.031 | −2.091 |
| 10523062 | Alb | albumin | 3.18E−04 | −2.036 | −3.421 |
| 10397364 | Mfsd7c | major facilitator superfamily domain containing 7C | 1.09E−04 | −2.049 | −3.001 |
| 10437195 | Igsf5 | immunoglobulin superfamily, members | 2.91E−06 | −2.051 | −2.333 |
| 10358677 | 1200016B10Rik | RIKEN cDNA 1200016B10 gene | 1.64E−04 | −2.059 | −2.524 |
| 10471844 | Nek6 | NIMA (never in mitosis gene a)-related expressed kinase 6 | 4.26E−05 | −2.065 | −2.306 |
| 10527538 | Rasl11a | RAS-like, family 11, member A | 1.65E−04 | −2.092 | −2.315 |
| 10481845 | Fam125b | family with sequence similarity 125, member B | 1.76E−04 | −2.093 | −2.167 |
| 10580486 | Brd7 | bromodomain containing 7 | 6.91E−06 | −2.11 | −2.332 |
| 10429859 | Oplah | 5-oxoprolinase (ATP-hydrolysing) | 1.90E−05 | −2.116 | −2.068 |
| 10363735 | Egr2 | early growth response 2 | 1.25E−04 | −2.121 | −2.145 |
| 10606868 | Bex1 | brain expressed gene 1 | 3.80E−05 | −2.121 | −3.373 |
| 10349295 | Tfcp2l1 | transcription factor CP2-like 1 | 9.10E−04 | −2.134 | −2.025 |
| 10458940 | Zfp608 | zinc finger protein 608 | 5.36E−05 | −2.143 | −2.283 |
| 10350977 | 4930523C07Rik | RIKEN cDNA 4930523C07 gene | 6.08E−04 | −2.145 | −1.952 |
| 10416437 | Lcp1 | lymphocyte cytosolic protein 1 | 1.21E−06 | −2.146 | −2.442 |
| 10474671 | Spred1 | sprouty protein with EVH-1 domain 1, related sequence | 4.74E−05 | −2.146 | −2.746 |
| 10367440 | Itga7 | integrin alpha 7 | 5.54E−05 | −2.152 | −2.826 |
| 10423556 | Pgcp | plasma glutamate carboxypeptidase | 8.33E−04 | −2.163 | −2.004 |
| 10517274 | Sepn1 | selenoprotein N, 1 | 2.05E−06 | −2.165 | −2.341 |
| 10355532 | Tns1 | tensin 1 | 7.43E−04 | −2.169 | −1.826 |

TABLE 2-continued

Genes with significantly altered expression in EpCam+ cells: LP tumor vs Kras tumor vs Normal lung EpCam+ cells
(log2 fold >1; or log2 fold <1)

| Symbol | Description | GenBank | p-value | log2 fold change for LKB1PTEN - Normal | log2 fold change for LKB1PTEN - Kras |
|---|---|---|---|---|---|
| 10512251 | AI464131 | expressed sequence AI464131 | 1.13E−05 | −2.171 | −1.856 |
| 10355530 | Tns1 | tensin 1 | 1.97E−04 | −2.181 | −1.861 |
| 10346374 | Aox1 | aldehyde oxidase 1 | 1.69E−04 | −2.182 | −2.97 |
| 10407946 | Stard3nl | STARD3 N-terminal like | 1.88E−04 | −2.191 | −1.944 |
| 10593856 | C230081A13Rik | RIKEN cDNA C230081A13 gene | 2.04E−05 | −2.192 | −2.403 |
| 10357363 | Nckap5 | NCK-associated protein 5 | 3.98E−05 | −2.208 | −1.869 |
| 10447079 | | | 1.99E−04 | −2.209 | −1.951 |
| 10345037 | Paqr8 | progestin and adipoQ receptor family member VIII | 3.10E−04 | −2.215 | −2.226 |
| 10569972 | Lass4 | LAG1 homolog, ceramide synthase 4 | 9.35E−04 | −2.217 | −2.458 |
| 10515716 | Szt2 | seizure threshold 2 | 1.37E−06 | −2.225 | −2.396 |
| 10439651 | Cd200 | CD200 antigen | 4.65E−04 | −2.227 | −2.043 |
| 10515729 | Szt2 | seizure threshold 2 | 4.02E−06 | −2.228 | −2.429 |
| 10403312 | Akr1c19 | aldo-keto reductase family 1, member C19 | 1.27E−04 | −2.235 | −3.617 |
| 10438909 | Atp13a3 | ATPase type 13A3 | 3.40E−04 | −2.238 | −2.211 |
| 10349671 | Slc26a9 | solute carrier family 26, member 9 | 4.99E−04 | −2.24 | −2.302 |
| 10502845 | Fam73a | family with sequence similarity 73, member A | 4.69E−04 | −2.249 | −1.823 |
| 10544348 | Trpv6 | transient receptor potential cation channel, subfamily V, member 6 | 1.23E−04 | −2.249 | −3.213 |
| 10445071 | Zfp57 | zinc finger protein 57 | 8.89E−07 | −2.256 | −2.996 |
| 10453026 | Prkd3 | protein kinase D3 | 1.44E−04 | −2.259 | −2.449 |
| 10603896 | Klhl13 | kelch-like 13 (Drosophila) | 1.56E−04 | −2.265 | −2.738 |
| 10450154 | H2-Aa | histocompatibility 2, class II antigen A, alpha | 4.39E−04 | −2.269 | −2.3 |
| 10515735 | Szt2 | seizure threshold 2 | 3.50E−06 | −2.27 | −2.416 |
| 10544689 | 4921507P07Rik | RIKEN cDNA 4921507P07 gene | 8.44E−05 | −2.271 | −3.401 |
| 10607679 | Txlng | taxilin gamma | 3.91E−04 | −2.285 | −2.098 |
| 10488374 | Foxa2 | forkhead box A2 | 1.87E−06 | −2.301 | −2.959 |
| 10513061 | Ctnnal1 | catenin (cadherin associated protein), alpha-like 1 | 1.70E−04 | −2.306 | −2.268 |
| 10515731 | Szt2 | seizure threshold 2 | 2.68E−06 | −2.307 | −2.567 |
| 10519951 | Pion | pigeon homolog (Drosophila) | 2.84E−05 | −2.308 | −1.836 |
| 10488322 | Ralgapa2 | Ral GTPase activating protein, alpha subunit 2 (catalytic) | 2.14E−06 | −2.311 | −2.053 |
| 10444229 | H2-DMa | histocompatibility 2, class II, locus DMa | 3.31E−05 | −2.318 | −2.997 |
| 10506201 | Ror1 | receptor tyrosine kinase-like orphan receptor 1 | 1.88E−04 | −2.329 | −2.264 |
| 10546432 | Adamts9 | a disintegrin-like and metallope ptidase (reprolysin type) with thrombospondin type 1 motif, 9 | 1.14E−05 | −2.332 | −4.134 |
| 10371616 | Chpt1 | choline phosphotransferase 1 | 1.90E−04 | −2.337 | −1.859 |
| 10384398 | Grb10 | growth factor receptor bound protein 10 | 2.05E−05 | −2.352 | −1.886 |
| 10482920 | Cd302 | CD302 antigen | 1.01E−04 | −2.353 | −2.527 |
| 10476819 | Plk1s1 | polo-like kinase 1 substrate 1 | 1.29E−05 | −2.354 | −2.002 |
| 10456005 | Cd74 | CD74 antigen (invariant polypeptide of major histocompatibility complex, class II antigen-associated) | 3.44E−05 | −2.37 | −2.44 |
| 10604713 | Arhgef6 | Rac/Cdc42 guanine nucleotide exchange factor (GEF) 6 | 2.30E−06 | −2.378 | −2.003 |

TABLE 2-continued

Genes with significantly altered expression in EpCam+ cells: LP tumor vs Kras tumor vs Normal lung EpCam+ cells
(log2 fold >1; or log2 fold <1)

| Symbol | Description | GenBank | p-value | log2 fold change for LKB1PTEN - Normal | log2 fold change for LKB1PTEN - Kras |
|---|---|---|---|---|---|
| 10440099 | St3gal6 | ST3 beta-galactoside alpha-2,3-sialyltransferase 6 | 2.57E−04 | −2.393 | −2.801 |
| 10559341 | | | 1.31E−05 | −2.395 | −1.86 |
| 10586700 | Rora | RAR-related orphan receptor alpha | 6.38E−06 | −2.396 | −2.208 |
| 10515690 | Szt2 | seizure threshold 2 | 2.37E−05 | −2.407 | −1.925 |
| 10546454 | Adamts9 | a disintegrin-like and metallopeptidase (reprolysin type) with thrombospondin type 1 motif, 9 | 1.21E−06 | −2.438 | −3.882 |
| 10581132 | Cdh16 | cadherin 16 | 2.19E−04 | −2.444 | −3.21 |
| 10352178 | Sccpdh | saccharopine dehydrogenase (putative) | 0.001 | −2.448 | −2.407 |
| 10591563 | Kank2 | KN motif and ankyrin repeat domains 2 | 2.75E−04 | −2.455 | −2.095 |
| 10422598 | Sepp1 | selenoprotein P, plasma, 1 | 4.94E−05 | −2.464 | −2.402 |
| 10539119 | Ggcx | gamma-glutamyl carboxylase | 2.59E−06 | −2.464 | −2.746 |
| 10398859 | Adssl1 | adenylosuccinate synthetase like 1 | 1.17E−04 | −2.48 | −3.365 |
| 10397145 | Acot2 | acyl-CoA thioesterase 2 | 7.22E−04 | −2.495 | −2.124 |
| 10426812 | Gpd1 | glycerol-3-phosphate dehydrogenase 1 (soluble) | 3.63E−06 | −2.534 | −2.564 |
| 10541071 | 8430408G22 Rik | RIKEN cDNA 8430408G22 gene | 0.001 | −2.536 | −2.682 |
| 10447224 | Dync2li1 | dynein cytoplasmic 2 light intermediate chain 1 | 2.19E−04 | −2.539 | −2.24 |
| 10543802 | Plxna4 | plexin A4 | 6.13E−06 | −2.541 | −3.118 |
| 10400460 | Mbip | MAP3K12 binding inhibitory protein 1 | 2.17E−06 | −2.547 | −2.897 |
| 10478048 | Lbp | lipopolysaccharide binding protein | 4.69E−04 | −2.589 | −3.001 |
| 10421046 | Dock5 | dedicator of cytokinesis 5 | 1.64E−06 | −2.591 | −2.559 |
| 10607089 | Acsl4 | acyl-CoA synthetase long-chain family member 4 | 1.19E−04 | −2.593 | −1.898 |
| 10495685 | Arhgap29 | Rho GTPase activating protein 29 | 1.19E−04 | −2.602 | −2.639 |
| 10577808 | Tacc1 | transforming, acidic coiled-coil containing protein 1 | 4.95E−05 | −2.612 | −2.456 |
| 10435791 | Mir568 | microRNA 568 | 8.91E−04 | −2.615 | −2.084 |
| 10475080 | Mapkbp1 | mitogen-activated protein kinase binding protein 1 | 1.19E−05 | −2.618 | −2.412 |
| 10410007 | Fbp1 | fructose bisphosphatase 1 | 2.75E−05 | −2.631 | −2.988 |
| 10547322 | Cacna1c | calcium channel, voltage-dependent, L type, alpha 1C subunit | 2.42E−04 | −2.635 | −2.389 |
| 10419096 | Sftpd | surfactant associated protein D | 1.26E−04 | −2.636 | −2.44 |
| 10355984 | Serpine2 | serine (or cysteine) peptidase inhibitor, clade E, member 2 | 2.21E−06 | −2.636 | −3.556 |
| 10515694 | Szt2 | seizure threshold 2 | 1.65E−06 | −2.642 | −2.242 |
| 10402195 | Tc2n | tandem C2 domains, nuclear | 2.84E−04 | −2.643 | −3.104 |
| 10374083 | Aebp1 | AE binding protein 1 | 4.68E−05 | −2.646 | −2.473 |
| 10600921 | Stard8 | START domain containing 8 | 6.74E−05 | −2.65 | −1.922 |
| 10592471 | Gramd1b | GRAM domain containing 1B | 1.09E−05 | −2.651 | −2.924 |
| 10421810 | 1190002H23 Rik | RIKEN cDNA 1190002H23 gene | 3.00E−05 | −2.655 | −3.203 |
| 10539933 | Txnrd3 | thioredoxin reductase 3 | 1.16E−04 | −2.66 | −2.356 |
| 10412394 | Nnt | nicotinamide nucleotide transhydrogenase | 3.81E−05 | −2.674 | −2.761 |
| 10493449 | Thbs3 | thrombospondin 3 | 3.63E−06 | −2.679 | −2.329 |
| 10519607 | 4930420K17 Rik | RIKEN cDNA 4930420K17 gene | 4.17E−06 | −2.682 | −2.49 |

TABLE 2-continued

Genes with significantly altered expression in EpCam+ cells: LP tumor vs Kras tumor vs Normal lung EpCam+ cells
(log2 fold >1; or log2 fold <1)

| Symbol | Description | GenBank | p-value | log2 fold change for LKB1PTEN - Normal | log2 fold change for LKB1PTEN - Kras |
|---|---|---|---|---|---|
| 10463070 | Entpd1 | ectonucleoside triphosphate diphosphohydrolase 1 | 6.88E−04 | −2.683 | −2.244 |
| 10435789 | | | 1.05E−04 | −2.688 | −2.096 |
| 10521832 | Pi4k2b | phosphatidylinositol 4-kinase type 2 beta | 3.66E−05 | −2.69 | −2.075 |
| 10419934 | Myh7 | myosin, heavy polypeptide 7, cardiac muscle, beta | 1.30E−07 | −2.703 | −3.433 |
| 10414192 | Mat1a | methionine adenosyltransferase 1, alpha | 1.18E−04 | −2.704 | −3.047 |
| 10463112 | Ccnj | cyclin J | 4.48E−04 | −2.72 | −2.299 |
| 10439766 | Pvrl3 | poliovirus receptor-related 3 | 1.95E−06 | −2.724 | −2.424 |
| 10519612 | 9330182L06Rik | RIKEN cDNA 9330182L06 gene | 1.36E−05 | −2.726 | −2.455 |
| 10372807 | Msrb3 | methionine sulfoxide reductase B3 | 2.44E−05 | −2.736 | −2.928 |
| 10419151 | Ear1 | eosinophil-associated, ribonuclease A family, member 1 | 1.13E−04 | −2.744 | −3.059 |
| 10448676 | Slc9a3r2 | solute carrier family 9 (sodium/hydrogen exchanger), member 3 regulator 2 | 7.43E−07 | −2.746 | −2.654 |
| 10414537 | Ang | angiogenin, ribonuclease, RNase A family, 5 | 4.00E−07 | −2.783 | −2.629 |
| 10578448 | Cyp4v3 | cytochrome P450, family 4, subfamily v, polypeptide 3 | 0.001 | −2.792 | −2.208 |
| 10525256 | Tmem116 | transmembrane protein 116 | 3.25E−05 | −2.796 | −2.345 |
| 10447190 | Plekhh2 | pleckstrin homology domain containing, family H (with MyTH4 domain) member 2 | 4.03E−05 | −2.796 | −2.854 |
| 10414211 | Mbl1 | mannose-binding lectin (protein A) 1 | 3.10E−05 | −2.798 | −2.371 |
| 10466735 | Fam189a2 | family with sequence similarity 189, member A2 | 3.03E−05 | −2.802 | −2.618 |
| 10434105 | Scarf2 | scavenger receptor class F, member 2 | 4.25E−06 | −2.816 | −2.669 |
| 10482004 | AI182371 | expressed sequence AI182371 | 7.90E−04 | −2.817 | −2.009 |
| 10523766 | Lrrc8c | leucine rich repeat containing 8 family, member C | 5.60E−07 | −2.817 | −2.966 |
| 10483046 | Dpp4 | dipeptidylpeptidase 4 | 8.72E−05 | −2.843 | −2.936 |
| 10400844 | Pygl | liver glycogen phosphorylase | 1.01E−06 | −2.844 | −3.38 |
| 10556381 | Mical2 | microtubule associated monoxygenase, calponin and LIM domain containing 2 | 4.45E−07 | −2.846 | −2.741 |
| 10427744 | Rai14 | retinoic acid induced 14 | 4.40E−06 | −2.869 | −3.052 |
| 10399559 | Atp6v1c2 | ATPase, H+ transporting, lysosomal V1 subunit C2 | 1.35E−05 | −2.883 | −2.96 |
| 10490826 | Zbtb10 | zinc finger and BTB domain containing 10 | 2.91E−05 | −2.894 | −2.28 |
| 10442396 | Abca3 | ATP-binding cassette, sub-family A (ABC1), member 3 | 6.43E−06 | −2.904 | −2.391 |
| 10386965 | Arhgap44 | Rho GTPase activating protein 44 | 1.18E−04 | −2.906 | −2.545 |
| 10543333 | Aass | aminoadipate-semialdehyde synthase | 2.18E−04 | −2.908 | −3.754 |

TABLE 2-continued

Genes with significantly altered expression in EpCam+ cells: LP tumor vs Kras tumor vs Normal lung EpCam+ cells
(log2 fold >1; or log2 fold <1)

| Symbol | Description | GenBank | p-value | log2 fold change for LKB1PTEN - Normal | log2 fold change for LKB1PTEN - Kras |
|---|---|---|---|---|---|
| 10546450 | Adamts9 | a disintegrin-like and metallopeptidase (reprolysin type) with thrombospondin type 1 motif, 9 | 2.53E−06 | −2.918 | −4.295 |
| 10431326 | Mlc1 | megalencephalic leukoencephalopathy with subcortical cysts 1 homolog (human) | 4.48E−06 | −2.92 | −2.39 |
| 10410501 | Irx1 | Iroquois related homeobox 1 (Drosophila) | 6.73E−06 | −2.923 | −2.376 |
| 10472350 | Gca | grancalcin | 2.51E−05 | −2.942 | −2.475 |
| 10387625 | Chrnb1 | cholinergic receptor, nicotinic, beta polypeptide 1 (muscle) | 9.00E−07 | −2.957 | −2.944 |
| 10467319 | Rbp4 | retinol binding protein 4, plasma | 4.33E−05 | −2.969 | −3.948 |
| 10369844 | Bicc1 | bicaudal C homolog 1 (Drosophila) | 1.50E−05 | −2.971 | −2.472 |
| 10471457 | St6galnac4 | ST6 (alpha-N-acetyl-neuraminyl-2,3-beta-galactosyl-1,3)-N-acetylgalactosaminide alpha-2,6-sialyltransferase 4 | 1.55E−06 | −2.976 | −3.337 |
| 10411171 | Pde8b | phosphodiesterase 8B | 1.40E−05 | −2.981 | −3.547 |
| 10451953 | Lrg1 | leucine-rich alpha-2-glycoprotein 1 | 1.27E−04 | −2.983 | −2.134 |
| 10540248 | Mitf | microphthalmia-associated transcription factor | 3.58E−04 | −2.986 | −2.17 |
| 10541114 | Rasgef1a | RasGEF domain family, member 1A | 2.61E−07 | −2.99 | −3.53 |
| 10378216 | Atp2a3 | ATPase, Ca++ transporting, ubiquitous | 1.80E−06 | −3.001 | −3.31 |
| 10355534 | Tns1 | tensin 1 | 5.65E−05 | −3.022 | −2.624 |
| 10565910 | Plekhb1 | pleckstrin homology domain containing, family B (evectins) member 1 | 4.08E−06 | −3.033 | −2.525 |
| 10539080 | St3gal5 | ST3 beta-galactoside alpha-2,3-sialyltransferase 5 | 1.70E−06 | −3.058 | −3.497 |
| 10452257 | Slc25a23 | solute carrier family 25 (mitochondrial carrier; phosphate carrier), member 23 | 6.87E−07 | −3.059 | −3.146 |
| 10453857 | Gata6 | GATA binding protein 6 | 7.54E−06 | −3.064 | −3.065 |
| 10559333 | | | 3.20E−05 | −3.081 | −2.491 |
| 10442932 | Tmem8 | transmembrane protein 8 (five membrane-spanning domains) | 3.37E−04 | −3.084 | −2.029 |
| 10511180 | Mxra8 | matrix-remodelling associated 8 | 1.35E−05 | −3.094 | −2.527 |
| 10403291 | Akr1c14 | aldo-keto reductase family 1, member C14 | 5.20E−04 | −3.103 | −2.352 |
| 10369040 | Ros1 | Ros1 proto-oncogene | 2.12E−05 | −3.127 | −4.575 |
| 10355514 | Tns1 | tensin 1 | 1.94E−05 | −3.13 | −2.928 |
| 10603151 | Gpm6b | glycoprotein m6b | 2.66E−05 | −3.162 | −2.628 |
| 10438433 | Olfr171 | olfactory receptor 171 | 9.85E−04 | −3.164 | −2.417 |
| 10590031 | Itga9 | integrin alpha 9 | 7.82E−06 | −3.172 | −2.659 |
| 10491721 | Spry1 | sprouty homolog 1 (Drosophila) | 2.29E−05 | −3.188 | −2.759 |
| 10577449 | Atp7b | ATPase, Cu++ transporting, beta polypeptide | 9.61E−04 | −3.197 | −2.564 |
| 10481949 | Traf1 | TNF receptor-associated factor 1 | 3.66E−06 | −3.198 | −2.955 |
| 10395466 | Dock4 | dedicator of cytokinesis 4 | 4.60E−06 | −3.202 | −3.472 |
| 10426315 | Lrrk2 | leucine-rich repeat kinase 2 | 3.85E−05 | −3.24 | −2.565 |

TABLE 2-continued

Genes with significantly altered expression in EpCam+ cells: LP tumor vs Kras tumor vs Normal lung EpCam+ cells
(log2 fold >1; or log2 fold <1)

| Symbol | Description | GenBank | p-value | log2 fold change for LKB1PTEN - Normal | log2 fold change for LKB1PTEN - Kras |
|---|---|---|---|---|---|
| 10439321 | Slc15a2 | solute carrier family 15 (H+/peptide transporter), member 2 | 5.10E−04 | −3.245 | −3.656 |
| 10467979 | Scd1 | stearoyl-Coenzyme A desaturase 1 | 8.39E−06 | −3.252 | −2.811 |
| 10605181 | Renbp | renin binding protein | 4.62E−06 | −3.258 | −3.354 |
| 10346410 | Aox3 | aldehyde oxidase 3 | 2.54E−04 | −3.283 | −3.602 |
| 10536297 | Ppp1r9a | protein phosphatase 1, regulatory (inhibitor) subunit 9A | 1.29E−06 | −3.286 | −3.223 |
| 10573779 | Nkd1 | naked cuticle 1 homolog (Drosophila) | 8.24E−05 | −3.29 | −3.439 |
| 10542066 | Tspan11 | tetraspanin 11 | 5.58E−07 | −3.325 | −3.823 |
| 10521892 | Slc34a2 | solute carrier family 34 (sodium phosphate), member 2 | 9.19E−06 | −3.339 | −3.077 |
| 10439710 | Phldb2 | pleckstrin homology-like domain, family B, member 2 | 2.68E−06 | −3.34 | −3.071 |
| 10573747 | Adcy7 | adenylate cyclase 7 | 1.29E−06 | −3.364 | −2.864 |
| 10368101 | D10Bwg1379e | DNA segment, Chr 10, Brigham & Women's Genetics 1379 expressed | 5.23E−08 | −3.423 | −3.203 |
| 10355536 | Tns1 | tensin 1 | 4.44E−05 | −3.442 | −3.021 |
| 10446334 | Glcci1 | glucocorticoid induced transcript 1 | 4.62E−06 | −3.484 | −3.499 |
| 10536294 | Peg10 | paternally expressed 10 | 5.36E−04 | −3.545 | −2.995 |
| 10357371 | Tmem163 | transmembrane protein 163 | 8.25E−05 | −3.557 | −3.116 |
| 10487238 | Hdc | histidine decarboxylase | 0,001 | −3.576 | −2.201 |
| 10369932 | Susd2 | sushi domain containing 2 | 1.20E−05 | −3.581 | −4.883 |
| 10426479 | Ano6 | anoctamin 6 | 3.13E−07 | −3.668 | −3.363 |
| 10371607 | Dram1 | DNA-damage regulated autophagy modulator 1 | 1.54E−06 | −3.673 | −3.311 |
| 10363455 | Pcbd1 | pterin 4 alpha carbinolamine dehydratase/dimerization cofactor of hepatocyte nuclear factor 1 alpha (TCF1) 1 | 2.61E−07 | −3.699 | −4.313 |
| 10452571 | Ptprm | protein tyrosine phosphatase, receptor type, M | 2.60E−07 | −3.7 | −3.897 |
| 10419223 | Fermt2 | fermitin family homolog 2 (Drosophila) | 4.38E−06 | −3.812 | −3.712 |
| 10601850 | Bex4 | brain expressed gene 4 | 3.75E−07 | −3.817 | −3.953 |
| 10356145 | Slc19a3 | solute carrier family 19, member 3 | 1.61E−05 | −3.874 | −3.654 |
| 10471721 | Ptgs1 | prostaglandin-endoperoxide synthase 1 | 2.22E−07 | −3.961 | −4.453 |
| 10469020 | Bend7 | BEN domain containing 7 | 1.25E−07 | −4.018 | −4.542 |
| 10584325 | Vsig2 | V-set and immunoglobulin domain containing 2 | 2.39E−07 | −4.094 | −4.366 |
| 10444407 | Ager | advanced glycosylation end product-specific receptor | 6.11E−08 | −4.124 | −4.173 |
| 10368175 | Pde7b | phosphodiesterase 7B | 9.73E−06 | −4.186 | −3.732 |
| 10528207 | Cd36 | CD36 antigen | 5.49E−05 | −4.264 | −3.856 |
| 10373834 | Sec14l4 | SEC14-like 4 (S. cerevisiae) | 1.57E−06 | −4.338 | −3.93 |
| 10358457 | Bex4 | brain expressed gene 4 | 2.57E−05 | −4.357 | −5.755 |
| 10421387 | Sftpc | surfactant associated protein C | 4.79E−05 | −4.362 | −4.3 |
| 10447065 | Fam82a1 | family with sequence similarity 82, member A1 | 1.71E−06 | −4.369 | −3.863 |
| 10347734 | Sgpp2 | sphingosine-1-phosphate phosphotase 2 | 3.96E−05 | −4.381 | −3.926 |
| 10501802 | Tmem56 | transmembrane protein 56 | 3.14E−04 | −4.391 | −3.162 |
| 10419261 | Bmp4 | bone morphogenetic protein 4 | 1.21E−06 | −4.413 | −5.173 |

TABLE 2-continued

Genes with significantly altered expression in EpCam+ cells: LP tumor vs Kras tumor vs Normal lung EpCam+ cells
(log2 fold >1; or log2 fold <1)

| Symbol | Description | GenBank | p-value | log2 fold change for LKB1PTEN - Normal | log2 fold change for LKB1PTEN - Kras |
|---|---|---|---|---|---|
| 10603746 | Maob | monoamine oxidase B | 2.13E−05 | −4.502 | −3.838 |
| 10466779 | Pip5k1b | phosphatidylinositol-4-phosphate 5-kinase, type 1 beta | 3.41E−07 | −4.613 | −4.614 |
| 10397835 | Slc24a4 | solute carrier family 24 (sodium/potassium/calcium exchanger), member 4 | 4.45E−07 | −4.629 | −4.039 |
| 10523145 | Cxcl15 | chemokine (C-X-C motif) ligand 15 | 3.63E−06 | −4.685 | −4.468 |
| 10349968 | Chi3l1 | chitinase 3-like 1 | 6.29E−06 | −4.706 | −4.998 |
| 10406031 | Lpcat1 | lysophosphatidylcholine acyltransferase 1 | 3.75E−07 | −4.759 | −4.306 |
| 10539091 | Sftpb | surfactant associated protein B | 4.99E−07 | −4.821 | −4.805 |
| 10413615 | Itih4 | inter alpha-trypsin inhibitor, heavy chain 4 | 2.64E−04 | −4.828 | −3.776 |
| 10408689 | Nrn1 | neuritin 1 | 6.72E−07 | −4.852 | −5.026 |
| 10552697 | Napsa | napsin A aspartic peptidase | 1.03E−07 | −4.967 | −4.772 |
| 10422635 | C6 | complement component 6 | 3.51E−04 | −5.024 | −3.343 |
| 10524698 | Pla2g1b | phospholipase A2, group IB, pancreas | 5.23E−08 | −5.104 | −4.82 |
| 10600169 | Bgn | biglycan | 2.09E−07 | −5.172 | −5.616 |
| 10576639 | Nrp1 | neuropilin 1 | 1.42E−05 | −5.286 | −4.383 |
| 10596106 | Cldn18 | claudin 18 | 5.24E−06 | −5.328 | −5.126 |
| 10414202 | Sftpa1 | surfactant associated protein A1 | 1.11E−07 | −5.357 | −5.271 |
| 10607848 | Egfl6 | EGF-like-domain, multiple 6 | 1.39E−05 | −5.389 | −5.344 |
| 10438626 | Etv5 | ets variant gene 5 | 1.03E−06 | −5.47 | −4.794 |
| 10438435 | Lamp3 | lysosomal-associated membrane protein 3 | 1.53E−07 | −7.118 | −6.562 |

TABLE 3

Metabolism profile: LP tumor vs Kras tumor vs normal lung

| Label | Average Kras | Average Normal | Average LP | Fold Change LP vs Normal | LP vs Normal T Test | Fold Change LP vs Kras | LP vs Kras T Test |
|---|---|---|---|---|---|---|---|
| UDP-nega | 529251.67 | 161649.845 | 2199651.3 | 13.60750622 | 2.3313E−08 | 4.156153689 | 0.046007334 |
| UDP-D-glucuronate | 55964.955 | 10572.7473 | 133524.67 | 12.62913629 | 0.004995484 | 2.385862139 | 0.228470305 |
| cystathionine | 363418.66 | 102123.61 | 1195672.2 | 11.70808803 | 2.02711E−05 | 3.290068325 | 0.00010257 |
| uracil | 14677824 | 3076356.29 | 28476362 | 9.256522806 | 1.23464E−06 | 1.940094197 | 1.0154E−05 |
| UDP-N-acetyl-glucosamine | 1182945.8 | 222126.758 | 1971905.5 | 8.877388227 | 1.17813E−05 | 1.66694486 | 7.58021E−06 |
| fructose-1,6-bisphosphate | 4162664.4 | 236366.613 | 1918207.2 | 8.115389956 | 1.05005E−08 | 0.460812365 | 0.001418535 |
| IDP-nega | 436528.73 | 138175.815 | 1074281.8 | 7.774745382 | 6.91505E−07 | 2.460964673 | 0.013652262 |
| ADP-nega | 3469983.5 | 1106641.29 | 8245851.1 | 7.451241144 | 2.47607E−07 | 2.376337279 | 0.012363715 |
| dGDP-nega | 3479897.4 | 1150020.17 | 8552648.7 | 7.436955388 | 1.12169E−06 | 2.457730138 | 0.008435066 |
| deoxyguanosine | 22159.135 | 21562.1512 | 144733.43 | 6.71283859 | 0.011006986 | 6.531547034 | 0.891325238 |
| GDP-nega | 43827.058 | 18093.896 | 113978.75 | 6.299292893 | 5.29402E−05 | 2.600647991 | 0.372974008 |
| adenosine 5-phosphosulfate | 24321.523 | 10549.2055 | 60091.68 | 5.696322854 | 5.14913E−05 | 2.470720252 | 0.082838098 |
| Methylmalonic acid | 10351989 | 2855631.64 | 14939812 | 5.231701218 | 4.20223E−08 | 1.443182735 | 5.4147E−11 |
| succinate | 8547058.9 | 2342227.81 | 12218023 | 5.216410996 | 6.79256E−08 | 1.429500253 | 4.70283E−10 |
| hypoxanthine | 5967048.5 | 795483.868 | 3826197.8 | 4.809899905 | 0.004177099 | 0.641221158 | 1.6479E−06 |
| N-Acetyl-L-alanine | 2627516.6 | 4960907.82 | 22698725 | 4.575518412 | 2.88151E−07 | 8.638851278 | 0.001534628 |
| deoxyinosine | 12763.953 | 11896.9522 | 53592.723 | 4.504743917 | 0.034742708 | 4.198755859 | 0.766567418 |
| FAD | 232311.06 | 84448.0909 | 372586.88 | 4.412022518 | 0.00039251 | 1.603827533 | 0.022030686 |
| uridine | 957311 | 91940.3791 | 390663.36 | 4.249094469 | 0.005474366 | 0.408084056 | 6.89682E−05 |
| Ascorbic acid | 16573624 | 5390181.49 | 21334040 | 3.957944691 | 3.76233E−06 | 1.287228476 | 6.79087E−05 |

TABLE 3-continued

Metabolism profile: LP tumor vs Kras tumor vs normal lung

| Label | Average Kras | Average Normal | Average LP | Fold Change LP vs Normal | LP vs Normal T Test | Fold Change LP vs Kras | LP vs Kras T Test |
|---|---|---|---|---|---|---|---|
| CDP-nega | 21957.443 | 21606.995 | 85382.54 | 3.951615647 | 0.000466398 | 3.888546588 | 0.943463946 |
| N-carbamoyl-L-aspartate-nega | 30331.232 | 24326.7475 | 94905.614 | 3.901286616 | 9.7668E−08 | 3.128973226 | 0.281805561 |
| xanthine | 17070766 | 2861802.89 | 10906682 | 3.811122701 | 0.001633943 | 0.638909929 | 3.88122E−07 |
| SBP | 197536.45 | 34752.0066 | 131776.02 | 3.791896861 | 2.5346E−05 | 0.667097256 | 0.001698857 |
| 6-phospho-D-gluconate | 71337.39 | 13491.4372 | 50715.169 | 3.759063508 | 4.00187E−08 | 0.710919885 | 0.002237585 |
| CDP-choline | 347944.26 | 137193.577 | 514335 | 3.748972907 | 4.96198E−10 | 1.478210932 | 0.000124439 |
| UDP-D-glucose | 2471704.4 | 566113.57 | 2077196.3 | 3.669221875 | 4.95089E−09 | 0.840390256 | 0.000496519 |
| 1-Methyl-Histidine | 1725464.6 | 1574846.03 | 5616783.4 | 3.566560323 | 2.23811E−08 | 3.255229519 | 0.338620922 |
| allantoate | 32643.666 | 27136.8625 | 95016.202 | 3.501370206 | 4.55453E−08 | 2.910708669 | 0.335150282 |
| Kynurenic acid | 46753.321 | 75622.767 | 252314.3 | 3.336486001 | 0.096737367 | 5.396714022 | 0.0120363 |
| anthranilate | 102221.42 | 17498.9106 | 57901.202 | 3.308846105 | 0.035150781 | 0.566429262 | 3.77896E−05 |
| N-acetyl-glucosamine | 58865.297 | 58381.8967 | 183325.46 | 3.140107919 | 0.000578341 | 3.114321407 | 0.967339159 |
| trehalose-6-Phosphate | 129073.21 | 43919.5048 | 132393.32 | 3.014453838 | 2.99522E−07 | 1.025722665 | 0.000666385 |
| inosine | 40249796 | 11642971.6 | 33976523 | 2.91820031 | 0.000840073 | 0.844141494 | 8.12618E−07 |
| sn-glycerol-3-phosphate | 19689304 | 4420844.27 | 12867436 | 2.910628714 | 1.89656E−05 | 0653524184 | 1.5785E−07 |
| dGTP | 1579489.8 | 1916470.83 | 5562810.2 | 2.902632313 | 0.002213305 | 3.521903177 | 0.613561157 |
| dephospho-CoA-posi | 55252.558 | 13105.0433 | 37867.636 | 2.889546777 | 0.021558689 | 0.685355338 | 0.049216531 |
| 2-Isopropylmalic acid | 29528366 | 12388433 | 35536587 | 2.868529634 | 5.1015E−07 | 1.203472861 | 2.63092E−05 |
| ATP-nega | 1558021.1 | 1908266.98 | 5460043.8 | 2.861257818 | 0.001791891 | 3.504473663 | 0.603072053 |
| UMP | 1598436.3 | 485503.424 | 1385256.5 | 2.853237317 | 3.09018E−07 | 0.866632289 | 0.001506937 |
| methylnicotinamide | 3996079.8 | 739643.647 | 2109678.1 | 2.852289906 | 0.011326296 | 0.527936929 | 0.000419106 |
| Geranyl-PP | 44649.604 | 30295.5849 | 81152.678 | 2.678696509 | 0.000233789 | 1.817545311 | 0.28552925 |
| guanosine | 278178.99 | 118148.301 | 314371 | 2.660816926 | 0.017065307 | 1.130103337 | 0.001459523 |
| cholesteryl sulfate | 2885118.4 | 5993158.06 | 15875634 | 2.648959618 | 0.000602093 | 5.502593389 | 0.014906643 |
| NADP+_nega | 137131.8 | 98213.0936 | 259303.82 | 2.640216433 | 0.00580191 | 1.890909471 | 0.427914246 |
| D-erythrose-4-phosphate | 646162.76 | 136251.607 | 353556.57 | 2.594880028 | 0.000112537 | 0.547163337 | 0.007351835 |
| N-acetyl-glucosamine-1-phosphate | 843715.91 | 520929.706 | 1324815.2 | 2.543174682 | 7.22638E−05 | 1.570214835 | 0.004213589 |
| CTP-nega | 240405.23 | 91570.7058 | 231087.76 | 2.523599247 | 0.000115665 | 0.961242649 | 0.016844737 |
| GMP | 9318230.4 | 2602203.13 | 6397388.2 | 2.458450737 | 0.00011035 | 0.6865454 | 0.004741399 |
| N-carbamoyl-L-aspartate | 66580.474 | 36272.892 | 88175.342 | 2.430888121 | 0.085498759 | 1.324342355 | 0.227022776 |
| glucose-1-phosphate | 461794.05 | 168394.31 | 407079.22 | 2.417416712 | 8.15663E−07 | 0.881516804 | 0.028905045 |
| glucose-6-phosphate | 1739257.8 | 362199.026 | 874890.69 | 2.41549707 | 0.002313943 | 0.503025319 | 0.049372773 |
| nicotinamide | 90882086 | 39632642.3 | 94966628 | 2.396172009 | 7.29651E−05 | 1.044943316 | 0.05409455 |
| xanthosine | 870019.76 | 136353.777 | 324839.92 | 2.382331682 | 0.012463016 | 0.373370743 | 8.24572E−08 |
| cytidine | 8321895.7 | 2565430.97 | 6025522.4 | 2.348736907 | 0.002155464 | 0.72405647 | 0.000790152 |
| fructose-6-phosphate | 1715650.2 | 386096.859 | 888656.45 | 2.30164124 | 0.001429217 | 0.517970664 | 0.047271395 |
| 2-deoxyglucose-6-phosphate | 1395067.6 | 906730.59 | 2029732.8 | 2.238518023 | 0.000514748 | 1.454935065 | 0.004341337 |
| 2-oxo-4-methylthiobutanoate | 12947.826 | 14346.5313 | 31807.032 | 2.217053846 | 0.061174079 | 2.456553941 | 0.617547696 |
| hexose-phosphate | 17799359 | 6332382.56 | 13164234 | 2.078875308 | 3.33461E−05 | 0.73959033 | 0.026223597 |
| 5-phosphoribosyl-1-pyrophosphate | 39574.98 | 16192.2749 | 33637.012 | 2.077349372 | 0.000148355 | 0.849956517 | 7.72239E−05 |
| ribose-phosphate | 8021606.1 | 1787254.81 | 3629919.7 | 2.031002876 | 0.000504641 | 0.452517816 | 1.74628E−05 |
| guanosine 5-diphosphate,3-diphosphate | 21334.242 | 14411.6944 | 29228.84 | 2.028133503 | 0.005643197 | 1.370043511 | 0.109534789 |
| cytosine | 2476485.8 | 803247.05 | 1621387.3 | 2.01854127 | 0.008213276 | 0.654712945 | 0.00072216 |
| Ng,NG-dimethyl-L-arginine | 4998037.9 | 3032838.67 | 6063416 | 1.999254389 | 0.017378556 | 1.213159262 | 0.004008523 |
| Aminoadipic acid | 117455.87 | 102109.481 | 204030.21 | 1.998151433 | 2.97154E−05 | 1.737079665 | 0.34572219 |
| Pyrophosphate | 985956.02 | 528022.872 | 1054470.1 | 1.997016048 | 0.000732882 | 1.069490041 | 0.003272645 |
| creatine | 26100081 | 44819955.2 | 87645262 | 1.95549643 | 9.17613E−06 | 3.358045575 | 0.00171655 |

TABLE 3-continued

Metabolism profile: LP tumor vs Kras tumor vs normal lung

| Label | Average Kras | Average Normal | Average LP | Fold Change LP vs Normal | LP vs Normal T Test | Fold Change LP vs Kras | LP vs Kras T Test |
|---|---|---|---|---|---|---|---|
| thymidine | 63080.291 | 80436.6925 | 156896.84 | 1.950563018 | 0.000756469 | 2.487256098 | 0.06645588 |
| deoxyribose-phosphate | 176499.52 | 121885.018 | 229071.92 | 1.879409965 | 4.75247E−05 | 1.297861404 | 0.006255346 |
| O-acetyl-L-serine | 23694.927 | 18325.5143 | 34030.103 | 1.85697942 | 0.007545665 | 1.436176705 | 0.267509258 |
| Pyroglutamic acid | 146148.49 | 130040.088 | 236336.15 | 1.817409955 | 0.01677119 | 1.617096097 | 0.577160972 |
| proline | 21398940 | 20083902.9 | 36166398 | 1.800765434 | 1.11848E−05 | 1.690102287 | 0.577272592 |
| adenine | 2876547.9 | 1455019.14 | 2607582.5 | 1.792129337 | 0.00016435 | 0.906497157 | 0.00449595 |
| D-sedoheptulose-1-7-phosphate | 3491113 | 1310636.02 | 2203013.9 | 1.680873916 | 0.009465175 | 0.631034834 | 0.072581499 |
| Guanidoacetic acid | 396953.91 | 281438.433 | 467583.17 | 1.661404837 | 0.014531817 | 1.177928114 | 0.239751611 |
| hydroxyproline | 2179662.4 | 1249033.5 | 2012642.5 | 1.611359889 | 0.021994022 | 0.923373479 | 0.010491527 |
| allantoin | 771759.11 | 848315.107 | 1359005 | 1.602004943 | 0.020959524 | 1.760918633 | 0.652628531 |
| lactate | 40874225 | 40547170.5 | 64493378 | 1.590576547 | 8.69998E−06 | 1.57784958 | 0.931369337 |
| D-gluconate | 97801.096 | 174286.618 | 276766.98 | 1.587999043 | 0.014317224 | 2.82989654 | 0.000845014 |
| Phenyllactic acid | 81245.352 | 76188.2212 | 119944.8 | 1.574322031 | 0.002376635 | 1.476328092 | 0.637594673 |
| sarcosine | 2419964.2 | 2318958.38 | 3644989.5 | 1.571821887 | 0.007378595 | 1.506216329 | 0.773799695 |
| NADP+_posi | 331356.32 | 311223.039 | 487680.6 | 1.566981033 | 0.09432915 | 1.471770942 | 0.87002798 |
| Indole-3-carboxylic acid | 69219.69 | 75765.2113 | 118600.44 | 1.565368029 | 0.009732829 | 1.713391672 | 0.503593699 |
| orotate | 219597.79 | 245298.231 | 382616.4 | 1.559800874 | 0.024684908 | 1.742350823 | 0.489909062 |
| acetylphosphate | 312873.91 | 127484.545 | 197041.63 | 1.545611923 | 0.004533425 | 0.629779682 | 0.000328379 |
| CDP-ethanolamine | 179396.56 | 138980.209 | 210568.34 | 1.515095853 | 0.001182723 | 1.173759078 | 0.06405091 |
| citrate | 16275875 | 19662073.9 | 28711283 | 1.460236758 | 0.009310237 | 1.76403932 | 0.076165701 |
| 2-ketohaxanoic acid | 43097.404 | 90733.6094 | 119773.9 | 1.320061027 | 0.185209685 | 2.779144239 | 7.4791E−06 |
| 2-hydroxygluterate | 316046.31 | 555146.298 | 712509.27 | 1.283462164 | 0.188170306 | 2.254445772 | 8.78916E−05 |
| Atrolactic acid | 7757.1508 | 12067.0596 | 15459.436 | 1.281127038 | 0.096145798 | 1.992927136 | 0.009940861 |
| Taurodeoxycholic acid | 16306.479 | 27447.4472 | 31679.619 | 1.154191811 | 0.556309994 | 1.942762635 | 0.001864033 |
| glucono-?-lactone | 9894.3502 | 14704.8712 | 16817.366 | 1.143659549 | 0.459543176 | 1.699693858 | 0.018766998 |
| p-aminobenzoate | 145745.32 | 198876.655 | 223192.03 | 1.122263596 | 0.544572882 | 1.531383854 | 0.065788348 |
| 2-dehydro-D-gluconate | 16369.494 | 33173.3138 | 35607.393 | 1.073374614 | 0.614457659 | 2.175228741 | 0.000280723 |
| 4-aminobutyrate | 15943.547 | 44641.6971 | 45477.194 | 1.018715626 | 0.950449819 | 2.852388739 | 0.007417527 |
| 2-Hydroxy-2-methylbutanedioic acid | 112885.45 | 411772.821 | 412970.04 | 1.002907484 | 0.991412571 | 3.65831053 | 3.07613E−05 |
| Citraconic acid | 868286.77 | 1608353.64 | 1581748.4 | 0.983458061 | 0.899519504 | 1.821688886 | 1.36412E−05 |
| myo-inositol | 8136691.6 | 21074131.1 | 16995725 | 0.80647334 | 0.222807877 | 2.08877584 | 0.000113133 |
| taurine | 55877911 | 116302507 | 92932095 | 0.799054961 | 0.000654348 | 1.663127576 | 7.56746E−12 |
| 2-Aminooctanoic acid | 47699092 | 89727407.1 | 57906312 | 0.645358133 | 0.034635956 | 1.213991915 | 0.001863374 |
| Maleic acid | 3525850.5 | 5081709.81 | 3233230.5 | 0.636248544 | 0.000242632 | 0.917007261 | 0.00066075 |
| Urea | 6019229.5 | 9795573.34 | 6195897.8 | 0.632520175 | 0.040098284 | 1.029350642 | 0.011584818 |
| valine | 389681.68 | 467827.325 | 295288.68 | 0.631191606 | 0.001076026 | 0.757768967 | 0.221354942 |
| Hydroxyisocaproic acid | 106867.56 | 115260.754 | 72386.048 | 0.628019907 | 0.088348159 | 0.677343499 | 0.647374835 |
| 2-keto-isovalerate | 3340523.8 | 4962760.43 | 3106811.9 | 0.626024953 | 0.001538527 | 0.930037347 | 0.001602038 |
| citrulline | 9660907.3 | 7797419.89 | 4808382.9 | 0.616663331 | 0.069509726 | 0.497715459 | 0.116777011 |
| Acetylcarnitine DL | 83192612 | 166312313 | 102282109 | 0.615000219 | 1.17904E−11 | 1.22946144 | 3.83245E−16 |
| fumarate | 3572440.8 | 5437693.15 | 3280092.6 | 0.603213997 | 5.58586E−05 | 0.918165694 | 0.000128021 |
| L-arginino-succinate | 547345.44 | 455663.616 | 272768.47 | 0.598618066 | 0.005512836 | 0.498347939 | 0.260844701 |
| homocysteic acid | 42614.388 | 155157.292 | 92800.796 | 0.598107862 | 0.005070958 | 2.177686948 | 5.52167E−07 |
| homocysteic acid | 42614.388 | 155157.292 | 92800.796 | 0.598107862 | 0.005070958 | 2.177686948 | 5.52167E−07 |
| 5-methoxytryptophan | 27523.823 | 30141.6699 | 17783.157 | 0.589985806 | 0.017398832 | 0.646100555 | 0.592906436 |
| betaine | 58321104 | 88677544 | 52171484 | 0.588328021 | 2.63504E−10 | 0.89455584 | 4.81481E−08 |
| NAD+_posi | 8963890.8 | 17150497.3 | 10028123 | 0.584713232 | 0.000989838 | 1.11872433 | 0.000880294 |
| N-acetyl-glutamine | 558272.46 | 245507.704 | 140985.99 | 0.574263016 | 0.088782607 | 0.252539762 | 0.037854167 |
| glutathione | 14118101 | 13299410 | 7373543.9 | 0.55442639 | 0.042882607 | 0.522275886 | 0.631908984 |
| Phosphorylcholine | 124413793 | 151156579 | 81769562 | 0.540959329 | 0.010031849 | 0.657238713 | 0.073782226 |

TABLE 3-continued

Metabolism profile: LP tumor vs Kras tumor vs normal lung

| Label | Average Kras | Average Normal | Average LP | Fold Change LP vs Normal | LP vs Normal T Test | Fold Change LP vs Kras | LP vs Kras T Test |
|---|---|---|---|---|---|---|---|
| glyoxylate | 64195.433 | 114067.612 | 61198.745 | 0.536512901 | 0.022171031 | 0.953319302 | 0.009759998 |
| glycolate | 17054.899 | 69781.5193 | 37125.237 | 0.532021045 | 0.002014207 | 2.176807786 | 6.25191E-08 |
| glycolate | 17054.899 | 69781.5193 | 37125.237 | 0.532021045 | 0.002014207 | 2.176807786 | 6.25191E-08 |
| Glycerophosphocholine | 93763925 | 126660894 | 66685282 | 0.526486747 | 3.28255E-08 | 0.711204037 | 0.002648978 |
| aconitate | 164050.8 | 530568.35 | 272415.77 | 0.513441425 | 0.023309435 | 1.660557439 | 0.000289024 |
| aconitate | 164050.8 | 530568.35 | 272415.77 | 0.513441425 | 0.023309435 | 1.660557439 | 0.000289024 |
| Cystine | 17716.166 | 43443.2807 | 21865.692 | 0.503315852 | 0.000268256 | 1.234222579 | 6.2149E-07 |
| N-Acetylputrescine | 7186.6492 | 13231.787 | 6618.4325 | 0.500191889 | 0.038910731 | 0.920934409 | 0.034957076 |
| Hydroxyphenylacetic acid | 180066.89 | 423521.098 | 210974.2 | 0.498143307 | 0.091265962 | 1.171643468 | 0.012102939 |
| D-glucarate | 54522.297 | 231766.382 | 109487.45 | 0.472404353 | 9.61296E-05 | 2.008122427 | 9.60618E-10 |
| D-glucarate | 54522.297 | 231766.382 | 109487.45 | 0.472404353 | 9.61296E-05 | 2.008122427 | 9.60618E-10 |
| glutamate | 34933949 | 72373676.6 | 33757962 | 0.466439789 | 6.03247E-06 | 0.966336862 | 2.36199E-07 |
| carnitine | 58039321 | 118511029 | 54197497 | 0.457320282 | 9.76914E-08 | 0.933806529 | 1.31326E-12 |
| spermidine | 203885.22 | 364715.63 | 163480.93 | 0.448242191 | 1.97444E-05 | 0.801828282 | 1.72192E-05 |
| 5-methyl-THF | 24803.397 | 82659.3541 | 36299.217 | 0.439142283 | 0.000426035 | 1.463477654 | 1.20991E-06 |
| betaine aldehyde | 580039 | 1060692.62 | 408960.49 | 0.385559852 | 7.33231E-06 | 0.705056883 | 4.49276E-06 |
| 2-oxobutanoate | 56195.927 | 302326.205 | 114583.88 | 0.379007434 | 0.000105965 | 2.039006816 | 9.24858E-08 |
| 2-oxobutanoate | 56195.927 | 302326.205 | 114583.88 | 0.379007434 | 0.000105965 | 2.039006816 | 9.24858E-08 |
| pyruvate | 17405.306 | 43600.539 | 16155.69 | 0.370538757 | 0.000402948 | 0.92820488 | 4.23036E-05 |
| acetoacetate | 60499.83 | 303975.174 | 111349.71 | 0.366311852 | 4.32655E-05 | 1.840496234 | 2.44492E-08 |
| acetoacetate | 60499.83 | 303975.174 | 111349.71 | 0.366311852 | 4.32655E-05 | 1.840496234 | 2.44492E-08 |
| thiamine-phosphate | 444804.38 | 138809.293 | 47657.852 | 0.343333298 | 0.005006605 | 0.107143398 | 0.003020597 |
| Thiamine pyrophosphate | 425006.29 | 411812.855 | 141164.03 | 0.342786835 | 3.55775E-05 | 0.332145732 | 0.893955934 |
| orotidine-S-phosphate | 5933.9622 | 15699.3236 | 5372.6486 | 0.342221661 | 0.018452033 | 0.905406618 | 0.022649228 |
| Acetyllysine | 1203630.5 | 4378556.62 | 1496553.1 | 0.341791429 | 0.003091158 | 1.243365878 | 0.000141638 |
| a-ketoglutarate | 155931.44 | 1265195.66 | 420854.62 | 0.332639952 | 3.28045E-05 | 2.698972244 | 2.19401E-08 |
| a-ketoglutarate | 155931.44 | 1265195.66 | 420854.62 | 0.332639952 | 3.28045E-05 | 2.698972244 | 2.19401E-08 |
| N6-Acetyl-L-lysine | 1489360.7 | 5564625.46 | 1771998.5 | 0.318439844 | 0.002919563 | 1.189771207 | 0.000164003 |
| D-glucosamine-1-phosphate | 14423.379 | 69906.4392 | 21337.231 | 0.305225546 | 0.004198992 | 1.479350368 | 0.000135952 |
| pantothenate | 869278.5 | 4469927.43 | 1362741 | 0.304868702 | 0.000717297 | 1.56766902 | 5.72128E-06 |
| pantothenate | 869278.5 | 4469927.43 | 1362741 | 0.304868702 | 0.000717297 | 1.56766902 | 5.72128E-06 |
| homocysteine | 48212.598 | 101975.982 | 30944.041 | 0.303444404 | 1.21745E-05 | 0.641824793 | 6.66068E-05 |
| Nicotinamide ribotide | 93249.772 | 598534.858 | 170042.14 | 0.284097306 | 2.40101E-06 | 1.823512673 | 2.42727E-09 |
| Nicotinamide ribotide | 93249.772 | 598534.858 | 170042.14 | 0.284097306 | 2.40101E-06 | 1.823512673 | 2.42727E-09 |
| oxaloacetate | 329374.88 | 1706785.03 | 475070.64 | 0.278342398 | 3.20114E-07 | 1.442340223 | 1.22334E-09 |
| arginine | 7389833.2 | 9560406.1 | 2591652.5 | 0.271081846 | 3.92409E-05 | 0.350705148 | 0.119630996 |
| cyclic-AMP | 1353244.2 | 2703830.41 | 719065.22 | 0.265943168 | 0.028368341 | 0.531363964 | 0.067516343 |
| deoxyadenosine | 24526.799 | 45368.6993 | 11660.102 | 0.257007643 | 1.08061E-05 | 0.47540254 | 0.016525265 |
| glycine | 47097.004 | 99096.9074 | 24673.276 | 0.248981296 | 1.70723E-05 | 0.523882083 | 4.61094E-05 |
| 3-methylphenylacetic acid | 106762.36 | 104996.924 | 25256.177 | 0.240542067 | 0.064032214 | 0.236564422 | 0.968048866 |
| p-hydroxybenzoate | 8101306.9 | 11343718 | 2722213 | 0.239975378 | 0.04954882 | 0.336021464 | 0.539376226 |
| Imidazoleacetic acid | 126567.03 | 242625.766 | 52322.115 | 0.215649458 | 8.63313E-08 | 0.413394491 | 0.011977589 |
| S-ribosyl-L-homocysteine-posi | 19571.952 | 30196.092 | 6170.4172 | 0.204344894 | 0.012462999 | 0.315268355 | 0.136087499 |
| 3-phospho-serine | 155227.73 | 128223.689 | 25836.39 | 0.201494673 | 0.001175672 | 0.166441849 | 0.589337956 |
| folate | 21107.517 | 47432.3485 | 8811.463 | 0.185769064 | 3.07947E-05 | 0.41745617 | 0.000114589 |
| aspartate | 8184138 | 18368956.1 | 3272680.8 | 0.17816368 | 1.128E-05 | 0.399880943 | 7.29852E-05 |
| choline | 2707025.6 | 4423728.42 | 681997.31 | 0.154167988 | 2.12816E-06 | 0.251936036 | 0.001945735 |
| glucosamine | 500620.68 | 1689898.49 | 226752.44 | 0.134181102 | 2.98584E-06 | 0.452942622 | 4.19781E-05 |
| 2,3-dihydroxybenzoic acid | 1207681.7 | 2645288.7 | 270649.94 | 0.102313952 | 0.000385566 | 0.224107011 | 0.010201239 |
| hydroxyphenyl-pyruvate | 22786.501 | 106447.102 | 10723.04 | 0.100735856 | 1.90194E-05 | 0.470587382 | 3.90935E-06 |
| S-adenosyl-L-methionine | 1825191.3 | 7867267.07 | 722777.16 | 0.091871441 | 2.90254E-07 | 0.396000779 | 1.226E-07 |
| S-methyl-5-thioadenosine | 15692.3 | 103985.084 | 9054.5749 | 0.087075709 | 2.21719E-06 | 0.5770075 | 1.07745E-07 |

TABLE 4

Summary of NGFR and MPO IHC staining on human slides

| Slides ID | Phenotype | P63 | NGFR | MPO |
|---|---|---|---|---|
| S1 | SCC | +++ | +++ | +++ |
| S2 | SCC | ++ | ++ | +++ |
| S3 | SCC | +++ | +++ | +++ |
| S4 | SCC | +++ | +++ | +++ |
| S5 | SCC | +++ | +++ | +++ |
| S6 | SCC | +++ | +++ | +++ |
| S7 | SCC | + | ++ | +++ |
| S8 | SCC | +++ | +++ | +++ |
| S9 | SCC | +++ | +++ | +++ |
| S10 | SCC | +++ | − | +++ |
| S11 | SCC | +++ | − | +++ |
| S12 | SCC | +++ | +++ | +++ |
| S13 | SCC | +++ | +++ | − |
| S14 | SCC | +++ | +++ | ++ |
| S15 | SCC | +++ | +++ | − |
| A1 | ADC | − | − | +++ |
| A2 | ADC | − | − | +/− |
| A3 | ADC | − | ++ | − |
| A4 | ADC | − | − | + |
| A5 | ADC | − | − | ++ |
| A6 | ADC | − | − | − |
| A7 | ADC | − | − | − |
| A8 | ADC | − | + | − |
| A9 | ADC | − | − | − |
| A10 | ADC | − | − | − |
| A11 | ADC | − | − | − |
| A12 | ADC | − | − | + |

Summary:

SCC p63 positive=15/15; ADC p63 positive=0/12; p<0.0001

SCC NGFR positive=13/15; ADC NGFR positive=2/12; p=0.001

SCC MPO strong positive=13/15; ADC MPO strong positive=4/12; p=0.007

TABLE 5

Genes with significantly altered expression in EpCam-CD45+ cells:
LP stroma vs Kras stroma vs Normal lung EpCam-CD45+ cells
(log2 fold >1; or log2 fold <1)

| Probe | Symbol | Description | p-value | log2 fold change for LKBIPTEN CD45 − LKBIPTEN EpCAM | log2 fold change for LKBIPTEN CD45-Kras CD45 |
|---|---|---|---|---|---|
| 10347291 | Cxcr2 | chemokine (C-X-C motif) receptor 2 | 0.004 | 3.95 | 5.004 |
| 10563712 | Mrgpra2a | MAS-related GPR, member A2A | 0.002 | 5.107 | 4.872 |
| 10429856 | Spatcl | spermatogenesis and centriole associated 1 | 4.54E−04 | 5.065 | 4.741 |
| 10435497 | Stfa2l1 | stefin A2 like 1 | 0.004 | 4.696 | 4.468 |
| 10499861 | S100a9 | S100 calcium binding protein A9 (calgranulin B) | 0.013 | 4.808 | 4.308 |
| 10579636 | Cyp4f18 | cytochrome P450, family 4, subfamily f, polypeptide 18 | 0.02 | 4.29 | 4.288 |
| 10487238 | Hdc | histidine decarboxylase | 0.004 | 2.867 | 4.246 |
| 10351197 | Sell | selectin, lymphocyte | 0.008 | 3.996 | 4.223 |
| 10478633 | Mmp9 | matrix metallopeptidase 9 | 0.004 | 4.962 | 4.187 |
| 10416837 | Irg1 | immunoresponsive gene 1 | 0.015 | 4.364 | 4 |
| 10372094 | | | 0.002 | 3.423 | 3.973 |
| 10493831 | S100a8 | S100 calcium binding protein A8 (calgranulin A) | 0.019 | 4.322 | 3.94 |
| 10471505 | Sh2d3c | SH2 domain containing 3C | 0.006 | 2.792 | 3.772 |
| 10519983 | Fgl2 | fibrinogen-like protein 2 | 0.008 | 2.888 | 3.761 |
| 10478973 | Cass4 | Cas scaffolding protein family member 4 | 0.002 | 3.413 | 3.73 |
| 10608637 | Gm5483 | predicted gene 5483 | 7.36E−04 | 4.271 | 3.639 |
| 10574276 | Gpr97 | G protein-coupled receptor 97 | 0.003 | 3.205 | 3.638 |
| 10594825 | Aqp9 | aquaporin 9 | 0.01 | 3.189 | 3.567 |
| 10353844 | Neurl3 | neuralized homolog 3 homolog (Drosophila) | 0.009 | 2.626 | 3.551 |
| 10563715 | Mrgpra2b | MAS-related GPR, member A2B | 0.004 | 4.308 | 3.513 |
| 10580033 | Cd97 | CD97 antigen | 0.002 | 2.928 | 3.459 |
| 10452307 | Tnfsf14 | tumor necrosis factor (ligand) superfamily, member 14 | 0.004 | 2.763 | 3.447 |
| 10439292 | BC100530 | cDNA sequence BC100530 | 0.003 | 4.16 | 3.397 |
| 10338926 | | | 0.005 | 2.211 | 3.377 |
| 10468527 | 5830416P10Rik | RIKEN cDNA 5830416P10 gene | 0.003 | 3.281 | 3.34 |
| 10437243 | Mefv | Mediterranean fever | 3.85E−04 | 3.435 | 3.28 |
| 10341789 | | | 0.005 | 2.012 | 3.206 |
| 10439296 | Stfa2 | stefin A2 | 0.004 | 3.146 | 3.205 |
| 10433101 | Gpr84 | G protein-coupled receptor 84 | 0.004 | 2.765 | 3.205 |
| 10341872 | | | 0.005 | 2.045 | 3.2 |
| 10340662 | | | 0.002 | 2.219 | 3.193 |

TABLE 5-continued

Genes with significantly altered expression in EpCam-CD45+ cells:
LP stroma vs Kras stroma vs Normal lung EpCam-CD45+ cells
(log2 fold >1; or log2 fold <1)

| Probe | Symbol | Description | p-value | log2 fold change for LKBIPTEN CD45 - LKBIPTEN EpCAM | log2 fold change for LKBIPTEN CD45- Kras CD45 |
|---|---|---|---|---|---|
| 10501164 | Csf1 | colony stimulating factor 1 (macrophage) | 0.003 | 3.939 | 3.192 |
| 10490304 | Sycp2 | synaptonemal complex protein 2 | 0.006 | 2.483 | 3.16 |
| 10404152 | Fam65b | family with sequence similarity 65, member B | 0.004 | 2.708 | 3.033 |
| 10338478 | | | 0.004 | 2.581 | 3.001 |
| 10474181 | Abtb2 | ankyrin repeat and BTB (POZ) domain containing 2 | 0.008 | 2.854 | 2.99 |
| 10365290 | Chst11 | carbohydrate sulfotransferase 11 | 0.003 | 2.461 | 2.93 |
| 10444752 | Ltb | lymphotoxin B | 0.005 | 2.785 | 2.851 |
| 10562705 | Gm2511 | predicted gene 2511 | 0.006 | 2.714 | 2.846 |
| 10379633 | Slfn1 | schlafen 1 | 0.004 | 3.705 | 2.745 |
| 10434291 | B3gnt5 | UDP-GlcNAc:betaGal beta-1,3-N-acetylglucosaminyltransferase 5 | 0.004 | 1.81 | 2.689 |
| 10444016 | Pram1 | PML-RAR alpha-regulated adaptor molecule 1 | 0.004 | 1.897 | 2.651 |
| 10551696 | Rasgrp4 | RAS guanyl releasing protein 4 | 0.005 | 2.064 | 2.622 |
| 10555510 | Pde2a | phosphodiesterase 2A, cGMP-stimulated | 0.005 | 1.543 | 2.578 |
| 10462603 | Fas | Fas (TNF receptor superfamily member 6) | 0.004 | 1.995 | 2.54 |
| 10344061 | | | 0.005 | 1.803 | 2.532 |
| 10481164 | Slc2a6 | solute carrier family 2 (facilitated glucose transporter), member 6 | 0.009 | 2.257 | 2.531 |
| 10424683 | Ly6g | | 0.007 | 3.302 | 2.462 |
| 10404996 | Ninj1 | ninjurin 1 | 0.004 | 2.126 | 2.379 |
| 10340031 | | | 0.009 | 1.844 | 2.372 |
| 10434845 | Il1rap | interleukin 1 receptor accessory protein | 0.003 | 2.034 | 2.37 |
| 10539739 | Asprv1 | aspartic peptidase, retroviral-like 1 | 0.004 | 3.626 | 2.339 |
| 10432236 | Rnd1 | Rho family GTPase 1 | 0.002 | 1.987 | 2.317 |
| 10560919 | Atp1a3 | ATPase, Na+/K+ transporting, alpha 3 polypeptide | 0.004 | 2.093 | 2.309 |
| 10359762 | Rcsd1 | RCSD domain containing 1 | 0.008 | 2.108 | 2.304 |
| 10566350 | Trim30b | tripartite motif-containing 30B | 3.79E−04 | 2.405 | 2.295 |
| 10589535 | Ngp | neutrophilic granule protein | 0.004 | 1.455 | 2.29 |
| 10448278 | Mmp25 | matrix metallopeptidase 25 | 0.003 | 1.569 | 2.281 |
| 10430382 | | | 0.002 | 2.564 | 2.279 |
| 10475782 | Dusp2 | dual specificity phosphatase 2 | 0.002 | 1.857 | 2.272 |
| 10549544 | | | 0.01 | 2.201 | 2.267 |
| 10361246 | G0sp2 | G0/G1 switch gene 2 | 0.002 | 1.946 | 2.251 |
| 10379636 | Slfn4 | schlafen 4 | 0.002 | 4.892 | 2.221 |
| 10585778 | Sema7a | sema domain, immunoglobulin domain (Ig), and GPI membrane anchor, (semaphorin) 7A | 0.003 | 2.016 | 2.216 |
| 10420668 | Mir15a | microRNA 15a | 0.011 | 2.35 | 2.188 |
| 10416653 | Kbtbd7 | kelch repeat and BTB (POZ) domain containing 7 | 0.005 | 2.05 | 2.186 |
| 10585555 | Pstpip1 | proline-serine-threonine phosphatase-interacting protein 1 | 0.003 | 2.077 | 2.107 |
| 10591416 | | | 0.005 | 2.043 | 2.103 |
| 10409152 | 1110007C09Rik | RIKEN cDNA 1110007C09 gene | 0.002 | 2.438 | 2.091 |
| 10370339 | Trpm2 | transient receptor potential cation channel, subfamily M, member 2 | 0.004 | 1.964 | 2.086 |
| 10339976 | | | 0.006 | 1.435 | 2.079 |
| 10409170 | Fgd3 | FYVE, RhoGEF and PH domain containing 3 | 0.019 | 2.955 | 2.007 |
| 10354191 | Rnf149 | ring finger protein 149 | 0.003 | 1.332 | 1.982 |
| 10435504 | Gm5416 | predicted gene 5416 | 0.009 | 2.22 | 1.957 |
| 10427131 | Soat2 | sterol O-acyltransferase 2 | 0.004 | 2 | 1.916 |
| 10367919 | Stx11 | syntaxin 11 | 0.001 | 2.415 | 1.883 |

TABLE 5-continued

Genes with significantly altered expression in EpCam-CD45+ cells:
LP stroma vs Kras stroma vs Normal lung EpCam-CD45+ cells
(log2 fold >1; or log2 fold <1)

| Probe | Symbol | Description | p-value | log2 fold change for LKBIPTEN CD45 - LKBIPTEN EpCAM | log2 fold change for LKBIPTEN CD45 - Kras CD45 |
|---|---|---|---|---|---|
| 10428008 | Ankrd33b | ankyrin repeat domain 33B | 0.011 | 1.51 | 1.86 |
| 10568221 | Sephs2 | selenophosphate synthetase 2 | 0.004 | 1.151 | 1.846 |
| 10343993 | | | 0.006 | 1.332 | 1.832 |
| 10479041 | Rbm38 | RNA binding motif protein 38 | 0.01 | 1.51 | 1.828 |
| 10389561 | Dhx40 | DEAH (Asp-Glu-Ala-His) box polypeptide 40 | 0.011 | 1.495 | 1.779 |
| 10420666 | Mir16-1 | microRNA 16-1 | 0.003 | 1.972 | 1.755 |
| 10388389 | Hic1 | hypermethylated in cancer 1 | 0.004 | 1.635 | 1.745 |
| 10573344 | Mir27a | microRNA 27a | 0.011 | 1.523 | 1.738 |
| 10343561 | | | 0.007 | 1.594 | 1.727 |
| 10476012 | Gm14047 | predicted gene 14047 | 0.007 | 1.748 | 1.719 |
| 10545930 | | | 0.004 | 2.895 | 1.701 |
| 10575209 | A430107J10Rik | RIKEN cDNA A430107J10 gene | 0.007 | 1.231 | 1.694 |
| 10376796 | Grap | GRB2-related adaptor protein | 0.009 | 1.474 | 1.683 |
| 10517070 | Zdhhc18 | zinc finger, DHHC domain containing 18 | 0.01 | 1.264 | 1.658 |
| 10415714 | Fam123a | family with sequence similarity 123, member A | 0.004 | 1.652 | 1.651 |
| 10342189 | | | 0.004 | 0.98 | 1.63 |
| 10395682 | | | 0.005 | 1.608 | 1.622 |
| 10573342 | Mir23a | microRNA 23a | 0.009 | 1.562 | 1.604 |
| 10433096 | Nfe2 | nuclear factor, erythroid derived 2 | 0.009 | 1.365 | 1.593 |
| 10472097 | Fmnl2 | formin-like 2 | 0.019 | 2.078 | 1.54 |
| 10584841 | Amica1 | adhesion molecule, interacts with CXADR antigen 1 | 0.017 | 1.5 | 1.536 |
| 10555470 | Arap1 | ArfGAP with RhoGAP domain, ankyrin repeat and PH domain 1 | 0.004 | 1.024 | 1.494 |
| 10400023 | Tspan13 | tetraspanin 13 | 0.011 | 1.44 | 1.484 |
| 10375439 | Med7 | mediator complex subunit 7 | 0.008 | 1.168 | 1.473 |
| 10562696 | 4931406B18Rik | RIKEN cDNA 4931406B18 gene | 0.019 | 1.602 | 1.471 |
| 10537509 | Mgam | maltase-glucoamylase | 0.004 | 1.854 | 1.463 |
| 10492824 | Tmem154 | transmembrane protein 154 | 0.011 | 1.581 | 1.461 |
| 10590801 | Birc3 | baculoviral IAP repeat-containing 3 | 0.005 | 1.246 | 1.454 |
| 10508465 | Marcksl1 | MARCKS-like 1 | 0.013 | 2.112 | 1.449 |
| 10603208 | Mid1 | midline 1 | 0.016 | 1.559 | 1.439 |
| 10385323 | Mir146 | microRNA 146 | 0.004 | 1.365 | 1.427 |
| 10575211 | Mir140 | microRNA 140 | 0.001 | 1.286 | 1.415 |
| 10458498 | Arap3 | ArfGAP with RhoGAP domain, ankyrin repeat and PH domain 3 | 0.006 | 1.281 | 1.403 |
| 10433161 | | | 0.007 | 1.658 | 1.402 |
| 10579958 | Il15 | interleukin 15 | 0.01 | 1.27 | 1.391 |
| 10433207 | | | 0.013 | 1.272 | 1.328 |
| 10393449 | Socs3 | suppressor of cytokine signaling 3 | 0.011 | 1.459 | 1.313 |
| 10409804 | Zcchc6 | zinc finger, CCHC domain containing 6 | 0.005 | 1.219 | 1.265 |
| 10516027 | Rlf | rearranged L-myc fusion sequence | 0.005 | 1.004 | 1.265 |
| 10416251 | Egr3 | early growth response 3 | 0.009 | 1.188 | 1.254 |
| 10576603 | | | 0.009 | 1.016 | 1.249 |
| 10391870 | Map3k14 | mitogen-activated protein kinase kinase kinase 14 | 0.006 | 1.133 | 1.234 |
| 10345445 | Arid5a | AT rich interactive domain 5A (MRF1-like) | 0.005 | 1.777 | 1.233 |
| 10454953 | Tmco6 | transmembrane and coiled-coil domains 6 | 0.008 | 1.364 | 1.222 |
| 10565775 | Dgat2 | diacylglycerol O-acyltransferase 2 | 0.004 | 1.991 | 1.206 |
| 10435501 | Stfa1 | stefin A1 | 0.009 | 2.068 | 1.195 |
| 10526675 | Tsc22d4 | TSC22 domain family, member 4 | 0.007 | 1.126 | 1.183 |
| 10560685 | Bcl3 | B cell leukemia/lymphoma 3 | 0.007 | 1.702 | 1.17 |
| 10351224 | F5 | coagulation factor V | 0.01 | 1.474 | 1.16 |
| 10343506 | | | 0.025 | 1.514 | 1.128 |

TABLE 5-continued

Genes with significantly altered expression in EpCam-CD45+ cells:
LP stroma vs Kras stroma vs Normal lung EpCam-CD45+ cells
(log2 fold >1; or log2 fold <1)

| Probe | Symbol | Description | p-value | log2 fold change for LKBIPTEN CD45 - LKBIPTEN EpCAM | log2 fold change for LKBIPTEN CD45 - Kras CD45 |
|---|---|---|---|---|---|
| 10582719 | Sipa1l2 | signal-induced proliferation-associated 1 like 2 | 0.016 | 1.437 | 1.106 |
| 10573346 | Mir24-2 | microRNA 24-2 | 0.006 | 1.079 | 1.044 |
| 10409162 | Susd3 | sushi domain containing 3 | 0.013 | 0.99 | 1.041 |
| 10405185 | Cks2 | CDC28 protein kinase regulatory subunit 2 | 0.004 | 0.83 | 1.018 |
| 10367803 | | | 0.022 | 1.366 | 1.013 |
| 10345715 | Map4k4 | mitogen-activated protein kinase kinase kinase kinase 4 | 0.005 | 0.847 | 0.998 |
| 10481670 | Cdk9 | cyclin-dependent kinase 9 (CDC2-related kinase) | 0.005 | 0.801 | 0.998 |
| 10381744 | Arf2 | ADP-ribosylation factor 2 | 0.015 | 0.938 | 0.962 |
| 10421950 | Dach1 | dachshund 1 (*Drosophila*) | 0.016 | 1.176 | 0.943 |
| 10558515 | Inpp5a | inositol polyphosphate-5-phosphatase A | 0.016 | 1.257 | 0.915 |
| 10569011 | Ifitm5 | interferon induced transmembrane protein 5 | 0.003 | 1.466 | 0.896 |
| 10409240 | Sema4d | sema domain, immunoglobulin domain (Ig), transmembrane domain (TM) and short cytoplasmic domain, (semaphorin) 4D | 0.003 | 2.082 | 0.85 |
| 10541895 | Tnfrsf1a | tumor necrosis factor receptor superfamily, member 1a | 0.01 | 0.658 | 0.838 |
| 10571321 | Ppp1r3b | protein phosphatase 1, regulatory (inhibitor) subunit 3B | 0.018 | 1.025 | 0.828 |
| 10339000 | | | 0.019 | 0.98 | 0.801 |
| 10475772 | Stard7 | START domain containing 7 | 0.015 | 0.749 | 0.775 |
| 10524983 | Med13l | mediator complex subunit 13-like | 0.004 | 1.084 | 0.767 |
| 10586039 | Tle3 | transducin-like enhancer of split 3, homolog of Drosophila E(spl) | 0.018 | 1.037 | 0.747 |
| 10352918 | Mir29c | microRNA 29c | 0.017 | 0.809 | 0.733 |
| 10564631 | Slco3a1 | solute carrier organic anion transporter family, member 3a1 | 0.003 | 1.64 | 0.704 |
| 10379321 | Rab11fip4 | RAB11 family interacting protein 4 (class II) | 0.021 | 0.72 | 0.587 |
| 10437160 | Ets2 | E26 avian leukemia oncogene 2, 3' domain | 0.004 | 1.19 | 0.54 |
| 10465379 | Snx15 | sorting nexin 15 | 0.012 | −0.643 | −0.732 |
| 10420986 | | | 0.019 | −1.239 | −0.904 |
| 10436978 | Cbr3 | carbonyl reductase 3 | 0.016 | −1.032 | −0.989 |
| 10431637 | Cpne8 | copine VIII | 0.012 | −1.113 | −1.064 |
| 10531261 | Rassf6 | Ras association (RalGDS/AF-6) domain family member 6 | 0.007 | −0.823 | −1.125 |
| 10512022 | | | 0.015 | −1.497 | −1.297 |
| 10359861 | Mgst3 | microsomal glutathione S-transferase 3 | 0.007 | −1.026 | −1.528 |
| 10537909 | Rny3 | RNA, Y3 small cytoplasmic (associated with Ro protein) | 0.007 | −1.336 | −1.899 |

What is claimed is:

1. A method of treating a subject afflicted with a lung cancer, wherein i) the lung cancer is selected from the group consisting of adenocarcinoma, lung squamous cell carcinoma (SCC), adeno-squamous carcinoma, or mixed tumors thereof, and ii) the lung cancer comprises at least one mutation selected from the group consisting of an activating KRAS mutation, an activating NRAS mutation, an activating HRAS mutation, an inhibiting LKB1 mutation, and an inhibiting PTEN mutation, comprising administering to the subject an agent that inhibits the copy number, amount, and/or activity of arginase 1 without administration of an additional immunotherapy, thereby treating the subject afflicted with the lung cancer.

2. The method of claim 1, wherein the agent is administered in a pharmaceutically acceptable formulation.

3. The method of claim 1, wherein the agent directly binds arginase 1.

4. The method of claim 1, wherein the arginase 1 is human arginase 1.

5. The method of claim 1, wherein the agent is selected from the group consisting of a blocking antibody, small molecule, antisense nucleic acid, interfering RNA, shRNA, siRNA, aptamer, ribozyme, dominant-negative protein, and combinations thereof.

6. The method of claim 1, wherein the lung cancer comprises at least one inhibiting LKB1 mutation and at least one inhibiting PTEN mutation.

7. The method of claim 1, wherein the lung cancer comprises at least one activating RAS mutation selected from the group consisting of KRAS, NRAS, HRAS, and any combination thereof.

8. The method of claim 1, wherein the lung cancer comprises 1) at least one inhibiting LKB1 mutation and at least one inhibiting PTEN mutation and 2) at least one activating RAS mutation selected from the group consisting of KRAS, NRAS, HRAS, and any combination thereof.

9. The method of claim 1, wherein the subject is a mammal, an animal model of cancer, or a human.

10. The method of claim 1, further comprising administering one or more additional anti-cancer agents.

11. A method of inhibiting hyperproliferative growth of a lung cancer cell or cells, wherein i) the lung cancer is selected from the group consisting of adenocarcinoma, lung squamous cell carcinoma (SCC), adeno-squamous carcinoma, or mixed tumors thereof, and ii) the lung cancer cell or cells comprise at least one mutation selected from the group consisting of an activating KRAS mutation, an activating NRAS mutation, an activating HRAS mutation, an inhibiting LKB1 mutation, and an inhibiting PTEN mutation, the method comprising contacting the cancer cell or cells with an agent that inhibits the copy number, amount, and/or activity of arginase 1 without contacting the cells with an additional immunotherapy, thereby inhibiting hyperproliferative growth of the cancer cell or cells.

12. The method of claim 11, wherein the step of contacting occurs in vivo, ex vivo, or in vitro.

13. The method of claim 11, wherein the agent is administered in a pharmaceutically acceptable formulation.

14. The method of claim 11, wherein the agent directly binds arginase 1.

15. The method of claim 11, wherein the arginase 1 is human arginase 1.

16. The method of claim 11, wherein the agent is selected from the group consisting of a blocking antibody, small molecule, antisense nucleic acid, interfering RNA, shRNA, siRNA, aptamer, ribozyme, dominant-negative protein, and combinations thereof.

17. The method of claim 11, wherein the lung cancer comprises at least one inhibiting LKB1 mutation and at least one inhibiting PTEN mutation.

18. The method of claim 11, wherein the lung cancer comprises at least one activating RAS mutation selected from the group consisting of KRAS, NRAS, HRAS, and any combination thereof.

19. The method of claim 11, wherein the lung cancer comprises 1) at least one inhibiting LKB1 mutation and at least one inhibiting PTEN mutation and 2) at least one activating RAS mutation selected from the group consisting of KRAS, NRAS, HRAS, and any combination thereof.

20. The method of claim 11, wherein the subject is a mammal, an animal model of cancer, or a human.

21. The method of claim 11, further comprising administering one or more additional anti-cancer agents.

* * * * *